(12) United States Patent
Jarvis et al.

(10) Patent No.: US 12,270,047 B2
(45) Date of Patent: Apr. 8, 2025

(54) ENGINEERED MULTI-COMPONENT SYSTEM FOR IDENTIFICATION AND CHARACTERISATION OF T-CELL RECEPTORS AND T-CELL ANTIGENS

(71) Applicant: GENOVIE AB, Södertälje (SE)

(72) Inventors: Reagan Micheal Jarvis, Karlskrona (SE); Ryan Edward Hill, Karlskrona (SE); Luke Benjamin Pase, Karlskrona (SE)

(73) Assignee: GENOVIE AB, Södertälje (SE)

(*) Notice: Subject to any disclaimer, the term of this patent is extended or adjusted under 35 U.S.C. 154(b) by 1016 days.

(21) Appl. No.: 16/863,119

(22) Filed: Apr. 30, 2020

(65) Prior Publication Data

US 2020/0339946 A1    Oct. 29, 2020

Related U.S. Application Data

(63) Continuation of application No. 16/347,684, filed as application No. PCT/EP2017/078376 on Nov. 7, 2017, now Pat. No. 12,012,610.

(30) Foreign Application Priority Data

Nov. 7, 2016    (DK) .................. PA 2016 70872

(51) Int. Cl.
| | |
|---|---|
| C12N 5/071 | (2010.01) |
| A61K 35/15 | (2015.01) |
| A61K 39/00 | (2006.01) |
| C07K 14/725 | (2006.01) |
| C12N 15/85 | (2006.01) |
| C12N 15/90 | (2006.01) |

(52) U.S. Cl.
CPC .......... *C12N 5/0602* (2013.01); *A61K 35/15* (2013.01); *C07K 14/7051* (2013.01); *C12N 15/85* (2013.01); *C12N 15/907* (2013.01); *A61K 2039/5154* (2013.01); *A61K 2039/5156* (2013.01); *C12N 2310/153* (2013.01); *C12N 2310/18* (2013.01); *C12N 2810/10* (2013.01)

(58) Field of Classification Search
CPC .......... A61K 35/15; A61K 2039/5154; A61K 2039/5156; C07K 14/7051; C12N 2310/153; C12N 2810/10; C12N 15/1093
See application file for complete search history.

(56) References Cited

U.S. PATENT DOCUMENTS

| | | |
|---|---|---|
| 9,678,061 B2 | 6/2017 | Dornmair et al. |
| 11,274,309 B2 | 3/2022 | Jarvis et al. |
| 2015/0203886 A1 | 7/2015 | Kishi et al. |
| 2017/0073664 A1 | 3/2017 | McCafferty et al. |
| 2017/0290858 A1 | 10/2017 | Zhao et al. |
| 2018/0245242 A1 | 8/2018 | Schendel et al. |
| 2019/0283017 A1 | 9/2019 | Jarvis et al. |
| 2019/0359934 A1 | 11/2019 | Jarvis et al. |
| 2020/0095574 A1 | 3/2020 | Jarvis et al. |
| 2020/0115432 A1 | 4/2020 | Jarvis et al. |
| 2020/0231974 A1 | 7/2020 | Jarvis et al. |

FOREIGN PATENT DOCUMENTS

| | | |
|---|---|---|
| CN | 105316362 A | 2/2016 |
| EP | 2 899 269 A1 | 7/2015 |
| JP | 2013-535209 A | 9/2013 |
| WO | WO-03/065977 A2 | 8/2003 |
| WO | WO-2008/095927 A1 | 8/2008 |
| WO | WO-2011/154147 A1 | 12/2011 |
| WO | WO-2012/017081 A1 | 2/2012 |
| WO | WO-2013/144257 A1 | 10/2013 |
| WO | WO-2014/153470 A2 | 9/2014 |
| WO | WO-2015/136072 A1 | 9/2015 |
| WO | WO-2015/164740 A1 | 10/2015 |
| WO | WO-2016/069282 A1 | 5/2016 |
| WO | WO-2016/073755 A2 | 5/2016 |

(Continued)

OTHER PUBLICATIONS

Baser et al. "A method for specifically targeting two independent genomic integration sites for co-expression of genes in CHO cells" Methods 95, pp. 3-12 (2016) (Available online Dec. 2015).

(Continued)

*Primary Examiner* — Paul J Holland
(74) *Attorney, Agent, or Firm* — KNOBBE, MARTENS, OLSON & BEAR LLP

(57) ABSTRACT

The present invention relates to A multicomponent system wherein a first component is an engineered antigen-presenting cell (eAPC) designated component A and a second component is a genetic donor vector, designated component C, for delivery of one or more ORFs encoding an analyte antigen-presenting complex (aAPX) and/or an analyte antigenic molecule (aAM), wherein component A a. Lacks endogenous surface expression of at least one family of aAPX and/or aAM and b. Contains at least two genomic receiver sites, designated component B and component D, each for integration of at least one ORF encoding at least one aAPX and/or aAM, and component C is matched to a component B, and wherein component C is designed to deliver c. A single ORF encoding at least one aAPX and/or aAM or d. Two or more ORF encoding at least one aAPX and/or aAM, wherein the genomic receiver sites B and D are synthetic constructs designed for recombinase mediated exchange (RMCE).

19 Claims, 50 Drawing Sheets

Figure 1:
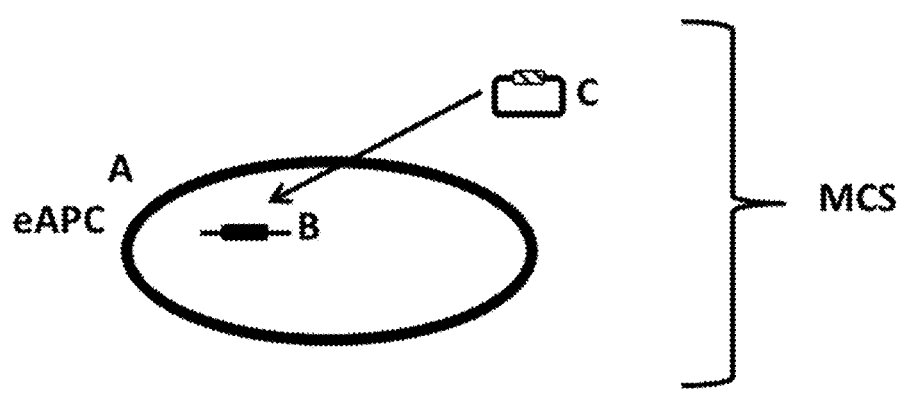

Specification includes a Sequence Listing.

(56) References Cited

FOREIGN PATENT DOCUMENTS

| WO | WO-2016/146618 A1 | 9/2016 |
| WO | WO-2016/193299 A1 | 12/2016 |

OTHER PUBLICATIONS

Brusko et al. (2010) Human Antigen-Specific Regulatory T Cells Generated by T Cell Receptor Gene Transfer. PLoS One 5(7):e11726. doi:10.1371/ournal.pone.0011726(Year:2010).

Office Action issued on Mar. 4, 2022, in U.S. Appl. No. 16/347,691 (US 2020-0231974).

Bhatta et al., "Engagement of CD45 alters early signaling events in human T cells co-stimulated through TCR + CD28," Cellular Immunology 353 (2020) 104130, 11 pages (Available online May 13, 2020).

CD3 (immunology)—Wikipedia; pp. 1-3, downloaded Apr. 19, 2021. Available online, URL: https://en.wikipedia.org/wiki/CD3_(immunology).

Office Action issued on Apr. 22, 2021 in U.S. Appl. No. 16/347,691 (US 2020-0095574).

Karste et al., "Not Limited to *E. coli*: Versatile Expression Vectors for Mammalian Protein Expression," In: Burgess-Brown N. (eds) Heterologous Gene Expression in *E.coli*. Methods in Molecular Biology, vol. 1586, pp. 313-324 (2017) (Available online May 2017).

Office Action issued on Jan. 12, 2021, in U.S. Appl. No. 16/347,691 (US 2020-0095574).

Turan et al., "Recombinase-Mediated Cassette Exchange (RMCE): Traditional Concepts and Current Challenges," Journal of Microbiology, vol. 407, pp. 193-221 (2011) (Available online Jan. 2011).

Restriction Requirement issued on Jun. 26, 2020, in U.S. Appl. No. 16/347,691 (US 2020-0095574).

Office Action issued on Apr. 27, 2022, in U.S. Appl. No. 16/347,684 (US 2019-0359934).

Restriction Requirement issued on May 6, 2022 in U.S. Appl. No. 16/347,716 (US 2020-0115432).

Office Action issued on Mar. 10, 2021 in U.S. Appl. No. 16/347,723 (US 2019-0283017).

Ziemann et al., "Gene name errors are widespread in the scientific literature," Genome Biology, vol. 17, No. 177, 3pages (2016).

U.S. Appl. No. 16/632,301, filed Jan. 17, 2020, Jarvis et al.

Butler et al., "A panel of human cell-based artificial APC enables the expansion of long-lived antigen-specific CD4 T cells restricted by prevalent HLA-DR alleles," International Immunology, vol. 22, No. 11, pp. 863-873 (Nov. 2010).

Dupont et al., "Artificial antigen-presenting cells transduced with telomerase efficiently expand epitope-specific, human leukocyte antigen-restricted cytotoxic T cells," Cancer Research, American Association for Cancer Research, vol. 65, No. 12, pp. 5417-5427, (Jun. 2005).

Guo et al., "Rapid cloning, expression, and functional characterization of paired αβ and γδT-Cell receptor chains from single-cell analysis," Molecular Therapy—Methods and Clinical Development, vol. 3, No. 15054, 12 pages, (Jan. 2016).

Hamana et al., "A novel, rapid and efficient method of cloning functional antigen-specific T-cell receptors from single human and mouse T-cells," Biochemical and Biophysical Research Communication, vol. 474, No. 4, pp. 709-714 (May 2016).

Han et al., "Linking T-cell receptor sequence to function al phenotype at the single-cell level," Nature Biotechnology, vol. 32, No. 7, pp. 684-692 (Jun. 2014).

Kobayashi et al., "A new cloning and expression system yields and validates TCRs from blood lymphocytes of patients with cancer within 10 days," Nature Medicine, vol. 19, No. 11, pp. 1542-1546 (Oct. 2013).

Latouche et al., "Induction of human cytotoxic T lymphocytes by artificial antigen-presenting cells," Nature Biotechnology, vol. 18, No. 4 pp. 405-409 (Apr. 2000).

Richman et al., "Display, engineering, and applications of antigen-specific T cell receptors," Biomolecular Engineering, vol. 24, No. 4, pp. 361-373 (Sep. 2007).

Turan et al., "Recombinase-mediated cassette exchange (RMCE)—A rapidly-expanding toolbox for targeted genomic modifications," Gene, vol. 515, No. 1, pp. 1-27, (Feb. 2013) (Available online Nov. 2012).

Zhang et al., "Transduction of Human T Cells with a Novel T-Cell Receptor Confers Anti-HCV Reactivity," PLoS Pathogens, vol. 6, No. 7, e1001018, 13 pages (Jul. 2010).

Figure 19
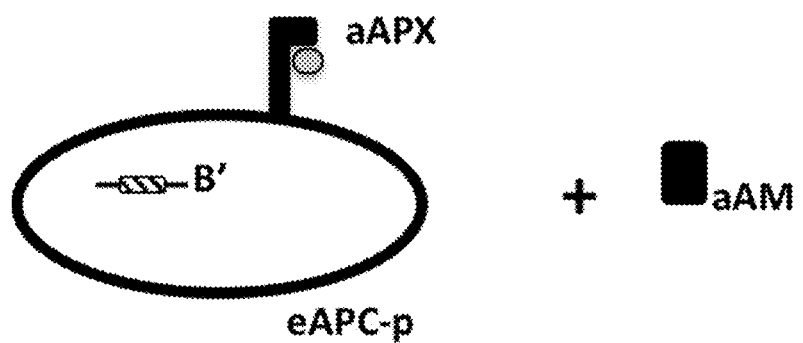
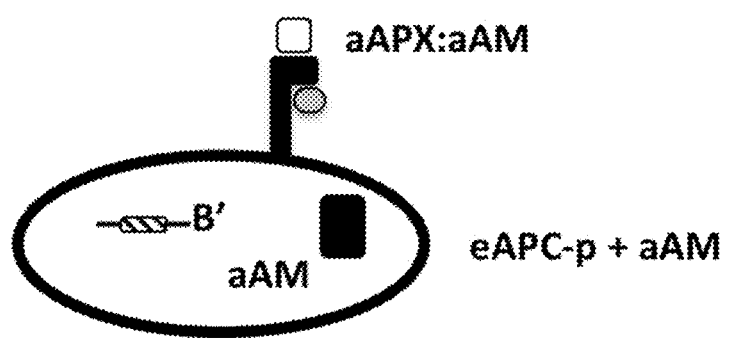

Figure 23
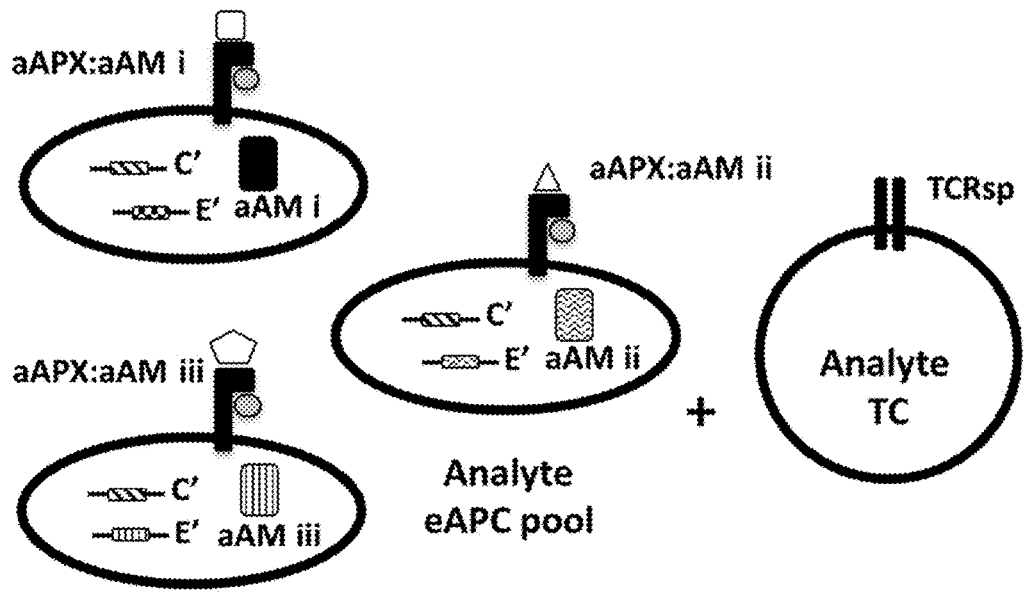
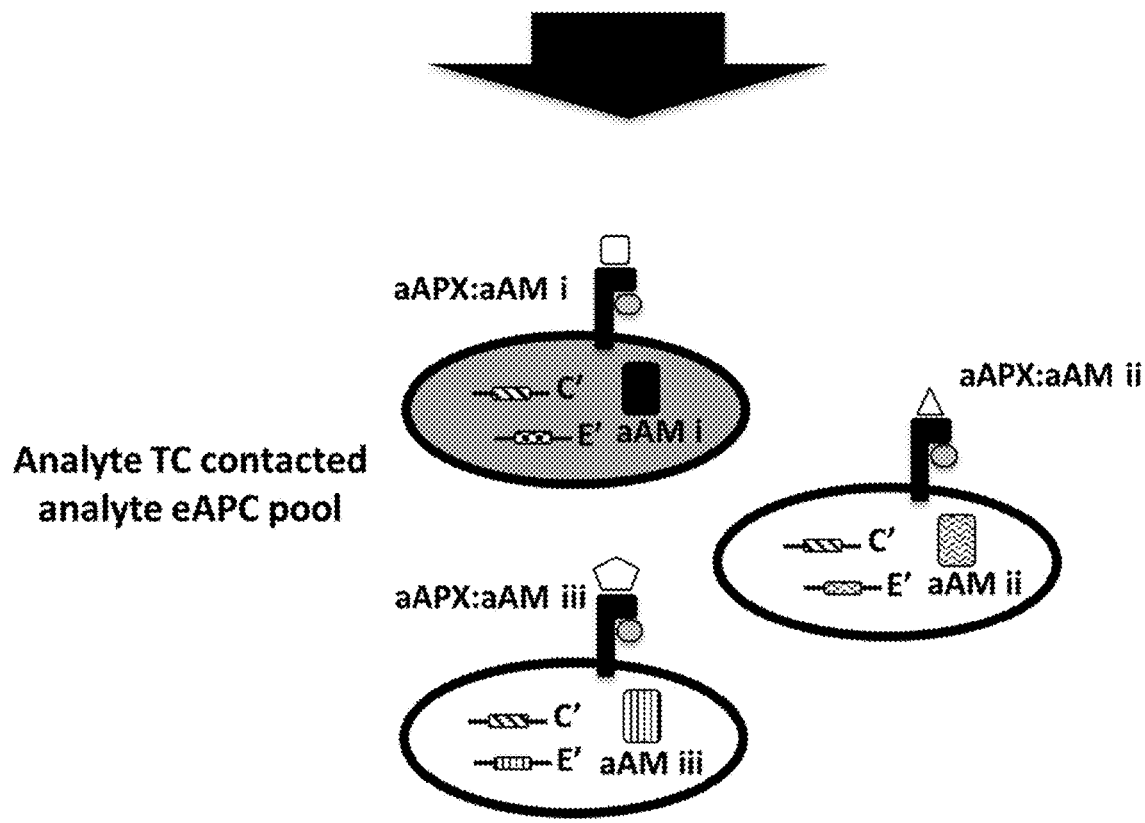

Figure 24
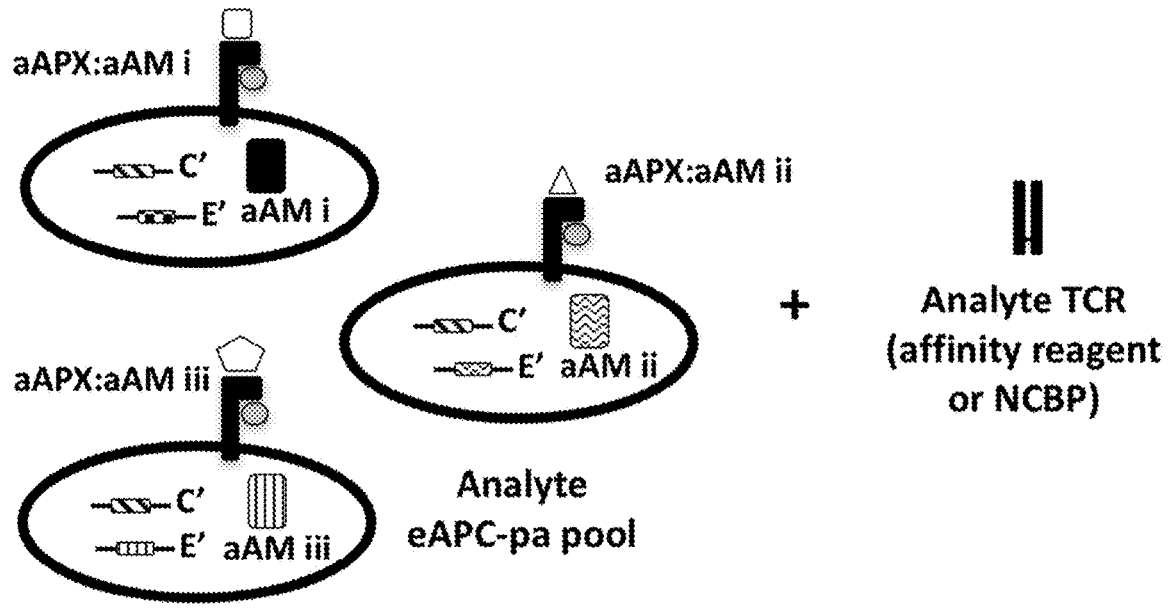
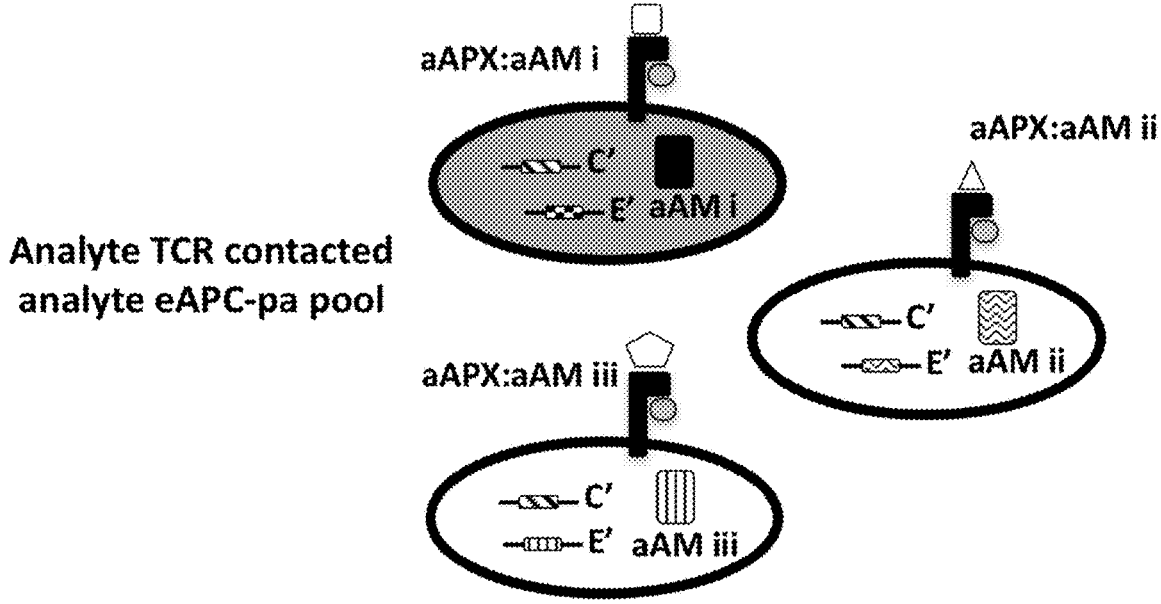

Figure 42

Table 1. Genetic characterization of monoclones containing component B

| Cell Line | Genomic location | | Copy number of integrated component B | | | |
|---|---|---|---|---|---|---|
| | Integrated into the genome | Integrated into the genomic integration site (AAVS1) | Reference gene copies/ul | Component B copies/ul | Observed Ratio | Expected ratio for a single integration of component B |
| ACL-469 | Yes | Yes | 151 | 51.8 | 0.343 | 0.33 |
| ACL-470 | Yes | Yes | 166 | 56.8 | 0.342 | 0.33 |

Table 2. Genetic characterization of monoclones containing components B and D

| Cell Line | Genomic location | | Copy number of integrated components B and D | | | |
|---|---|---|---|---|---|---|
| | Integrated into the genome | Integrated into the genomic integration site (AAVS1) | Reference gene copies/ul | Component B and D copies/ul | Observed Ratio | Expected ratio for a single integration of component B and D |
| ACL-472 | Yes | Yes | 183 | 124 | 0.675 | 0.66 |

Figure 44
a)
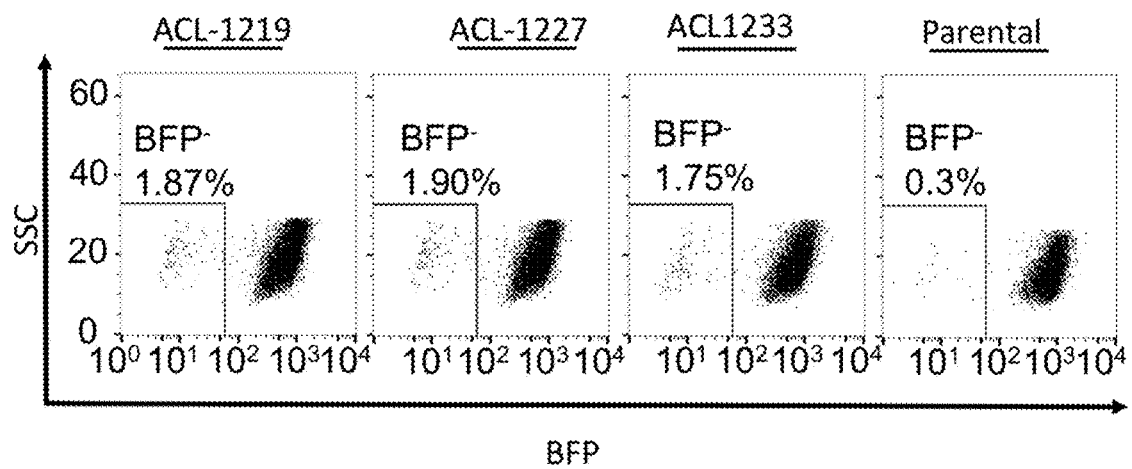
b)
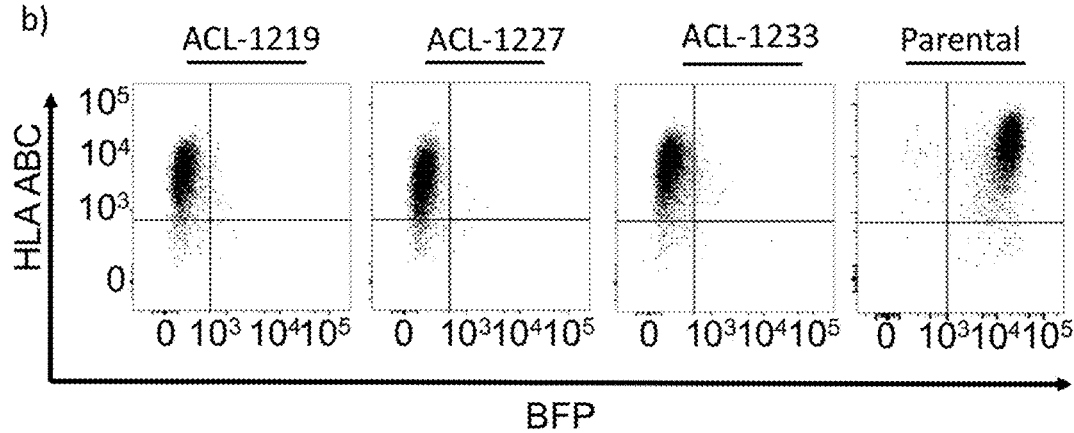
c)
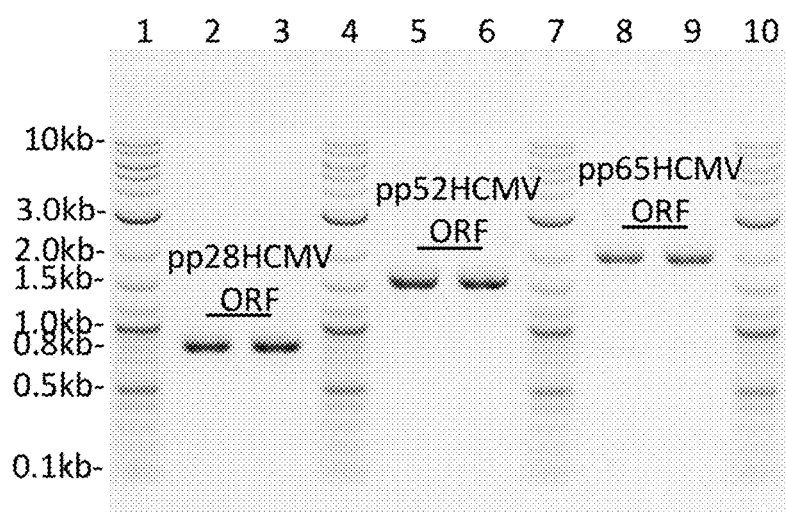

Figure 49

| ID | eAPC line ID | eAPC allele | Peptide sequence | Identified peptides | Intensity | PEP score |
|----|--------------|-------------|------------------|---------------------|-----------|-----------|
| 1 | ACL-900 | HLA-A*02:01 | NA | NA | 0 | 0 |
| 2 | ACL-900 | HLA-A*02:01 | NLVPMVATV | NLVPMVATV | 3.4E+07 | 6.55E-07 |
| 4 | ACL-900 | HLA-A*02:01 | NLGPMAAGV | NA | 0 | 0 |
| 10 | ACL-963 | HLA-A*24:02 | NA | NA | 0 | 0 |
| 11 | ACL-963 | HLA-A*24:02 | VYALPLKML | VYALPLKML | 7.9E+06 | 0.026368 |
| 12 | ACL-963 | HLA-A*24:02 | NLVPMVATV | NA | 0 | 0 |
| 13 | ACL-900 | HLA-A*02:01 | VYALPLKML | NA | 0 | 0 |

ENGINEERED MULTI-COMPONENT SYSTEM FOR IDENTIFICATION AND CHARACTERISATION OF T-CELL RECEPTORS AND T-CELL ANTIGENS

CROSS REFERENCE TO RELATED APPLICATIONS

This present application is a continuation application of U.S. application Ser. No. 16/347,684, filed May 6, 2019, which is the U.S. National Phase of PCT/EP2017/078376, filed Nov. 7, 2017, and claims priority to Denmark Application No. PA 2016 70872, filed Nov. 7, 2016.

SEQUENCE LISTING

The instant application contains a Sequence Listing which has been submitted electronically in ASCII format and is hereby incorporated by reference in its entirety.

FIELD OF THE INVENTION

The present invention relates to the construction, assembly and use of a multi-component system, comprised of at least three components being, an engineered antigen-presenting cell (eAPC), an engineered genomic receiver site and a matching genetic donor vector. The present invention is used for rapid, high-throughput generation of stable derivative cells that present various forms of antigenic molecules for identification and characterisation of these antigens and cognate TCR sequences.

INTRODUCTION TO THE INVENTION

Immune surveillance by T lymphocytes (T-cells) is a central function in the adaptive immunity of all jawed vertebrates. Immune surveillance by T-cells is achieved through a rich functional diversity across T-cell subtypes, which serve to eliminate pathogen-infected and neoplastic cells and orchestrate adaptive immune responses to invading pathogens, commensal microorganisms, commensal non-self factors such as molecular components of foodstuffs, and even maintain immune tolerance of self. In order to respond to various foreign and self factors, T-cells must be able to specifically detect molecular constituents of these foreign and self factors. Thus T-cells must be able to detect a large cross-section of the self and non-self molecules that an individual encounters, with sufficient specificity to mount efficient responses against pathogenic organisms and diseased self, while avoiding the mounting of such responses against health self. The highly complex nature of this task becomes clear when considering the practically unlimited diversity of both foreign and self molecules, and that pathogenic organisms are under evolutionary pressure to evade detection by T-cells.

The T-Cell/Receptor (TCR)

T-cells are primarily defined by the expression of a T-cell receptor (TCR). The TCR is the component of the T-cell that is responsible for interacting with and sensing the targets of T-cell adaptive immunity. In general terms, the TCR is comprised of a heterodimeric protein complex presented on the cell surface. Each of the two TCR chains are composed of two extracellular domains, being the variable (V)-region and the constant (C)-region, both of the immunoglobulin superfamily (IgSF) domain, forming antiparallel β-sheets. These are anchored in the cell membrane by a type-I transmembrane domain, which adjoins a short cytoplasmic tail. The quality of the T-cells to adapt and detect diverse molecular constituents arises from variation in the TCR chains that is generated during T-cell genesis. This variation is generated by somatic recombination in a similar manner to antibody genesis in B-cells.

TCR Chain Diversity

The T cell pool consists of several functionally and phenotypically heterogeneous subpopulations. However, T cells may be broadly classified as αβ or γδ according to the somatically rearranged TCR form they express at their surface. There exist two TCR chain pair forms; TCR alpha (TRA) and TCR beta (TRB) pairs; and TRC gamma (TRG) and TCR delta (TRD) pairs. T-cells expressing TRA:TRB pairs are referred to as αβ T-cells, while T-cells expressing TRG:TRD pairs are often referred to as γδ T-cells.

TCRs of both αβ and γδ forms are responsible for recognition of diverse ligands, or 'antigens', and each T-cell generates αβ or γδ receptor chains de novo during T-cell maturation. These de novo TCR chain pairs achieve diversity of recognition through generation of receptor sequence diversity in a process called somatic V(D)J recombination after which each T-cell expresses copies of a single distinctly rearranged TCR. At the TRA and TRG loci, a number of discrete variable (V) and functional (J) gene segments are available for recombination and juxtaposed to a constant (C) gene segments, thus referred to as VJ recombination. Recombination at the TRB and TRD loci additionally includes a diversity (D) gene segment, and is referred to as VDJ recombination.

Each recombined TCR possess potential for unique ligand specificity, determined by the structure of the ligand-binding site formed by the α and β chains in the case of a T-cells or γ and δ chains in the case of γδ T-cells. The structural diversity of TCRs is largely confined to three short hairpin loops on each chain, called complementarity-determining regions (CDR). Three CDRs are contributed from each chain of the receptor chain pair, and collectively these six CDR loops sit at the membrane-distal end of the TCR extracellular domain to form the antigen-binding site.

Sequence diversity in each TCR chain is achieved in two modes. First, the random selection of gene segments for recombination provides basal sequence diversity. For example, TRB recombination occurs between 47 unique V, 2 unique D and 13 unique J germline gene segments. In general, the V gene segment contributes both the CDR1 and CDR2 loops, and are thus germline encoded. The second mode to generate sequence diversity occurs within the hypervariable CDR3 loops, which are generated by random deletion of template nucleotides and addition of non-template nucleotides, at the junctions between recombining V, (D) and J gene segments.

TCR:CD3 Complex

Mature αβ and γδ TCR chain pairs are presented at the cell surface in a complex with a number of accessory CD3 subunits, denoted ε, γ, δ and ζ. These subunits associate with αβ or γδ TCRs as three dimers (εγ, εδ, ζζ). This TCR:CD3 complex forms the unit for initiation of cellular signalling responses upon engagement of a αβ or γδ TCR with cognate antigen. The CD3 accessories associated as a TCR:CD3 complex contribute signalling motifs called immunoreceptor tyrosine-based activation motifs (ITAMs). CD3ε, CD3γ and CD3δ each contribute a single ITAM while the CD3ζ homodimer contains 3 ITAMs. The three CD3 dimers (εγ, εδ, ζζ) that assemble with the TCR thus contribute 10 ITAMs. Upon TCR ligation with cognate antigen, phosphorylation of the tandem tyrosine residues creates paired docking sites for proteins that contain Src homology 2 (SH2)

domains, such as the critical ζ-chain-associated protein of 70 kDa (ZAP70). Recruitment of such proteins initiate the formation of TCR:CD3 signalling complexes that are ultimately responsible for T-cell activation and differentiation.

αβ T-Cells

αβ T-cells are generally more abundant in humans than their γδ T-cell counterparts. A majority of αβ T-cells interact with peptide antigens that are presented by HLA complexes on the cell surface. These peptide-HLA (pHLA)-recognising T-cells were the first to be described and are by far the best characterised. More rare forms of αβ T-cells have also been described. Mucosal-associated invariant T (MAIT) cells appear to have a relatively limited α and β chain diversity, and recognise bacterial metabolites rather than protein fragments. The invariant natural killer T-cells (iNK T-cells) and germlineencoded mycolyl-reactive T-cells (GEM T-cells) are restricted to recognition of glycolipids that are cross-presented by non-HLA molecules. iNK T-cells are largely considered to interact with CD1d-presented glycolipids, whereas GEM T-cells interact with CD1b-presented glycolipids. Further forms of T-cells are thought to interact with glycolipids in the context of CD1a and CD1c, however, such cells are yet to be characterised in significant detail.

Conventional αβ T-Cells

The key feature of most αβ T-cells is the recognition of peptide antigens in the context of HLA molecules. These are often referred to as 'conventional' αβ T-cells. Within an individual, self-HLA molecules present peptides from self and foreign proteins to T-cells, providing the essential basis for adaptive immunity against malignancies and foreign pathogens, adaptive tolerance towards commensal organisms, foodstuffs and self. The HLA locus that encodes HLA proteins is the most gene-dense and polymorphic region of the human genome, and there are in excess of 12,000 alleles described in humans. The high degree of polymorphism in the HLA locus ensures a diversity of peptide antigen presentation between individuals, which is important for immunity at the population level.

HLA Class I and II

There are two forms of classical HLA complexes: HLA class I (HLAI) and HLA class II (HLAII). There are three classical HLAI genes: HLA-A, HLA-B, HLA-C. These genes encode a membrane-spanning α-chain, which associates with an invariant β2-microglobulin (β2M) chain. The HLAI α-chain is composed of three domains with an immunoglobulin fold: α1, α2 and α3. The α3 domain is membrane-proximal and largely invariant, while the α1 and α2 domains together form the polymorphic membrane-distal antigen-binding cleft. There are six classical HLAII genes: HLA-DPA1, HLA-DPB1, HLA-DQA1, HLA-DQB1, HLA-DRA, and HLA-DRB1. These genes encode paired DP, DQ and DR heterodimeric HLA complexes comprising a α-chain and a β-chain. Each chain has two major structural domains with an immunoglobulin fold, where the α2 and β2 domain comprise membrane-proximal and largely invariant modules similar to that of HLAI α3 domain. The HLAII α2 and β2 domains together form the membrane-distal antigen-binding cleft and are regions of high polymorphism.

The antigen-binding cleft of HLAI and HLAII comprises two anti-parallel α-helices on a platform of eight anti-parallel β-sheets. In this cleft the peptide antigen is bound and presented in an extended conformation. The peptide-contacting residues in HLAI and HLAII are the location of most of the sequence polymorphism, which constitutes the molecular basis of the diverse peptide repertoires presented by different HLA alleles. The peptide makes extensive contacts with the antigen-binding cleft and as a result each HLA allele imposes distinct sequence constraints and preferences on the presented peptides. A given peptide will thus only bind a limited number of HLAs, and reciprocally each allele only accommodates a particular fraction of the peptide collection from a given protein. The set of HLAI and HLAII alleles that is present in each individual is called the HLA haplotype. The polymorphism of HLAI and HLAII genes and the co-dominant expression of inherited alleles drives very large diversity of HLA haplotype across the human population, which when coupled to the enormous sequence diversity of αβ TCRs, presents high obstacles to standardisation of analysis of these HLA-antigen-TCR interactions.

αβ TCR Engagement of HLAI and HLAII

αβ TCRs recognize peptides as part of a mixed pHLA binding interface formed by residues of both the HLA and the peptide antigen (altered self). HLAI complexes are presented on the surface of nearly all nucleated cells and are generally considered to present peptides derived from endogenous proteins. T-cells can thus interrogate the endogenous cellular proteome of an HLAI-presenting cell by sampling pHLAI complexes of an interacting cell. Engagement of HLAI requires the expression of the TCR co-receptor CD8 by the interacting T-cell, thus HLAI sampling is restricted to $CD8^+$ αβ T-cells. In contrast, the surface presentation of HLAII complexes is largely restricted to professional APC, and are generally considered to present peptides derived from proteins exogenous to the presenting cell. An interacting T-cell can therefore interrogate the proteome of the extracellular microenvironment in which the presenting cell resides. The engagement of HLAII requires the expression of the TCR co-receptor CD4 by the interacting T-cell, thus HLAII sampling is restricted to $CD4^+$ αβ T-cells.

Thymic Selection of αβ TCRs

The role of αβ TCRs as described above is the detection of pHLA complexes, such that the TCR-presenting T-cell can raise responses germane to the role of that T-cell in establishing immunity. It should be considered that the αβ TCR repertoire generated within an individual must account for the immense and unforeseen diversity of all foreign antigens likely to be encountered in the context of a specific haplotype and prior to their actual occurrence. This outcome is achieved on a background where extremely diverse and numerous αβ TCRs are generated in a quasi-randomised manner with the potential to recognise unspecified pHLA complexes while only being specifically instructed to avoid strong interactions with self pHLA. This is carefully orchestrated during T-cell maturation in a process call thymic selection.

During the first step of T-cell maturation in the thymus, T-cells bearing αβ TCRs that are incapable of interacting with self-pHLA complexes with sufficient affinity, are deprived of a survival signal and eliminated. This step called positive selection assures that the surviving T-cells carry a TCR repertoire that is at least potentially capable of recognizing foreign or altered peptides presented in the right HLA context. Subsequently, αβ TCR that strongly interact with self-pHLA and thus have the potential to drive autoimmunity are actively removed through a process of negative selection. This combination of positive and negative selection results in only T-cells bearing αβ TCRs with low affinity for self-pHLA populating the periphery. This establishes an αβ T-cell repertoire that is self-restricted but not self-reactive. This highly individualised nature of T-cell genesis against HLA haplotype underscores the challenges in standardised analysis αβ TCR-antigen-HLA interactions. Moreover, it forms the basis of both graft rejection and graft versus host disease and the general principle that αβ TCRs identified in one individual may have completely different effect in a second individual, which has clear implications for TCR-based and T-cell based therapeutic and diagnostic strategies emerging in clinical practice.

Unconventional αβ T-Cells

The non-HLA-restricted, or 'unconventional', forms of αβ T-cells have very different molecular antigen targets. These unconventional αβ T-cells do not engage classical HLA complexes, but rather engage conserved HLA-like proteins such as the CD1 family or MR1. The CD1 family comprises four forms involved in antigen cross-presentation (CD1a,b,c and d). These cell surface complexes have an α-chain resembling HLAI, which forms heterodimers with β2-M. A small hydrophobic pocket presented at the membrane distal surface of the α-chain forms a binding site for pathogen-derived lipid-based antigens. Innate like NK T-cells (iNK T-cells) form the best-understood example of lipid/CD1 family recognition with GEM T-cells representing another prominent example. 'Type I' iNK T-cells are known to interact strongly with the lipid α-GalCer in the context of CD1d. These iNK T-cells display very limited TCR diversity with a fixed TCR α-chain (Vα10/Jα18) and a limited number of β-chains (with restricted vβ usage) and they have been likened to innate pathogen-associated molecular patterns (PAMPS) recognition receptors such as Toll-like and Nod-like receptors. In contrast, 'type II' NK T-cells present a more diverse TCR repertoire, and appear to have a more diverse mode of CD1d-lipid complex engagement. GEM T-cells recognise mycobacteria-derived glycolipids presented by CD1b, however, the molecular details of antigen presentation by CD1a, b and c as well as their T-cell recognition are only beginning to be understood.

MAIT cells largely express an invariant TCR α-chain (TRAV1-2 ligated to TRAJ33, TRAJ20, or TRAJ12), which is capable of pairing with an array of TCR β-chains. Instead of peptides or lipids MAIT TCRs can bind pathogen-derived folate- and riboflavin-based metabolites presented by the HLAI-like molecule, MR1. The limited but significant diversity in the TCRs observed on MAIT TCRs appear to enable the recognition of diverse but related metabolites in the context of the conserved MR1.

It is not well-understood how non-classical HLA-restricted αβ T-cell TCRs are selected in the thymus during maturation. However, it appears likely that the fundamental process of negative and positive selection outlined above still applies and some evidence suggests that this occurs in specialized niches within the thymus.

γδ T-Cells

In contrast to the detailed mechanistic understanding of αβ TCR genesis and pHLA engagement, relatively little is known about the antigen targets and context of their γδ T-cell counterparts. This is in part due to their relatively low abundance in the circulating T-cell compartment. However, it is broadly considered that γδ T-cells are not strictly HLA restricted and appear to recognize surface antigen more freely not unlike antibodies. Additionally, more recently it has become appreciated that γδ T-cells can dominate the resident T-cell compartment of epithelial tissues, the main interaction site of the immune system with foreign antigen. In addition, various mechanisms for γδ T-cell tumour immunosurveillance and surveillance of other forms of dysregulated-self are beginning to emerge in the literature. The specific antigen targets of both innate-like and adaptive γδ T-cells remain poorly defined but the tissue distribution and fast recognition of PAMPs suggests a fundamental role for γδ T-cells both early in responses to foreign antigens as well as early in life when the adaptive immune system is still maturing.

The diverse functions of γδ T-cells appear to be based on different Vγ Vδ gene segment usage and can be broadly understood in two main categories in which γδ T-cells with largely invariant TCRs mediate innate-like recognition of PAMPs very early during infection. Beyond PAMPs these type of γδ T-cells are furthermore believed to recognize self-molecules, including phosphoantigens that could provide very early signatures of cellular stress, infection and potentially neoplastic development. Recognition of PAMPs and such so-called danger associated molecular patterns (DAMPS) as well as the large numbers of tissue-restricted innate-like γδ T-cells strongly suggests that these cells are suited to respond rapidly to antigenic challenge without the need for prior activation, homing and clonal expansion.

A second form of γδ T-cells are considered to be more adaptive in nature, with a highly diverse γδ TCR repertoire and the ability to peripherally circulate and access lymphoid tissues directly. Such antigen-specific γδ T-cells to common human pathogens such as CMV have been described and they appear to form a memory response. However, it has also been observed that γδ T-cells show only relatively limited clonal proliferation after activation and little data is available on the extent of TCR diversity and specific responses of γδ T-cells in peripheral circulation, or in tissues. Furthermore, while it is generally considered that γδ TCRs do not interact with pHLA complexes, and thus do not engage with peptide antigens in this context only few antigen targets of γδ T-cells have been characterised and the underlying molecular framework is only poorly understood.

The low frequency of peripheral γδ T-cells and the difficulty to study tissue-resident T-cells in humans has limited our knowledge of how this important and diverse type of T-cells participate in adaptive immune responses. This emerging area of research would require more reliable technologies with which to capture and characterise rare γδ T-cells, isolate their TCR pairs, and to identify their cognate antigens.

Antigens and Antigen-Presenting Cells

In the context of T-cells and TCRs, antigens may be defined as any molecule that may be engaged by a TCR and resulting in a signal being transduced within the T-cell. The most well characterised T-cell antigens are peptides presented in an HLAI and HLAII complex, and which are engaged by conventional αβ T-cells. However, in recent years it has become apparent that non-conventional αβ T-cells and γδ T-cells are able to engage a wide range of biomolecules as antigens, including lipids, lipopeptides, glycopeptides, glycolipds and a range of metabolites and catabolites. In addition, it has emerged that γδ T-cells may be able to engage fully folded proteins directly in an antibody-like fashion. Therefore, the view of T-cell antigens being largely restricted to HLA-presented peptides has expanded over the past two decades to include almost any biomolecule. With this concept in mind, it is relevant to define what may be considered an antigen-presenting cell (APC).

As defined in the above sections, HLAI and HLAII have a disparate expression profiles across cell types. It is widely accepted that nearly all nucleated cells present HLAI complexes on the cell surface, and are thus competent to present peptide antigens for T-cell sampling. In contrast, HLAII has a restricted expression profile, and at least in steady state conditions is only expressed on the surface of cells that have a specialist role in antigen presentation, including dendritic cells (DC), macrophage and B-cells. These specialist cell types are often referred to as professional APC. For the purposes of this document, the term APC is used to describe any nucleated cell that is capable of presenting an antigen for sampling by αβ or γδ T-cells. Such antigens are not restricted to those presented as 'cargo' in specific antigen-presenting complexes such as HLA and HLA-like molecules, but may also include any cell-surface presented moiety that is able to engage a αβ or γδ TCR-bearing cell.

Therapeutic Use of TCRs

Adoptive transfer of primary T-cells was first trialled in a clinical setting in the early 1990s, starting with ex vivo expanded T-cells polarised towards viral antigens to confer viral immunity in immunocompromised patients. Similar approaches using primary T-cells expanded ex vivo against specific cancer antigens were soon after trialled in treatment of malignancies. One limitation in these early approaches that continues to be a challenge today is a lack of understanding of the nature and diversity of T-cells clashing with the need to finely-optimize their composition in the therapeutic product. At present, the use of ex vivo expanded primary T-cells has largely been abandoned by the pharmaceutical industry with the exception of a handful of initiatives using primary T-cells with specificity for viral antigens.

In recent years the ability to reliably introduce genetic material into primary human cells has seen a variety of experimental genetically modified T-cell therapeutics arise. Such therapeutic cell products aim to harness the power of T-cell responses and redirect T-cell specificity towards a disease-associated antigen target, for example, an antigen uniquely expressed by malignant cells. These have largely relied on the transfer of a chimeric antigen receptor (CAR) into recipient T-cells, rather than actual TCR chain pairs. A CAR represents a targeting moiety (most often a single-chain antibody element targeting a surface expressed protein of malignant cells) grafted to signal receptor elements such as the ζ-chain of the CD3 complex, to produce a synthetic chimeric receptor that mimics CD3-TCR function. These so-called CAR T-cell (CAR-T) products have met mixed success in clinical trials to date and despite their potential are not easy to translate beyond tumours with inherent unique molecular targets such as B-cell malignancies. Alternatively, the transfer of full-length TCR chain pair ORFs into T-cells is of emerging interest. Such TCR-engineered T-cell therapeutics are at present limited by challenging manufacturing processes, and like the CAR-T products, a dearth of validated antigen targets and targeting constructs. To date this has been focused on the use of αβ TCRs for recognition of peptide antigens presented by HLAI on malignant cells and a fundamental challenge of this approach is the need for antigens that are specific to malignant cells.

It has been considered that since the TCR-pHLA interaction is of relatively low-affinity, native TCRs are likely to be suboptimal for TCR-engineered T-cell therapies. Several approaches have been devised to affinity-mature TCRs in vitro, in much the same manner as single-chain antibody affinity maturation. These TCR affinity maturation approaches generally also utilise a single-chain formats, wherein the V-region of one chain is fused to V-region of another chain to make a single polypeptide construct. Such single polypeptides may then be used in phage- or yeast-display systems adapted from antibody engineering workflows, and passed through rounds of selection based on target binding. Two inherent limitations exist in such a single-chain TCR approach in terms of yielding functional TCR chain pairs. Firstly, the selection is based on binding affinity to the target. However, it has been well documented that TCR affinity does not always correlate to the strength or competency of TCR signalling output. Secondly, the selection of single-chain constructs based on affinity does not always translate to equivalent affinities once they are reconstituted as full-length receptors.

In a therapeutic context, there exists an additional and crucial limitation in affinity-matured TCR pairs. That is, considering their sequences have been altered, the resulting constructs by definition have no longer been subject to thymic selection, wherein TCRs that react strongly to self-antigens are deleted from the repertoire. Therefore, these modified TCRs carry an inherent risk of being auto-reactive, which is very difficult to rule out in vitro using current methods. For the same reason, any selected or engineered TCR for therapeutic application needs to be individualised. If TCRs are artificially engineered or native TCRs applied across individuals, cross-reactivities have to be ruled out on the basis of the HLA haplotype and presented peptide repertoire of each specific individual in order to avoid potentially catastrophic autoimmunity. This is due to the fact that thymic selection is conducted on a background of all available HLA molecules specific only to that given individual. The likelihood of such cross-reactivity is unclear. However, the ability of our TCR repertoire to recognize pHLA complexes of other individuals of the same species as foreign is a fundamental property of adaptive immunity and underpins graft rejection and graft versus host disease. Recent clinical trials using a matured TCR chain pair against the cancer-specific melanoma associated antigen (MAGE) highlighted the potential problem of bypassing thymic selection. When autologous T-cells harbouring the matured TCRs were infused back to two cancer patients, these patients rapidly developed a fatal heart disease. Subsequent studies determined that the MAGE-specific matured TCRs were cross-reactive with an HLAI-presented peptide from the heart protein titin. This strongly suggests that cross-reactivity is a distinct possibility in therapeutic use of TCRs.

A distinct avenue of utilising TCRs for therapeutic purposes is in their use as affinity reagents in much the same manner as antibody therapeutic substances. Single-chain TCR molecules have been trialled for delivery of conjugated drug substances to specific HLA-antigen expressing cell populations. Such an approach is generally considered safer than CAR-T or TCR engineered T-cell therapeutics, as administration of the drug substance may simply be withdrawn. However, the potential for cross-reactivity and off target effects that are difficult to predict remains a potential limitation in this setting.

TCR Repertoire Detection in Clinical Diagnostics

In a related aspect, there is an emerging interest in using the detection of the abundance of specific TCR sequences for clinical diagnostic purposes. With the rise of deep-sequencing methods in particular, it is possible to capture the full TCR diversity within an individual globally and for matched as pairs in specific contexts. This potentially represents a means to diagnose specific conditions and disease states simply by detecting the abundance of expanded T-cell clones, as proxy readout for established immune response against a disease-associated antigen in the patient. However, such global approaches are currently limited to very strong immune responses with established clinical time-points and suffer from the underlying difficulty in identifying the specific antigen target of any particular TCR identified via sequencing.

Therapeutic and Diagnostic Use of T-Cell Antigens

The fundamental strength of harnessing adaptive immune responses translates into a central technical challenge in that the exquisite specificity of the TCR-antigen interaction requires detailed knowledge of the antigens specifically associated with each pathogen, cancer cell or autoimmune disease. Furthermore, each antigen may be presented by a specific antigen presenting complex, or allele thereof, such that antigen discovery has been performed for each relevant HLA gene and allele. For several infectious diseases like HIV, influenza and CMV that are associated with strong adaptive immune responses and generally display conserved epitope response hierarchies, the most important epitopes have been mapped in context of some common HLA. Similarly, the fields of cancer, allergy and autoimmunity have seen increased and systematic efforts to map the associated T-cell antigens. However, these are challenging procedures and the efforts to systematically describe T-cell antigens associated with different clinical contexts are hindered by the absence of efficient, robust, fast and scalable protocols.

Specifically, cancer cells represent a challenging and important aspect as most of the peptides presented on the surface of malignant cells are self antigens or very similar to self antigens. Therefore, thymic selection will have deleted TCRs that could strongly recognize these peptides, while at the same time the tumour has evolved to evade immune recognition. This means that potent immune responses against established tumours are relatively rare and targets difficult to predict or discover. However, these responses do exist and, importantly, are generally associated with better outcome. The target of such responses, tumour-associated-antigens (TAA), will in most cases have distinguishing characteristics from self and be derived from proteins that are overexpressed during cancer development, otherwise absent from the cell type at this stage of development or specifically altered through genetic mutation or post-translational modifications such as phosphorylation.

When available, the knowledge of such epitopes makes it possible to interrogate the associated T-cell response for fundamental discovery, diagnostic purposes and for example as a test of vaccine efficacy. Importantly, they also provide highly specific targets for T-cell tolerization in allergy and autoimmunity and, crucially, point towards valuable targets for specific immunotherapy and against malignant cells. Malignancies represent a particularly valuable target as the promise of cellular immunotherapies and the progress in the T-cell manipulations are slowed by a lack of validated target TAAs that go beyond the few cases where specific markers for the type of cancer happen to be available.

In the light of the potential of cellular therapy and lack of validated targets the identification of promising TCR antigens remains one of the most pressing bottlenecks of TCR-based immunotherapy, particularly in the effort to treat cancer.

Technological Aspects of TCR and T-Cell Antigen Analyses

Overall, the development of TCR-based therapies is still in its early stages, and success has been limited. Diagnostic approaches, while of immense potential, have seldom been deployed into controlled clinical studies that aim to assess patient disease states or response to therapy. Underdeveloped techniques for the reliable capture of native TCR chain pairs, and the systematic analysis of TCR-antigen interactions at high-throughput and in a functional context of cell-cell communication, has been the main hurdle to the development of TCR-based therapies and diagnostics.

Deep sequencing approaches have led to an improved understanding of T-cell receptor diversity in heath and disease. However, these approaches have generally focused on short stretches spanning the CDR3 regions, mainly of the TCR β-chain. Most studies have ignored the contribution of the TCR α-chain, and few have sought to analyse paired as chains as well as the antigen specificity of TCRs determined to be of interest. Recent workflows using single cell encapsulation and genetic barcoding has enabled the pairing of native TCR αβ or γδ chain pairs and analysis of full-length sequences, however, such workflows remain experimental.

Isolated TCR chain pairs may be analysed in terms of antigen specificity in either biophysical or functional modes. Biophysical analysis requires the recombinant production of both the TCR as well as the analyte antigen in soluble form. In the case of HLA-restricted TCRs this would thus require the generation of all individual TCRs as well as the cognate pHLA complexes. This is technically highly challenging, slow and very low-throughput. Furthermore, such analysis would only provide interaction affinities, which are not well-correlated with functional characteristics in predictable ways.

Until recently, the detailed functional analysis of isolated TCR sequences in a cellular context has been limited to laborious protocols of transfection of analyte TCR chain pairs into primary T-cells or immortal T-cell lines, and detection of cellular responses by traditional flow cytometric analysis of cell activation, or detection of secreted factors from the transfected cells upon antigen challenge. In a recent publication by Guo et al, rapid cloning, expression, and functional characterization of paired TCR chains from single-cells was reported (Molecular Therapy—Methods and clinical development (2016) 3:15054). In this study, analyte human αβ TCR pairs were expressed in a reporter cell line that lacked αβ TCR expression, and which contained a green fluorescent protein (GFP) reporter system linked to the Nur77 promoter that is activated upon TCR stimulation. This system remains inefficient due to the lack of standardised TCR integration into the reporter cell line genome, and does not provide a systematic manner for cell-bound antigen challenge by an APC element.

Similar to workflows for identification of TCRs against known T-cell antigens, the de novo discovery of novel T-cell antigens in health and disease remains highly challenging. Most approaches remain biophysical in nature, and aim to produce candidate antigens that may be tested in immunisation protocols, or through identifying cognate TCRs as addressed above. Little or no standardisation exists in the field of T-cell antigen discovery, and the field is largely restricted to academic study.

With the accumulating interest in TCRs and their cognate in both therapeutic and diagnostic use, and the emergence of means to capture significant numbers of native TCR αβ and γδ chain pairs, there remains a lack of reliable high-throughput and standardised technologies for the systematic analysis of TCR-antigen interactions. Importantly, there is a lack of standardised systems for functional analysis of TCR chain pairs in the native context of cell-cell communication wherein both the TCR and antigen are presented by a viable cell. Moreover, there is a lack of systematic means to present large libraries of candidate antigens to analyte TCR-bearing cells or reagents.

Therapeutic Use of T-Cell Antigens

With the rapidly expanding knowledge of T-cell biology, there is an expanding interest in the use of T-cell antigens within therapeutic formulations. Predominantly this takes the form of some type immunisation strategy. Most prominently, the use of next-generation sequencing approaches can identify large number so mutagenised sequences in tumour cells. Such sequences can represent potential T-cell antigens unique to the cancer cell, and thus may represent immunogens for personalised therapeutic vaccines against the sequenced tumour. However, with the large number of genetic mutations observable, there exists no high-throughput manner to analyse these potential T-cell antigens for their ability to be presented by the patient HLA repertoire, nor whether these antigens are immunogenic. At present, predictions of mutant peptide binding are conducted computationally across a very small number of HLA alleles. These predictive models loosely inform whether a given peptide sequence will bind to an HLA, and do not generally predict the potential immunogenicity of the bound antigen. Moreover, such computational models are unreliable for antigens that do not present canonical 'anchoring' residues relative to the HLA allele against which they are being analysed. Other immunisation approaches required detailed knowledge of T-cell antigens, including tolerisation therapies for allergy and autoimmune syndromes, and prophylactic vaccination against pathogens, for example. In the latter instance of prophylactic vaccines, there still exists surprisingly scarce knowledge about T-cell antigens from common pathogens in all but a handful of HLA alleles. There exists a need for systematic approaches to expand this knowledge to develop effective vaccines for common and emergent pathogens.

DETAILED DESCRIPTION OF THE INVENTION

The present invention addresses the above-mentioned needs. In particular, the present invention relates to the construction, assembly and use of a multi-component system, comprised of at least three components being, an engineered antigen-presenting cell (eAPC), an engineered genomic receiver site and a matching genetic donor vector. The present invention is used for rapid, high-throughput generation of stable derivative cells that present various forms of antigenic molecules for identification and characterisation of these antigens and cognate TCR sequences. Specifically, the eAPC is engineered by genome editing to render the APC null for cell surface presentation of human leukocyte antigen (HLA) molecules, HLA-like molecules and distinct forms of antigen-presenting molecules and antigenic molecules. In addition, the eAPC as part of the multicomponent system, contains genomic receiver sites for insertion of antigen-presenting molecule encoding open reading frames (ORFs), and optionally insertion of genetically encoded analyte antigens. The system further comprises of genetic donor vectors designed to target the genomic receiver sites of the APC as to rapidly deliver analyte antigen molecule- and/or antigen-presenting complex encoding ORFs. The multicomponent system may be used as an analytical system in clinical immunodiagnostics.

Furthermore, the present invention relates to the use the multicomponent system to identify and characterise T-cell antigens and cognate TCRs for production of immunotherapeutics and immunodiagnostics.

The present invention enables a highly standardised system for assembly of various analyte eAPC forms in a systemised manner. This standardisation and systemisation is achieved through highly defined and controllable genome integration of antigen-presenting complex and antigenic molecule ORF with matched donor vector/genomic receiver site subsystems. This controllable and predictable system provides significant efficiency to the process generating eAPC populations, reducing cycle time and costs for such a process. Previous systems have relied on random integration using unguided genome integration and/or viral approaches. Moreover, the design of the system is partly to ensure controllable copy-number of integrated ORF, usually a single copy, which permits tight control over achievable expression levels of integrated ORF product. More importantly, the ability of single-copy integration of ORF from a vector pool allows so-called 'shotgun integration', wherein each cell integrated with a donor vector may only receive a single ORF from a library of vectors, potentially encoding a diverse population of ORF. This enables the conversion of ORF libraries encoded in donor vectors, into eAPC libraries expressing a single desired analyte ORF per clonal eAPC sub-population; essentially representing a cell-based array system akin to a bacteriophage or yeast display system. Such array systems can facilitate the identification of unknown analyte antigen sequences within a library of sequences, based on their TCR or other affinity reagent reactivity when presented by an eAPC, and then recovery of the unknown 'reactive' sequence from the carrier eAPC. Moreover, the shotgun integration permits the efficient production of each analyte antigen within target cells. When compared to transient transfection of large pool so of analyte antigen sequences, which would result in minute levels of transcript available for any given analyte antigen, each cell in a eAPC library generated by shotgun integration would robustly express a single analyte for surface presentation by and eAPC, facilitating the identification of said analyte antigen by various means.

The present invention relates to the provision of an engineered multi-component system the components of which are used to prepare one or more analyte eAPC. These analyte eAPC are then combined with one or more analyte TCR (collectively the eAPC:TCR system, eAPC:T) to obtain one or more outputs, wherein the analyte TCR may be provided as soluble or immobilised reagents, presented on surface of cells or presented by non-cell based particles (NCBP). The eAPC present candidate analyte antigens to the analyte TCR.

The minimal form of multicomponent system comprises a first component as an eAPC, designated component A, containing a second component as a genomic receiver site component B, and a third component is a genetic donor vector, designated component C (FIG. 1).

An eAPC represents the base component of the multi-component system, to which all other components of the system relate. Therefore, the eAPC contains certain features, that are native or engineered, that make the eAPC suitable for use to create analyte eAPC populations, and their use.

In the present context the eAPC, component A
i. Lacks endogenous surface expression of at least one family of antigen-presenting complex (aAPX) and/or analyte antigenic molecule (aAM) and
ii. Contains at least one genomic receiver site, designated component B wherein i) may be obtained by selection of a naturally occurring cell population lacking said expression of aAPX and/or aAM, or may be engineered to lack such expression, and ii) which is synthetic and which may be introduced by means of directed or undirected genome integration.

The selection of an eAPC cell candidate that lacks desired aAPX and/or aAM expression from naturally occurring cell populations can be achieved by methods well known in the art. This may be directly achieved by staining of target cells with affinity reagents specifically for the aAPX and/or aAM that are desired to be lacking from the eAPC, and selection of cells lacking target aAPX and/or aAM expression.

Engineering of cells to lack aAPX and/or aAM expression may be achieved by untargeted and targeted means. Untargeted mutagenesis of the cell can be achieved by providing a chemical, radiological or other mutagen to the cell, and then selecting cells lacking target aAPX and/or aAM expression. Targeted mutation of the genomic loci can be achieved via different means, including but not limited to site directed mutagenesis via i. zinc-finger nucleases
    ii. CRISPR/Cas9 mediated targeting
    iii. Synthetic transcription activator-like effector nucleases (TALEN)

wherein said site-directed nucleases induce site-specific DNA-repair error mutagenesis at target loci, after which mutated cells are obtained by selecting cells lacking target aAPX and/or aAM expression.

The component A, eAPC, may optionally include additional T-cell co-stimulation receptors, wherein such features permit robust or varying forms of communication of the analyte eAPC to the analyte TCR-presenting cells (analyte TC), wherein the tuneable communication is relevant to identification or characterisation of specific analyte TCR and/or analyte antigens. In the present context, different forms of CD28 ligation on the analyte TC can be promoted by inclusion of one or more of CD80, CD86 and/or further B7 family proteins.

The component A, eAPC, may optionally additionally include introduced cell surface adhesion molecule components, or ablation of endogenous cell surface adhesion molecules, to promote the eAPC engagement with analyte TC and formation of the immunological synapse, or to avoid tight binding and formation of deleterious cell clustering within the combined eAPC:T system, respectively. Such adhesion molecules that may be introduced as additional ORFs to component A, or genetically ablated from A, can be selected from the integrin family of adhesion proteins.

Figure 17:
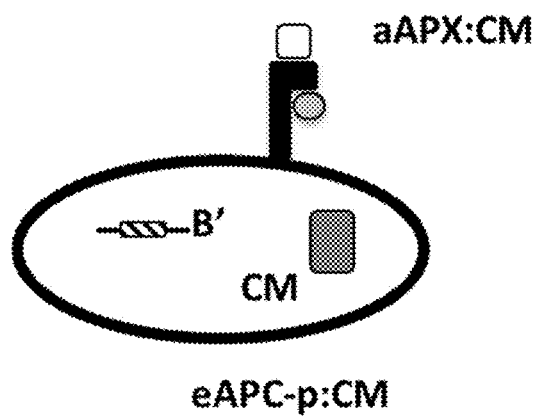

An eAPC may optionally possesses the ability to process and load antigen as cargo into aAPX, designated aAPX: aAM, by native processing and loading machinery. An eAPC that possesses the ability to process and load antigen as cargo into aAPX by native processing and loading machinery, will also process and load cargo molecules (CM) that are intrinsic to the eAPC or the culture system in which it is contained, wherein aAPX that is loaded with a CM is designated as an aAPX:CM complex (FIG. 17).

The second component of the minimal multicomponent system is a genetic donor vector, component C, which is used for integration of at least one ORF encoding at least one aAPX and/or aAM (FIG. 1).

Component C is a genetic donor vector that is coupled with the genomic receiver site of Component B contained within the genome of the eAPC, Component A. Component C is designed for the integration of one or more ORFs encoding an aAPX and/or an aAM, encoded in the genetic donor vector, into the genomic receiver site, B, wherein integration results in the expression of aAPX and/or an aAM by the target eAPC.

In the present context, a paired genetic donor vector and genomic receiver site is described as an integration couple.

Figure 2:
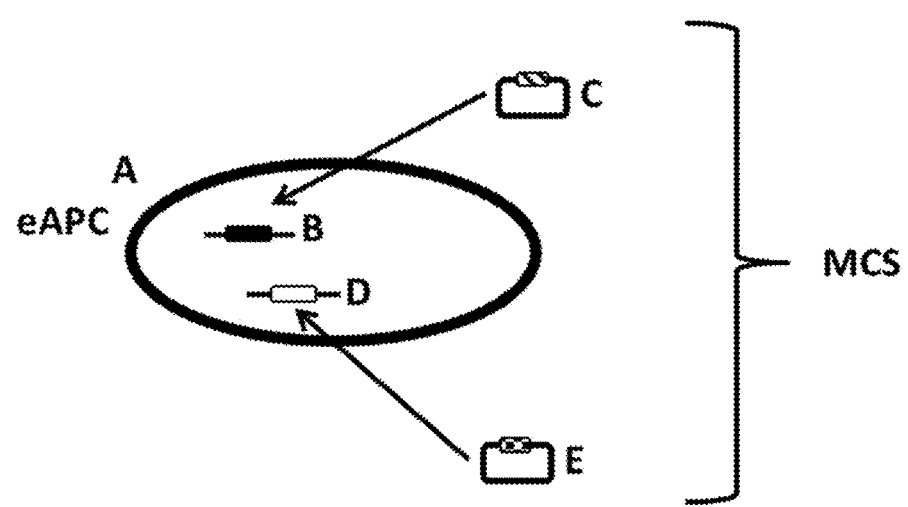

In an expanded form of the multicomponent system, component A eAPC may further contain a second genomic receiver site, designated component D, which is coupled to a second genomic donor vector, designated component E, that is also added to the system (FIG. 2). A multicomponent system may further comprise one or more additional integration couples.

Figure 3:
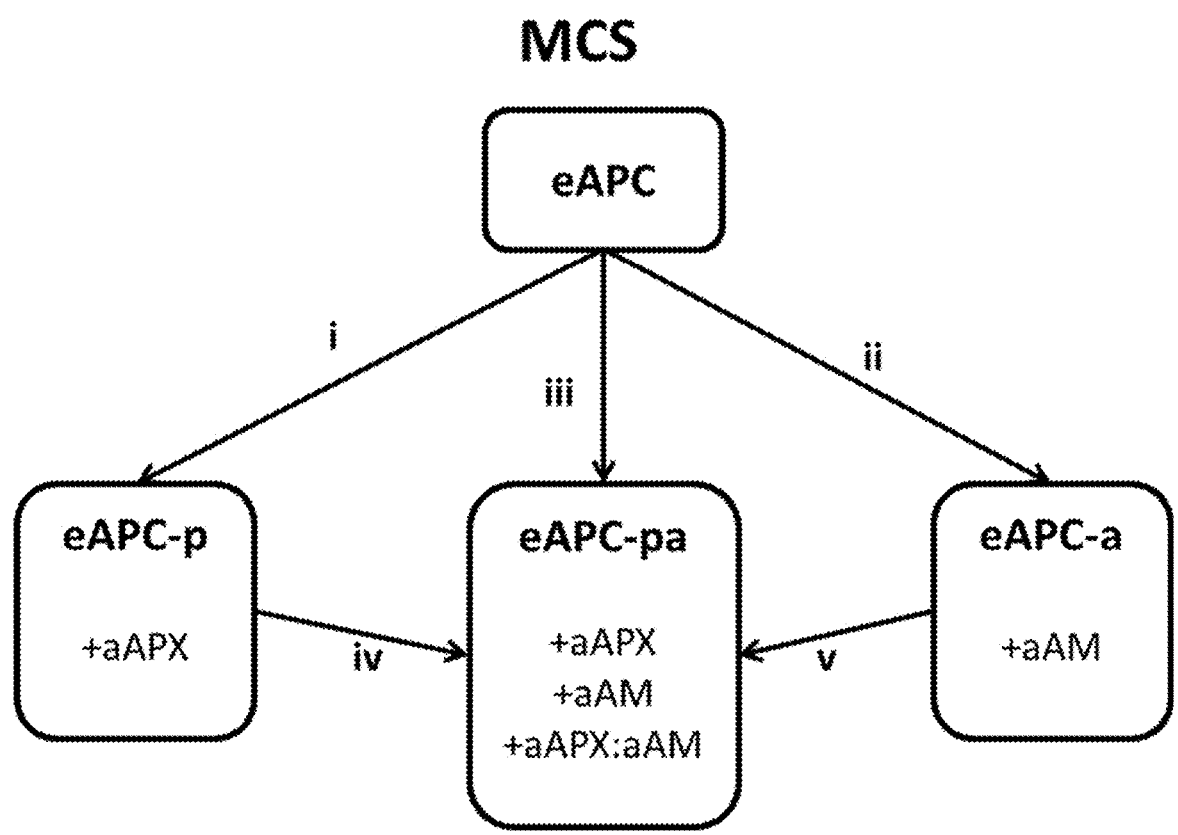

A multicomponent system, comprising an eAPC and either one or two integration couples, is used for preparation of the derivative eAPC forms i. eAPC-p
    ii. eAPC-a
    iii. eAPC-pa wherein each genetic donor vector may contain one or more ORFs encoding one or more aAPX and/or an aAM, to integrate said ORFs into the coupled genomic receiver sites, such that i) expresses at least one aAPX, ii) expresses at least one aAM and iii) expresses at least one aAPX and at least one aAM (FIG. 3).

Figure 4:
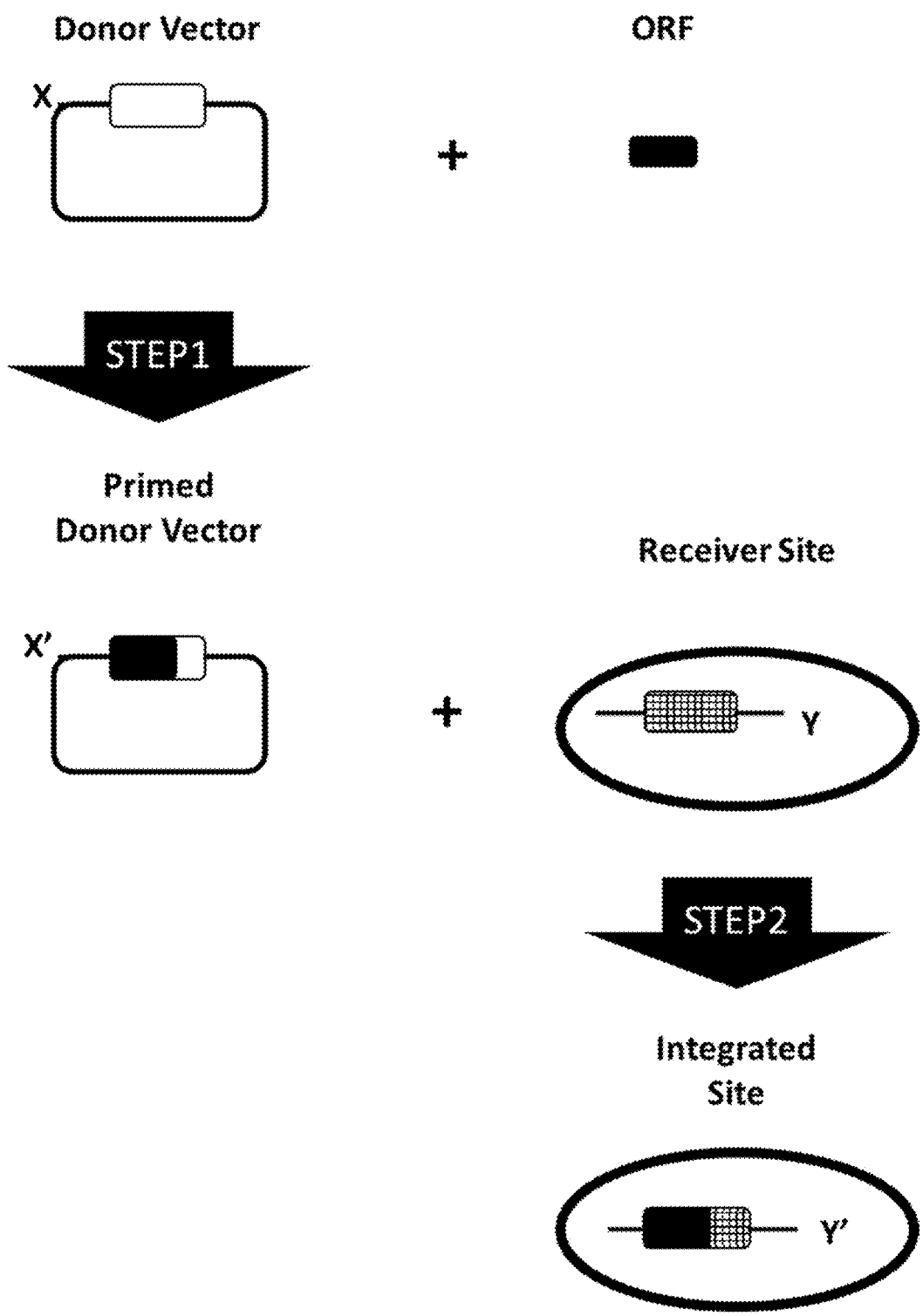

The genetic donor vector and genomic receiver sites operate as an integration couple subsystem of the multicomponent system. A genetic donor vector must first be combined with target ORFs, such that base donor vector now encodes those target ORFs. The assembled primed donor vector is then introduced to the target eAPC to exchange target ORF(s) to the genomic receiver site, thus integrating the target ORFs to the coupled receiver site of the target cell (FIG. 4).

A multicomponent system that comprises genetic donor vectors component C and/or E may be combined with at least one ORF encoding at least one aAPX and/or aAM to obtain component C' and/or E', wherein the combination is defined as the ligation of genetic material into the correct coding frame(s), and in the correct orientation(s), of the genetic donor vector.

The combination of one or more ORFs into genetic donor vectors C and/or E may be performed multiple times with a library of unique ORFs as i. single discrete reactions to obtain a discrete library of C' and/or E' vectors encoding multiple ORFs
    ii. a single reaction to obtain a pooled library of C' and/or E' vectors encoding multiple ORFs wherein the discrete library may be combined with component A multiple times as to obtain a discrete library of eAPC with unique ORFs encoding unique aAPX and/or aAM, or a pooled library may be combined with component A as a single event as to obtain a pooled library of eAPCs each with unique ORFs encoding unique aAPX and/or aAM.

The efficient integration of a predictable copy number of one or more ORFs into the genomic receiver site is highly advantageous for operation of a standardised eAPC, where analyte eAPC populations may be rapidly prepared and characterised. Thus, the genomic receiver site(s) and coupled donor vector(s) are critical to the function of the eAPC. Furthermore, it is strongly desirable to have an eAPC wherein component B and D, are insulated from one another, such that the donor vector component C cannot integrate at component B, and vice versa. In addition, it is also desirable that the component B and/or component D are amenable to a method of preparation of an eAPC wherein the introduction of a single defined aAPX- and/or aAM-containing construct is rapid, repeatable, with a high likelihood of correct integration and delivery of only a single analyte.

The genomic receiver site may be selected from the following i. A synthetic construct designed for recombinase mediated cassette exchange (RMCE)
    ii. A synthetic construct designed for site directed homologous recombination
    iii. A native genomic site for site directed homologous recombination wherein i) is preferred. The RMCE method may employ selected heterospecific sites that are specific for individual recombinase enzymes, such that each component B and D possess insulated specificity.

The genomic receiver site, component B and/or component D, comprises at least one of the following genetic elements i. Heterospecific recombinase sites
ii. Homologous arms
iii. Eukaryotic promoter
iv. Eukaryotic conditional regulatory element
v. Eukaryotic terminator
vi. Selection marker
vii. Splice acceptor site
viii. Splice donor site
ix. Non-protein coding gene
x. Insulator
xi. Mobile genetic element
xii. Meganuclease recognition site
xiii. Internal ribosome entry site (IRES)
xiv. viral self-cleaving peptide element
xv. Akozak consensussequence.

The preferred genomic receiver site would comprise two different arrangements using the following selected elements from the previously stated list of element. The first arrangement is for receiving a single ORF encoding one or more aAPX and/or aAM and/or a selection mark of integration, via RMCE integration wherein the arrangement is

5'-[A][B][C][D][E][F]-3' wherein
A) is element iii) a constitutive or inducible Eukaryotic promoter
B) is element i) heterospecific recombinase site 1
C) is element xv) a Kozak consensus sequence
D) is element vi) a FACS and/or MACS compatible encoded protein marker
E) is element i) heterospecific recombinase site 2
F) is element v) Eukaryotic terminator.

The second arrangement is for receiving two ORF encoding one or more aAPX and/or aAM and/or a selection marker of integration, via RMCE integration wherein the arrangement is

5'-[A][B][C][D][E][F][G][H][I]-3' wherein
A) is element iii) a constitutive or inducible Eukaryotic promoter
B) is element i) heterospecific recombinase site 1
C) is element xv) a Kozak consensus sequence
D) is element vi) a FACS and/or MACS compatible encoded protein marker 1
E) is element v) a Eukaryotic bidirectional transcriptional terminator
F) is element vi) a FACS and/or MACS compatible encoded protein marker 2
G) is element xv) a Kozak consensus sequence
H) is element i) heterospecific recombinase site 2
I) is element iii) a constitutive or inducible Eukaryotic promoter;
furthermore, in this second arrangement the elements F, G, and I are encoded in the antisense direction.

Component C and/or E comprises at least one of the following genetic elements
i. Heterospecific recombinase sites
ii. Homologous arms
iii. Eukaryotic promoter
iv. Eukaryotic conditional regulatory element
v. Eukaryotic terminator
vi. Selection marker
vii. Splice acceptor site
viii. Splice donor site
ix. Non-protein coding gene
x. Insulator
xi. Mobile genetic element
xii. Meganuclease recognition site
xiii. Internal ribosome entry site (IRES)
xiv. Viral self-cleaving f element
xv. Akozak consensussequence
xvi. Selection marker of integration
xvii. An antibiotic resistance cassette
xviii. A bacterial origin of replication
xix. A yeast origin of replication
xx. A cloning site In a preferred embodiment of the genetic donor vector, component C and/or component E, would comprise of two different possible arrangements using the following selected elements from the previously stated list of elements.

The first arrangement is for delivering a single ORF encoding one or more aAPX and/or aAM and/or a selection mark of integration, via RMCE integration wherein the arrangement is

5'-[A][B][C][D][E]-3' wherein
A) is element i) heterospecific recombinase site 1
B) is element xv) a Kozak consensus sequence
C) is element xx) a cloning site of a single ORF encoding one or more aAPX and/or aAM and/or element xvi) a selection marker of integration
D) is element i) heterospecific recombinase site 2
E) is element xvii) An antibiotic resistance cassette and element xviii) a bacterial origin of replication, in no specific orientation
furthermore, the elements viii and/or xiv may be used to link multiple aAPX and/or aAM and/or element xvi together.

The second arrangement is for delivering two ORF encoding one or more aAPX and/or aAM and/or a selection mark of integration, via RMCE integration wherein the arrangement is

5'-[A][B][C][D][E][F]-3' wherein
A) is element i) heterospecific recombinase site 1
B) is element xv) a Kozak consensus sequence
C) is element xx) a cloning site for introduction of two or more ORF, with eukaryotic terminators, encoding one or more aAPX and/or aAM and/or element xvi) a selection marker of integration
D) is element xv) a Kozak consensus sequence (antisense direction)
E) is element i) heterospecific recombinase site 2
F) is element xvii) An antibiotic resistance cassette and element xviii) a bacterial origin of replication, in no specific orientation
furthermore, the elements viii and/or xiv may be used to link multiple aAPX and/or aAM and/or element xvi together within each ORF.

Preparing Analyte eAPC Using the Multicomponent System

Figure 27:
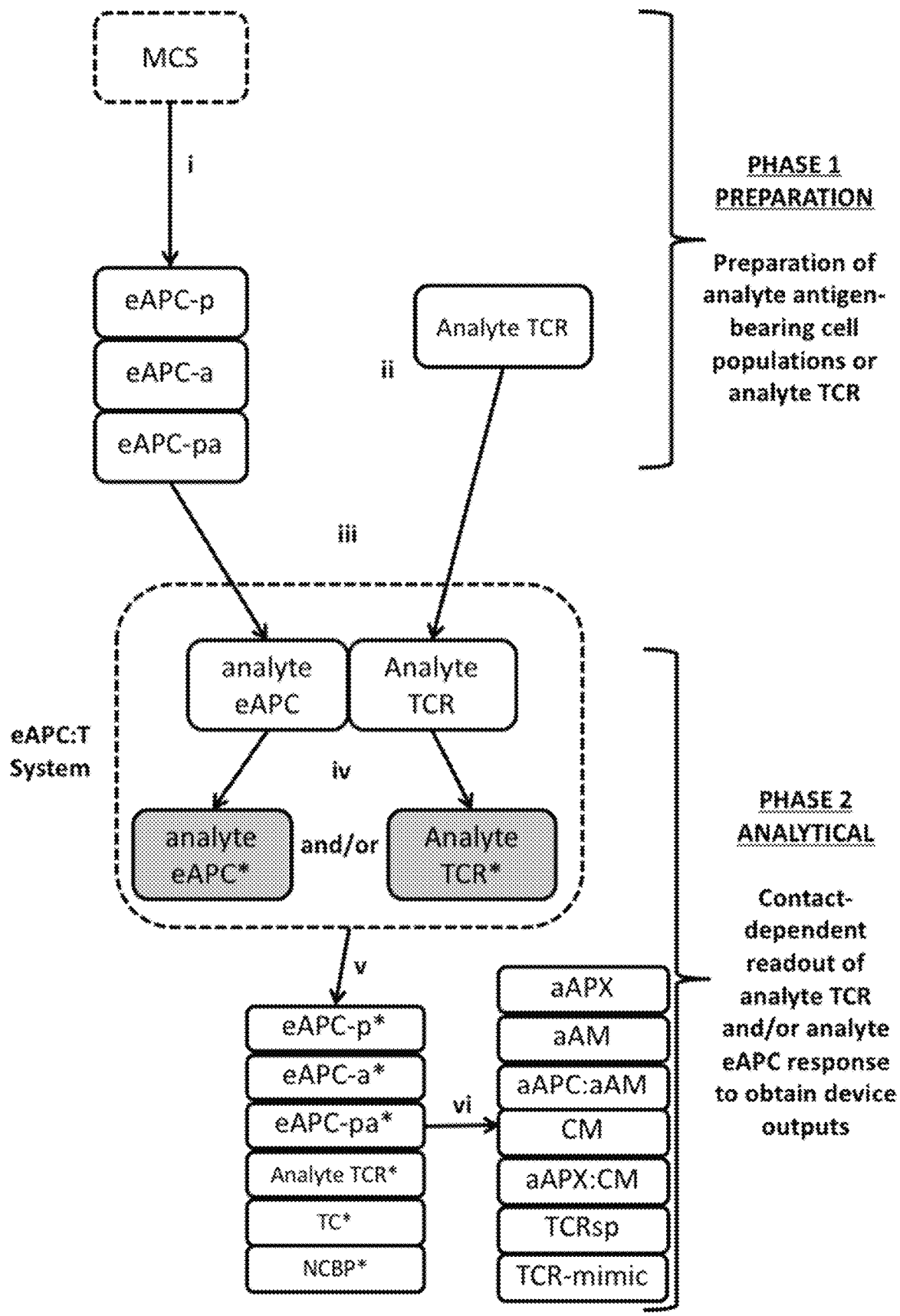

The above described multicomponent system may be used in multiple ways to prepare distinct forms of analyte eAPC, or libraries thereof, that serve to present analyte aAPX, aAM, aAPX:aAM and aAPX:CM to the analyte TCR within the combined eAPC:T system in operation (see FIG. 27).

Figure 5:
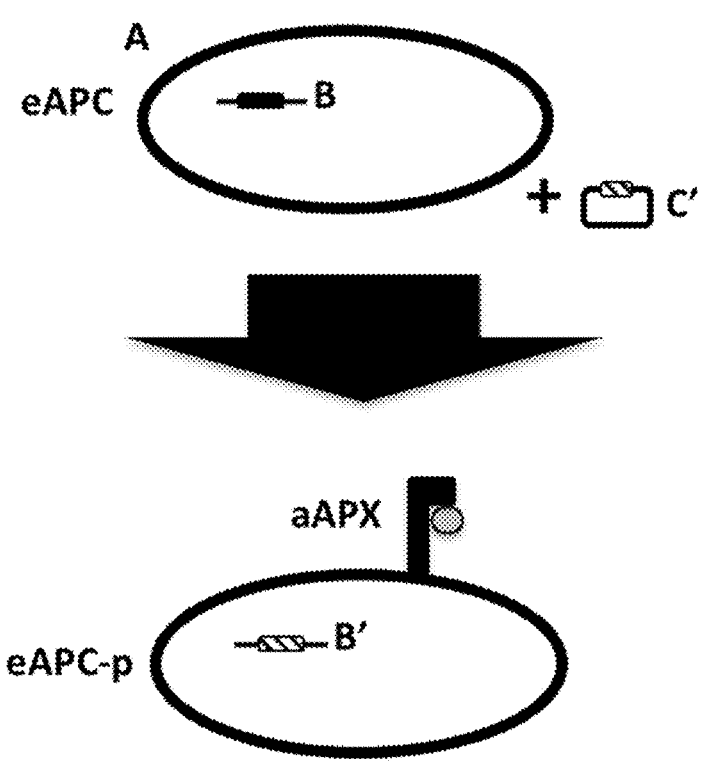

The multicomponent system comprising a single integration couple may be used to prepare an eAPC-p from component A in one step, by providing component C' combined with an ORF for an aAPX, such that this aAPX is integrated to site B, to create B'. The resulting cell line expresses the provided aAPX, and it is presented at the cell surface (FIG. 5).

Figure 6:
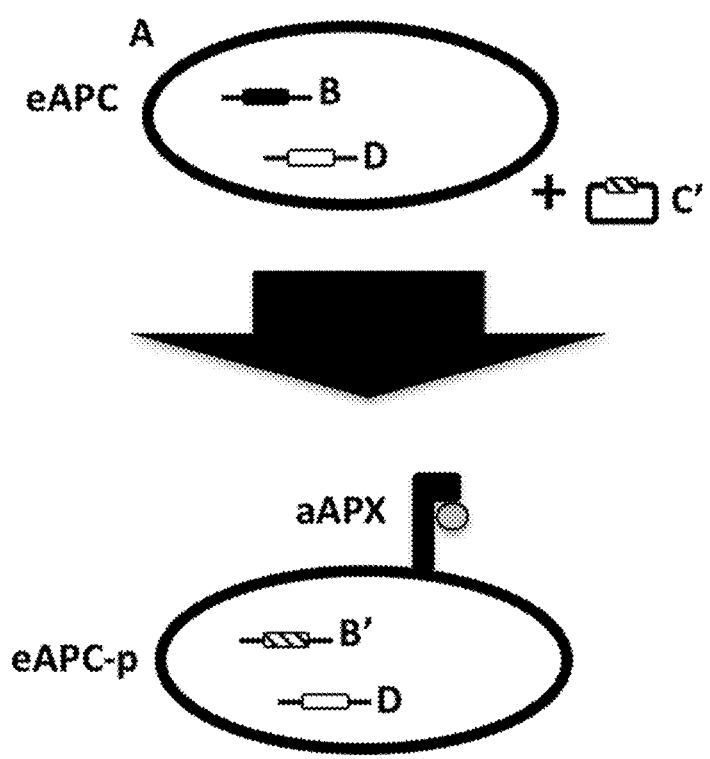

A multicomponent system comprising two integration couples may be used to prepare an eAPC-p from component A in one step, by providing component C' combined with an ORF for an aAPX, such that this aAPX is integrated to site B, to create B'. The resulting cell line expresses the provided aAPX, and it is presented at the cell surface. The second integration couple D/E remains unmodified and may be used for downstream integration steps (FIG. 6).

Figure 7:
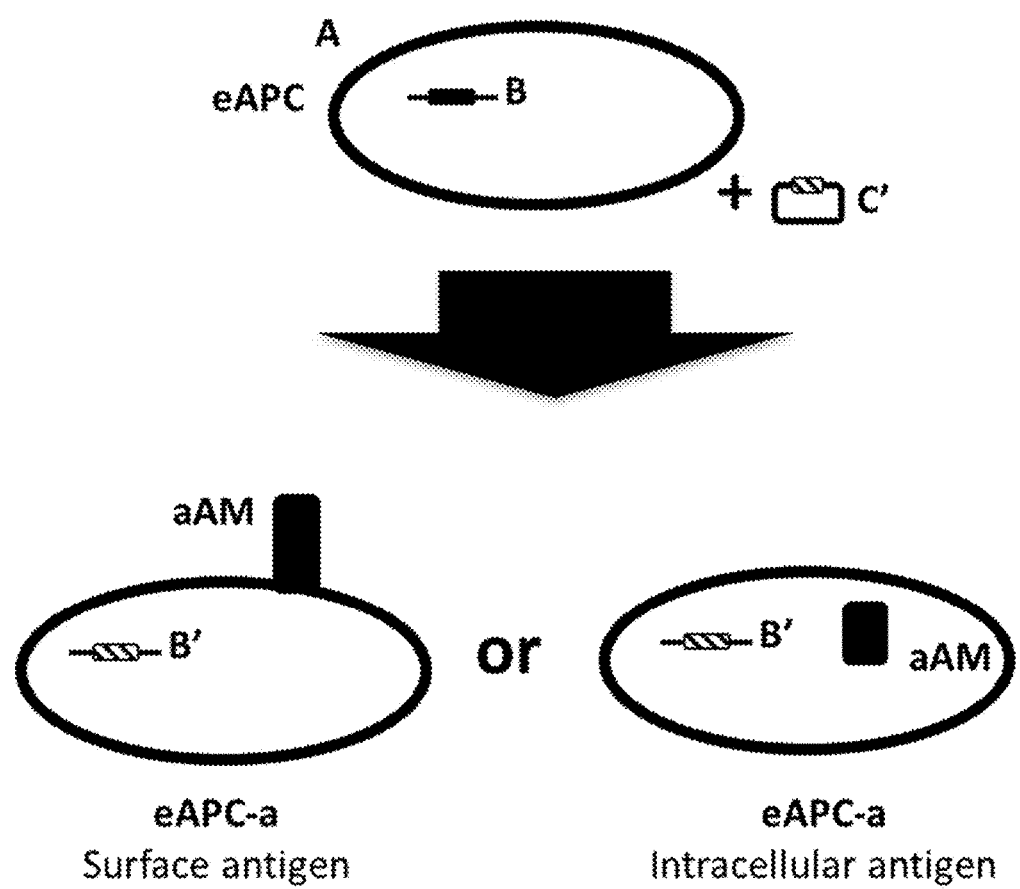

A multicomponent system comprising a single integration couple may be used to prepare an eAPC-a from component A in one step, by providing component C' combined with an ORF for an aAM, such that this aAM is integrated to site B, to create B'. The resulting cell line expresses the provided aAM, and is presented either at the cell surface or retained intracellularly (FIG. 7).

Figure 8:
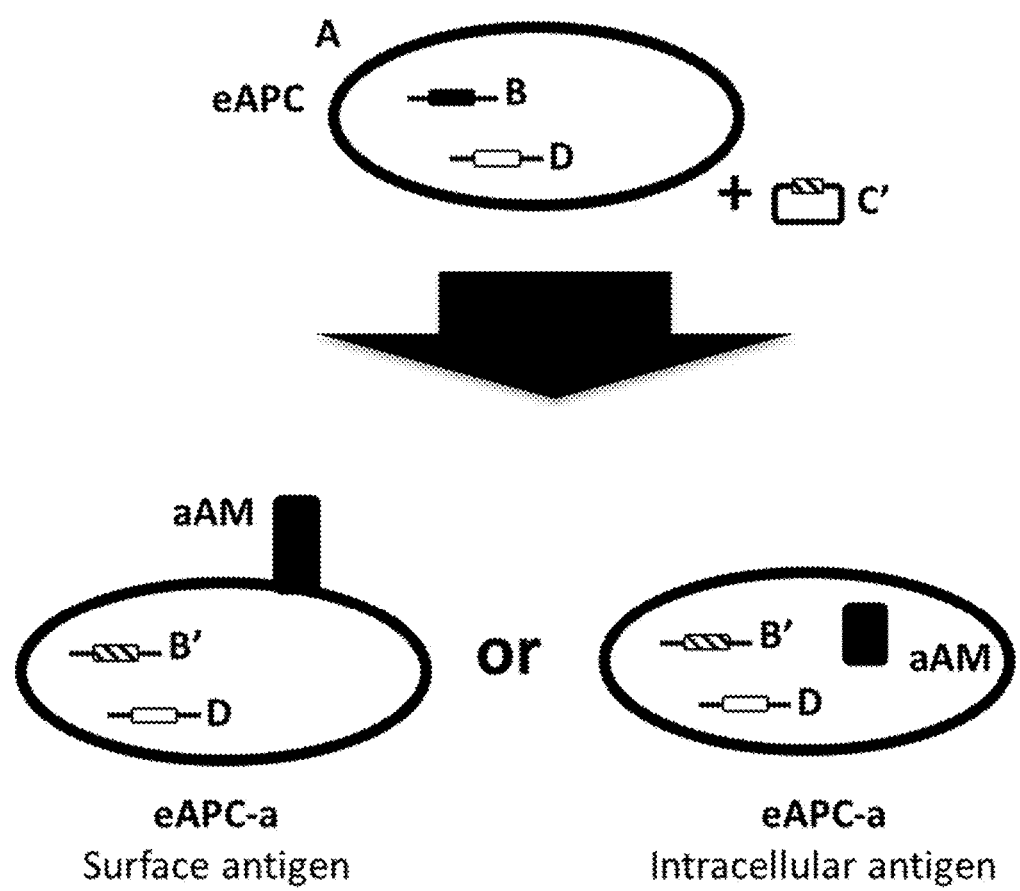

A multicomponent system comprising two integration couples may be used to prepare an eAPC-a from component A in one step, by providing component C' combined with an ORF for an aAM, such that this aAM is integrated to site B, to create B'. The resulting cell line expresses the provided aAM, and is presented either at the cell surface or retained intracellularly. The second integration couple D/E remains unmodified and may be used for downstream integration steps (FIG. 8).

Figure 9:
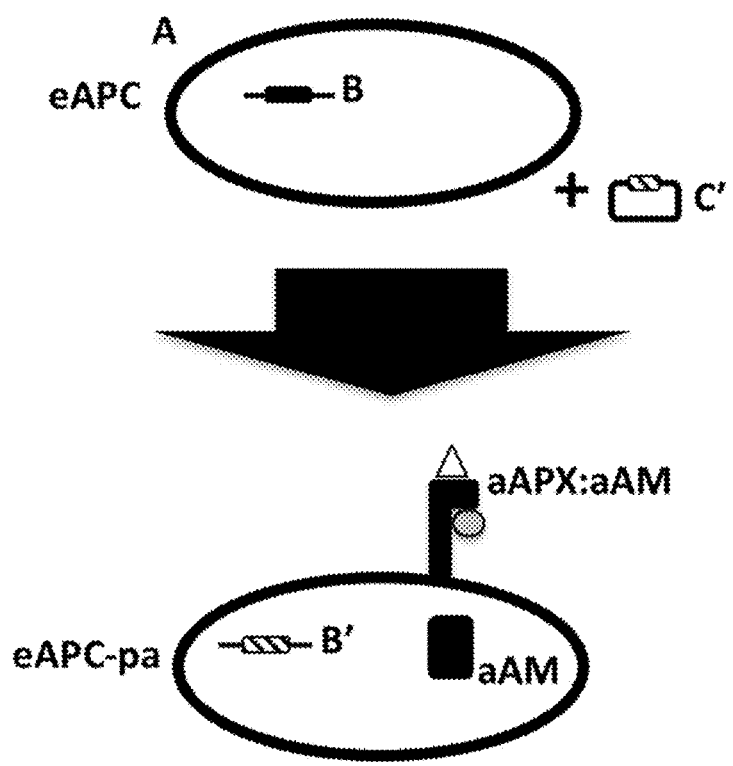

A multicomponent system comprising a single integration couple may be used to prepare an eAPC-pa from component A in one step, by providing component C' combined with two ORFs, one encoding and aAPX and the other an aAM, such that both aAPX and aAM are integrated to site B, to create B'. The resulting cell line expresses the provided aAPX and aAM, and may present an aAPX:aAM at the cell surface (FIG. 9).

Figure 10:
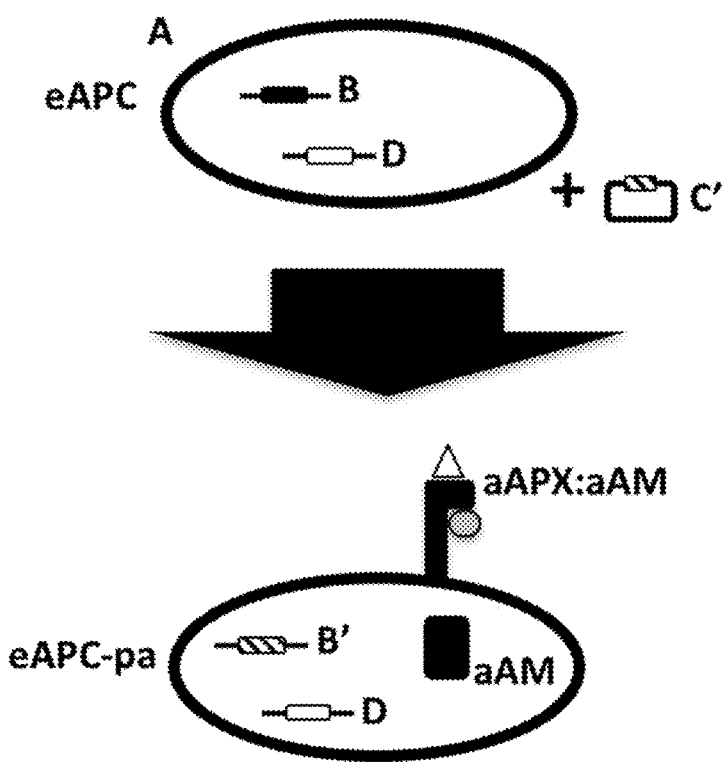

A multicomponent system comprising two integration couples may be used to prepare an eAPC-pa from component A in one step, by providing component C' combined with two ORFs, one encoding and aAPX and the other an aAM, such that both aAPX and aAM are integrated to site B, to create B'. The resulting cell line expresses the provided aAPX and aAM, and may present an aAPX:aAM at the cell surface. The second integration couple D/E remains unmodified and may be used for downstream integration steps (FIG. 10).

Figure 11:
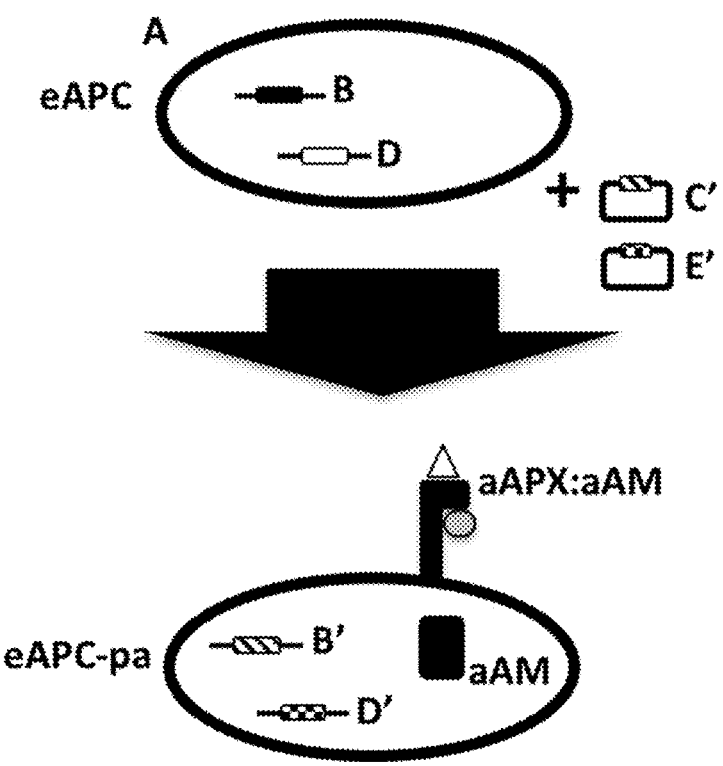

A multicomponent system comprising two integration couples may be used to prepare an eAPC-pa from component A in one step, by providing component C' and E' each combined with one ORF encoding either an aAPX or an aAM, such that both aAPX and aAM are integrated to site B or D, to create B' and D'. The resulting cell line expresses the provided aAPX and aAM, and may present an aAPX:aAM at the cell surface (FIG. 11).

Figure 12:
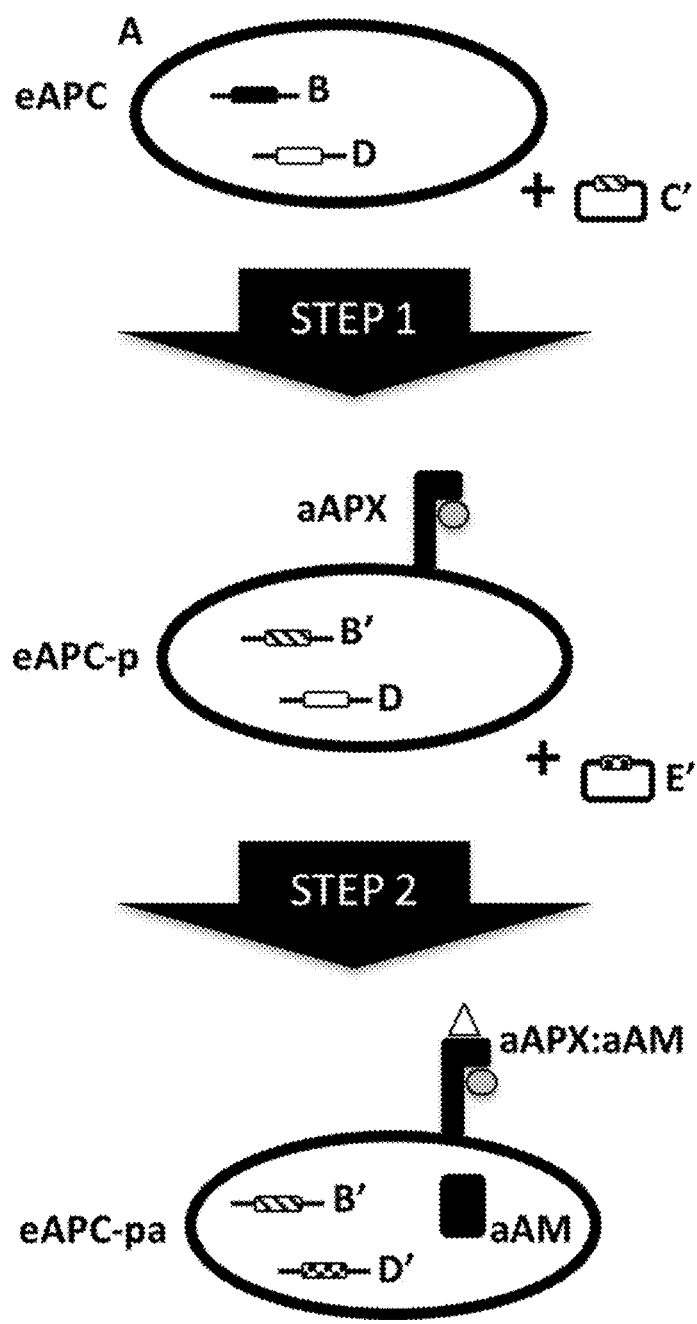

A multicomponent system comprising two integration couples may be used to prepare an eAPC-pa from component A in two steps, by first providing component C' combined with an ORF encoding an aAPX such that this aAPX is integrated to site B, to create B'. The resulting cell line expresses the provided aAPX, and it is presented at the cell surface (eAPC-p intermediate). The second integration couple D/E remains unmodified. In the second step E' is provided wherein the donor vector is combined with an ORF encoding an aAM such that this aAM is integrated to site E, to create E'. The resulting cell line expresses the provided aAM, and this may be processed and loaded as cargo in the aAPX to form an aAPX:aAM complex on the cell surface (FIG. 12).

Figure 13:
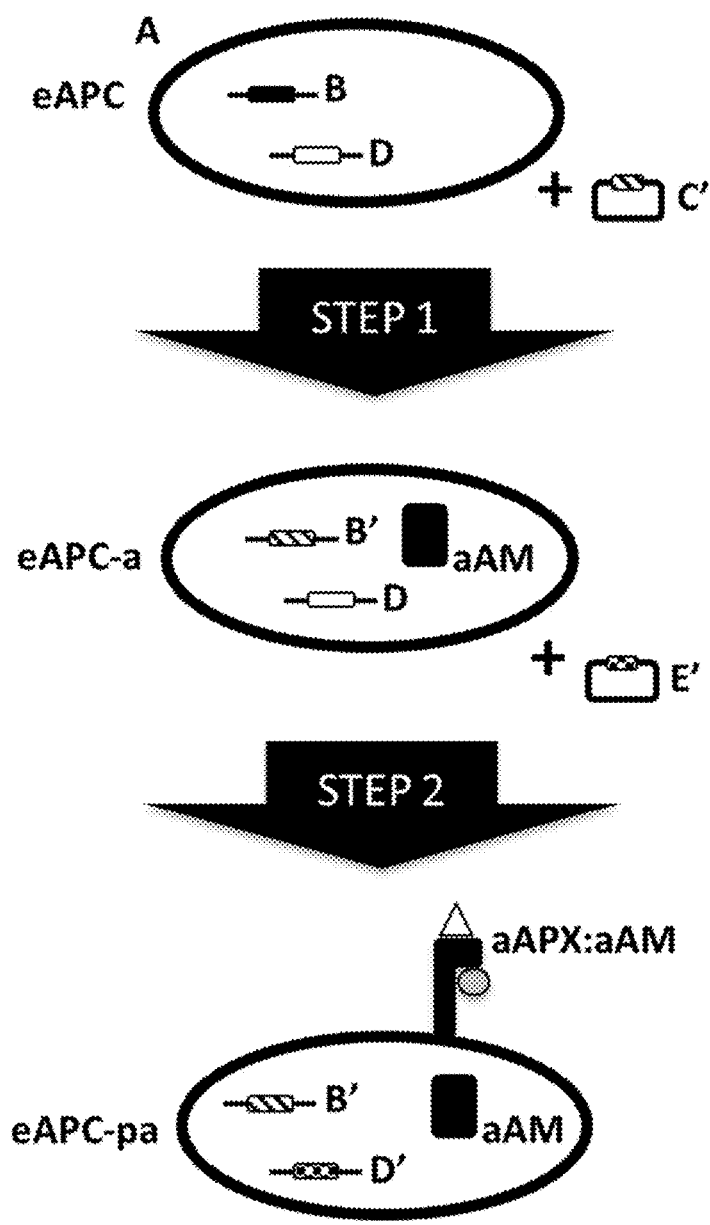

A multicomponent system comprising two integration couples may be used to prepare an eAPC-pa from component A in two steps, by first providing component C' combined with an ORF encoding an aAM such that this aAM is integrated to site B, to create B'. The resulting cell line expresses the provided aAM (eAPC-a intermediate). The second integration couple D/E remains unmodified. In the second step E' is provided wherein the donor vector is combined with an ORF encoding an aAPX such that this aAPX is integrated to site E, to create E'. The resulting cell line expresses the provided aAPX, which is presented on the cell surface. The aAM integrated in the first step may be processed and loaded as cargo in the aAPX to form an aAPX:aAM complex on the cell surface (FIG. 13).

In the abovementioned examples of preparing analyte eAPC-p, eAPC-a and eAPC-pa populations from eAPC, the multicomponent system is used to provide known aAPX and aAM candidates in a defined manner to prepare discrete populations of analyte eAPC expressing defined aAPX and/or aAM. Such a process may be repeated many times to build libraries of eAPC-p, eAPC-a and eAPC-pa to provide to the combined eAPC:T system in operation of the system. An alternative approach is to take pooled libraries of candidate aAPX and/or aAM ORFs combined with genetic donor vectors, and integrate these in a single reaction to obtain pooled libraries of analyte eAPC-p, eAPC-a or eAPC-pa that express multiple aAPX, aAM and/or aAPX:aAM. This process of converting a pool of vectors to a pool of eAPC-p, -a, and/or -pa will be referred to as shotgun integration. This is particularly useful when analysing large libraries of candidate aAM against a fixed aAPX, or vice versa.

Figure 14:
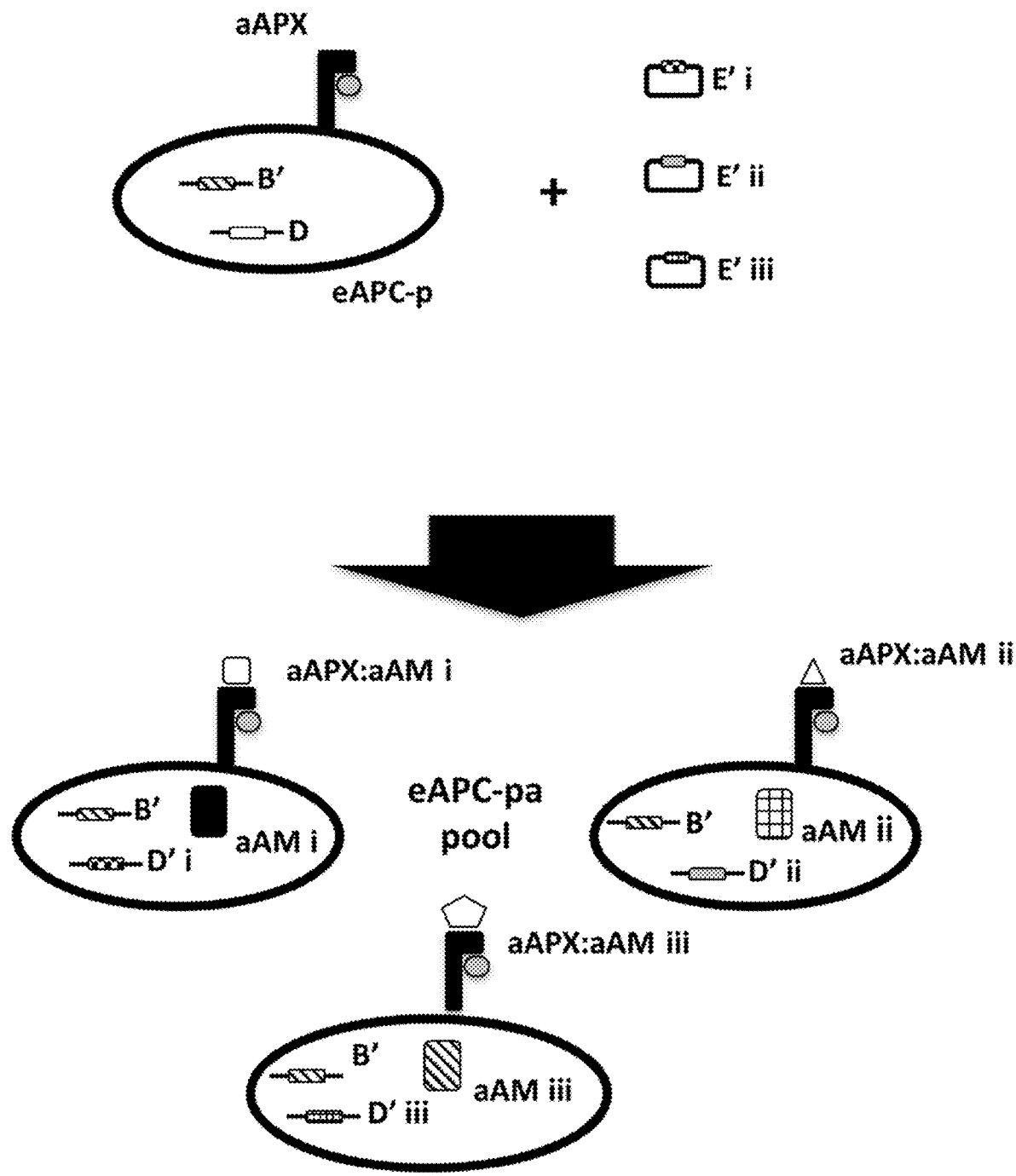

A multicomponent system comprising two integration couples may be used to prepare an eAPC-pa from component A in two steps, by first providing component C' combined with an ORF encoding an aAPX such that this aAPX is integrated to site B, to create B'. The resulting cell line expresses the provided aAPX on the cell surface (eAPC-p intermediate). The second integration couple D/E remains unmodified. In the second step a library of multiple E' is provided wherein the library of donor vectors comprises a pool of vectors each combined with a single ORF encoding an aAM such that each aAM is integrated to site E, to create E', within single cells. The resulting pool of cells contains a collection of cells, wherein each cell has integrated a single random aAM ORF from the original pool of vectors. The aAM integrated in the second step may be processed and loaded as cargo in the aAPX integrated in the first step to form an aAPX:aAM complex on the cell surface (FIG. 14).

A multicomponent system comprising two integration couples may be used to prepare an eAPC-pa from component A in two steps, by first providing component C' combined with an ORF encoding an aAM such that this aAM is integrated to site B, to create B'.

Figure 15:
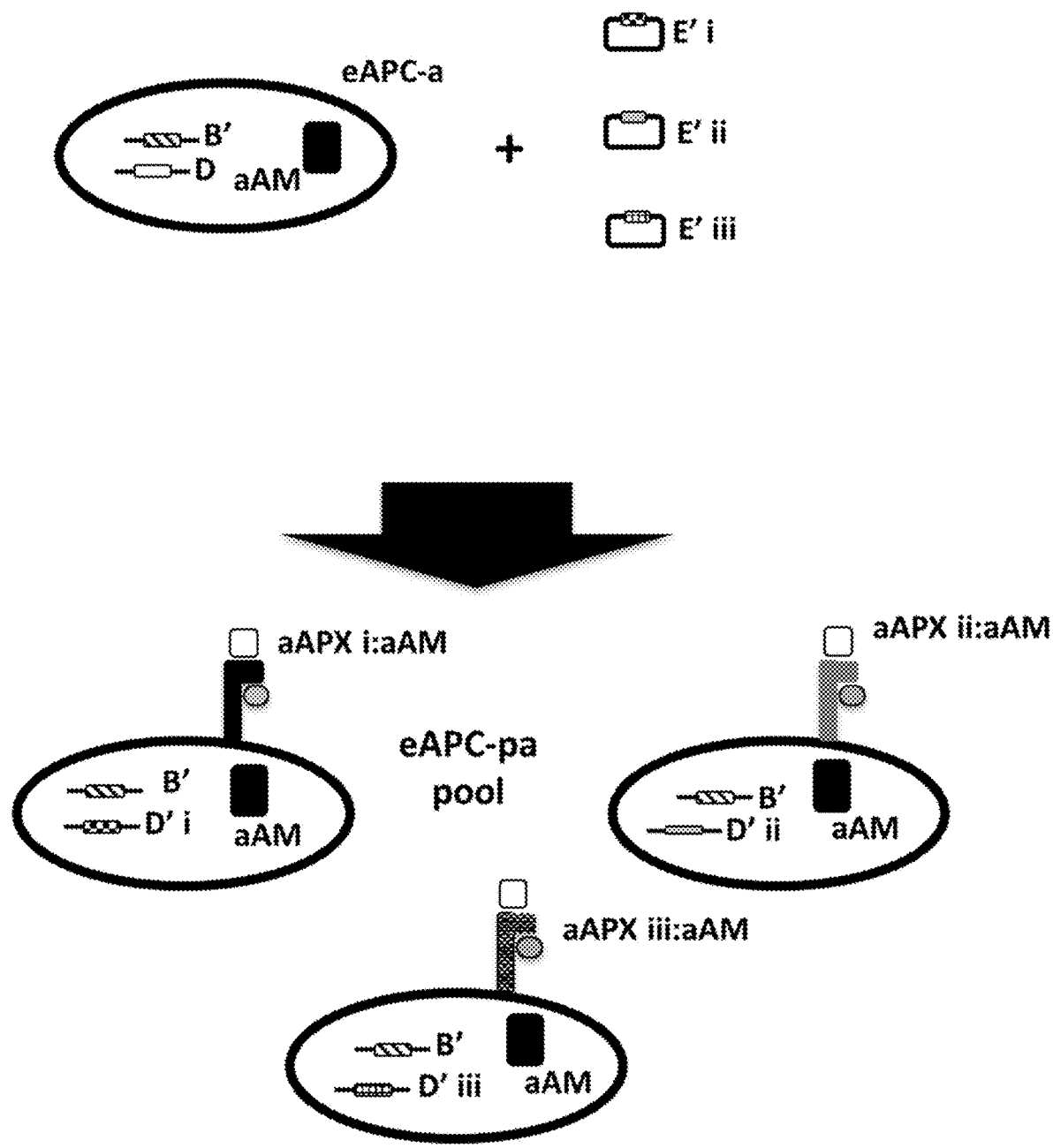

The resulting cell line expresses the provided aAM, an eAPC-a intermediate. The second integration couple D/E remains unmodified. In the second step a library of multiple E' is provided wherein the library of donor vectors comprises a pool of vectors each combined with a single ORF encoding an aAPX such that each aAPX is integrated to site E, to create E', within single cells. The resulting pool of cells contains a collection of cells, wherein each cell has integrated a single random aAPX ORF from the original pool of vectors. The aAM integrated in the first step may be processed and loaded as cargo in the aAPX integrated in the second step to form an aAPX:aAM complex on the cell surface (FIG. 15).

Figure 16:
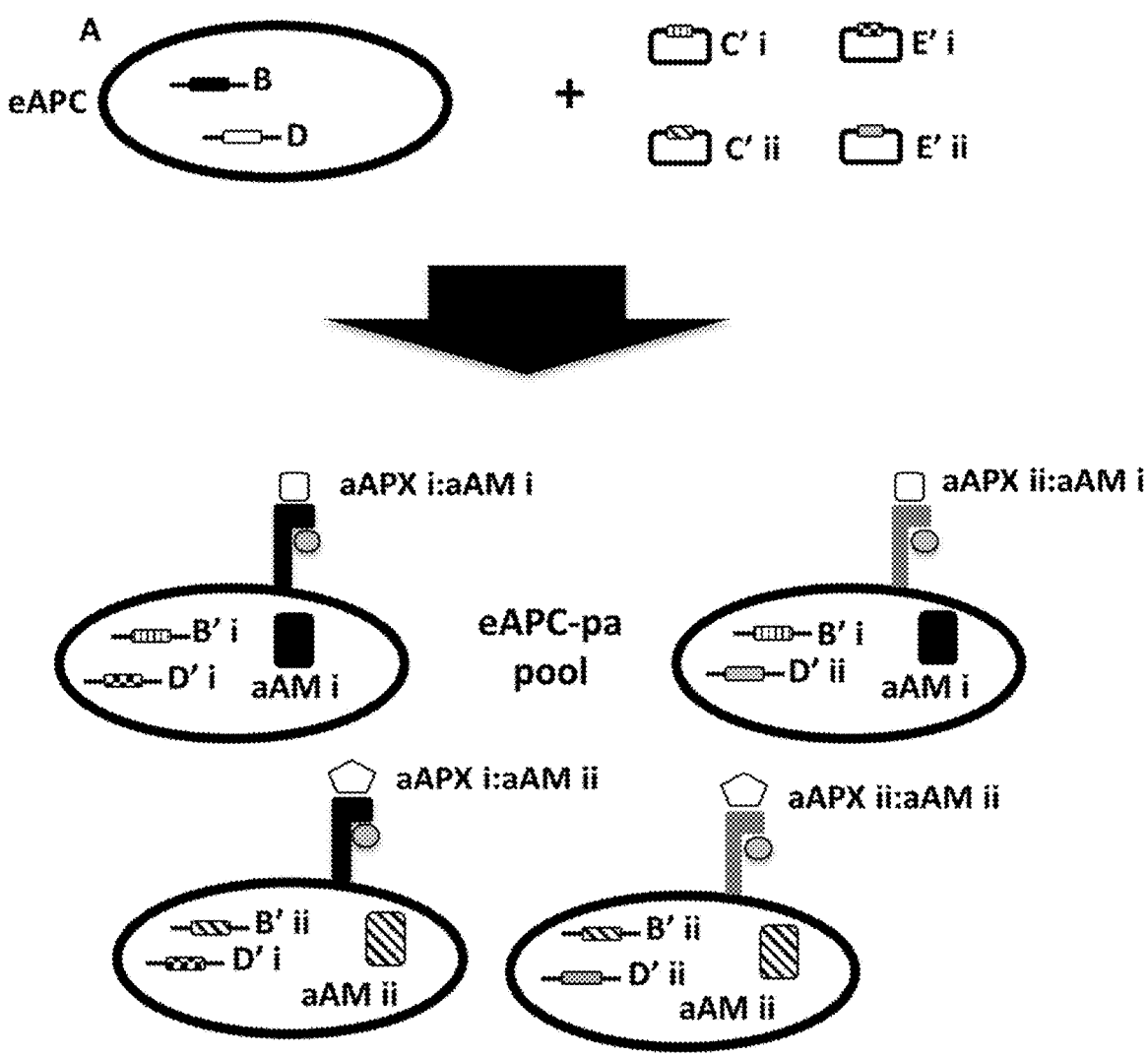

A multicomponent system comprising two integration couples may be used to prepare an eAPC-pa from component A in one step, by providing component C' and E' each combined with a library of ORFs encoding either a library of aAPX or a library of aAM, such that both aAPX and aAM are integrated to site B or D, to create B' and D'. The resulting pool of cells contains a collection of cells wherein each cell has integrated a single random aAPX ORF and a single random aAM ORF from the original pool of vectors. Within each cell in the pooled library, an integrated aAM may be processed and loaded as cargo in the aAPX integrated into the same cell to form an aAPX:aAM complex on the cell surface. Such a pooled library would contain all possible combinations of aAPX:aAM from the set of aAPX and aAM provided (FIG. 16).

In the above-mentioned shotgun integration methods for providing pooled libraries of eAPC-pa, the robustness of the system relies on a single copy of the genomic receiver site. This is to ensure just a single analyte may be introduced into each cell via the integration couple. This single-copy genomic receiver site is an optional aspect of an eAPCS, as multiple copies of the same genomic receiver site may be beneficial in providing integration steps where multiple 'alleles' from a library of provided vectors may be obtained in the prepared eAPC.

In the present context, an aAPX may be selected from one of the following
  i. One or more members of HLA class I
  ii. One or more members of HLA class
  iii. One or more non-HLA antigen-presenting complex.

In the present context, an aAPX may be selected from one of the following
  i. a polypeptide or complex of polypeptides provided as analyte antigen
  ii. a peptide derived from a polypeptide provided as analyte antigen
  iii. a peptide provided as analyte antigen
  iv. a metabolite provided as analyte antigen
  v. a polypeptide or complex of polypeptides translated from the analyte antigenic molecule ORF(s)
  vi. a peptide derived from a polypeptide translated from the analyte antigenic molecule ORF(s)
  vii. a peptide derived from altering the component A proteome
  viii. a polypeptide derived from altering the component A proteome
  ix. a metabolite derived from altering the component A metabolome.

Contacting Analyte eAPC with Analyte TC

The present invention relates to the provision of an engineered multicomponent system. The component A and one or more component C' and/or one or more Component E' are used to prepare one or more analyte eAPC populations. These analyte eAPC are then combined with one or more analyte TCR to compile an eAPC:TCR analytical system (eAPC:T) to obtain one or more outputs (FIG. 27), wherein in the eAPC provides the analyte antigen and wherein the analyte TCR may be represented by:
  i. a TCR molecule and/or
  ii. a molecule with affinity for the analyte antigen, and
wherein the analyte TCR may be present to the eAPC in different modes within an eAPC:T system, represented as:
  i. an analyte TCR presenting cell (TC) and/or
  ii. a soluble or immobilised affinity reagent and/or
  iii. a non-cell based particle (NCBP),
wherein i) an analyte TCR presenting cell (TC) is considered any TC that is able to present an analyte TCR to the eAPC; ii) an affinity reagent is considered any reagent that is prepared as analyte to probe TCR binding and/or stimulation at the cell surface of the eAPC in an eAPC:T system. Such reagents will often represent analyte TCR multimer reagent (e.g. TCR 'tetramers') used to stain eAPC. Affinity reagents in this context could also represent antibodies or similar entities; iii) a non-cell based particle (NCBP) acts in a similar manner to an affinity reagent, inasmuch that the particle presents an analyte TCR or other entity that is to be assessed for analyte antigen engagement at the surface of a eAPC within and eAPC:T system. However, an NCBP is considered as a larger entity that can further carry genetic or other information that is to act as an identifier, either directly or by proxy, of the presented analyte TCR or other binding entity. A typical example of an NCBP would be a bacteriophage in a phage-display scenario, wherein phage may display antibody fragment antigen binding (FAB). Positively labelled eAPC may be recovered along with the phage, and sequenced to identify FABs specific for the analyte antigen at the surface of a eAPC.

Furthermore, the cellular presentation of the analyte TCR may be in the form of any of the following
  i. a primary T-cell
  ii. a recombinant T-cell
  iii. an engineered TCR presenting cell
  iv. an engineered cell presenting a molecule with affinity for the analyte antigen collectively referred to as analyte TC.

An analytical eAPC:T system is comprised of a selection of one or more of analyte eAPC populations and more analyte TCR (FIG. 27). The analyte eAPC populations are prepared using the multicomponent system as described above (FIGS. 3 to 16). The eAPC:T system is provided in a format that permits physical contact between the analyte eAPC and analyte TCR, wherein such contact is permissive of complex formation between one or more analyte antigens presented by the analyte eAPC and analyte TCR.

An analyte antigen represents any entity that an analyte TCR can putatively engage in the eAPC:T system, and may be represented by;
  i. aAPX (analyte Antigen-presenting complex) and/or
  ii. aAM (analyte antigenic molecule) and/or
  iii. aAPX:aAM (analyte Antigen-presenting complex presenting an analyte antigenic molecule) and/or
  iv. CM (a non-analyte cargo molecule) and/or
  v. aAPX:CM (analyte Antigen-presenting complex presenting a cargo molecule)
wherein an aAPX represents a complex that is able to present an aAM; an aAM is any molecule that is directly recognised by a TCR or when loaded in an aAPX; an aAPX:aAM is an aAPX with a loaded aAM; a CM is a cargo molecule that may be loaded in the aAPX, but which is not an analyte, thus may be derived from an analyte antigen presenting cell (APC) or the assay system itself; aAPX:CM is an aAPX with a CM loaded.

In the present context, an eAPC:T system comprises of:
  i. an input of a single analyte eAPC; or
  ii. an input of a pooled library of analyte eAPC
     and combined with one of the following:
  iii. an input of a single analyte TC; or
  iv. an input of a single analyte affinity reagent; or
  v. an input of a single analyte NCBP; or
  vi. an input of a pooled library of analyte TC; or
  vii. an input of a pooled library of analyte affinity reagent; or
  viii. an input of a pooled library of analyte NCBP Contacting in Buffer System A contact between an analyte eAPC and analyte TC is performed in a permissive cell culture system or buffered media, wherein said system comprises media that is permissive to the function of both analyte eAPC and analyte TC cells or analyte affinity reagent, or analyte NCBP.

A contact between a soluble analyte TCR, immobilised analyte TCR and/or analyte NCBP and an analyte eAPC may be performed in a permissive buffered system, wherein said system comprises a buffered medium that is permissive to function of both the analyte TCR and analyte eAPC cells.

Labelling eAPC with Affinity Reagents or NCBP

An analyte eAPC obtained from the multi-component system may be used for characterisation of an analyte antigen presented by the eAPC. Such characterisation may be conducted in a manner where the analyte eAPC is contacted with an immobilised or soluble affinity reagent or NCBP in such a manner as to label the eAPC (FIG. 24).

Labelling of an eAPC may be considered to be detected by direct observation of the label through such methods as flow cytometry, microscopy, spectrometry or luminometry or alternatively by means of capture with an immobilised affinity reagent or NCBP for identification of the analyte antigen.

Signal Responses Definition

Figure 20:
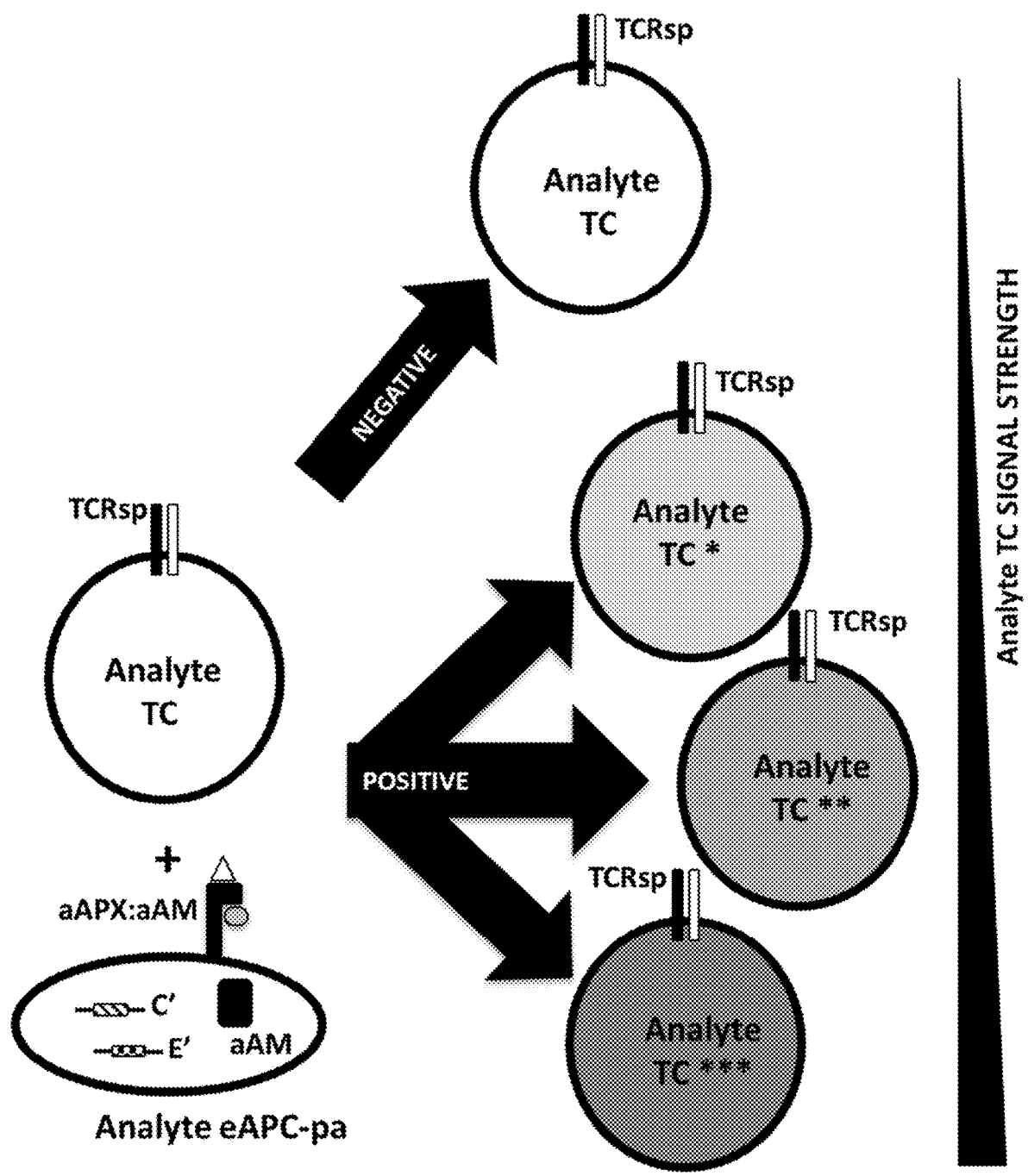

An analyte eAPC prepared from the multi-component system is used for characterisation of a signal response of the analyte eAPC to analyte TCR, wherein such a signal response may be either binary or graduated, and may be measured as intrinsic to intrinsic to the eAPC (FIG. 21) and/or the analyte TC, if included (FIG. 20). Such signals may be detected through methods such as flow cytometry, microscopy, spectrometry or luminometry or other methods known to those skilled in the art.

General Method—Selecting an eAPC

The method for selecting one or more analyte eAPC from an input analyte eAPC or a library of analyte eAPC, from the combined eAPC:T system, to obtain one or more analyte eAPC wherein the expressed analyte antigen binds to one or more analyte TCR, comprises
  i. Combining one or more analyte eAPC with one or more analyte TCR resulting in a contact between an analyte antigen and the analyte TCR, and at least one of
  ii. Measuring a formation, if any, of a complex between one or more analyte antigen with one or more analyte TCR and/or
  iii. Measuring a signal from a labelled analyte TCR and/or
  iv. Measuring a signal response by the analyte eAPC, if any, induced by the formation of a complex between one or more analyte antigen with one or analyte TCR and/or
  v. Measuring a signal response by the analyte TC, if any, induced by the formation of a complex between one or more analyte antigen with one or analyte TCR and/or and
  vi. Selecting one or more analyte eAPC based on step ii, iii, iv and/or v wherein the selection is made by a positive and/or negative measurement
wherein i, iv and vi or i, v and vi comprise the preferred arrangement.

General Method—Selecting an Analyte TCR

The method for selecting one or more analyte TCR from an input analyte TCR or a library of analyte TCR, to obtain one or more analyte TCR wherein the expressed analyte antigen binds to one or more analyte TCR comprises
  i. Combining one or more analyte APC with one or more analyte TCR, resulting in a contact between an analyte antigen presented by the analyte APC with one or more analyte TCR and
  ii. Measuring a formation, if any, of a complex between one or more analyte antigen with one or more analyte TCR and/or
  iii. Measuring a signal from a labelled analyte TCR and/or
  iv. Measuring a signal response in the one or more analyte TC, if any, induced by the formation of a complex between the analyte TCR with the analyte antigen and/or
  v. Measuring a signal response, if any, by the analyte APC induced by the formation of a complex between one or more analyte TCR with one or more analyte antigen and
  vi. Selecting one or more analyte APC from step ii, iii, iv and/or v wherein the selection is made by a positive and/or negative measurement
wherein i, iv and v comprise the preferred arrangement.

General Method for Signal Response

A method for selecting analyte eAPC and/or analyte TC and/or affinity reagents and/or NCBP from the combined eAPC:T system on the basis of a reported signal response comprises
  i. Determining a native signalling response and/or
  ii. Determining a synthetic signalling response, if the eAPC contains such a response circuit, and/or if the analyte TC contains an equivalent synthetic reporter circuit.

An induced native or synthetic signal response that is intrinsic to APC and/or analyte TC is measured by detecting an increase or decrease in one or more of the following
  i. a secreted biomolecule
  ii. a secreted chemical
  iii. an intracellular biomolecule
  iv. an intracellular chemical
  v. a surface expressed biomolecule
  vi. a cytotoxic action of the analyte TC upon the analyte eAPC
  vii. a paracrine action of the analyte TC upon the analyte eAPC such that a signal response is induced in the analyte APC and is determined by detecting an increase or decrease any of i to v
  viii. a proliferation of the analyte TC
  ix. an immunological synapse between the analyte TC and the analyte eAPC
wherein said detected signal responses are compared to the non-induced signal response state intrinsic to analyte eAPC and/or analyte TC prior to assemble of the combined eAPC:T system and/or a parallel assembled combined system wherein analyte eAPC and/or analyte TC may present control analyte antigen and/or analyte TCR species and/or soluble analyte antigen that are known not to induce a signal response within the combined eAPC:T system in use.

Method of Selection by Labelling and/or Signal Response

A method for selecting analyte eAPC and/or analyte affinity reagents and/or analyte NCBP from the combined eAPC:T system on the basis of a measureable labelling of an eAPC by said affinity reagent or NCBP comprises;
  i. Determining a labelling of the eAPC by an affinity reagent or NCBP and may also comprise
  ii. Determining a native signalling response and/or
  iii. Determining a synthetic signalling response, if the eAPC contains such a response circuit.
wherein selecting an eAPC and/or affinity reagent and/or NCBP by detecting labelling of the eAPC may comprise detection of the surface labelling of the eAPC by an affinity reagent and/or NCBP via including a detectable label on the affinity reagent and/or NCBP. Such detectable labels may be fluorescent, luminescent, spectrometric, chemical, radiochemical or affinity moieties. Thus, such selection of eAPC may be conducted on the basis of FACS, MACS or equivalent high-throughput screening and selection methodologies.

SUMMARY

Within the combined eAPC:T system, measuring a signal response in the one or more analyte eAPC or one or more analyte TC, or the labelling of an eAPC, which may be mediated by the formation of a complex between the analyte antigen with the analyte TCR (FIG. 27 step iv) is critical to selection of primary system outputs (FIG. 27 step v), wherein the primary system outputs are single cells or pools of cells, and/or or single affinity reagent or pools of affinity reagents and/or or single NCBP or pools of NCBP. Wherein the selection of cells or reagents may be made on the presence or absence of a reported signal response in either and/or both of the contacted analyte eAPC or analyte TC cells, or through the measurable labelling of eAPC with an affinity reagent or NCBP Obtaining Primary System Outputs from the eAPC:T System The present invention relates to the provision of an engineered multicomponent system. The component A and one or more component C' and/or one or more Component E' are used to prepare one or more analyte eAPC populations. These analyte eAPC are then combined with one or more analyte TCR via the eAPC:T system to obtain one or more outputs. The analyte TCR are provided as soluble or immobilised reagents, presented on surface of cells or presented by non-cell based particles (NCBP). The cellular presentation of the analyte TCR may be in the form of any of the following i. a primary T-cell
    ii. a recombinant T-cell
    iii. an engineered TCR presenting cell
    iv. an engineered cell presenting a molecule with affinity for the analyte antigen collectively referred to as analyte TC.

The system is comprised of a selection of one or more of analyte eAPC populations and more analyte TCR (FIG. 27). The analyte eAPC populations are prepared using the multicomponent system as described above (FIGS. 3 to 16). The eAPC:T system is provided in a format that permits physical contact between the analyte eAPC and analyte TCR, wherein such contact is permissive of complex formation between one or more analyte antigens presented by the analyte eAPC and analyte TCR wherein the analyte antigen is any of the following i. aAPX and/or
    ii. aAM and/or
    iii. aAPX:aAM and/or
    iv. CM and/or
    v. aAPX:CM and wherein the analyte TCR is provided as, presented by an analyte TC, or presented by either a soluble or immobilised analyte affinity reagent, or presented as by an analyte NCBP, for potential engagement with analyte antigens presented by an analyte eAPC, such that complex formation may lead to stabilisation of such a complex and wherein leads to labelling of the eAPC and/or the induction of signalling within the analyte eAPC and/or the analyte TC, may be reported and measured.

The modes of induced signal response reporting, and/or labelling of the eAPC are described above, and it is these reported responses and/or labelling that are required to be measured in obtaining the primary output of the multicomponent system compiled as an eAPC:T system.

Primary outputs from the eAPC:T system are selected cell populations and/or selected affinity reagents or selected NCBP, wherein the selection is made on the basis of;

i. a measurable labelling of eAPC by affinity reagent or NCBP and/or
    ii. a detected signal response in an eAPC and/or
    iii. lack of a detected signal response in an eAPC and/or
    iv. a detected signal response in an analyte TC and/or
    v. a lack of detected signal response in an analyte TC;

wherein a primary output may be represented as a single cell, or a pool of cells and/or one or more eAPC-associated affinity regent or NCBP.

A selection of analyte affinity reagent, NCBP or analyte TC and/or analyte eAPC from the combined eAPC:T system may be made on the basis of a response in the contacting cell. That is, an analyte TC may be selected on that basis of a reported response, or lack thereof, in the contacting analyte eAPC. Conversely, an analyte eAPC may be selected on that basis of a reported response, or lack thereof, in the contacting analyte TCR, or in the case wherein the analyte TC is an analyte affinity reagent or NCBP, the analyte affinity reagent or NCBP can selected from the eAPC response.

Primary eAPC and/or analyte TC outputs from the system are selected cells, wherein selection is made based on the presence or absence of a reported signal response in either analyte TC or eAPC, and these cells may comprise one or more of eAPC and/or one or more analyte TC wherein the selected cells may comprise a single cell, a pool of cells of the same identity, a pool of cells of different identities (FIG. 27 step v).

Primary analyte affinity reagents or NCBP outputs from the system are selected cells with or without associated affinity reagent or NCBP, wherein selection is made based on the presence or absence of a labelling or reported signal response by the analyte eAPC, wherein selected affinity reagent or NCBP may comprise a single affinity reagent or NCBP, a pool of affinity reagent or NCBP of the same identity, a pool of affinity reagent or NCBP of different identities (FIG. 27 step v).

Outputs from Binary Composition

The reported signals in the analyte eAPC and/or analyte TC in a combined eAPC:T system may be used to select analyte cell populations to provide the primary outputs. In the present context, a primary output of an analyte eAPC may be achieved in a an instance wherein the combined eAPC:T system is of binary composition of one or more analyte eAPC with an analyte TCR (e.g. FIG. 24) by selecting the desired analyte eAPC population that is labelled with the analyte TCR from the binary system.

A primary output of an analyte affinity reagent or analyte NCBP may be achieved in a an instance wherein the combined eAPC:T system is of binary composition of one or more analyte eAPC with an analyte affinity reagent or analyte NCBP (e.g. FIG. 24) by selecting the desired analyte eAPC population that is labelled with the analyte affinity reagent or analyte NCBP from the binary system.

A primary output of eAPC and/or analyte TC types may be achieved from an instance wherein the combined eAPC:T system is of fixed analyte eAPC and pooled library analyte TC nature (e.g. FIG. 22), or from an instance wherein the combined eAPC:T system is of fixed analyte TC and pooled library of analyte eAPC (e.g. FIG. 23) nature by selecting the desired analyte APC and/or analyte TC population from the combined culture system.

A primary output an analyte eAPC may be achieved from an instance wherein the combined eAPC:T system is of fixed analyte TCR and pooled library analyte eAPC nature (e.g. FIG. 24), or from an instance wherein the combined eAPC:T system is of fixed eAPC and pooled library of soluble analyte affinity reagent or NCBP nature by selecting the desired analyte eAPC population from the combined culture system.

A primary output an analyte affinity reagent or analyte NCBP may be achieved from an instance wherein the combined eAPC:T system is of fixed soluble analyte affinity reagent or analyte NCBP and pooled library analyte eAPC nature (e.g. FIG. 24), or from an instance wherein the combined eAPC:T system is of fixed eAPC and pooled library of analyte affinity reagent or analyte NCBP nature by selecting the desired analyte affinity reagent or analyte NCBP population from the combined culture system.

Modes of Obtaining Outputs

There are several distinct modes in which the primary outputs may be obtained, wherein each mode entails a step of cell sorting. Sorting may be achieved through fluorescence-activated cell sorting (FACS) and/or magnetic-activated cell sorting (MACS) and/or distinct affinity-activated cell sorting methods.

Primary output eAPC and/or analyte TC cells, and/or eAPC-associated affinity reagents or NCBP, may be obtained by single cell sorting to obtain a single cell and/or cell sorting to a pool to obtain a pool of cells Primary output eAPC and/or analyte TC cells may be obtained by single cell sorting to obtain a single cell, and optionally subsequent outgrowth of the single cells to obtain monoclonal pool of selected eAPC or analyte TC cells.

Primary output eAPC and/or analyte TC cells may be obtained also by cell sorting to a pool to obtain a pool of cells, and optionally subsequent outgrowth of the pool of cells to obtain a pool of selected eAPC and/or TC cells.

Obtaining Terminal System Outputs from the eAPC:T System

Subsequent to the above-described methods of obtaining primary outputs, wherein primary outputs are selected analyte eAPC and/or analyte TC and/or analyte NCBP that are selected on the basis of a measured signal response, or stable complex formation, such that the terminal outputs from the eAPC:T system may be obtained via further processing of the selected eAPC and/or analyte TC and/or NCBP primary outputs (FIG. 27, step vi.

Terminal outputs from the multicomponent system are the identities of
  i. aAPX and/or
  ii. aAM and/or
  iii. aAPX:aAM and/or
  iv. CM and/or
  v. aAPX:CM and/or
  vi. TCR
presented by the analyte APC or analyte TC or analyte affinity reagent or analyte NCBP, and obtained as primary outputs from the multicomponent system by their selection from the combined eAPC:T system.

Within the eAPC:T system, it is often the case that analyte molecules that are presented by the analyte eAPC and analyte TC are genetically encoded. It may also be the case that an analyte NCBP has a genetically encoded identity, in the case of where the NCBP is a bacteriophage, for example. Therefore, to identify the analyte molecules presented by the analyte eAPC or analyte TC or analyte NCBP, genetic sequencing of the prepared analyte eAPC, TC and NCBP may be performed.

The selected primary outputs may be processed such that genetic sequence is obtained for the genome or transcriptome of the sorted and/or expanded cells to determine the identity of
  i. aAPX and/or
  ii. aAM and/or
  iii. aAPX:aAM
  iv. CM and/or
  v. aAPX:CM and/or
  vi. analyte TCR
wherein the obtained identities represent terminal outputs from the eAPC:T system. NCBP that possess a genetic component may be processed such that genetic sequence is obtained for the genome or transcriptome of the sorted NCBP to determine the identity of analyte TCR, wherein the obtained identities represent terminal outputs from the eAPC:T system.

eAPC may be processed such that genetic sequence is obtained for component B' and/or component D' of the sorted and/or expanded TC cells to determine the identity of analyte antigen, wherein the obtained identify of analyte antigen represents a terminal output from the eAPC:T system.

Analyte TC may be processed such that genetic sequence is obtained for the genome or transcriptome of the sorted and/or expanded TC cells to determine the identity of analyte TCR, wherein the obtained identify of TCR represents a terminal output from the eAPC:T system.

Genetic sequencing can be achieved by a range of modes, and from arrange genetic material sources, with and without specific processing. The sequencing step may be preceded by
  i. Extracting of genomic DNA and/or
  ii. Extracting of components B' and/or D' RNA transcript and/or
  iii. Amplifying by a PCR and/or a RT-PCR of the DNA and/or RNA transcript of component B' and/or D'

The sequencing step may be destructive to the eAPC or TC, NCBp, or pool thereof, obtained as primary outputs from the multicomponent system.

If it is desirable to obtain primary outputs from the eAPC:T system wherein the sequencing step has been destructive to the primary output eAPC, the sequence information obtained as terminal output of the multicomponent system may be used to prepare equivalent output eAPC as analyte eAPC.

In the above described scenarios of genetically encoded analyte molecules, the terminal outputs of the eAPC:T system may be obtained by obtaining sequence information from component B' and/or D', and/or from the cell genome and/or transcriptome. However, in some embodiments the antigen information will not be genetically encoded. Post-transnationally modified antigens, antigens provided to the combined eAPC:T system through non-genetic means, antigens that are emergent from a induced or modified state of the analyte eAPC proteome or metabolite, CM intrinsic to the eAPC:T system, may not reasonably be identified through genetic sequencing means.

Figure 18:
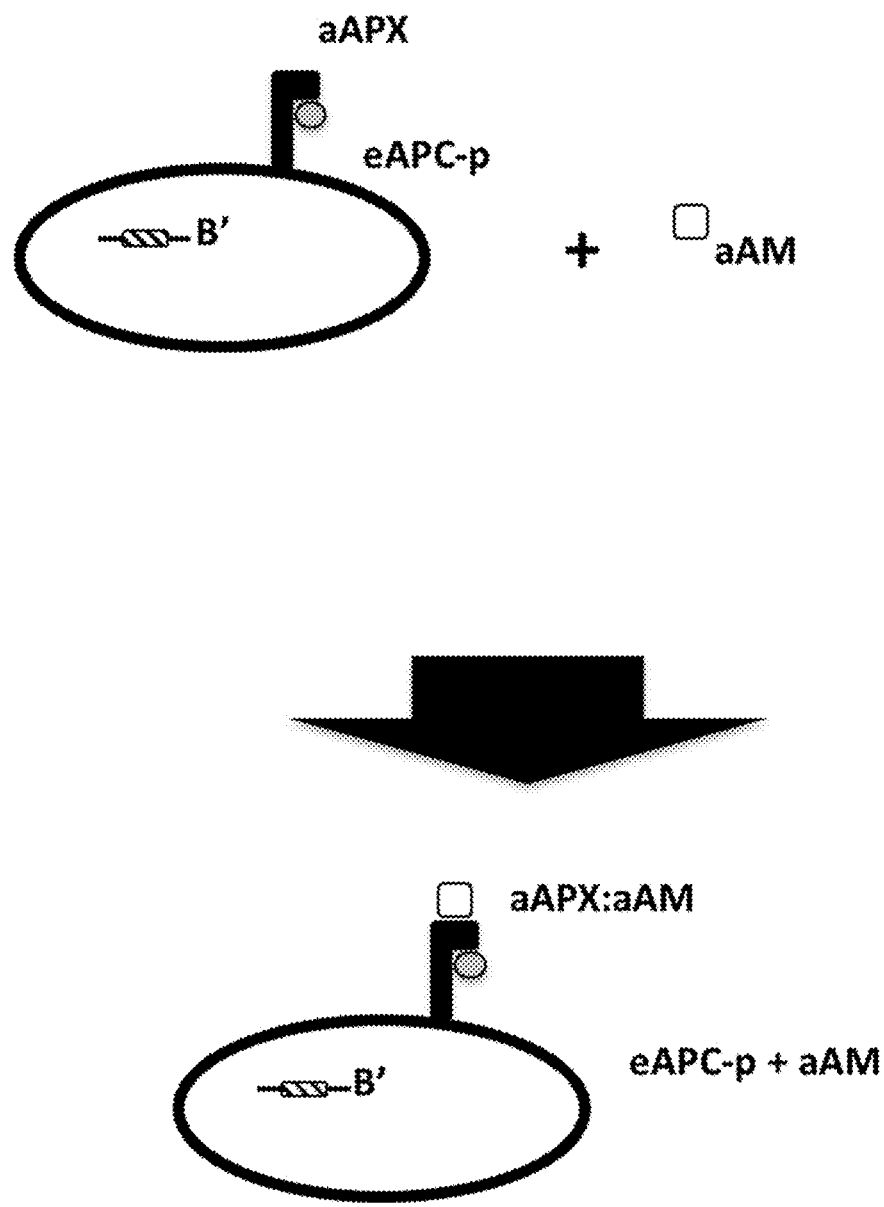

In the important case of aAM that may be provided to the eAPC:T system by non-genetic means, there are two distinct modes through which an APC may present a provided aAM as an aAPX:aAM complex. In the first scenario the aAM is provided in a form that may directly bind to the aAPX and forms an aAPX:aAM complex at the cells surface (FIG. 18). An example of such an aAM would be a peptide antigen for an HLA complex. In the second scenario, the aAM is provided is in a form that may be taken up by the analyte eAPC and processed such that it is loaded as cargo in the aAPX and forms an aAPX:aAM complex at the cells surface (FIG. 19).

A method to select and identify an aAM cargo or a CM cargo, wherein the cargo is a metabolite and/or a peptide, that is loaded in an aAPX of an eAPC selected and obtained by as a primary output of the multicomponent system, comprises
  i. isolating an aAPX:aAM or an aAPX:CM or the cargo aM or the cargo CM and
  ii. identifying the loaded cargo
wherein the identified loaded cargo (CM or aAM) represent terminal outputs of the multicomponent system.

Figure 25:
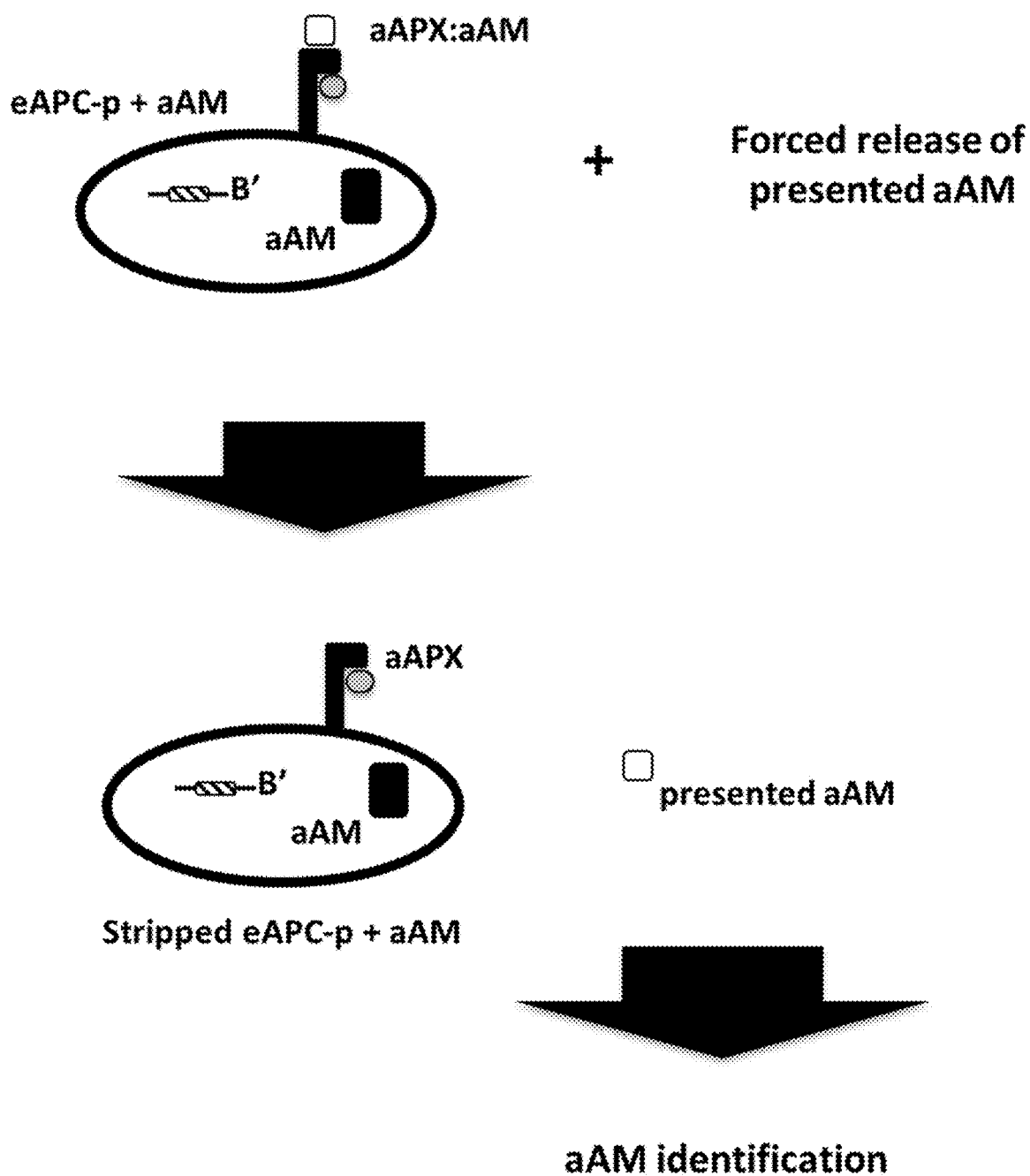
Figure 26:
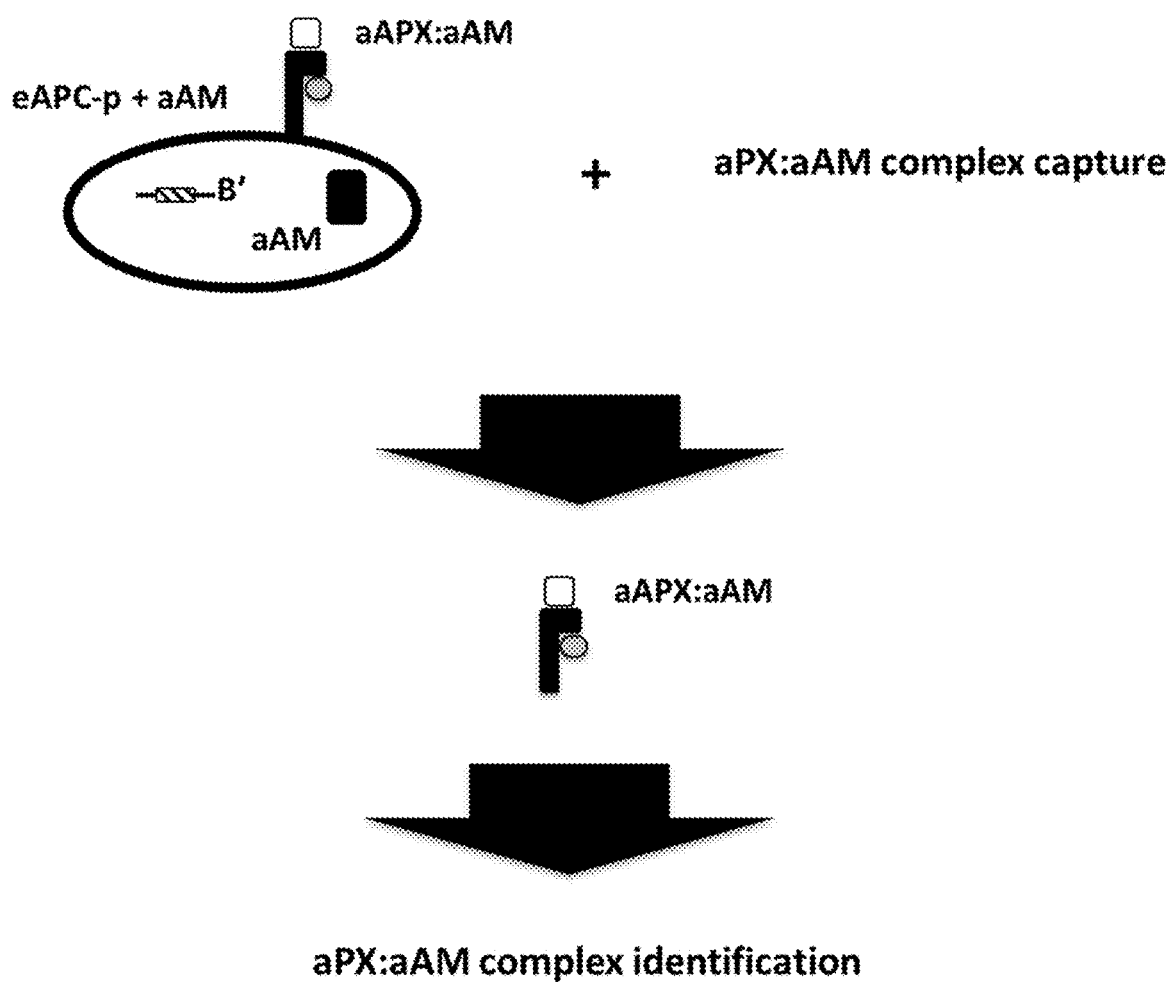

There are generally two modes through which a cargo molecule may be identified from a selected APC. First, a forced release of the cargo from the aAPX:aAM or aAPX:CM results in isolation of the aAM or CM that is available for subsequent identification (FIG. 25). An example of this would be acid-washing of the eAPC to liberate peptide aAM from HLA complexes. Secondly, the capture of the aAPX:aAM or aAPX:CM, for example, by liberation of the complex and immunoaffinity isolation methods, results in isolation of the aAPX:aAM or aAPX:CM complexes, such that aAM or CM can be identified (FIG. 26).

Methods for identifying isolated aAM and/or CM directly, or from the isolated aAPX:aAM or an aAPX:CM complexes, can comprise
  i. Mass spectrometry analysis
  ii. Peptide sequencing analysis
wherein the contain aAM and/or CM identities are terminal outputs from the multicomponent system.

Determining the Affinity of the analyte TCR for analyte antigen using the eAPC:T system Subsequent to the above-described methods of obtaining primary outputs, wherein primary outputs are selected analyte eAPC cells that are selected on the basis of a measured signal response, the eAPC primary outputs may be subjected to an affinity analysis to determine the affinity of the analyte antigen to a cognate analyte TCR wherein the analyte antigen is any of the following
  i. aAPX and/or
  ii. aAM and/or
  iii. aAPX:aAM and/or
  iv. CM and/or
  v. aAPX:CM
and wherein the analyte TCR is either provided as a soluble affinity reagent or presented by an analyte TC or analyte NCBP, such that the affinity of the analyte antigen is determined according to the following method
  i. Labelling the selected analyte eAPC with the analyte TCR at range of concentrations
  ii. Conducting FACS analysis on the stained analyte eAPC of step a
  iii. Determining the intensity of fluorescent labelling of the analyte eAPC over the range of concentrations of analyte TCR
  iv. Calculating the affinity of the analyte antigen to the analyte TCR In the present context, the affinity of the analyte antigen may also be determined by the previously described method but wherein a labelled reference may also be included, such that the affinity is calculated using the using the ratio of the analyte antigen fluorescence intensity to the reference fluorescence intensity wherein the labelled reference is selected from
  i. The analyte eAPC labelled with an affinity reagent to one of the analyte antigen
  ii. a cell or particle presenting a labelled reference analyte antigen.

LEGENDS TO FIGURES

The invention is further illustrated in the following non-limiting figures.

FIG. 1—Description of the components of a single integration couple Multicomponent System.

An example of a MCS comprising three components. The first component A is the eAPC line itself with all required engineered features of that cell. The eAPC A contains one further component B, which is a genomic integration site for integration of aAPX and/or aAM. One additional component, C represents a genetic donor vector for site-directed integration of ORFs into sites B, wherein the arrow indicates coupled specificity. The paired integration site/donor vector couple may be formatted to integrate a single ORF or a pair of ORFs to introduce aAPX and/or aAM expression.

FIG. 2—Description of the components of a dual integration couple Multicomponent System.

An example of a MCS comprising five components. The first component A is the eAPC line itself with all required engineered features of that cell. The eAPC A contains two further components, B and D, which are genomic integration sites for integration of aAPX and/or aAM. Two additional components, C and E, represent genetic donor vectors for site-directed integration of ORFs into sites B and D, respectively, wherein arrows indicate paired specificity. Each paired integration site/donor vector couple may be formatted to integrate a single ORF or a pair of ORFs to introduce aAPX and/or aAM expression.

FIG. 3—Preparation of different analyte antigen presenting eAPC

The MCS begins with the eAPC and uses a donor vector(s) to create cells expressing analyte antigen-presenting complex (aAPX), and/or analyte antigenic molecule (aAM) at the cell surface. An eAPC presenting aAPX alone is termed eAPC-p, and may be created by introduction of aAPX encoding ORF(s) to the eAPC (step i). An eAPC expressing aAM alone is termed eAPC-a, wherein aAM may be expressed at the cell surface and available for TCR engagement, or require processing and loading as cargo into an aAPX as the aAPX:aAM complex. An eAPC A may be created by introduction of aAM encoding ORF(s) to the eAPC (step ii). An eAPC presenting an aAM as cargo in an aAPX is termed an eAPC-pa. An eAPC-pa be produced either; introduction of aAM and aAPX encoding ORFs to an eAPC simultaneously (step iii); introduction of aAM encoding ORF(s) to an eAPC-p (step iv); introduction aAPX encoding ORF(s) to an eAPC-a (step v).

FIG. 4—Operation of the genetic donor vector and genomic receiver site integration couple A genetic donor vector and genomic receiver site form an integration couple, wherein one or more ORFs encoded within the genetic donor vector can integrated specifically to its coupled genomic receiver site. Step 1 in operation of the integration couple is to introduce one or more target ORFs to the donor vector. The initial donor vector is denoted X, and is modified to a primed donor vector X', by introduction of target ORF(s). Step 2 entails combination of the primed donor vector, X', with a cell harbouring a genomic receiver site, Y. Introduction of the ORF encoded by the primed donor vector into the receiver site results in the creation of a cell harbouring an integrated site, Y'.

FIG. 5—Example of preparation of an eAPC-p in one step with one integration couple eAPC A contains genomic receiver site B. Primed genetic donor vector C' is coupled to B and encodes an aAPX. When the A eAPC is combined with the C' donor vector. The resulting cell has the ORF of C' exchanged to the B genomic receiver site to create site B' and introduce aAPX expression. This results in expression of the aAPX on the cell surface and creation of an eAPC-p.

FIG. 6—Example of preparation of an eAPC-p in one step with one integration couple and one unused integration site eAPC A contains genomic receiver sites B and D. Primed genetic donor vector C' is coupled to B and encodes an aAPX. When the A eAPC is combined with the C' donor vector. The resulting cell has the ORF of C' exchanged to the B genomic receiver site to create site B' and introduce aAPX expression. This results in expression of the aAPX on the cell surface and creation of an eAPC-p. Genomic receiver site D remains unused.

FIG. 7—Example of preparation of an eAPC-a in one step with one integration couple eAPC A contains genomic receiver site B. Primed genetic donor vector C' is coupled to B and encodes an aAM. When the A eAPC is combined with the C' donor vector. The resulting cell has the ORF of C' exchanged to the B genomic receiver site to create site B' and introduce aAM expression. This results in one of two forms of eAPC-a, expressing aAM at the cell surface or intracellularly.

FIG. 8—Example of preparation of an eAPC-a in one step with one integration couple and one unused integration site eAPC A contains genomic receiver sites B and D. Primed genetic donor vector C' is coupled to B and encodes an aAM. When the A eAPC is combined with the C' donor vector. The resulting cell has the ORF of C' exchanged to the B genomic receiver site to create site B' and introduce aAM expression. This results in one of two forms of eAPC-a, expressing aAM at the cell surface or intracellularly. Genomic receiver site D remains unused.

FIG. 9—Example of preparation of an eAPC-pa in one step with one integration couple eAPC A contains genomic receiver site B. Genetic donor vector C' is coupled to B. Donor vector C' encodes an aAPX as well as an aAM.

The A eAPC is combined with donor vectors C'. The resulting cell has the ORFs C' exchanged to the B genomic receiver site to create site B' and deliver an ORF for an aAPX and an aAM. This results in expression of the aAPX on the cell surface, aAM intracellularly, and thus loading of the aAM as cargo in the aAPX in formation of the aAPX:aAM complex at the cell surface.

FIG. 10—Example of preparation of an eAPC-pa in one step with one integration couple and one unused integration site eAPC A contains distinct genomic receiver sites B and D. Genetic donor vector C' is coupled to B. Donor vector C' encodes an aAPX as well as an aAM. The A eAPC is combined with donor vectors C'. The resulting cell has the ORFs C' exchanged to the B genomic receiver site to create site B' and deliver an ORF for an aAPX and an aAM. Genomic receiver site D remains unused. This results in expression of the aAPX on the cell surface, aAM intracellularly, and thus loading of the aAM as cargo in the aAPX in formation of the aAPX:aAM complex at the cell surface. This creates an eAPC-pa cell line. Genomic receiver site D remains unused.

FIG. 11—Example of preparation of an eAPC-pa in one step with two integration couples eAPC A contains distinct genomic receiver sites B and D. Distinct genetic donor vectors C' and E' are independently coupled to B and D, respectively. Donor vector C' encodes an aAPX and donor vector E' encodes an aAM. The A eAPC is combined with donor vectors C' and E' simultaneously. The resulting cell has the ORF C' exchanged to the B genomic receiver site to create site B' and deliver an ORF for an aAPX. Simultaneously, the ORF of E' exchanged to the D genomic receiver site to create site D' and deliver an ORF for an aAM. This results in expression of the aAPX on the cell surface, aAM intracellularly, and thus loading of the aAM as cargo in the aAPX in formation of the aAPX:aAM complex at the cell surface. This creates an eAPC-pa cell line.

FIG. 12—Example of preparation of an eAPC-pa in two steps with two integration couples via eAPC-p eAPC A contains distinct genomic receiver sites B and D. Distinct genetic donor vectors C' and E' are independently coupled to B and D, respectively. Donor vector C' encodes an aAPX and donor vector E' encodes an aAM. In STEP1 the A eAPC is combined with the C' donor vector. The resulting cell has insert C' exchanged to the B genomic receiver site to create site B' and deliver an ORF for an aAPX. This results in expression of the aAPX on the cell surface and creation of an eAPC-p. Genomic receiver site D remains unused. In STEP2 the eAPC-p created in STEP1 is combine with the E' donor vector. The resulting cell has insert E' exchanged to the D genomic receiver site to create site D' and deliver an ORF for an aAM. This results in expression of the aAM on the cell surface as cargo of the expressed aAPX, and creation of an eAPC-pa.

FIG. 13—Example of preparation of an eAPC-pa in two steps with two integration couples via eAPC-a eAPC A contains distinct genomic receiver sites B and D. Distinct genetic donor vectors C' and E' are independently coupled to B and D, respectively. Donor vector C' encodes an aAM and donor vector E' encodes an aAPX. In STEP1 the A eAPC is combined with the C' donor vector. The resulting cell has insert C' exchanged to the B genomic receiver site to create site B' and deliver an ORF for an aAM. This results in expression of the aAM on the cell surface and creation of an eAPC-a. Genomic receiver site D remains unused. In STEP2 the eAPC-a created in STEP1 is combine with the E' donor vector. The resulting cell has insert E' exchanged to the D genomic receiver site to create site D' and deliver an ORF for an aAPX. This results in expression of the aAPX on the cell surface with the aAM as cargo and creation of an eAPC-pa.

FIG. 14—Shotgun preparation of an eAPC-pa pool from an eAPC-p

The eAPC-p contains the exchanged genomic receiver site B' expressing an aAPX and the distinct genomic receiver site D. The pool of genetic donor vectors E' i-iii are coupled to D. Donor vectors E' i-iii each encode a single aAM gene. The eAPC-p is combined with donor vectors E' i, E' ii, E' iii simultaneously. The resulting cell pool has either of inserts E' i-iii exchanged to the D genomic receiver site in multiple independent instances to create sites D' i-iii each delivering a single ORF for an aAM gene. The resulting eAPC-pa cell pool comprises a mixed population of three distinct cell cohorts each expressing a discrete combination of B' presenting as aAPX:aAM either of the aAM genes contained in the initial vector library.

FIG. 15—Shotgun preparation of an eAPC-pa pool from an eAPC-a eAPC-a contains the exchanged genomic receiver site B' expressing an aAM and the distinct genomic receiver site D. The pool of genetic donor vectors E' i-iii are coupled to D. Donor vectors E' i-iii each encode a single aAPX gene. The eAPC-a is combined with donor vectors E' i, E' ii, E' iii simultaneously. The resulting cell pool has either of inserts E' i-iii exchanged to the D genomic receiver site in multiple independent instances to create sites D' i-iii each delivering a single ORF for an aAPX gene. The resulting eAPC-pa cell pool comprises a mixed population of three distinct cell cohorts each expressing a discrete combination of the aAM encoded in B' and either of the aAPX genes contained in the initial vector library.

FIG. 16—Shotgun preparation of pooled eAPC-pa libraries from eAPC containing combinatorial paring of aAM and aAPX genes eAPC A contains distinct genomic receiver sites B and D. Distinct genetic donor vectors C' and E' are coupled to B and D, respectively. Donor vectors C' i and C' ii each encode a single aAM gene, and donor vectors E' i and E' ii each encode a single aAPX gene. The eAPC A is combined with donor vectors C' i, C' ii, E' i and E' ii simultaneously. The resulting cell pool has insert C' i or C' ii exchanged to the B genomic receiver site multiple independent instances to create sites B' i and B' ii, each delivering a single ORF for an aAM. The resulting cell pool further has insert E i or E ii exchanged to the D genomic receiver site multiple independent instances to create sites E' i and E' ii, each delivering a single ORF for an APX gene. The resulting eAPC-pa cell pool comprises a mixed population of four distinct cell cohorts each expressing a discrete randomised aAPX:aAM pair at the surface comprised of one of each gene contained in the initial vector library.

FIG. 17—Generation of eAPC-p:CM from eAPC-p expressing intrinsic cargo CM

In the absence of the expression of an aAM from a genomic recombination site the aAPX molecule on an eAPC-p can present intrinsic cargo molecule CM on the surface as aAPX:CM complex.

FIG. 18—Generation of a eAPC-p+aAM from a eAPC-p and the addition of a soluble, presentable antigen aAM eAPC-p contains the exchanged genomic receiver site B' expressing an aAPX. A soluble, directly presentable antigen aAM is combined with the eAPC-p. This results in the formation of the aAPX:aAM complex on the cell surface and the generation of an eAPC-p+aAM.

FIG. 19—Generation of an eAPC-p+aAM from an eAPC-p and soluble aAM eAPC-p contains the exchanged genomic receiver site B' expressing an aAPX. A soluble antigen aAM is combined with the eAPC-p, this results in expression of the aAPX on the cell surface, the presence of aAM intracellularly, and thus loading of the aAM as cargo in the aAPX in formation of the aAPX:aAM complex on the cell surface and the generation of an eAPC-p+aAM.

FIG. 20—Operation of a combined eAPC:T system showing possible analyte TC output states The analyte eAPC contains sites C' and E' integrated with one ORF each to encode one aAPX and one aAM, with the aAM loaded as cargo in aAPX at the cell surface. The analyte TC expresses a TCRsp at the surface. When analyte TC and eAPC-pa populations are contacted, four analyte TC response states can be achieved, one negative and three positive. The negative state is the resting state of the analyte TC, with no signal strength denoting failure of the eAPC aAPX:aAM complex to stimulate the analyte TC presented TCRsp. Three positive states show increasing signal strength*,  and * denote low, medium and high signal strength, respectively as also denoted by darker shading of the cells. This indicates a graded response of analyte TCRsp expressed by analyte TC population towards analyte aAPX: aAM presented by the eAPC-pa.

Figure 21:
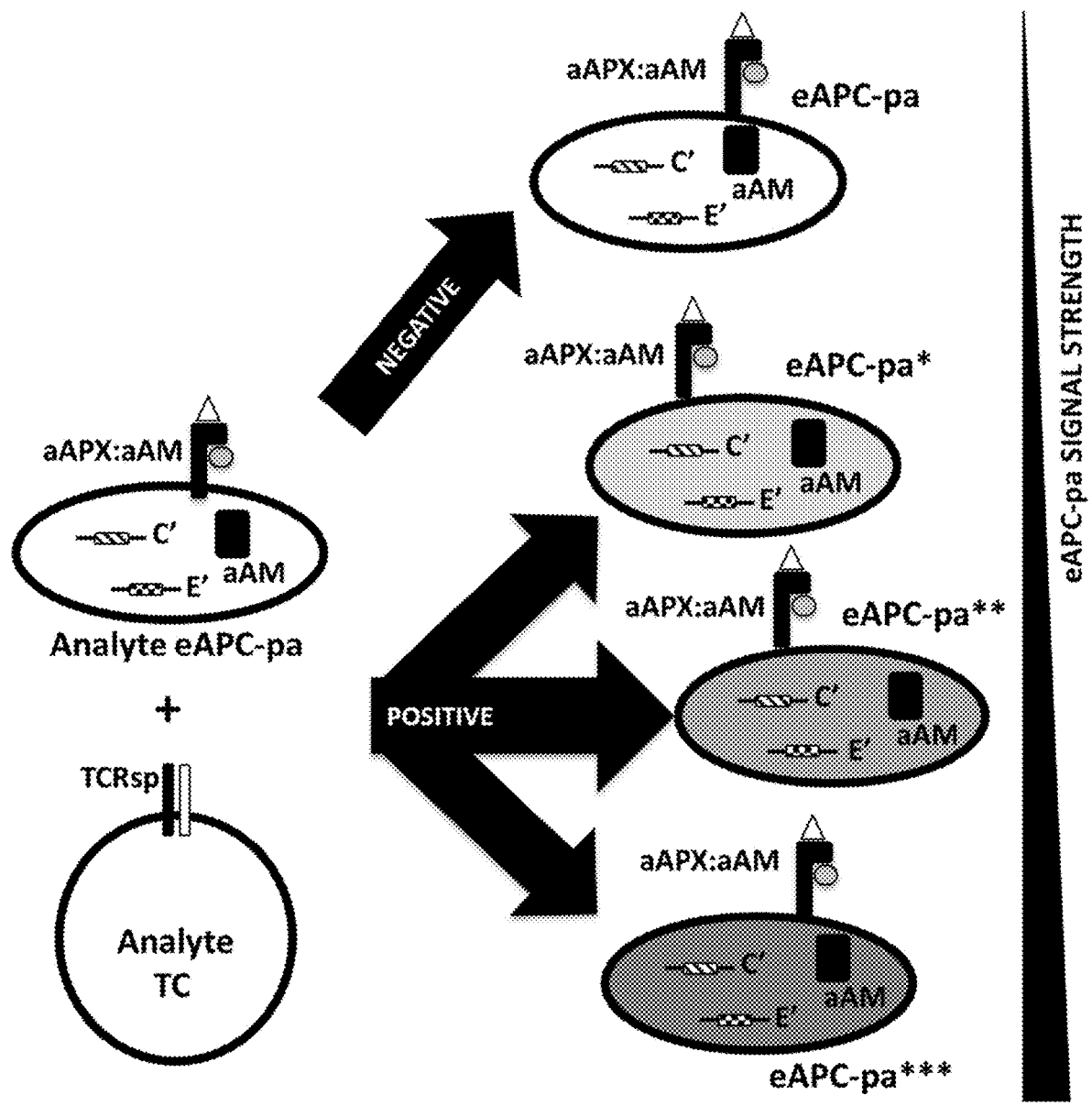

FIG. 21—Operation of a combined eAPC:T system showing possible eAPC-pa output states The analyte eAPC-pa contains sites C' and E' integrated with one ORF each to encode one aAPX and one aAM, with the aAM loaded as cargo in aAPX at the cell surface. The analyte TC expresses a TCRsp at the surface. When analyte TC and eAPC-pa populations are contacted, four eAPC response states can be achieved, one negative and three positive. The negative state is the resting state of the analyte eAPC, denoting failure of the TCRsp chain pair to stimulate the aAPX:aAM complex presented by the analyte eAPC. Three positive states show increasing signal strength from the contacted aAPX:aAM. Three positive states show increasing signal strength*,  and * denote low, medium and high signal strength, respectively as also denoted by darker shading of the cells. This indicates a graded response of analyte aAPX:aAM towards the analyte TCRsp presented by the analyte TC.

Figure 22:
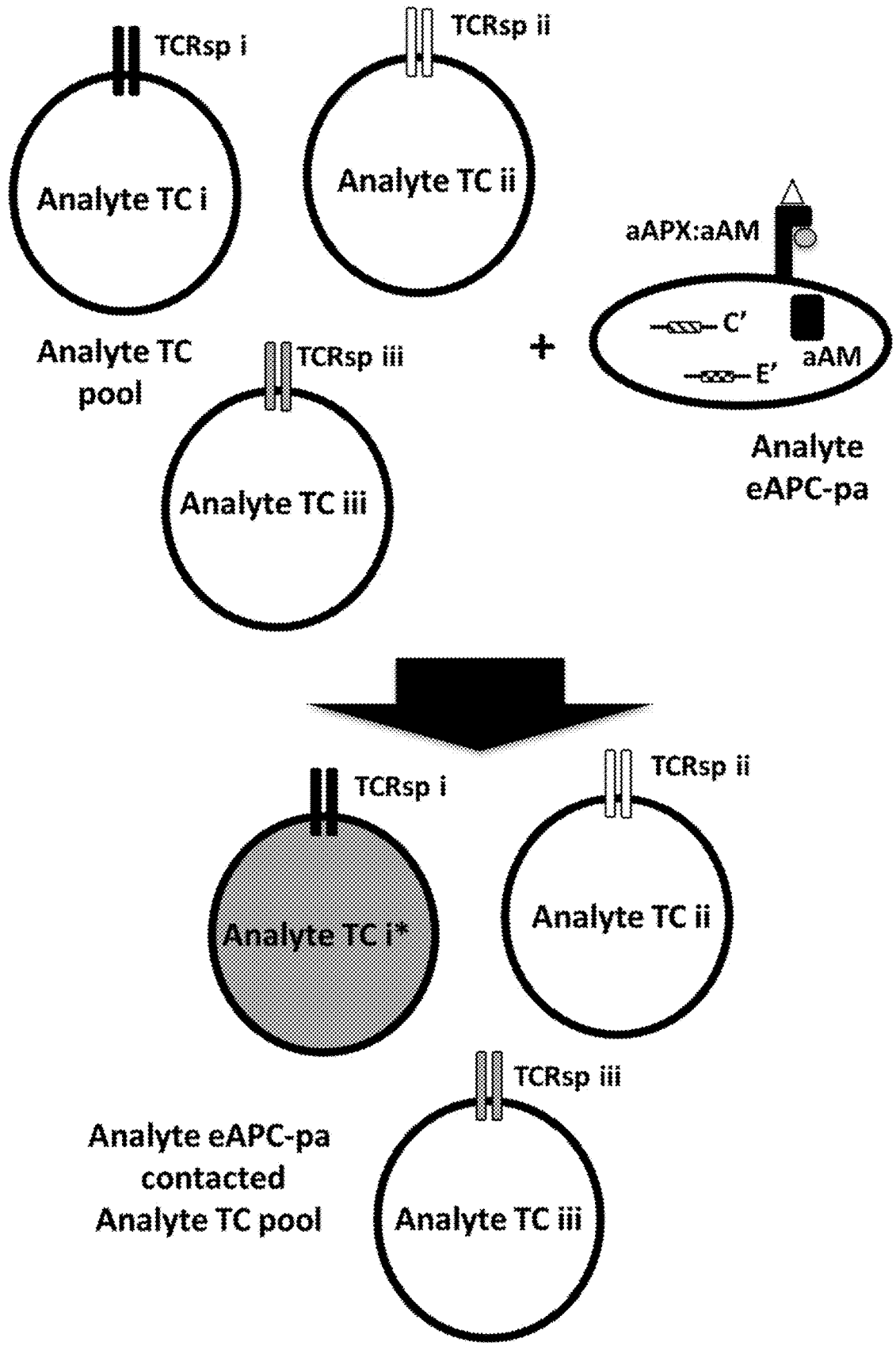

FIG. 22—Combined operation of a combined eAPC:T system to identify TCR chain pairs reactive with analyte aAPX:aAM from a library of analyte TC expressing discrete analyte TCRsp The analyte TC pool expresses varied TCRsp at the surface. The analyte eAPC-pa contain sites C' and E' integrated with a distinct set of ORF to encode one aAPX and one aAM, with the aAM loaded as cargo in aAPX at the cell surface. In the present example, only the TCRsp expressed from analyte TC i is specific for the aAPX:aAM presented by the analyte eAPC-pa, such that when analyte TC pool and analyte eAPC-pa population are contacted, only the cell cohort of the analyte TC expressing TCRsp i engagement.

FIG. 23—Combined operation of a combined eAPC:T system to identify aAM reactive with analyte analyte TC from a library of analyte eAPC-pa expressing discrete analyte aAPX:aAM complexes The analyte eAPC contain sites C' and E' integrated with a distinct set of ORF each to encode one aAPX and one aAM, with the aAM loaded as cargo in aAPX at the cell surface. The analyte TC express a defined TCRsp at the surface. In the present example, only the complex aAPX: aAM i is specific for the TCRsp presented by the analyte TC, such that when analyte eAPC pool and analyte TC population are contacted, only the cell cohort expressing aAM i express a distinct signal *.

FIG. 24—Operation of a combined eAPC:T system to identify aAPX:aAM complex reactive with a specific analyte TCR The analyte eAPC-pa pool contain sites C' and E' integrated with a distinct set of ORF each to encode one aAPX and one aAM i-iii, with the aAM loaded as cargo in aAPX at the cell surface. An analyte TCR, in the form of soluble, immobilised or NCBP presented specific for a distinct aAPX:aAM complex expressed by a subpopulation of the analyte eAPC-pa pool by is contacted with the analyte eAPC-pa pool. In the present example, only the aAPX:aAM i formed from for the analyte TCR such that, only the cell cohort of the analyte eAPC-pa pool that bears aAM i responds to the analyte TCR (dark grey).

FIG. 25—Identification of the aAM presented by an eAPC-p+aAM through forced release of the aAM eAPC-p+aAM contains the exchanged genomic receiver site B' expressing an aAPX as well as internalized aAM that is presented on the surface as aAPX:aAM complex. The aAM is released from the aAPX:aAM surface complex through incubation and the released aAM available for identification.

FIG. 26—Identification of the aAM presented by an eAPC-p+aAM through capture of the aAPX:aAM complex eAPC-p+aAM contains the exchanged genomic receiver site B' expressing an aAPX as well as internalized aAM that is presented on the surface as aAPX:aAM complex. The aAPX:aAM surface complex is captured for identification of loaded aAM.

FIG. 27—Operation of the multicomponent system for preparing analyte eAPC for assembly of a combined eAPC:T system The overall system in which the engineered multicomponent cellular system (MCS) operates comprises contacting prepared analyte engineered antigen-presenting cells (eAPC) with various analyte TCR in assembly of combined eAPC:T system. It is from the combined eAPC:T system that primary outputs are derived, and from these primary outputs that terminal outputs are derived. Operation of the overall system comprises two phases, the preparation phase, and the analytical phase. In one aspect of Phase 1, the multicomponent system is used to prepare analyte eAPC are prepared, and such analyte populations may comprise eAPC-p, eAPC-a and/or eAPC-pa. Such analyte eAPC present various forms of antigenic moieties; analyte antigen-presenting complexes (aAPX); analyte antigenic molecules (aAM); aAPX with loaded aAM cargo (aAPX:aAM); a cargo molecule (CM); an aAPX loaded with CM (aAPX:CM); wherein the analyte antigens represent those to be tested for affinity or signal induction against the analyte TCR (step i). In another aspect of Phase1, cells (analyte TC), non-cell based particles, soluble reagents, immobilized reagents presenting analyte TCR chain pairs, or other affinity reagents with specificity to the analyte antigen are prepared collectively referred to as analyte TCR (step ii). Phase 2 of the overall system is the contacting of analyte eAPC populations and analyte TCR prepared in Phase 1, resulting in the assembly of a combined eAPC:T system (step iii). Contacted analyte eAPC potentially bind to analyte TCR wherein such binding may result in a stable complex formation. Formation of a stable complex may induce a signal response in analyte eAPC and/or analyte TC entities, and/or the stable complex may be directly selected. Within the combined eAPC:T system, outputs of the analyte eAPC, or analyte TC may change their signal state (denoted with *, and the darker shading) such that those responding species may be identified (step iv). The altered state may also be in the form of direct selection of eAPC forming a stable complex with the analyte TCR. Based on altered signal states within the eAPC:T system, specific analyte eAPC and/or analyte TC may be selected on their ability to induce are response in one another, or selected on the basis of failure to induce such a response, and/or in direct selection of the stable complex itself. Selection based on this responsiveness or stable complex yields the primary outputs of the combined eAPC:T system (step v). By obtaining the analyte cells, or analyte TCR from step v, the presented analyte aAPX, aAM, aAPX:aAM, CM, aAPX:CM and/or TCR and/or other affinity reagents with specificity to the analyte antigen, may be identified as the terminal output of the system operation (step vi).

Figure 28:
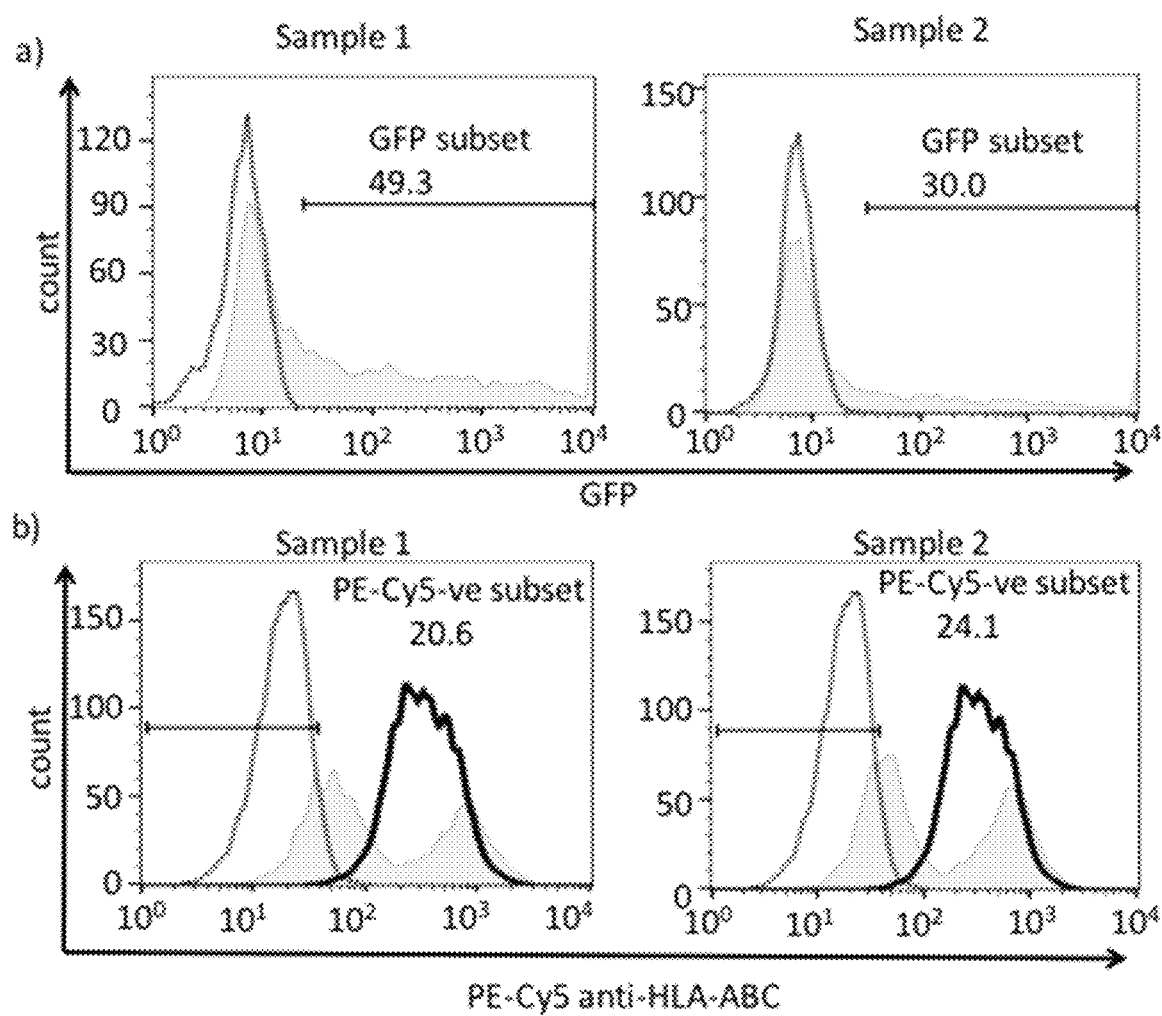

FIG. 28—Selection of cells with targeted mutagenesis of the HLA-A, HLA-B and HLA-C loci in HEK239 cell line a) GFP fluorescence signal in two independent cell populations 48 hours after transfection with plasmids encoding Cas9-P2A-GFP and gRNAs targeting the HLA-A, HLA-B and HLA-C loci (grey histogram) compared to HEK293 control cells (dashed lined histogram). Cells that had a GFP signal within the GFP subset gate were sorted as a polyclonal population. b) Cell surface HLA-ABC signal observed on the two sorted polyclonal populations when labelled with a PE-Cy5 anti-HLA-ABC conjugated antibody (grey histogram). Single cells that showed a low PE-Cy5 anti-HLA-ABC signal and were displayed within the sort gate were sorted to establish monoclones. Non-labelled HEK293 cells (dashed line histogram) and PE-Cy5 anti-HLA-ABC labelled HEK293 cells (full black lined histogram) served as controls.

Figure 29:
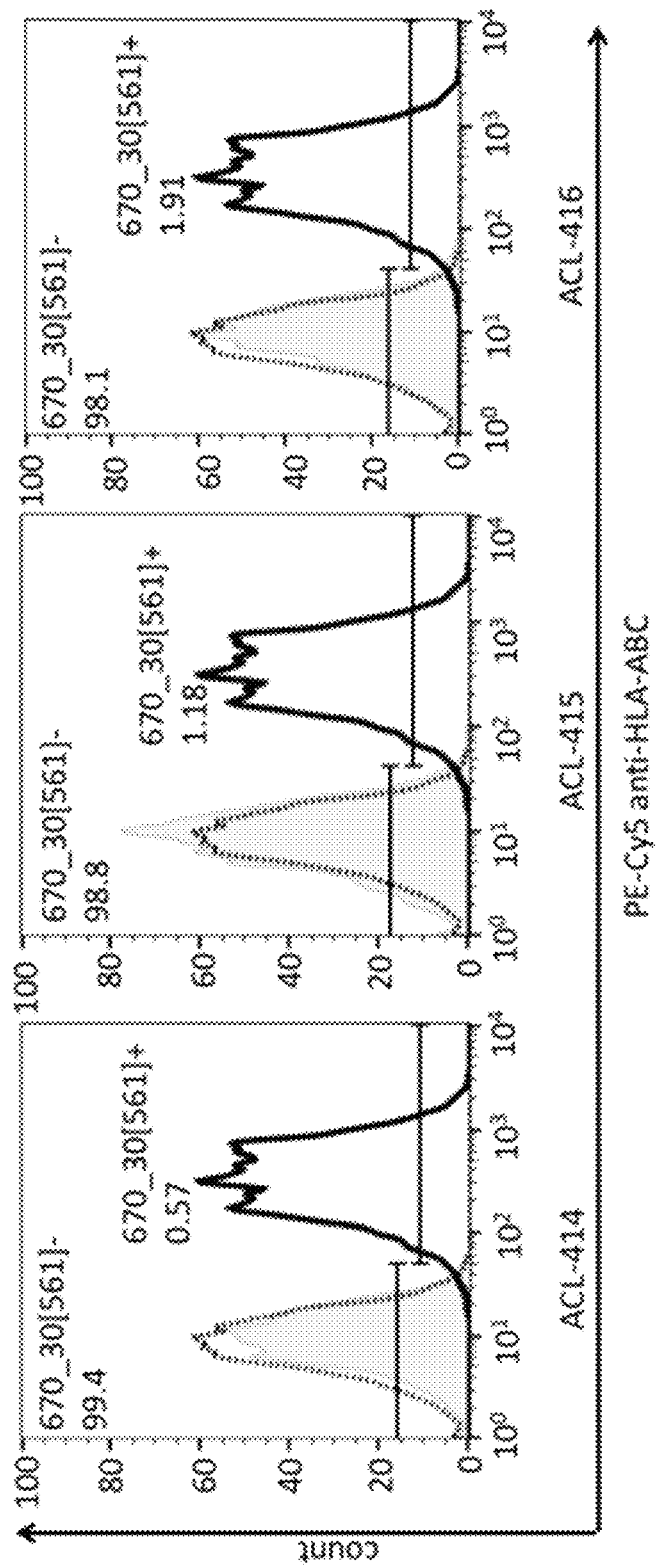

FIG. 29—Phenotypic analysis of HLA-ABC$^{null}$ monoclones:

Monoclone populations were stained with the PE-Cy5 anti-HLA-ABC conjugated antibody, and were analysed by flow cytometry (grey histogram). Non-labelled HEK293 cells (dashed lined histogram) and PE-Cy5 anti-HLA-ABC labelled HEK293 cells (full black lined histogram) served as controls. All three monoclone lines showed a fluorescent signal matching to non-labelled controls demonstrating that each line lacked HLA-ABC surface expression.

Figure 30:
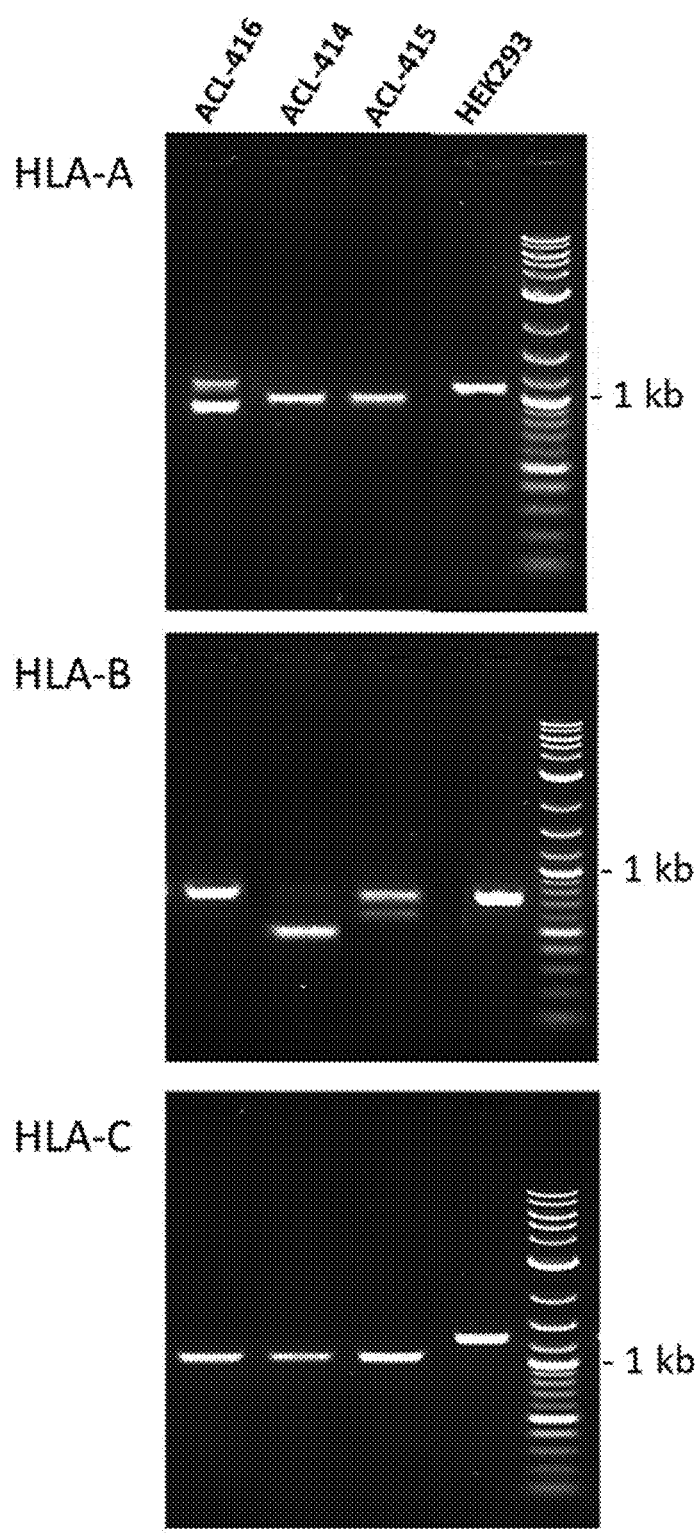

FIG. 30—Genetic characterization of a selection of monoclones lacking surface HLA-ABC expression demonstrating a genomic deletion in the targeted HLA alleles.

PCR amplicons were generated with primers that spanned the gRNA genomic target sites of a specific HLA alleles and their size determined by electrophoresis. The expected size of the wild type HLA-A amplicon is 1067 bp, HLA-B amplicon is 717 bp and HLA-C amplicon is 1221 bp.

Figure 31:
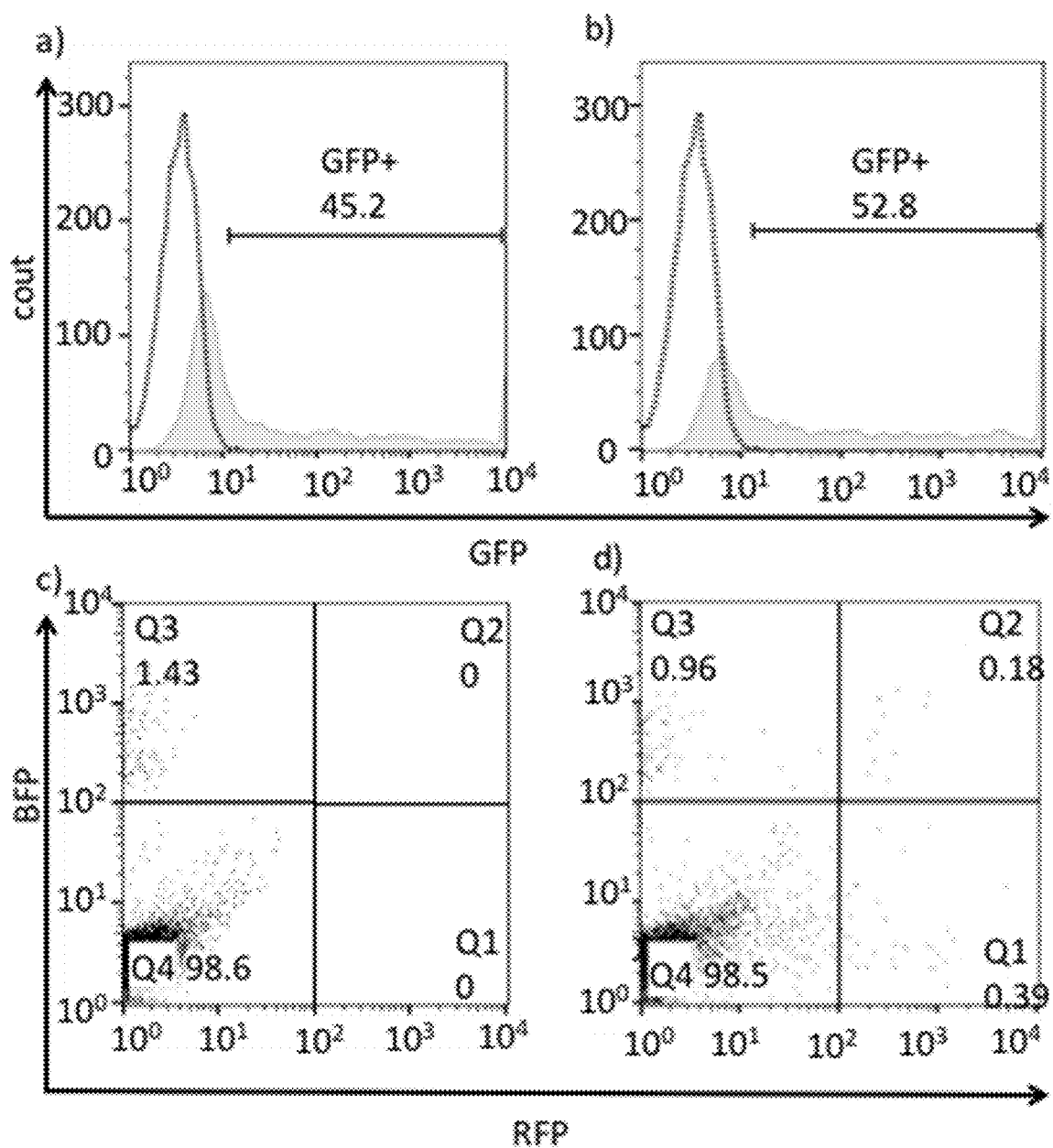

FIG. 31—Selection of cells with targeted genomic integration of synthetic Component B with or without synthetic Component D a) GFP fluorescence signal 48 hours after transfection with plasmids encoding Cas9-P2A-GFP, gRNAs targeting the AAVS1 locus and component B genetic elements flanked by AAVS1 left and right homology arms (grey histogram). HEK293 cells server as a GFP negative control (dashed line histogram). Cells that had a GFP signal within the GFP+ gate were sorted as a polyclonal population. b) GFP fluorescence signal 48 hours after transfection with plasmids encoding Cas9-P2A-GFP, gRNAs targeting the AAVS1 locus and component B and D, both flanked by AAVS1 left and right homology arms (grey histogram). HEK293 cells server as a GFP negative control (dashed line histogram). Cells that had a GFP signal within the GFP+ gate were sorted as a polyclonal population c) Maintained BFP but no detectable RFP signal observed in the D1 sorted polyclonal population. Single cells that showed high BFP signal in quadrant Q3 were sorted to establish eAPC containing synthetic component B monoclones. d) Maintained BFP and RFP signal observed in the D2 sorted polyclonal population. Single cells that showed high BFP and RFP signals in quadrant Q2 were sorted to establish eAPC monoclones containing synthetic component B and synthetic component D.

Figure 32:
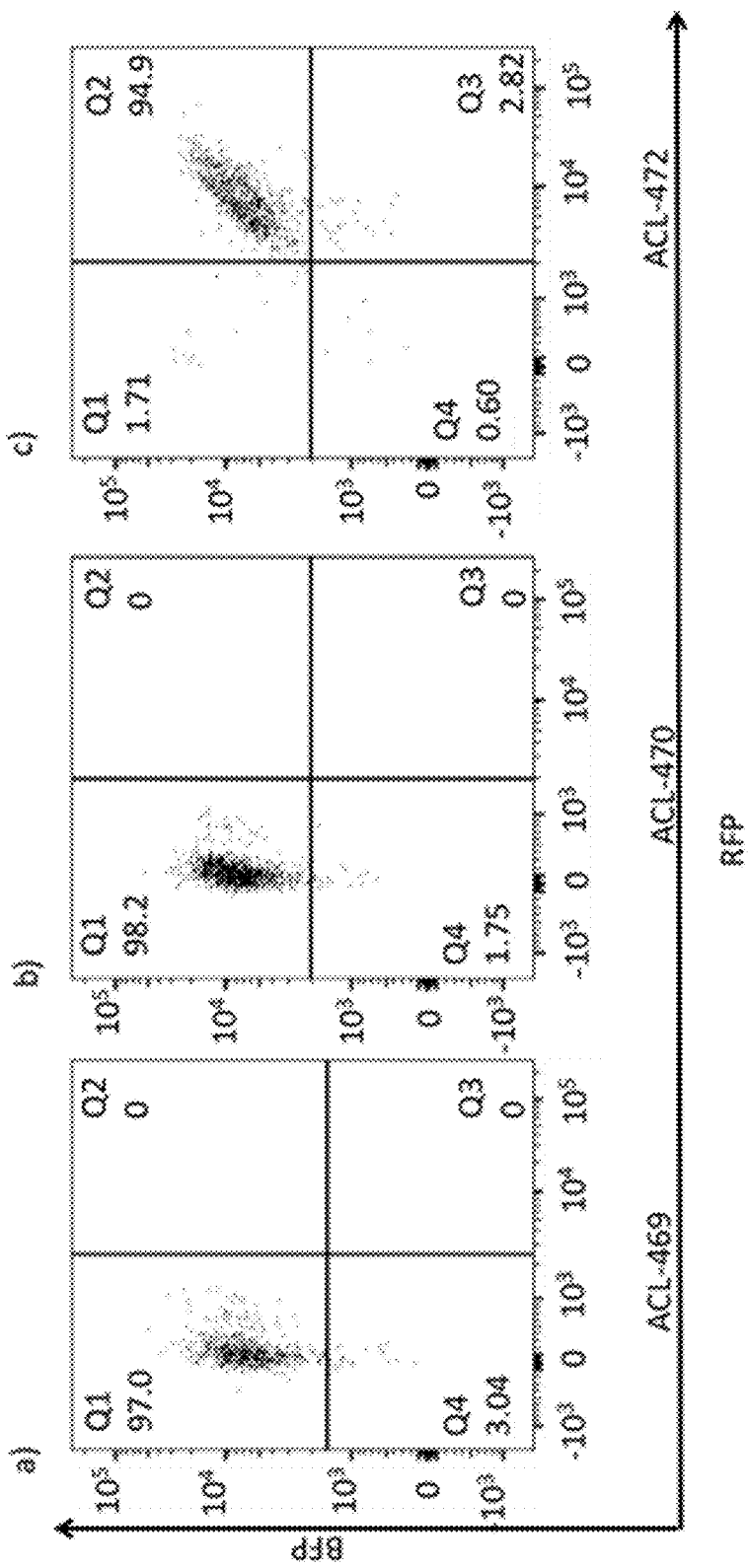

FIG. 32—Phenotypic analysis of eAPC monoclones a and b) Monoclone populations that display maintained BFP expression suggest the integration of synthetic component B. c) Monoclone populations that display maintained BFP and RFP expression suggest the integration of both synthetic component B and synthetic component D.

Figure 33:
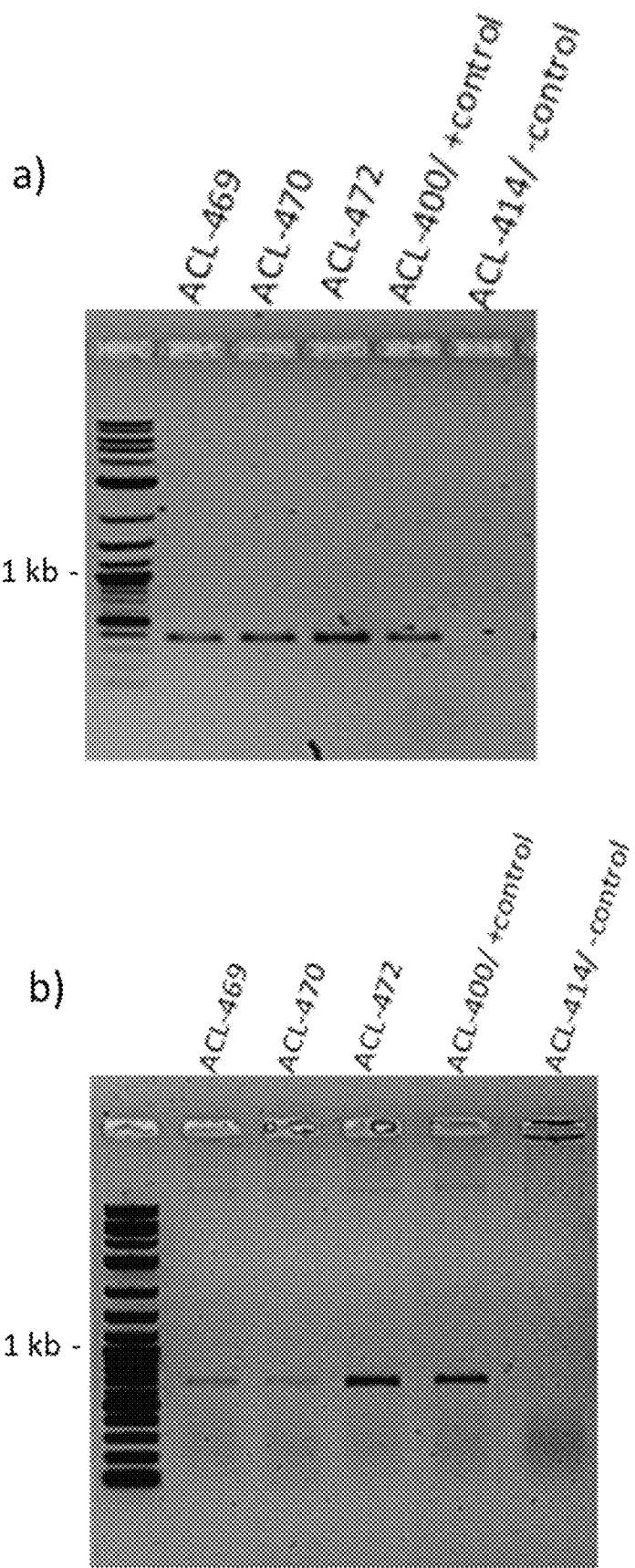

FIG. 33—Genetic characterization of a selection of monoclones for integration of Component B or Component B and D in the AAVS1 locus.

a) PCR amplicons were generated with primers that prime within component B and/or D and size determined by electrophoresis. The expected size of a positive amplicon is 380 bp indicating stable integration of component B and/or D. b) PCR amplicons were generated with primers that prime on AAVS1 genomic sequence distal to region encoded by the homologous arms and the SV40 pA terminator encoded by component B and/or D and size determined by electrophoresis. The expected size of a positive amplicon is 660 bp indicating integration of component B and/or D occurred in the AAVS1 site.

Figure 34:
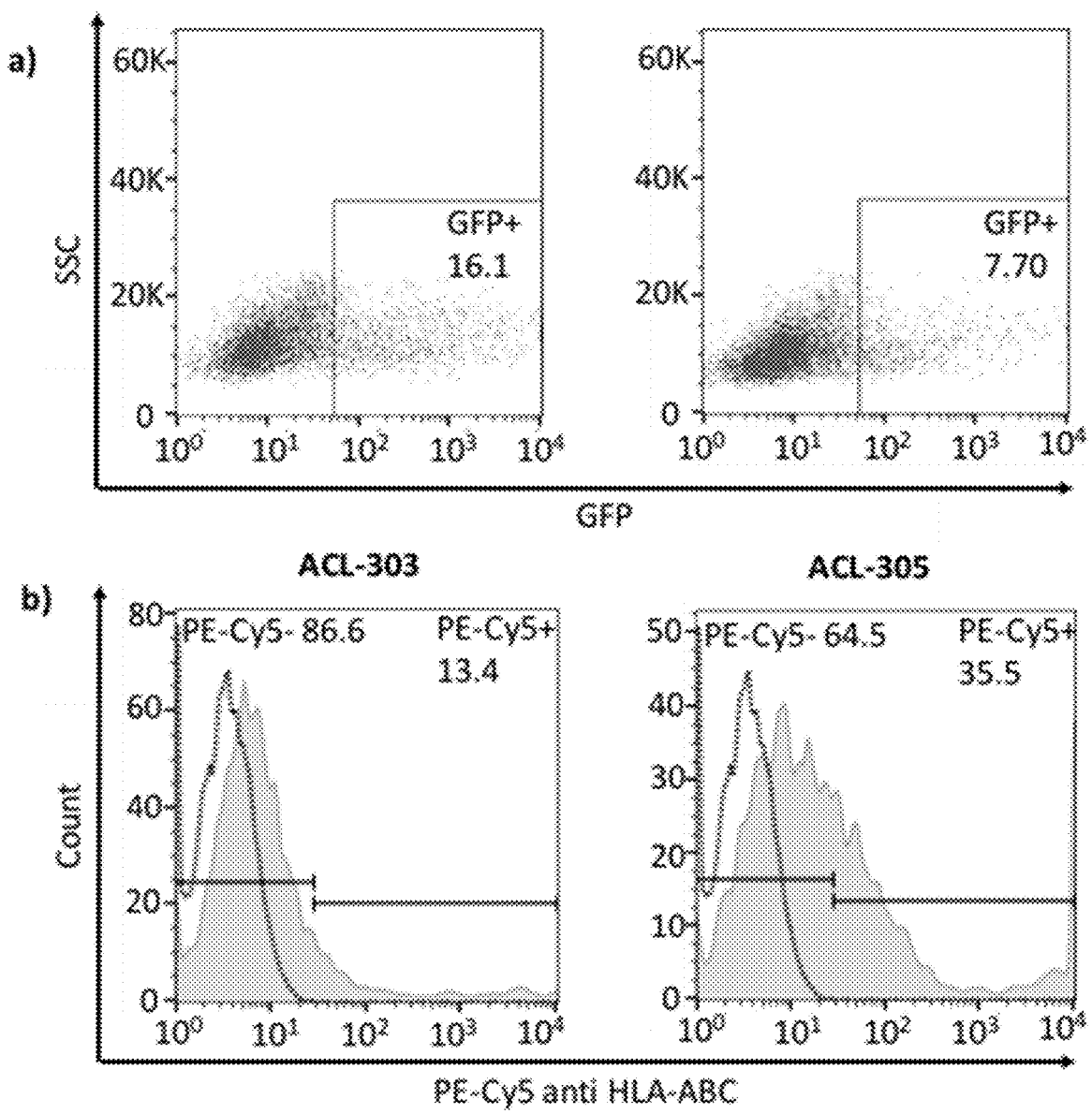

FIG. 34—Selection of cells with targeted genomic integration of component C' into component B a) GFP fluorescence signal 48 hours after transfection with plasmids encoding Cas9-P2A-GFP, gRNAs targeting the AAVS1 locus and component $C^{tHLA-A*24:02}$ (left panel) or component $C^{tHLA-B*-07:02}$ (right panel). Cells that had a GFP signal within the GFP+ gate were sorted as a polyclonal population ACL-303 or ACL-305.

b) Analyte HLA cell surface expression observed on the two sorted polyclonal populations when labelled with a PE-Cy5 anti-HLA-ABC conjugated antibody (grey histogram). Single cells that showed a high PE-Cy5 anti-HLA-ABC signal and were displayed within the right sort gate were sorted to establish monoclones. Signal detected from PE-Cy5 anti-HLA-ABC labelled ACL-128, the HLA-ABC$^{null}$ and HLA-DR,DP,DQ$^{null}$ eAPC cell line (dashed line histogram) served as controls.

Figure 35:
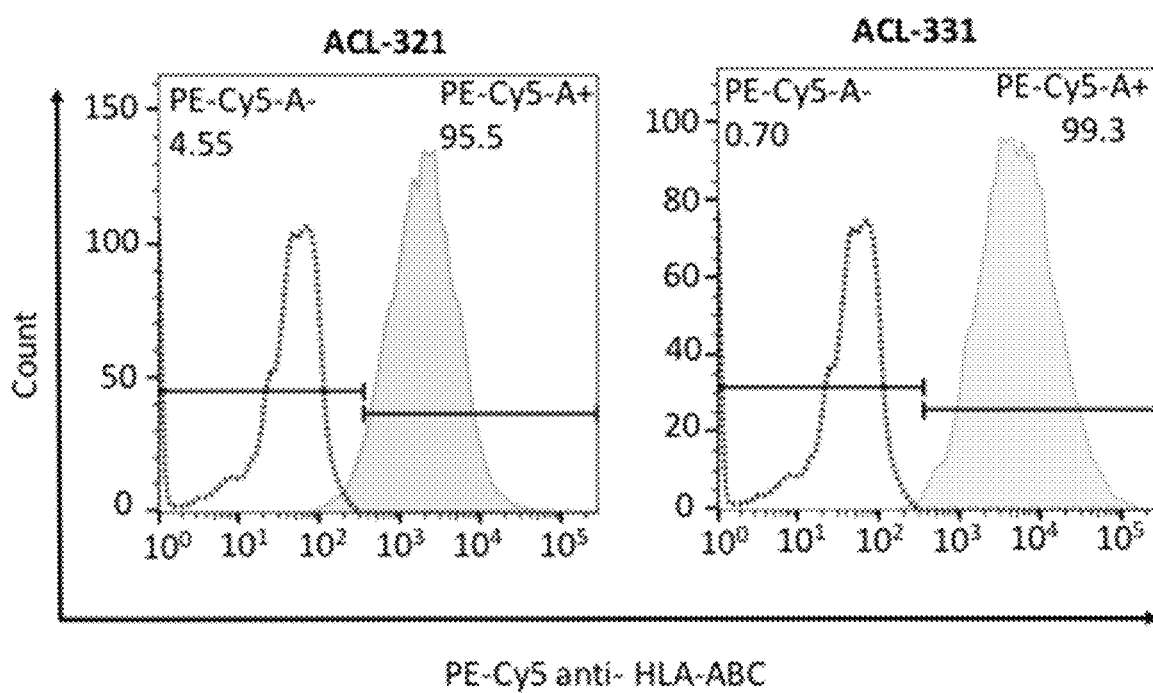

FIG. 35—Phenotypic analysis of eAPC-p monoclones expressing analyte HLA class I protein on the cell surface Monoclone populations were stained with the PE-Cy5 anti-HLA-ABC conjugate antibody, and were analysed by flow cytometry (grey histogram). ACL-128, the HLA-ABC$^{null}$ and HLA-DR,DP,DQ$^{null}$ eAPC cell line (dashed line histogram) served as controls. ACL-321 and ACL-331 monoclone cell lines showed a stronger fluorescent signal compared to the HLA-ABC$^{null}$ and HLA-DR,DP,DQ$^{null}$ eAPC cell line control, demonstrating that each line expresses their analyte aAPX, HLA-A*24:02 or HLA-B*-07:02 ORF, respectively, and therefore are eAPC-p cell lines.

Figure 36:
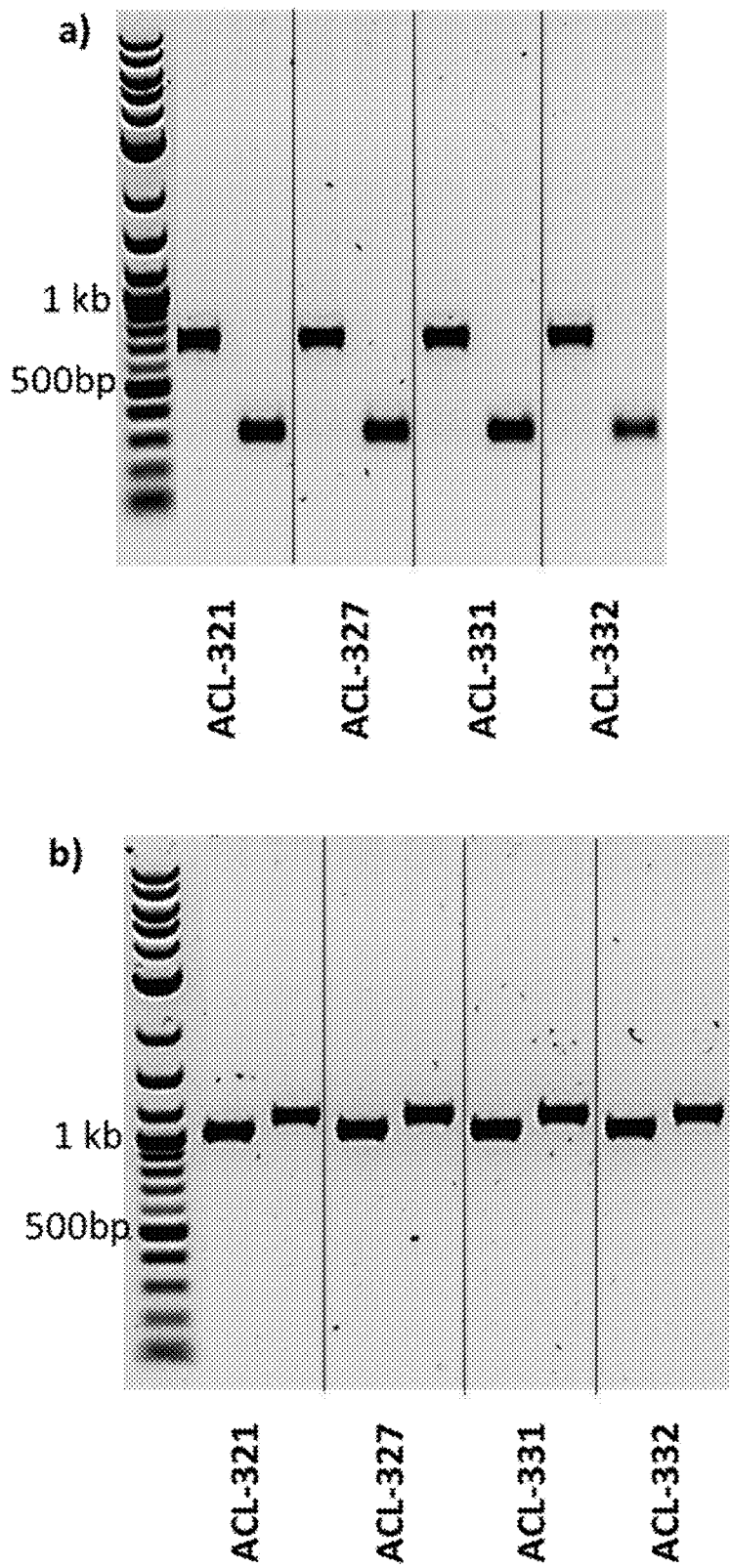

FIG. 36—Genetic characterization of a selection of monoclones demonstrating that their genomes integrated component C', and that the integration occurred in the AAVS1 genomic receiver site, generating component B' a) PCR amplicons confirm the presence of HLA insert, a band of 810 bp indicated correct CMV promoter amplicon and 380 bp is the amplicon generated from SV40 pA terminator.

b) PCR amplicons were generated with two set of primers that primed on AAVS1 genomic sequence distal to region encoded by the homologous arms and a primer that is unique to the SV40 pA terminator linked to the analyte HLA ORF. The expected size of a positive amplicon 1 kb and 1.1 kb indicate generation of component B'.

Figure 37:
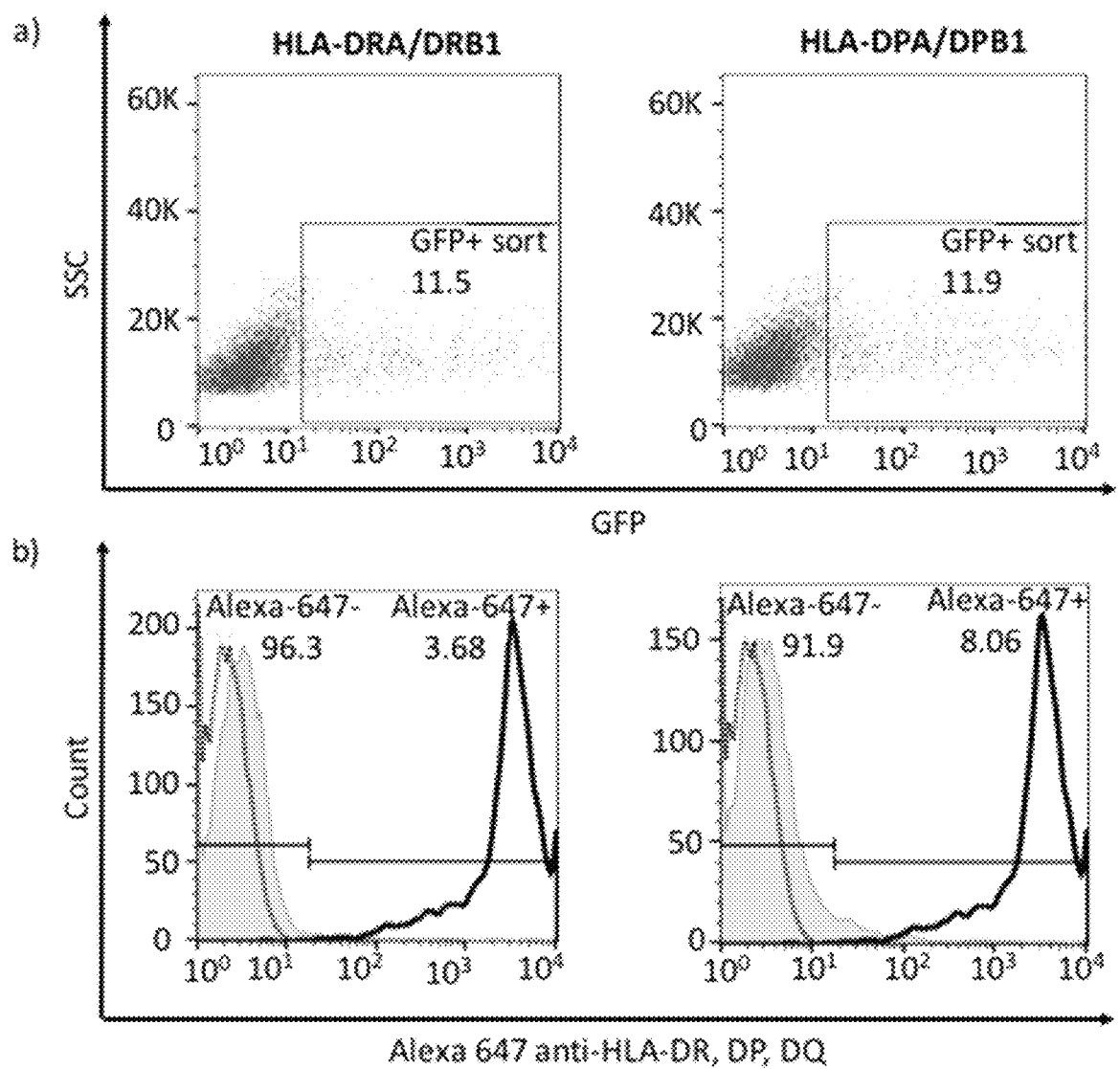

FIG. 37—Selection of cells with targeted genomic integration of component C' into component B a) GFP fluorescence signal 48 hours after transfection with plasmids encoding Cas9-P2A-GFP, gRNAs targeting the AAVS1 locus and component $C^{tHLA-DRA*01:01/HLA-DRB1*01:01}$ (left panel) or component $C^{tHLA-DPA1*01:03/HLA-DPB1*04:01}$ (right panel). Cells that had a GFP signal within the GFP+ gate were sorted as a polyclonal population.

b) Analyte HLA cell surface expression observed on the two sorted polyclonal populations when labelled with an Alexa 647 anti-HLA-DR,DP,DQ conjugated antibody (grey histogram). Single cells that showed a high Alexa 647 anti-HLA-ABC signal and were displayed within the right sort gate were sorted to establish monoclones. Signal detected from Alexa 647 anti-HLA-ABC labelled ACL-128 (HLA-ABC$^{null}$ and HLA-DR,DP,DQ$^{null}$ eAPC cell line) (dashed line histogram) and ARH wild type cell line (full black lined histogram) served as controls FIG. 38—Phenotypic analysis of eAPC-p monoclones expressing analyte HLA class II protein on the cell surface Monoclone populations were stained with a Alexa 647 anti-HLA-DR,DP,DQ conjugated antibody, and analysed by flow cytometry (grey histogram). ACL-128 (HLA-ABC$^{null}$ and HLA-DR,DP,DQ$^{null}$ eAPC cell line) (dashed histogram) and ARH wild type cell line (full black lined histogram) served as controls. ACL-341 and ACL-350 monoclone cell lines showed a stronger fluorescent signal compared to the HLA-ABC$^{null}$ and HLA-DR,DP,DQ$^{null}$ eAPC cell line control, demonstrating that each line expressed their analyte aAPX, HLA-DRA*01:01/HLA-DRB1*01:01 or HLA-DPA1*01:03/HLA-DPB1*04:01, respectively, and therefore are eAPC-p cell lines.

Figure 39:
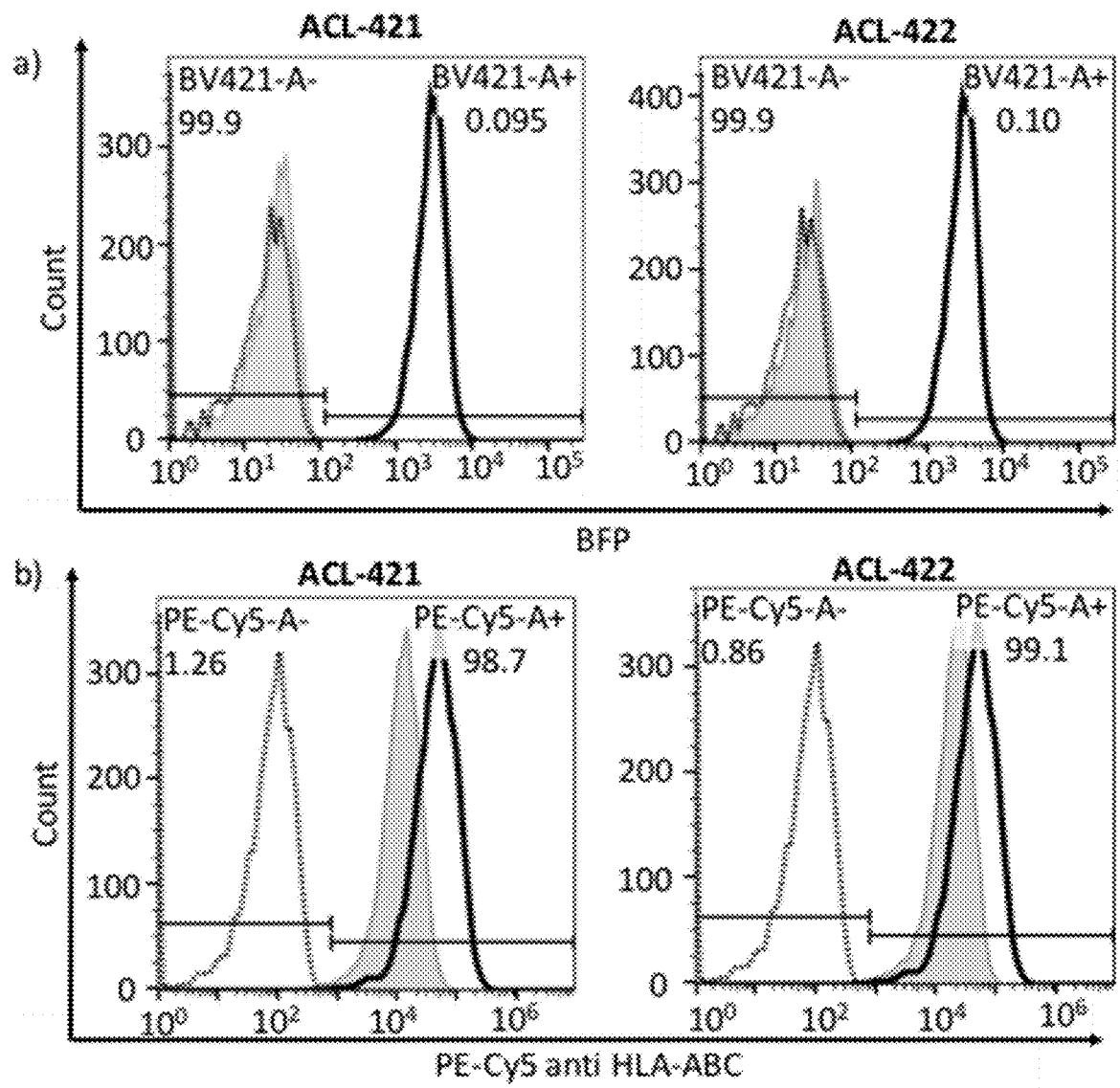

FIG. 39—eAPC-p monoclones generated by RMCE integration of analyte HLA class I protein a) eAPC-p monoclone populations ACL-421 and ACL-422 lost BFP fluorescence (grey histogram). Their parent eAPC cell line ACL-385 (full black line histogram) and the BFP negative ARH wild type cell line (dash line histogram) served as a control b) eAPC-p monoclone populations ACL-421 and ACL-422 gained HLA-A*02:01 expression when stained with the PE-Cy5 anti-HLA-ABC conjugate antibody (grey histogram). Their parent ACL-385 HLA-ABC$^{null}$ and HLA-DR,DP,DQ$^{null}$ eAPC cell line (dash line histogram) and ARH wild type cell line (full black line histogram) served as negative and positive PE-Cy5 anti-HLA-ABC labeling control, respectively.

These results strongly indicated a successful RMCE occurred between the BFP ORF and HLA-A*02:01 ORF in both ACL-421 and ACL-422 cell lines.

Figure 40:
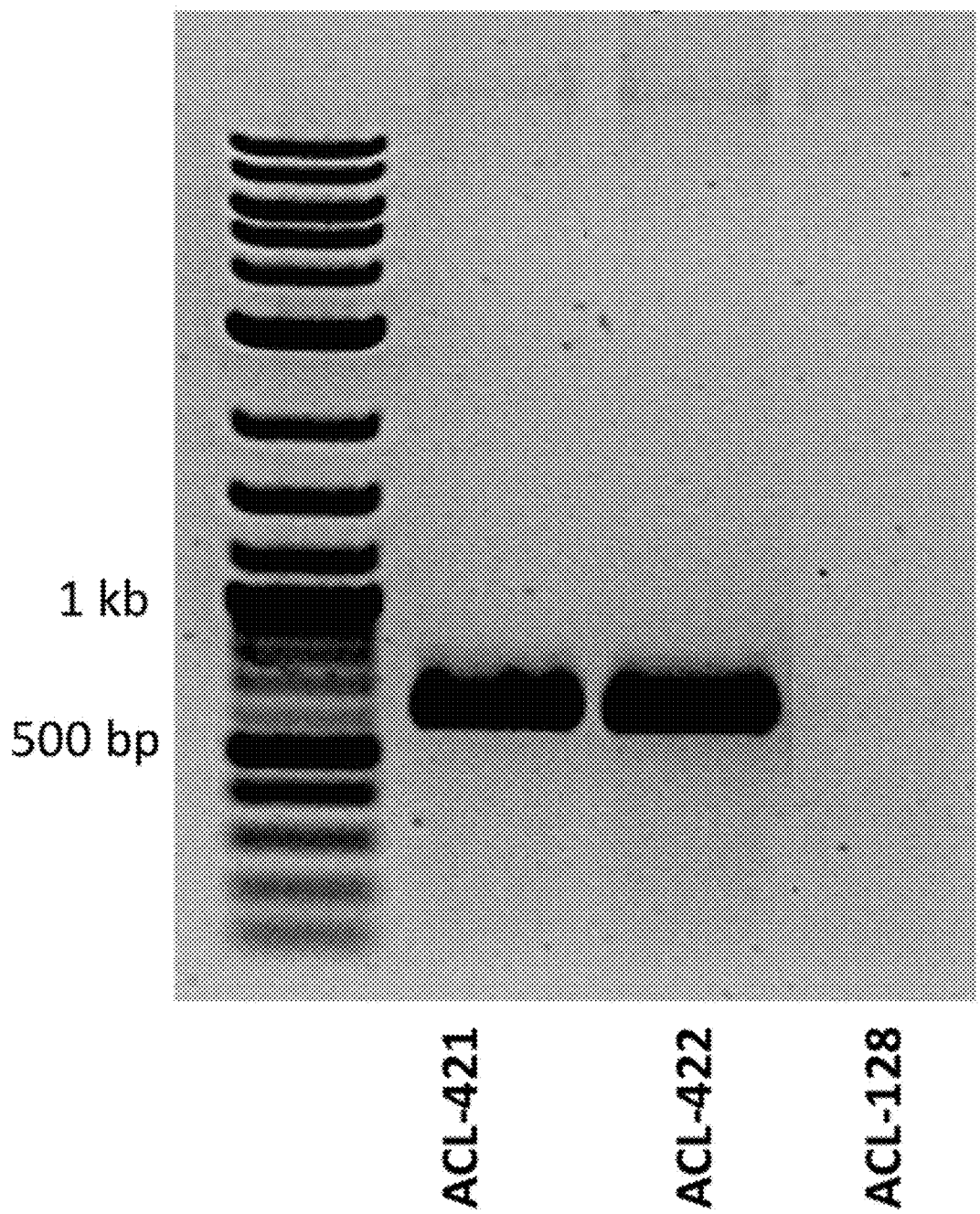

FIG. 40—Genetic characterization of a selection of monoclones confirmed HLA-A*02:01 integration by RMCE An amplicon of 630 bp indicated presence of HLA-A2 in monclones ACL-421 and 422 but not in the control line, ACL-128.

Figure 41:
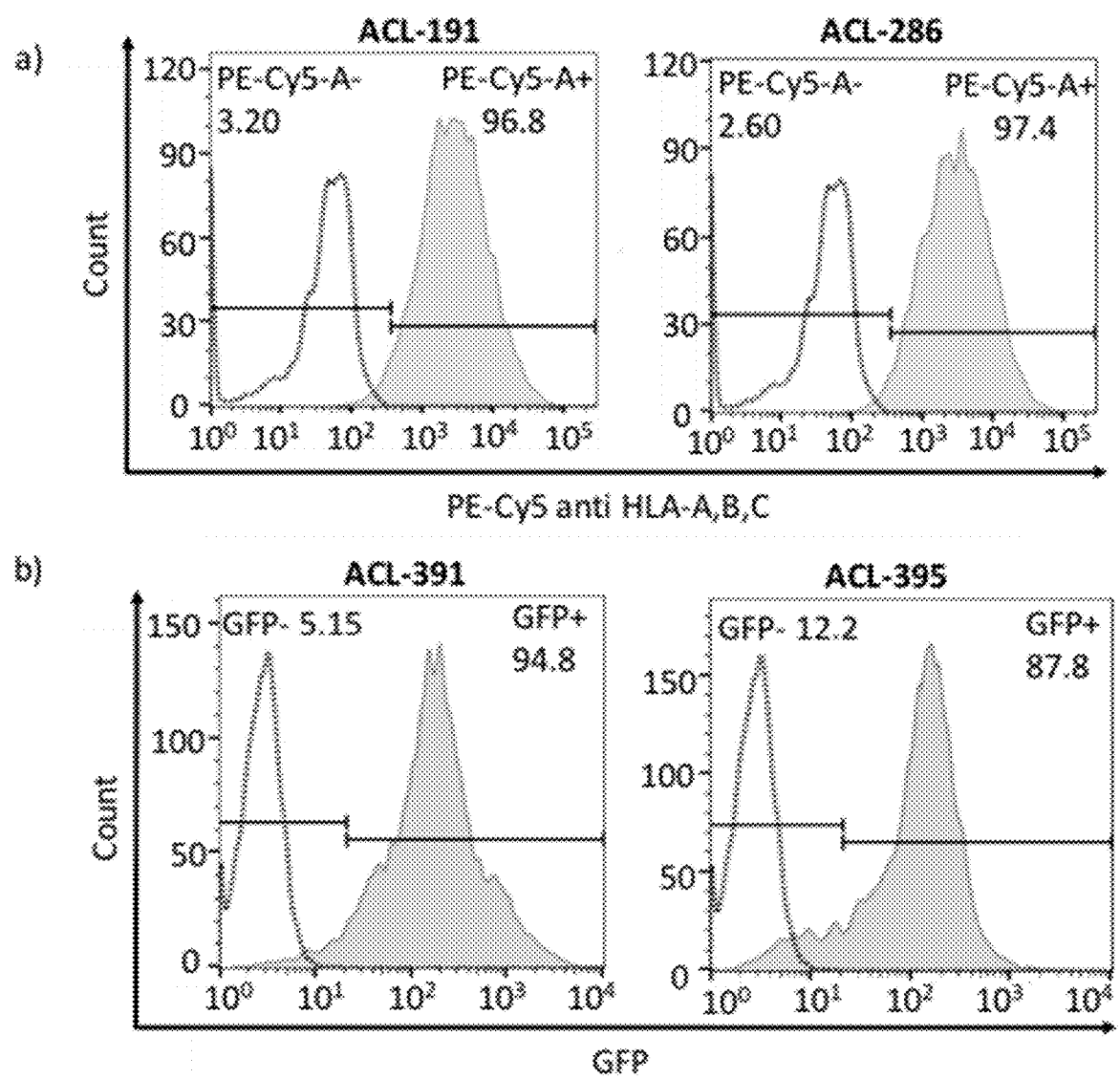

FIG. 41—Phenotypic analysis of eAPC-pa monoclones expressing analyte HLA class I protein on the cell surface and aAM a) eAPC-p Monoclone populations were stained with the PE-Cy5 anti-HLA-ABC conjugated antibody, and were analysed by flow cytometry (grey histogram). ACL-128, the HLA-ABC$^{null}$ and HLA-DR,DP,DQ$^{null}$ eAPC cell line (dashed line histogram) served as control. ACL-321 and ACL-331 monoclone cell lines showed stronger fluorescent signal compared to controls demonstrating that each line expressed their analyte aAPX, HLA-A*02:01 or HLA-B*35:01 ORF, respectively, and therefore were eAPC-p cell lines.

b) eAPC-pa Monoclone populations were assessed for GFP fluorescence by flow cytometry (grey histogram). ACL-128, the HLA-ABC$^{null}$ and HLA-DR,DP,DQ$^{null}$ eAPC cell line (dashed line histogram) served as control. ACL-391 and ACL-395 monoclone cell lines showed a stronger fluorescent signal compared to controls demonstrating that each line expresses analyte aAM selection marker and therefore inferred aAM expression, in a cell line which also expressing HLA-LA-A*02:01 or HLA-B*35:01 ORF, respectively. Therefore ACL-391 and ACL-395 were eAPC-pa lines.

FIG. 42—Genetic characterization of monoclones containing component B or B and D:

Table 1) The copy-number of component B is determined by digital drop PCR, in which the number of component B and reference gene DNA molecules are measured and the ratio calculated Monoclones ACL-469 and ACL-470 contained a ratio of 1 component B molecule to 3 reference gene molecules; and Table 2) The copy-number of both component B and D is determined by digital drop PCR, in which the number of component B, D and reference gene DNA molecules is measured and the ratio calculated. The monoclone ACL-472 contained a ratio of 2 component B and D molecules to 3 reference gene molecules.

Figure 43:
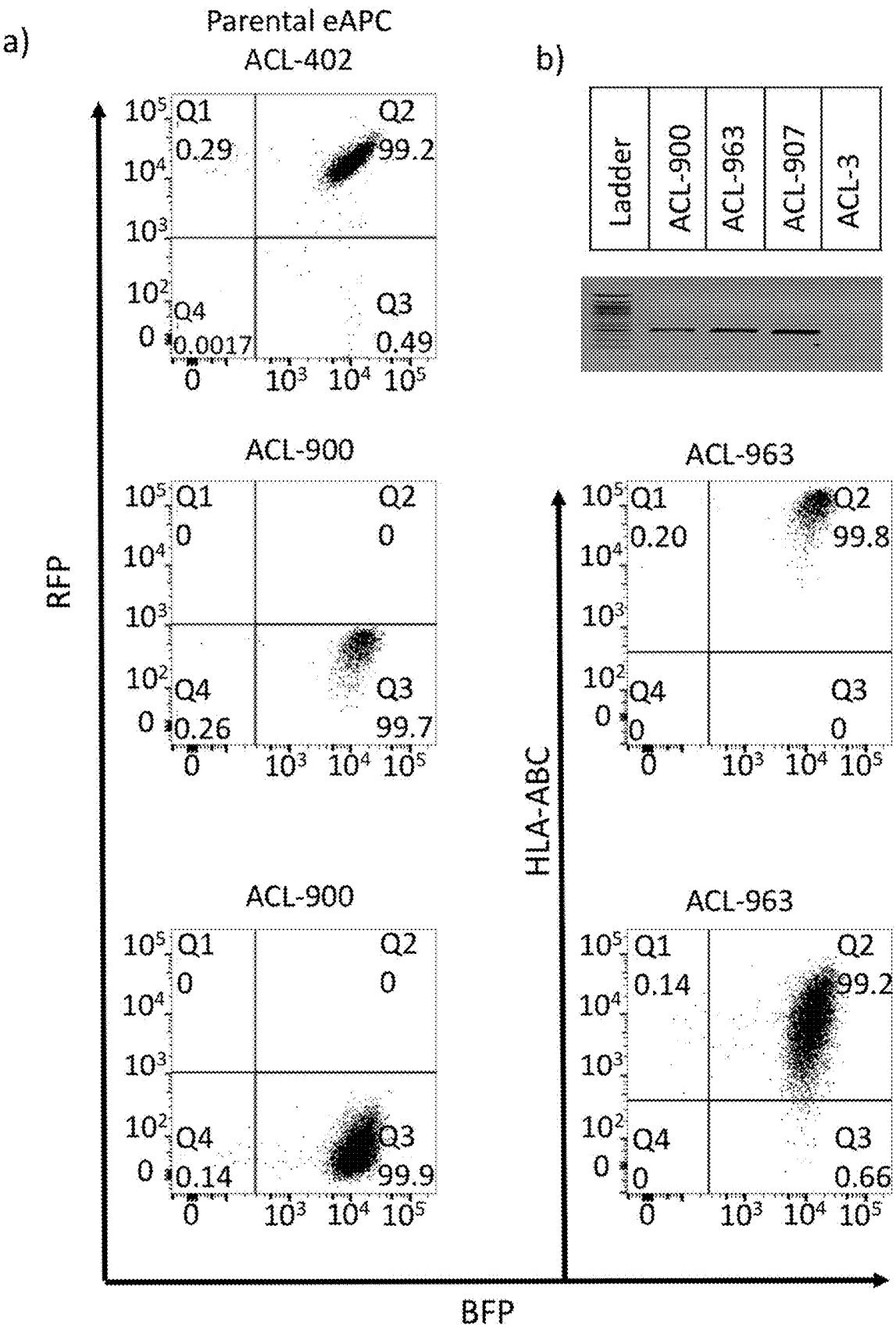

FIG. 43—An eACP-p constructed in one step wherein Component C' encoded a single HLAI ORF.

An eAPC-p was created through RMCE by electroporation of the cell line ACL-402 with the plasmid that encodes expression of the Tyr-recombinase, Flp (V4.1.8), together with one Component C' plasmid encoding an aAPX, selected from either HLA-A*02:01 (V4.H.5 or HLA-A*24: 02 (V4.H.6). At 10 days post electroporation, individual cells positive for HLAI surface expression and diminished fluorescent protein signal, RFP, encoded by Component B selection marker, were sorted. Resulting monoclonal eAPC-p lines were analysed by flow cytometry in parallel with the parental eAPC line, and two examples are presented a) Individual outgrown monoclone lines (ACL-900 and ACL-963) were analysed by flow cytometry for loss of RFP, presence of BFP and gain of HLA-ABC (aAPX). Left-hand plots display BFP vs RFP, the parental cell has both BFP and RFP (Q2, top plot, 99.2%), whereas ACL-900 (Q3, middle plot, 99.7%) and ACL-963 (Q3, bottom plot, 99.9%) both lack RFP signal, indicating integration couple between Component B/C' has occurred. Right-hand plots display BFP vs HLA-ABC (aAPX), wherein both ACL-900 (Q2, top plot, 99.2%) and ACL-963 (Q2, bottom plot, 99.2%) show strong signal for HLA-ABC (aAPX), further reinforcing that B/C' integration. Both ACL-900 and ACL-963 have strong BFP signal, indicating that Component D remains open and isolated from the Component B/C' integration couple. b) To further characterize ACL-900 and ACL-963, and a third eAPC-p not presented in a) ACL-907, genomic DNA was extracted and PCR conducted using primers that target adjacent and internal of Component B' (Table 5, 8.B.3, 15.H.2), thereby selectively amplifying only successful integration couple events. Comparison is made to an unmodified parental line, ACL-3 wherein the Component B is lacking. Amplicon products specific for Component B' were produced for all three eAPC-p monoclones whereas no product was detected in the ACL-3 reaction, confirming the specific integration couple event between Component B and Component C' had occurred.

FIG. 44—An eAPC-pa constructed from eAPC-p in one step, wherein Component D' encodes a single analyte antigen molecule (aAM) ORF.

Multiple eAPC-pa were constructed from a parental eAPC-p (ACL-905) in parallel, wherein the genomic receiver site, Component D, is targeted for integration by a primed genetic donor vector, Component E', comprising of a single ORF that encodes an aAM. The eAPC-p (ACL-900, example 8) was independently combined with a vector encoding expression of the RMCE recombinase enzyme (Flp, V4.1.8) and each Component E' of either V9.E.6, V9.E.7, or V9.E.8 by electroporation. At 10 days post electoporation, individual eAPC-pa were selected and single cell sorted (monoclones) based on diminished signal of the selection marker of integration BFP, encoded by Component D. Resulting monoclonal eAPC-pa lines were analysed by flow cytometry in parallel with the parental eAPC line, and three examples are presented. In addition, resulting monoclones were also genetically characterized to confirm the integration couple event. a) Monoclones for eAPC-pa, ACL-1219, ACL-1227 and ACL-1233, were analysed and selected by flow cytometry for loss of BFP signal and retention of the HLA-ABC signal. Plots of BFP vs SSC are displayed with a BFP– gate. An increase in the number of BFP– events compared to parental eAPC-p is observed, indicating that an integration couple between Component D/E' has occurred. Single cells from the BFP– gate were selected, sorted and outgrown. b) Selected monoclones of ACL-1219, ACL-1227, ACL-1233 were analysed by flow cytometry to confirm loss of BFP and retention of HLA-ABC signals. Plots of BFP vs HLA-ABC are presented, wherein all three monoclones can be observed having lost the BFP signal in comparison to parental eAPC-p (right most plot), indicating a successful integration couple event. c) To demonstrate that the monoclones contained the correct fragment size for aAM ORF, a polymerase chain reaction was conducted, utilising primers targeting the aAM ORF (Table 5, 10.D.1, 15.H.4) and representative agarose gel is presented. Results from two monoclones representing each aAM ORF are shown. Lane 1: 2_log DNA marker, Lanes 2-3: pp28 ORF (expected size 0.8 kb), Lane 4: 2_log DNA marker, Lanes 5-6: pp52 ORF (expected size 1.5 kb), Lane 7: 2_log DNA marker, Lanes 8-9: pp65 ORF (expected size 1.9 kb), Lane 10: 2_log DNA marker. All monoclones analysed had the expected amplicon size for the respective aAM, further indicating the integration couple had occurred.

Figure 45:
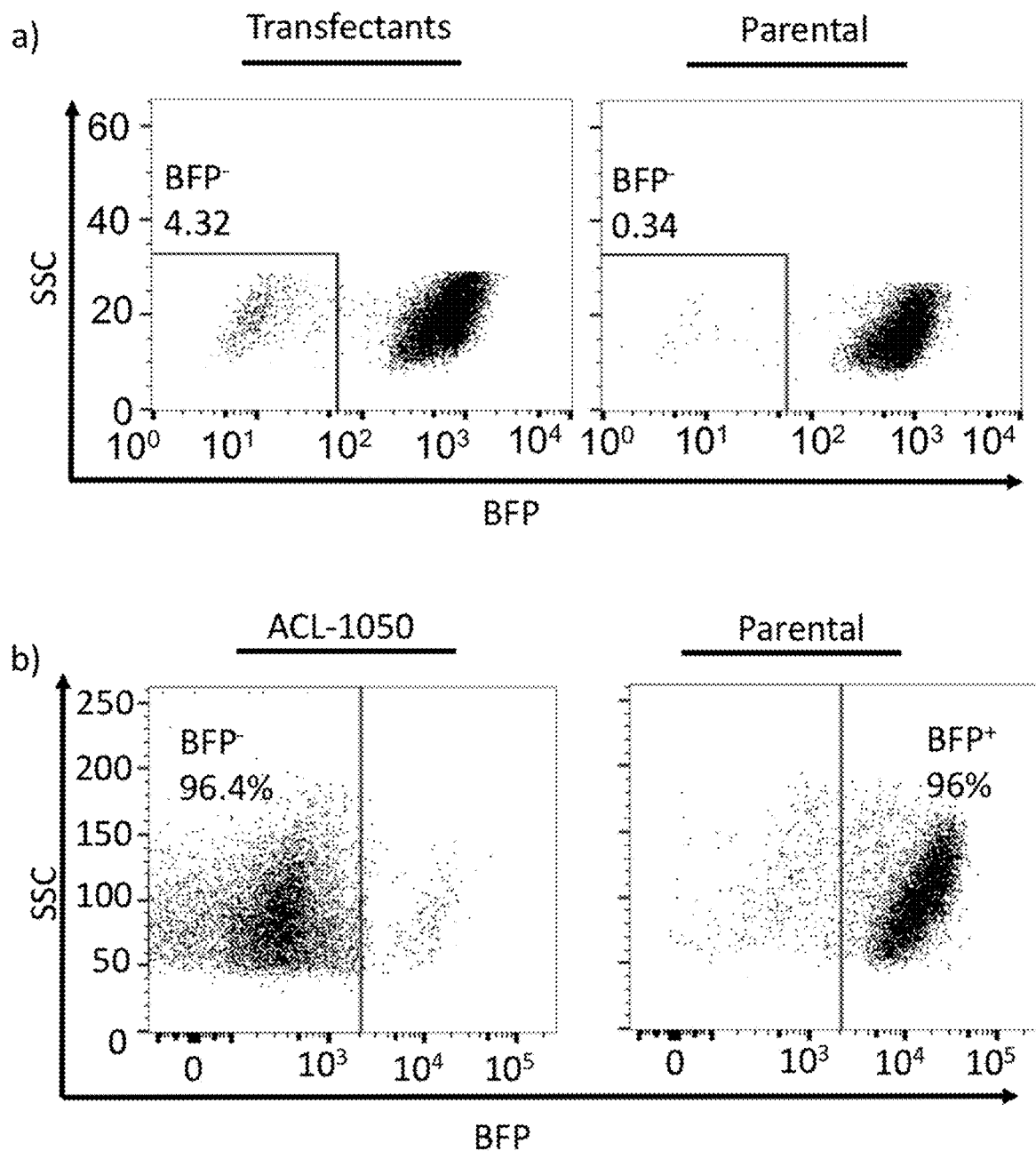
Figure 45:
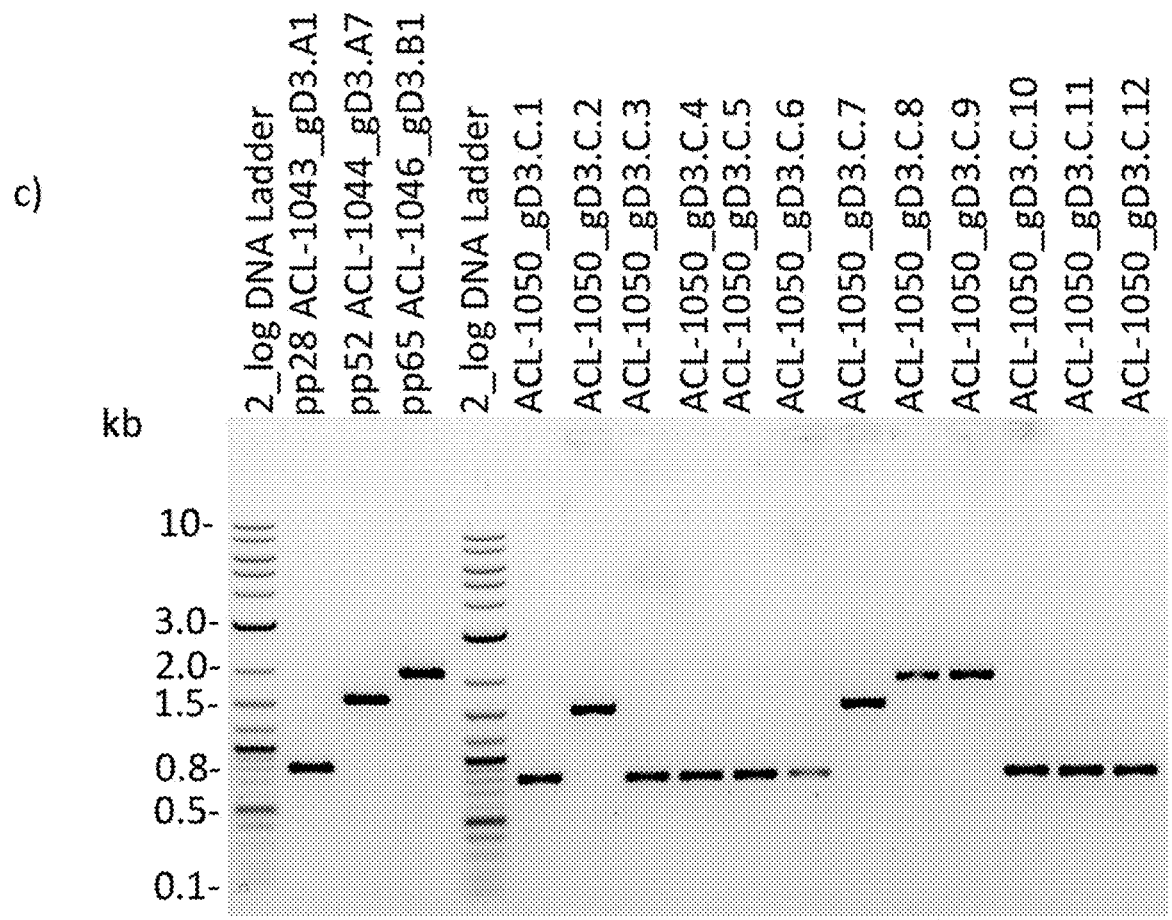

FIG. 45—Shotgun integration of multiple antigens into eAPC-p to create a pooled eAPC-pa library in a single step A pooled library of eAPC-pa were generated from a pool of primed Component E vectors (Component E') collectively encoding multiple aAM ORF (HCMVpp28, HCMVpp52 and HCMVpp65) by integration in a single step into the parental eAPC-p, wherein each individual cell integrates a single random analyte antigen ORF derived from the original pool of vectors, at Component D', such that each generated eAPC-pa expresses a single random aAM, but collectively the pooled library of eAPC-pa represents all of aAM ORF encoded in the original pooled library of vectors. The library of eAPC-pa was generated by electroporation by combing the eAPC-p (ACL-905, aAPX: HLA-A*02:01) with a pooled vector library comprised of individual vectors encoding an ORF for one of HCMVpp28, HCMVpp52 or HCMVpp65 (V9.E.6, V9.E.7, and V9.E.8), and being mixed at a molecular ratio of 1:1:1. Resulting eAPC-pa populations were analysed and selected by flow cytometry, in parallel with the parental eAPC-p line. a) At 10 days post electroporation putative eAPC-pa cells (Transfectants) were analysed and selected by flow cytometry, compared in parallel with the parental line (ACL-905). Plots display BFP vs SSC, gated for BFP– populations, wherein an increase in BFP– cells are observed in the BFP– gate compared to the parental line. Bulk cells were sorted form the transfectants based on BFP– gate, denoted ACL-1050. b) After outgrowth, ACL1050 cells were analysed by flow cytometry for loss of BFP. Plots displayed are BFP vs SSC, wherein ACL-1050 has been enriched to 96.4% BFP– compared to parental line ~4% BFP–. Subsequently, single cells were sorted from the BFP– pollution of ACL1050. c) To demonstrate that the polyclone ACL-1050 was comprised of a mixture of HCMVpp28, HCMVpp52 and HCMVpp65 encoding cells, 12 monoclones were selected at random, outgrown and were used for genetic characterisation. Cells were characterised by PCR utilising primers targeted to the aAM ORF (Component D') (Table 5, 10.D.1, 15.H.4), to amplify and detect integrated aAM. All 12 monoclones screened by PCR have detectable amplicons are of the expected size for one of pp28 (0.8 kb), pp52 (1.5 kb) or pp65 (1.9 kb). In addition, all 3 aAMs were represented across the 12 monoclones. In comparison, amplicons from three discrete monoclones, wherein in the aAM was known, were amplified in parallel as controls; all three controls produced the correct sized amplicons of pp28 (0.8 kb), pp52 (1.5 kb) and pp65 (1.9 kb). Thus, it is confirmed that the pool is comprised of eAPC-pa wherein each cell has a single randomly selected aAM form the original pool of three vectors.

Figure 46:
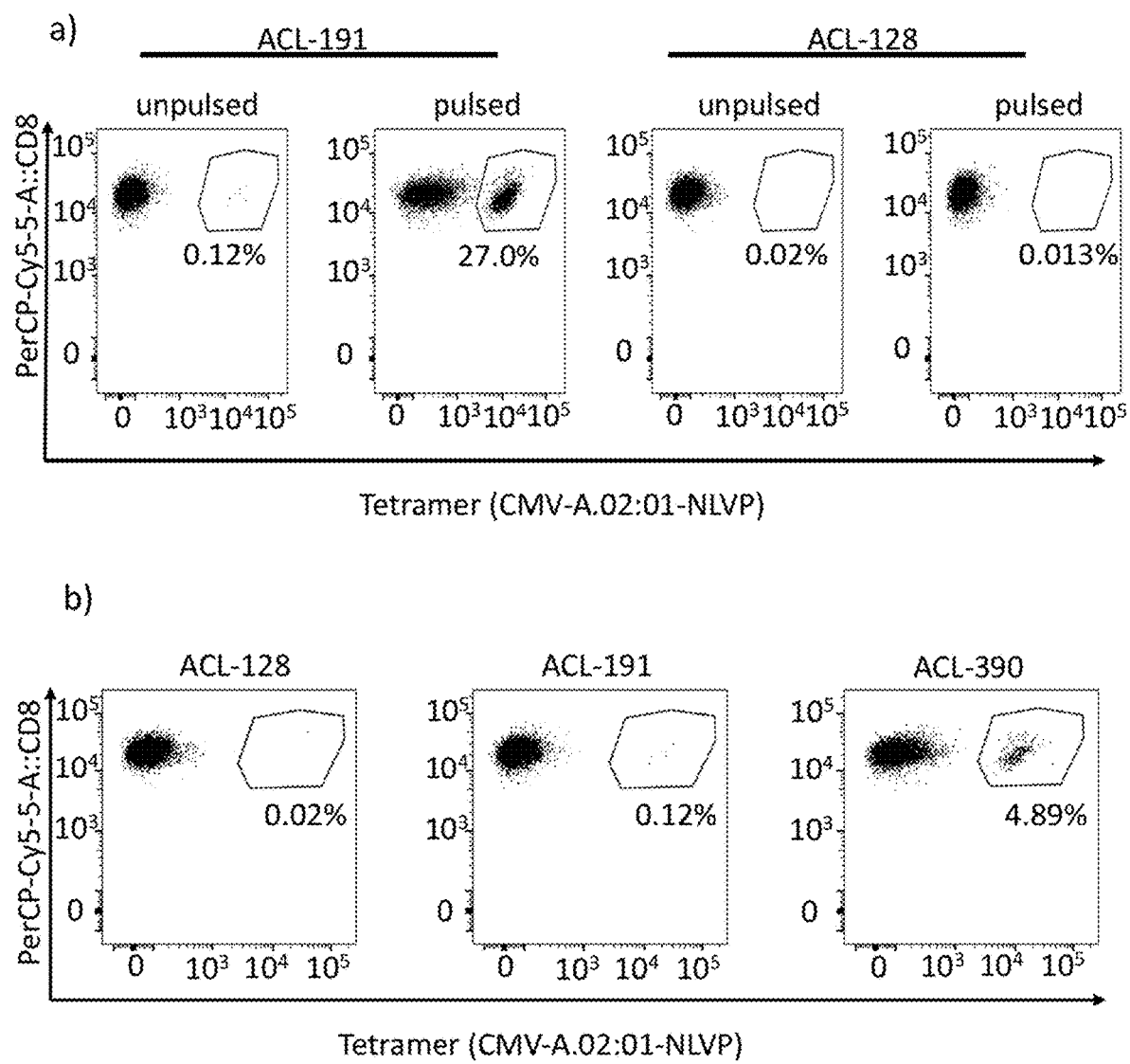

FIG. 46—eAPC-pa induced antigen-specific outgrowth of primary CD8 cells

Seven different eAPC:T systems were compiled using primary CD8+ T cells as the analyte TC, and three different eAPC cell lines, ACL-191 (eAPC-p, aAPX: HLA-A*02:01), ACL-390 (eAPC-pa, aAPX:aM: HLA-A*02:01, HCMVpp65) or ACL-128 (eAPC, HLA-1 null, i.e. no aAPX). Furthermore, eAPC:T systems comprising of ACL-191 or ACL-128, where applicable used exogenously provided aAM (as soluble NLVPMVATV peptide). Systems were compiled as described below, and after 9 days of co-culture the cells were analysed for specific staining with CMV-A.0201-NLVP tetramer (aAPX:aAM) to detect outgrowth of antigen-specific T-cells by flow cytometry. a) Four eAPC:T systems were compiled comprising of analyte TC (CD8+ T-cells), and 1) ACL-191 with no aAM (unpulsed), 2) ACL-191 pulsed with aAM, 3) ACL-128 unpulsed, or 4) ACL-128 pulsed with aAM. Systems with aAM were provided with NLVPMVATV peptide (aAM), derived from HCMVpp65 protein, at a peptide concentration of 1 µM for 4 hours as described in materials and methods section. Flow cytometry plots of CD8 vs CMV-A.0201-NLVP are displayed, wherein plots represent data for eAPC:T system (left-to-right) 1), 2), 3), 4). A clear population (27%) of CD8+CMV-A.0201-NLVP+ cells (gated) are observed in plot 2 (ACL-191 pulsed with aAM), in contrast all other eAPC:T systems, plots 1, 3, 4, lacking either aAPX or aAM or both, have positive cells of between 0.02-0.12%. Thus, specific analyte TC can be outgrown in an antigen dependent nature by aAPX:aAM presented by eAPC-p cells when provided with exogenous aAM. b) Three eAPC:T systems were compiled comprising of analyte TC (CD8+ T-cells), and 1) ACL-128 (eAPC), 2) ACL-191 (eAPC-p), or 3) ACL-390 (eAPC-pa), and wherein no exogenous aAM is provided. ACL-390 has an integrated aAM ORF, HCMVpp65. Flow cytometry plots of CD8 vs CMV-A.0201-NLVP are displayed, wherein plots represent data for eAPC:T system (left-to-right) 1), 2), 3). A clear population (4.89%) of CD8+CMV-A.0201-NLVP+ cells (gated) are observed in plot 3 (ACL-390 with endogenous aAM), in contrast the other eAPC:T systems, plots 1 and 2, lacking either aAM or aAPX and aAM, have positive cells of between 0.02-0.12%. Thus, this data supports that eAPC-pa are capable of processing endogenous aAM ORF into aAM by native cellular machinery, and present the aAM in complex with aAPX, such that it can stimulate an antigen specific outgrowth of analyte TC.

Figure 47:
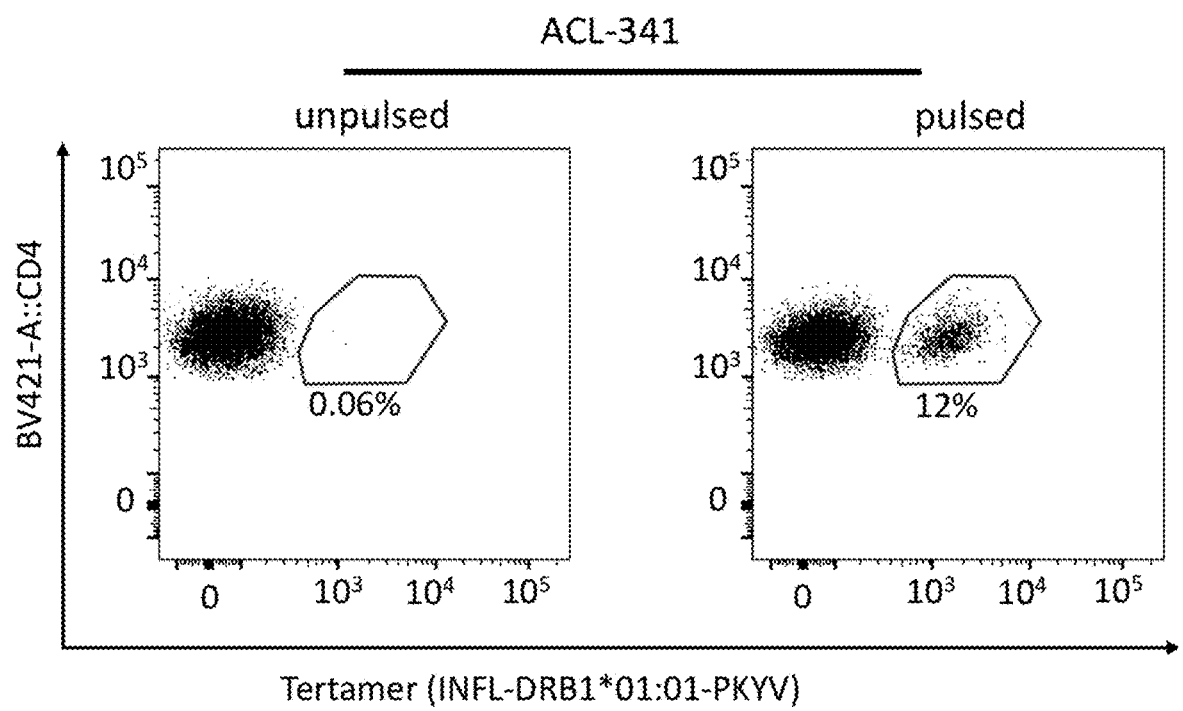

FIG. 47—eAPC-p and exogenous aAM induced antigen-specific outgrowth of primary CD4 cells Two different eAPC:T systems were compiled using primary CD4+ T cells as the analyte TC, and one eAPC-p cell lines, ACL-341 (aAPX: HLA-DRB1*01:01). Furthermore, where applicable exogenously aAM (as PKYVKQNTLKLAT peptide, SEQ ID NO:1) was also provided to the system. Systems were compiled as described below, and after 9 days of co-culture the cells were analysed for specific staining with INFL-DRB1*01:01-PKYV tetramer (aAPX:aAM, SEQ ID NO:2) to detect outgrowth of antigen-specific T-cells by flow cytometry. Two eAPC:T systems were compiled comprising of analyte TC (CD4+ T-cells), and 1) ACL-341 with no aAM (unpulsed), 2) ACL-341 pulsed with PKYVKQNTLKLAT peptide (aAM, SEQ ID NO:1), at a peptide concentration of 1 µM for 2 hours as described in materials and methods section. Flow cytometry plots of CD4 vs with INFL-DRB1*01:01-PKYV are displayed, wherein plots represent data for eAPC:T system (left-to-right) 1) and 2). A clear population (12%) of CD4+/INFL-DRB1*01:01-PKYV+ cells (gated) are observed in plot 2 (ACL-341 pulsed with aAM), in contrast the control eAPC:T systems, plots 1, lacking either aAM, has positive cells of between 0.06%. Thus, specific analyte TC CD4+ cells can be outgrown in an antigen dependent nature by aAPX:aAM presented by eAPC-p cells when provided with exogenous aAM.

Figure 48:
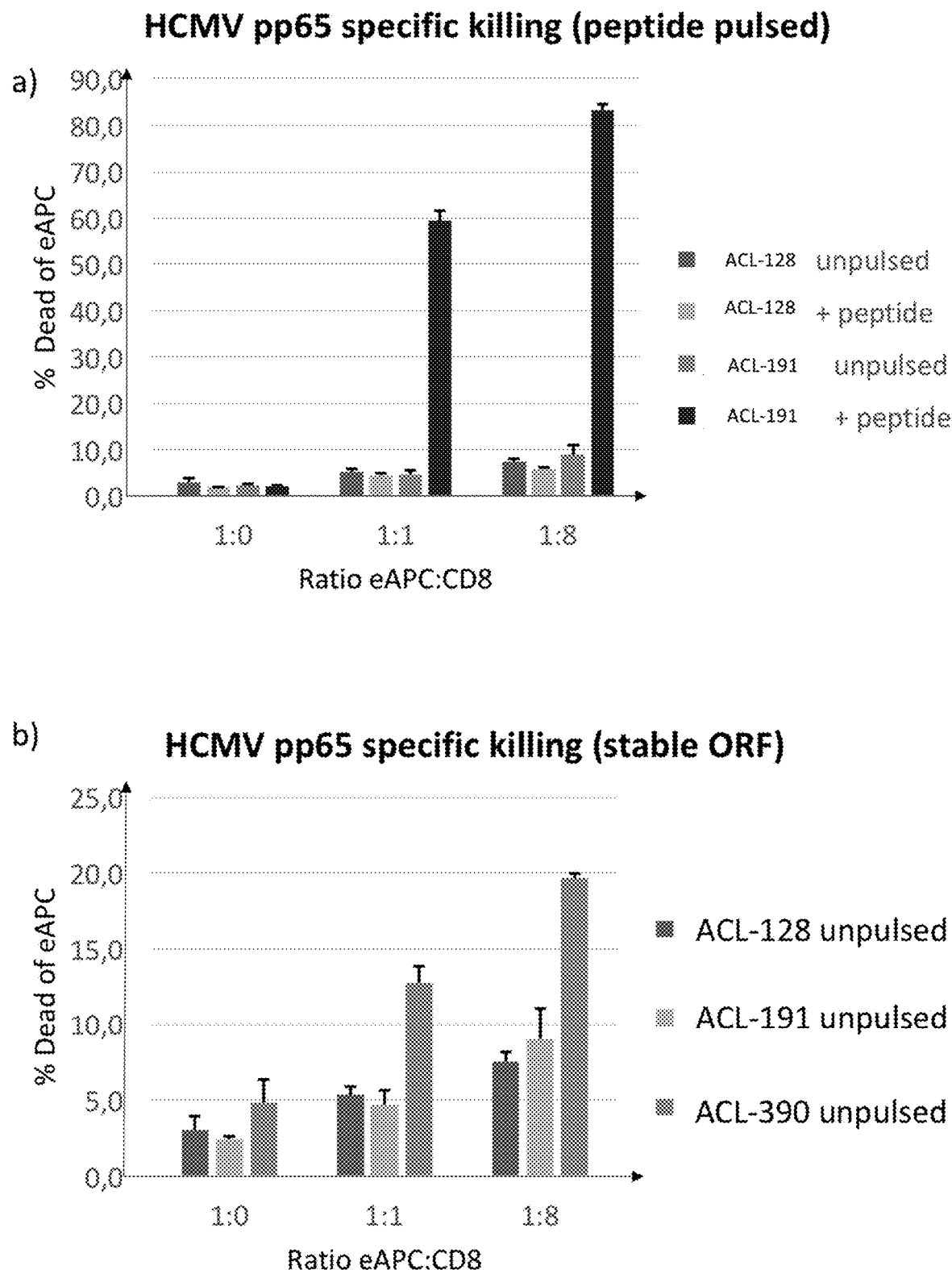

FIG. 48—Antigen-specific cytotoxicity of eAPC-pa cells co-cultured with primary CD8 cells Seven different eAPC:T systems were compiled using primary CD8+ T cells as the analyte TC, and three different eAPC cell lines, ACL-191 (eAPC-p, aAPX: HLA-A*02:01), ACL-390 (eAPC-pa, aAPX:aM: HLA-A*02:01, HCMVpp65) or ACL-128 (eAPC, HLA-I null, i.e. no aAPX). Furthermore, eAPC:T systems comprising of ACL-191 or ACL-128, where applicable, used exogenously provided aAM (as NLVPMVATV peptide, SEQ ID NO: 3). Systems were compiled as described below, and the co-culture the cells were analysed for cytotoxic action against the eAPC-p or -pa by staining with AnnexinV and PI to detect dead cells by flow cytometry. a) Four eAPC:T systems were compiled comprising of analyte TC (CD8+ T-cells), and 1) ACL-128 unpulsed, 2) ACL-128 pulsed with aAM, 3) ACL-191 with no aAM (unpulsed), 4) ACL-191 pulsed with aAM. Systems with aAM were provided with NLVPMVATV peptide (aAM), derived from HCMVpp65 protein, at a peptide concentration of 1 µM for 2 hours as described in materials and methods section. In addition, systems were compiled with ratios of eAPC:CD8 of 1:0, 1:1 and 1:8. Plotted is a bar graph of the percentage dead eAPC cells as detected by flow cytometry (CD80+Annexin+PI+). A clear killing of the eAPC-p cells is observed only in system 4 (ACL-191+peptide) comprised of both eAPC and CD8+ cells, ratios 1:1 or 1:8 (eAPC:CD8). No significant increase in death above is background is observed in systems 1, 2, and 3 lacking either aAPX, aAM or both. Thus, eAPC-p pulsed with exogenous aAM can be used to stimulate antigen specific cytotoxic action in primary CD8+ T-cells (analyte TC). b) Three eAPC:T systems were compiled comprising of analyte TC (CD8+ T-cells), and 1) ACL-128 (eAPC), 2) ACL-191 (eAPC-p), or 3) ACL-390 (eAPC-pa), and wherein no exogenous aAM is provided. ACL-390 has an integrated aAM ORF, HCMVpp65. Plotted is a bar graph of the percentage dead eAPC cells as detected by flow cytometry (CD80+Annexin+PI+). A clear killing of the eAPC-p cells is observed only in system 3 (ACL-390), comprised of both eAPC and CD8+ cells, at ratios 1:1 or 1:8 (eAPC:CD8). No significant increase in death above background is observed in systems 1 and 2 lacking either aAM or aAPX:aAM. Thus, this data supports that eAPC-pa are capable of processing endogenous aAM ORF into aAM by native cellular machinery, and present the aAM in complex with aAPX, such that it can stimulate an antigen specific cytotoxic action by primary CD8+ T-cells (analyte TC).

FIG. 49—Analyte Antigen Molecules identification from eAPC-pa cells via mass spectrometry Mass-spectrometry results are presented for peptide fractions derived from the following procedures. Two eAPC-p lines, ACL-900 (aAPX: HLA-A*02:01) and ACL-963 (aAPX: HLA-A*24:02) were pulsed with known antigenic peptides, wherein for each eAPC-p four discrete pulses were conducted, consisting of one of the following aAM as peptides; NLVPMVATV (APD-2, SEQ ID NO: 3), NLGPMAAGV (APD-21, SEQ ID NO: 4), or VYALPLKML (APD-11, SEQ ID NO: 5), or no peptide. APD-2 is known to complex with HLA-A*02:01, APD-11 with HLA-A*24:02, and APD-21 is a triple mutant (V3G, T8G, V6A) of APD-2 in which these mutations disrupt the ability for the peptide to complex with HLA-A*02:01. Pulsed cells were harvested and lysed. Cleared lysate was mixed with nickel agarose resin and the HLAs were pulled down using 6x-His capture. The bound fraction was eluted in 10% acetic acid and ultrafiltered over 3kD columns. The peptide fraction was subjected to liquid extraction and removal of the organic phase was subjected to solid phase extraction. The eluted peptide fraction w submitted to mass spectrometry. Peptides NLVPMVATV (SEQ ID NO: 3), VYALPLKML (SEQ ID NO: 5) and NLGPMVAGV (SEQ ID NO: 4) were successfully identified in their respective pulsed experiment (IDs 2, 3, 11) and were not identified in any other sample. The HLA-mismatched peptides NLVPMVATV (ID 12, HLA-A*24:02, SEQ ID NO: 3) and VYALPLKML (ID 13, HLA-A*02:01, SEQ ID NO: 5) and the triple mutant NLGPAAGV (SEQ ID NO: 4) was not identified. Thus, the capture and enrichment of aAPX:aAM complexes of eAPC-p cells can be used to identify, confirm and/or determine the HLA-restricted presentation of an analyte antigen molecule in antigen presenting complexes.

MATERIALS AND METHODS

Electroporation of ARH-77 Cells

Per reaction, $4 \times 10^6$ cells were electroporated in 500 ul RPMI 1640 with Glutamax-I (Life Technologies) using the Gene Pulser Xcell™ (Bio-Rad) with the following setting Square Wave 285V, pulse length 12.5 ms and 2 pulses with 1s interval. The DNA concentration used for the Cas9 plasmid V1.A.8 was 10 ug/ml and 7.5 ug/ml for the gRNA targeting the integration site (V2.1.10 and V2.1.1 for integration in HLA endogenous locus and V2.J.6 to target the AAVS1 site) (Table 3).

The integration vectors were electroporated at a concentration of 7.5 ug/ul. For HDR integration in the HLA locus, HLA class I V1.C.6 and V1.C.9 plasmids were used. For HDR integration in AAVS1 locus, HLA class I V1.F.8 and V1.F.10 and HLA class II V1.1.5 and V1.1.7. Variants of pp65 ORF were integrated into previously created HLA monoallelic lines. Plasmids V1.G.9 and V1.H.1 containing a form of pp65 linked with a GFP marker were used for this purpose. To generate an ARH-77 HLA-null line with one RMCE site, plasmids with heterospecific recombinase sites flanking a marker were used, V4.B.2 for RFP and V4.B.3 for BFP. The same plasmids were co-electroporated to produce a stable line containing two RMCE sites. A monoallelic HLA line was also created using RMCE, where vector V4.D.2 was electroporated into a cell containing one RMCE site. After electroporation, cells were incubated in culture medium RPMI 1640 with Glutamax-I+10% FBS (37° C., 5% $CO_2$) for two days, before analysis.

Transfection of HEK293 Cells

One day prior to transfection, cells were seeded at a density of $1.2-1.4 \times 10^6$ cells/60 mm dish in 90% DMEM+2 mML-glutamine+10% HI-FBS (Life Technologies). The following day, cells with 65% confluency were transfected with a total amount of 5 ug DNA and jetPEI® (Polyplus transfection reagent, Life Technologies) at a N/P ratio of 6. The medium was replaced before transfection. Stock solutions of DNA and jetPEI @ were diluted in sterile 1M NaCl and 150 mM NaCl respectively. The final volume of each solution was equivalent to 50% of the total mix volume. The PEI solution was then added to the diluted DNA and the mixture was incubated at room temperature for 15 min. Finally the DNA/PEI mixtures were added to the 60-mm dishes, being careful not to disrupt the cell film.

The cells were incubated for 48 hours at (37° C., 5% CO2, 95% relative humidity) prior to GFP expression analysis. For deletion of HLA class I genes, cells were transfected with 0.42 ug of DNA vectors encoding the Cas9_GFP (V1.A.8), gRNAs targeting HLA-A, B and C (V2.A.1, V2.A.7 and V2.B.3 respectively) and an empty vector (V1.C.2). For integration of RMCE sites in the AAVS1 locus, cells were transfected with 0.5 ug of V1.A.8; 0.625 ug of gRNA V2.J.6 and 0.75 ug of plasmids encoding two markers flanked by RMCE sites (V4.B.2 for RFP and V4.B.3 for BFP), empty vector V1.C.2 was used to complete 5 ug of DNA.

Sorting of Polyclonal GFP-Expressing Cells

Cells electroporated or transfected with Cas9-P2A-GFP (V1.A.8) or with a plasmid encoding a GFP selection marker (V1.A.4) were sorted for transient GFP expression, using the FACSJAzz™ cell sorter (BD Biosciences). HEK 293 cells were harvested with TrypLE™ Express Trypsin (ThermoFisher Scientific) and resuspended in a suitable volume of DPBS 1× (Life Technologies) prior to cell sorting, in DMEM 1× medium containing 20% HI-FBS and Anti-Anti 100× (Life Technologies). ARH-77 cells were washed and resuspended in an adequate volume of DPBS before sorting in RPMI 1640 with Glutamax-I with 20% HI-FBS and Anti-Anti 100× (Life Technologies).

Sorting Polyclonal and Monoclonal Cells with Stable Expression of Component of Interest To obtain a population of cells constitutively expressing the integrated protein or marker, cells were sorted 7 to 15 days after the first GFP+selection. For cells expected to express a surface protein, antibody staining was performed prior to sorting. For HLA class I genes, PE-Cy™5 Mouse Anti-Human HLA-ABC antibody (BD Biosciences) was used. Staining of HLA-DR and HLA-DP was done with Alexa Fluor® 647 Mouse Anti-Human HLA-DR, DP, DQ (BD Biosciences). In the case of HEK 293 derived cell lines, cells were harvested with TrypLE™ Express Trypsin (ThermoFisher Scientific) and washed in a suitable volume of DPBS 1× (Life Technologies) prior to cell sorting in DMEM 1× medium containing 20% HI-FBS and Anti-Anti 100× (Life Technologies). ARH-77 derived cell lines were washed in an adequate volume of DPBS before sorting in RPMI 1640 with Glutamax-I with 20% HI-FBS and Anti-Anti 100× (Life Technologies).

TABLE 3

| Vectors | |
|---|---|
| ID | Name |
| V1.A.4 | pcDNA3.1_GFP |
| V1.A.8 | SpCas9-2A-GFP |
| V1.C.2 | pMA-SV40pA |
| V1.C.6 | HLA-A 02:01 6xHis + Exon2/3-HA-L + R |
| V1.C.9 | HLA-B 35:01 6xHis + Exon2/3-HA-L + R |
| V1.F.8 | AAVS1-S_A24_6xH |

TABLE 3-continued

Vectors

| ID | Name |
|---|---|
| V1.F.10 | AAVS1-L__B07__6xH |
| V1.G.10 | AAVS1-I__GFP__HCMVpp65 |
| V1.G.9 | AAVS1-I__GFP__HCMVpp65 ANET |
| V1.H.1 | AAVS1-I__GFP__HCMVpp65 AIN |
| V1.I.5 | AAVS1__DRA__Flag-DRB1__6xHis |
| V1.I.7 | AAVS1__DPA1__Flag-DPB1__6xHis |
| V2.A.1 | HLA-A-sg-sp-opti1 |
| V2.A.7 | HLA-B-sg-sp-3 |
| V2.B.3 | HLA-C-sg-sp-4 |
| V2.I.10 | HLA-A-ex2-3__sg-sp-opti__1 |
| V2.J.1 | HLA-A-ex2-3__sg-sp-opti__2 |
| V2.J.6 | AAVSl_sg-sp-opti__3 |
| V4.B.2 | AAVS__Efla-intron__F14__RFPnls__F15 |
| V4.B.3 | AAVS__Efla-intron__FRT__BFPnls__F3 |
| V4.D.2 | pMA__FRT__HLA-A*02:01-6xHis__F3 |
| V4.H.5 | pMA__F14__HLA-A*02:01-6xHis__F15 |
| V4.H.6 | pMA__F14__HLA-A*24:02-6xHis__F15 |
| V4.H.7 | pMA__F14__HLA-B*07:02-6xHis__F15 |
| V4.H.8 | pMA__F14__HLA-B*35:01-6xHis__F15 |
| V4.I.8 | CMVpro__FLPo__Sv40pA__V2 |
| V9.E.6 | FRT__HCMVpp28-3xMYC__F3 |
| V9.E.7 | FRT__HCMVpp52-3xMYC__F3 |
| V9.E.8 | FRT__HCMVpp52-3xMYC__F3 |

For HLA knockout or integration, selection of cells was done based on loss or gain of HLA expression, respectively. Cells with integrated RMCE sites were sorted based on the expression of BFP and RFP markers, and HLA monoclones with integrated pp65 mutants were sorted for GFP expression (Table 4). Monoclonal sorting of cells expressing the gene of interest was done in 96-well plates, containing 200 ul of growth medium. One to two plates were sorted per sample. Polyclonal sorting of the remaining cells was done immediately after, in FACS tubes, using the Two-way sorting setting in the cell sorter Influx™ (BD Biosciences).

Phenotypic Screening of Monoclonal Populations

A sample of 20,000 cells of the outgrown monoclones population was transferred into microtiter plates for analysis, cells were resuspended in 250 ul of DPBS 1× (Life Technologies) and analyzed on the LRSFortessa™ (BD Biosciences). BFP and RFP expression was detected using the PMTs for BV421 and PE-Texas Red fluorophore, respectively. For proteins with surface expression, cells were first stained using PE-Cy™5 Mouse Anti-Human HLA-ABC antibody (BD Biosciences) or Alexa Fluor® 647 Mouse Anti-Human HLA-DR, DP, DQ (BD Biosciences). Staining solution was prepared using the recommended antibody volume diluted in 100 ul of staining buffer (DPBS+2% FBS). Cells were incubated for 1 hour at 4° C. and then washed twice with 500 ul of staining buffer, prior to analysis. Selected monoclones were maintained in normal growth medium. HEK239 cells grow in DMEM+2 mML-glutamine+10% HI-FBS (Life Technologies) and ARH-7 cells grow in RPMI 1640 with Glutamax-I+10% HI-FBS. The confluence of cells was monitored every day, until they reached 10-12×10$^6$. DNA was extracted from 5×10$^6$ cells using the QIAamp DNA Minikit (Qiagen). The remaining cells were further expanded and cryopreserved at a density of 3×10$^6$ cells/ml, in 70% growth medium+20% HI-FBS+10% DMSO.

TABLE 4

| FACSJazz and Influx filters | | |
|---|---|---|
| Protein | Fluorochrome | Filter |
| Cas9/GFP | GFP | 488-513/17 |
| Cas9/GFP | GFP | 488-530/40 |
| HLA-A, B, C | PE-Cy5 | 561-670/30 |
| HLA-DR, DP, DQ | Alexa 647 | 640-670/30 |
| BFP | BFP | 405-460/50 |
| RFP | RFP | 561-585/29 |
| HLA-ABC (protein YG72) | PE-Cy7 | 561-750LP |
| Myc (protein R43) | Alexa647 | 640-670/30 |
| Phosphatidylserine (stained by Annexin V) | BV711 | 405-710/50 |
| CD80 APC | APC | 640-670/30 |
| CD8APC-H7 | APC-H7 | 640-780/60 |
| CD8 | APC-H7 | 640-750/LP |
| DNA (stained by Propidium iodide) | Propidium Iodide | 561-585/15 |
| CD3 | APC | 640-670/30 |
| CD3 | FITC | 488-530/40 |
| CD8 | PerCP-Cy5.5 | 488-710/50 |
| CD8 | PerCP-Cy5.5 | 488-695/40 |
| CD4 | BV510 | 405-520/35 |
| CD4 | BV421 | 405-460/50 |
| CD25 | PE | 561-585/29 |
| CMV-A.02:01-NLVP | PE | 561-585/15 |
| INFL-DRB1-0101-PKYV (SEQ ID NO: 2) | PE | 561-585/15 |
| Dead cell marker | APC-H7 | 640-780/60 |

Confirmation of integration in correct genomic location Monoclones with desired phenotypic characteristics were screened and assessed at a molecular level, this was done by PCR using Q5@ Hot Start High-Fidelity DNA Polymerase (NBE), in 20 ul reactions, using the components and volumes recommended by the manufacturer. To determine whether HLA I ORFs were integrated in the HLA locus, primers 9.C.4 and 9.D.6 were used; correct right homologous arm recombination was indicated by 1 kb amplicons (table 5). For HLA integration in the AAVS1 locus, four sets of primers were used: 9.C.3 and 9.C.8 to assess correct left homologous arm recombination (1.1 kb), 9.C.4 and 9.D. 1 to assess right homologous arm recombination (660 bp), 1.C.5 and 9.C.5 to amplify the CMV promoter of the internal construct (810 bp), and 1.C.2 and 9.C.10 to obtain an amplicon for the SV40 pA terminator of the internal construct (380 bp). Assessment of RMCE site integration in HEK293 and ARH-77 HLA-null lines was done using primer sets 2 and 4. To confirm HLA class I deletion in HEK293 cells, specific HLA primers were used as follows: 4.A.3 and 4.A.4 targeting HLA-A, 4.A.7 and 4.B.1 for HLA-B and 4.B.5 and 8.A.1 for HLA-C. Initially, a PCR Master Mix was prepared with all components (Q5® Reaction Buffer, dNTPs, Hot-Start Q5@ DNA polymerase, primers Fwd and Rev, 100 ng of DNA template and H$_2$0). PCR reactions were run using C1000 Touch™ Thermal Cycler (Bio-Rad). PCR products were run on a 1% Agarose gel in 1×TAE buffer, using the PowerPac Basic (Bio-Rad), stained with 10,000 dilution of sybersafe and analyzed with Fusion SL (Vilber Lourmat).

TABLE 5

Primers

| ID | Name | Sequence |
|---|---|---|
| 1.C.2 | pMA-sv40_OE_F1 | CCTGATCATAATCAAGCCATATCAC |
| 1.C.3 | pMA-sv40_OE_R1 | GTGATATGGCTTGATTATGATCAGG |
| 1.C.5 | pMA-CMV_OE_R1 | |
| 4.A.3 | HLA-A-GT-Rg3 | TCCCGTTCTCCAGGTATCTG |
| 4.A.4 | HLA-A-GT-Fg2 | GTGTCGGGTTTCCAGAGAAG |
| 4.A.7 | HLA-B-GT-Fg2 | GGGTCCCAGTTCTAAAGTCC |
| 4.B.1 | HLA-B-GT-Rg2 | GGGGATTTTGGCCTCAACTG |
| 4.B.5 | HLA-C-GT-Fg2 | TCTTCCTGAATACTCATGACG |
| 4.I.9 | HLA-A-02_GT_Rg4 | GGAGATCTACAGGCGATCAG |
| 6.I.9 | HLA-A-Exon3_HA-RE-BglII_F1 | GGTTAGATCTGGGAAGGAGACGCTGCAG |
| 8.A.1 | HLA-C-04-GT-Rg1 | GATCCCATTTTCCTCCCCTC |
| 8.B.2 | CMV-pA-HLA-Ex3_Probe_F1 | ATGTCTGGATCTGCGGATCAGCGCACG |
| 9.C.3 | CMV-pro_GT_R1 | ATGGGCTATGAACTAATGACC |
| 9.C.4 | sv40pA_GT_F1 | CATTCTAGTTGTGGTTTGTCC |
| 9.C.5 | AAVS1_GT_F1 | CTTACCTCTCTAGTCTGTGC |
| 9.C.7 | AAVS1_GT_F3 | CCATTGTCACTTTGCGCTG |
| 9.C.8 | AAVS1_GT_F4 | TCCTGGACTTTGTCTCCTTC |
| 9.C.10 | AAVS1_GT_R2 | AGAGATGGCTCCAGGAAATG |
| 9.D.1 | AAVS1_GT_R3 | AAGAGAAAGGGAGTAGAGGC |
| 9.D.2 | AAVS1_GT_R4 | CCCGAAGAGTGAGTTTGC |
| 9.D.6 | HLA-A-intron4_GT_R1 | GCTAAAGGTCAGAGAGGCTC |
| 9.D.7 | sv40pA-GT-F2 | CTGCATTCTAGTTGTGGTTTGTC |
| 9.D.9 | AAVS1_GT_R6 | |
| 9.J.2 | sv40pA-AAVS1-probe-FAM-F1 | TGCGGATCAGGATTGGTGACAGAA |
| 10.A.9 | TRAC_TCRA-ex1_R1 | GACTTGTCACTGGATTTAGAGTCTCT |
| 10.A.10 | TRAC_TCRA-promoter_F1 | CTGATCCTCTTGTCCCACAGATA |
| 10.6.6 | TRAC_probe (HEX) | ATCCAGAACCCTGACCCTGCCG |
| 8.B.3 | Pan-HLA_GT_F1 | AAGGAGGGAGCTACTCTCAG |
| 15.H.2 | SV40pA_GT_R1 | CCTCTACAGATGTGATATGGCTTG |
| 10.C.4 | 3xMyc_OE_R1 | GGAGAACAAAAGCTCATCTCTGAGGAG |
| 10.D.1 | CtermCysLink_OE_R1 | AGATCCAGATCCACCGGATGTAGAGCAAC |
| 15.H.4 | Ef1a_intron_GT_F2 | TGGGTGGAGACTGAAGTTAG |

Identification of Gene Copy Number

DNA of selected monoclones was analyzed by using specific primers targeting the gene of interest and a probe recognizing a fragment of the integrated gene and extending to the homologous arm. For HLA class I integration in the HLA locus, primers 4.I.9 and 9.C.4 were used to amplify the gene of interest and 8.B.2 was used as the probe, conjugated with FAM. For constructs integrated in the AAVS1 locus, primers 9.D.6 and 9.D.7 and probe 9.J.2, also conjugated with FAM, were used. In all cases, a reference gene (TRAC) was simultaneously screened to determine copy numbers, using primers 10.A.9 and 10.A.10 together with the fluorescent probe 10.B.6 conjugated with HEX. Integration copy number considered that ARH-77 cells are diploid and HEK293 cells are triploid for reference gene (TRAC). Prior to Droplet Digital PCR, DNA was digested with MfeI (NEB) to separate tandem integrations. The reaction setup and cycling conditions were followed according to the protocol for ddPCR™ Supermix for Probes (No dUTP) (Bio-Rad), using the QX200™ Droplet Reader and Droplet Generator and the C1000 Touch™ deep-well Thermal cycler (Bio-Rad). Data was acquired using the QuantaSoft™ Software, using Ch1 to detect FAM and Ch2 for HEX.

TABLE 6 ddPCR Primers/probes

| ID | Name | Sequence |
|---|---|---|
| 21.I.1 | HCMVpp65_GT_F2 | TCGACGCCCAAAAAGCAC |
| 21.I.2 | HCMVpp28_GT_F1 | TGCCTCCTTGCCCTTTG |
| 21.I.3 | HCMVpp52_GT_F1 | CGTCCCTAACACCAAGAAG |
| 20.H.10 | Myc-Tag_GT_R1 | AAGGTCCTCCTCAGAGATG |
| 20.H.9 | Linker-Myc_Probe_Fam | CTTTTGTTCTCCAGATCCAGATCCACC |
| 10.A.9 | TRAC-TCRA-ex1-F1 | CTGATCCTCTTGTCCCACAGATA |
| 10.A.10 | TRAC-TCRA-ex1-F1 | GACTTGTCACTGGATTTAGAGTCTCT |
| 10.B.6 | TRAC-probe (HEX) | ATCCAGAACCCTGACCCTGCCG |

TABLE 7

Summary of ACL cell lines, associated components and if applicable the aAPX and/or aAM integrated at Component B/B' and Component D/D'

| ID | Components | aAPX (B') | aAM (D') | Designation |
|---|---|---|---|---|
| ACL-3 | None | Wild Type | — | — |
| ACL-128 | None | Null | — | — |
| ACL-402 | B, D | | — | eAPC |
| ACL-900 | B', D | HLA-A*02:01 | — | eAPC-p |
| ACL-963 | B', D | HLA-A*24:02 | — | eAPC-p |
| ACL-905 | B', D | HLA-A*02:01 | — | eAPC-p |
| ACL-1219 | B', D' | HLA-A*02:01 | pp28 ORF | eAPC-pa |
| ACL-1227 | B', D' | HLA-A*02:01 | pp52 ORF | eAPC-pa |
| ACL-1233 | B', D' | HLA-A*02:01 | pp65 ORF | eAPC-pa |
| ACL-1050 | B', D' | HLA-A*02:01 | pp28, pp52, pp65 | eAPC-pa |
| ACL-1043 | B', D' | HLA-A*02:01 | pp28 ORF | eAPC-pa |
| ACL-1044 | B', D' | HLA-A*02:01 | pp52 ORF | eAPC-pa |
| ACL-1046 | B', D' | HLA-A*02:01 | pp65 ORF | eAPC-pa |
| ACL-191 | B', D | HLA-A*02:01 | | eAPC-p |
| ACL-390 | B', D' | HLA-A*02:01 | pp65 ORF | eAPC-pa |
| ACL-341 | B', D | HLA-DRB1*01.01 | | eAPC-p |

Flp-Mediated Integration of HLA-A*02:01 Sequences in eAPC Cell Line eAPC cells were electroporated with vectors encoding Flp, DNA encoding a marker to track delivery (vector encoding GFP) and vector containing HLA-A*02:01. The HLA-A*02:01 sequence also encoded a linker and 3×Myc-tag at the 3'end. The electroporation conditions used were 258 V, 12.5 ms, 2 pulses, 1 pulse interval.

Ratio between each integrating vector and the Flp-vector was 1:3. Cells electroporated with only GFP-vector and non-electroporated cells were used as controls respectively in order to set the gates for GFP sort after two days. On the following day (2 days after electroporation), cells were analyzed and sorted based on GFP expression. Cells were sorted using the BD Influx Cell Sorter.

3 days after electroporation, a sort based on GFP-expression was performed in order to enrich for electroporated cells. 7-8 days after electroporation, the cells were harvested and surface stained for HLA-ABC expression. BFP+ve RFP−ve HLA+ve cells were single cell sorted for monoclonal.

To genotype the cells, 100 ng of DNA was used as template to run a PCR reaction to check if integrations had occurred at the expected integration site. A forward primer targeting the integration cassettes (Pan_HLA_GT_F1 (Insert SEQ ID NO)) and a reverse primer (SV40 pA_GT_R1 Insert SEQ ID NO) targeting just outside the integration site was used and the PCR product was run on a 1% agarose gel.

Flp-Mediated Integration of HCMV ORF Sequences in eAPC-p Cell Line eAPC-p cells were electroporated with vectors encoding Flp, DNA encoding a marker to track delivery (vector encoding GFP) and vectors containing HCMV pp28, pp52 or pp65 aAM-ORF. The HCMV-ORF sequences also encoded a linker and 3×Myc-tag at the 3'end. The electroporation conditions used were 258 V, 12.5 ms, 2 pulses, 1 pulse interval.

Ratio between each integrating vector and the Flp-vector was 1:3. Cells electroporated with only GFP-vector and no electroporated cells were used as controls respectively in order to set the gates for GFP sort after two days. On the following day (2 days after electroporation), cells were analyzed and sorted based on GFP expression. Cells were sorted using the BD Influx Cell Sorter.

Flp-Mediated Shotgun Integration of 3 HCMV ORF Sequences in eAPC-p Cell Line eAPC-p cells were electroporated with vectors encoding Flp, DNA encoding a marker to track delivery (vector encoding GFP) and vectors containing HCMV pp28, pp52 or pp65 aAM-ORF. The HCMV-ORF sequences also encoded a linker and 3×Myc-tag at the 3'end. The electroporation conditions used were 258 V, 12.5 ms, 2 pulses, 1 pulse interval. For the shotgun integration, the vectors containing HCMV-ORFs were pooled in a ratio 1:1:1 and the mixture was electroporated into the eAPC-p cell. The resulting eAPC-pa cells were polyclonal. Individual monoclone cells were sorted and genetically characterized to demonstrate that the polyclone was made up of cells containing all three HCMV-ORFs.

PCR Reactions to Assess the RMCE-Integration of the HCMV ORFs into Component D

Primers used to assess integration of the HCMV ORF annealed to the linker (forward primer 10.D.1 (Insert SEQ ID) and EF1alpha promoter (reverse primer 15.H.4). Expected size was 0.8 kb for pp28, 1.5 kb for pp52, 1.9 kb for pp65.

TABLE 8

PCR reagents for assess integration of the aAM ORF

| Reaction Component | Volume per reaction |
|---|---|
| 5xPhusion buffer | 4 ul |
| DNTPs | 0.2 ul |
| Phusion DNA polymerase | 0.15 ul |
| 10.D.1 | 0.5 ul |
| 15.H.4 | 0.5 ul |
| H20 | up to 20 ul |
| DNA (100 ng) | 1 ul (100 ng/ul) |
| DMSO 3% | 0.6 ul |

TABLE 9

PCR cycle conditions

| Step | Temperature | Time |
|---|---|---|
| Initial Denaturation | 98° C. | 30 sec |
| 30 cycles | 98° C. | 10 sec |
|  | 60° C. | 10 sec |
|  | 72° C. | 15 sec |
| Final extension | 72° C. | 10 min |

PCR products were run on a 1% Agarose gel in 1×TAE buffer, using the PowerPac Basic (Bio-Rad), stained with 10,000 dilution of sybersafe and analyzed with Fusion SL (Vilber Lourmat).

Outgrowth of Antigen-Specific CD8+ Cells

Peripheral blood mononuclear cells (PBMCs) were isolated from a healthy blood donor that is known to have CD8$^+$ T cells specific for CMV-A.0201-NLVP, using Ficoll Paque Plus (GE Healthcare). Cells were stained with surface antibodies against CD markers.

Specific T-cell populations were sorted using BD Influx Cell Sorter, pelleted and resuspended to 200 000 cells/ml in OSG medium+10% HS.

eAPCs Pulsing with Peptide Multimer

HLA-A*02:01 eAPCs were pulsed with 1 µM peptide (NLVPMVATV (SEQ ID NO: 3) or in complete OSG medium+10% HS) for 4 hours. Cells were washed 3 times in phosphate buffered saline (PBS) and resuspended to 100 000 cells/ml in OSG medium+10% human serum (HS).

Co-Culturing Antigen-Specific CD8+ with eAPCs

CD8+ cells were co-cultured with eAPCs in 96 well polysterene (wp) round bottom plates at a 1:1 ratio, i.e. 5000 cells of each cell type in total 10000 cells per well in 100 µL culture volume. Restimulation was performed at day 9 of culture such that 150 µL of the cultures was kept and restimulated with 5000 freshly pulsed eAPC cells at a volume of 50 µL per well.

In a parallel experiment CD8+ T cells were co-cultured with eAPC-pa cell line, stably expressing pp65, in 96 wp round bottom at a 1:1 ratio, 5.000 cells of each cell type=>10.000 cells per well in 100 µL culture volume. Unpulsed HLA null and eAPC-pa cells were included as controls. No restimulation was performed.

Phenotyping

Phenotyping was performed at day 14. Five replicates and a pool of 20 wells was phenotyped per condition. Cells were stained separately with 100× diluted DCM (Zombie NIR) followed by staining with 50× diluted multimer (Table 4) for 10 min and thereafter addition of surface markers (Table 4) in 25 µL per sample for 30-60 min. Cells were resuspended in Stain Buffer (PBS+2% FBS) and data were acquired on LSRFortessa and analysed in FlowJo.

Outgrowth of Antigen-Specific CD4+ Cells

Peripheral blood mononuclear cells (PBMCs) were isolated from a healthy blood donor that is known to have CD4$^+$ T cells specific for INFL-DRB1*01:01-PKYV, using Ficoll Paque Plus (GE Healthcare). Cells were stained with surface antibodies against CD markers. Specific T-cell populations were sorted using BD Influx Cell Sorter, pelleted and resuspended to 100000 or 400000 cells/ml in OSG medium+ 10% HS.

eAPCs Pulsing with Peptide Multimer

HLA DRB1*01:01 eAPCs were pulsed with 1 µM peptide (PKYVKQNTLKLAT (SEQ ID NO: 1) or in complete OSG medium+10% HS) for 2 hours. Cells were washed 3 times in phosphate buffered saline (PBS) and resuspended to 5000 cells/ml in OSG medium+10% human serum (HS).

Co-Culturing Antigen-Specific CD4+ with eAPCs

CD4+ cells were co-cultured with eAPC in 96 wp round bottom i.e. 250 eAPCs and 5.000 vs. 20.000 CD4+ cells in 100 µL culture volume. Cultures were maintained in OSG+ 10% HS. Some cultures were dosed with 100 U/mL IL-2 at day 1. Cultures with no IL-2 addition were dosed with media. Cultures expanded for 14 days got an additional dose of IL-2 at day 7.

Phenotyping

Phenotyping was performed at day 14. Five replicates and a pool of 20 wells was phenotyped per condition. Cells were stained separately with 100× diluted DCM (Zombie NIR) followed by staining with 50× diluted multimer (Table 4) for 10 min and thereafter addition of surface markers (Table 4) in 25 µL per sample for 30-60 min. Cells were resuspended in Stain Buffer (PBS+2% FBS) and data were acquired on LSRFortessa and analysed in FlowJo.

Cytotoxic Assay

Peptide Pulsing of eAPCs

2×10$^6$ cells were pulsed with 1 µM NLVPMVATV (SEQ ID NO: 3) peptide in 2 ml complete Roswell Park Memorial Institute (RPMI) medium overnight, harvested, washed 3× with PBS and resuspended in complete RPMI.

Preparation of Antigen-Specific CD8+ T Cells

Antigen-specific CD8+ T cells were derived from PBMCs from a healthy donor. Cells were stained with surface antibodies against CD markers. Specific T-cell populations were sorted using BD Influx Cell Sorter, counted and stored in liquid nitrogen. One day prior to the experiment the cells were thawed and rested overnight in complete OSG medium. Cells were counted and resuspended in complete OSG medium.

Co-Culturing eAPCs and Antigen Specific CD8+ Cells

Peptide pulsed and unpulsed eAPCs were co-cultured with the cytotoxic CD8+ T cells. 10 000 eAPCs were seeded per well in a 96-well plate (in 50 µl complete RPMI). eAPCs were co-cultured with the CD8+ T cells in increasing ratios. The ratios tested were eAPCs alone 1:0 (eAPC:CD8+), 1:1 (eAPC:CD8+), 1:8 (eAPC:CD8+) in a total volume of 100 ul. Cells were co-cultured for 4-5 hours.

Staining

Cells were transferred from the wells to microtubes (one well→one microtube), 400 µl RPMI was added per tube. Cells were centrifuged for 3 min at 400 g, supernatant aspirated and cell pellets were resuspended in 25 µl stain mix or RPMI (unstained controls) (Stain mix: AnnexinV BV711+CD80 APC+CD8 APC-H7) and incubated for 20 min at RT and 450 rpm. Staining was ended by addition of 400 μl RPMI per tube, subsequent centrifugation and removal of the supernatant. Stains are described in Table 4. Cell pellets were resuspended in 150 μl RPMI containing 1 μg/ml propidium iodide (stained samples) or 150 μl RPMI (unstained samples) and samples were transferred to 96-well plates for Fortessa acquisition.

Metal Affinity Chromatography

Peptides used for the pulsing experiments were purchased from Genscript Biotech. APD-2: NLVPMVATV (SEQ ID NO: 3) pp65 is wild type peptide and restricted to binding to HLA-A*02:01, APD-21: NLGPMAAGV (SEQ ID NO: 4) pp65 V3G,T8G, V6A triple mutant peptide of ADP-2 NLVPMVATV (SEQ ID NO:3) pp65, APD-11: VYALPLKML (SEQ ID NO: 5) is a wild type peptide restricted to binding to HLA-A*24:02

Cells were cultured in RPMI supplemented with 10% FBS at 37° C. and 5% $CO_2$. On the day of the experiment, cells were harvested, washed twice in warm PBS 1×, re-seeded at $2 \times 10^6$ cells/ml and pulsed with 1 μM peptides for 2 hours. Pulsed cells were harvested, washed twice with ice-cold PBS and lysed in ice-cold lysis buffer (150 mM Sodium chloride (NaCl), 50 mM Tris pH 8, 1% 3-[(3-cholamidopropyl)dimethylammonio]-1-propanesulfonate (CHAPS), 5 mM Imidazole, 0.2 mM iodoacetamide and 1× Halt protease inhibitor cocktail (Thermo Scientific)), vortexed and incubated at 4° C. for 20 minutes.

Cleared lysate was mixed with HisPur™ nickel-nitrilo-acetic acid (Ni-NTA) Resin (Thermo Scientific) and rotated for 2 hours at 4° C. After removal of the lysate unbound fraction, the resin was washed twice with high salt buffer (250 mM NaCl, 50 mM Tris pH 8, 25 mM Imidazole) and twice with low salt buffer (50 mM NaCl, 50 mM Tris pH 8). Washed beads were harvested in low salt wash buffer and transferred to spin columns (Thermo Scientific). The bound fraction was eluted in 10% acetic acid and ultrafiltered over 3kD Nanosep Omega columns (Pall). The peptide fraction was subjected to liquid extraction by mixing 1:1 with water-saturated ethyl-acetate, extensive vortexing and removal of the organic phase. Subsequent solid phase extraction was performed on stage tips assembled with 2 layers Empore Styrene Divinylbenzene-Reversed Phase Sulphonate (SDB-RPS) matrix 47 mm disks (3M). The SDB-RPS membrane was activated with acetonitrile and equilibrated with SDB wash buffer (0.2% TFA, milli-Q, pH≤2) prior to sample loading. The SDB membrane was then washed twice prior to elution of the absorbed peptide fraction in elution buffer (80% acetonitrile (ACN), 1% NH3, milli-Q, pH≥10). Samples were transferred to HPLC-glass vials, vacuum-dried and stored at −20° C. prior to LC-MS/MS analysis.

Mass Spectrometry

Peptides were re-suspended in 10 ul Solvent A (3% ACN, 0.1% formic acid (FA), MQ) prior LC-MS/MS analysis. Each sample was analyzed on a Q Exactive HF (Thermo Fisher, Germany) connected to a Dionex nano-UHPLC system (Thermo Fisher Scientific) by injecting 8 μl from each sample vial. The UHPLC was equipped with a trap column (Acclaim PepMap 100, 75 μm×2 cm, nanoviper, C18, 3 μm, 100 Å; Thermo Fisher Scientific) and an analytical column (PepMap RSLC C18, 2 μm, 100 Å, 50 μm×50 cm; Thermo Fisher Scientific) heated to 50° C. MobileQ-phase buffers for nLC separation consisted of Solvent A and Solvent B (95% ACN, 0.1% FA, MQ). The peptides were eluted during a 30 min gradient and directly sprayed into the mass spectrometer. The flow rate was set to 400 nL/min, and the LC gradient was as follows: 2-5% solvent B within 5 min, 5-40% solvent B within 30 min, 40-47% solvent B within 5 min, 47-100% solvent B within 5 min and 100% B for κ min and 2% solvent B for 5 min. Nano spray was achieved with an applied voltage of 1.8 kV.

The mass spectrometer was programmed in a data☐dependent acquisition (DDA) mode (top 10 most intense peaks) and was configured to perform a Fourier transform survey scan from 400 to 1600 m/z (resolution 60,000 at 200 m/z), AGC target 1e6, maximum injection time 250 ms. MS2 scans were acquired on the 10 most-abundant MS1 ions of charge state 1-7 using a quadrupole isolation window of 1.2 m/z for HCD fragmentation and dynamic exclusion at 30 s.

Data Analysis

Raw MS files were searched using MaxQuant (version 1.5.6.5) against a peptide fasta-file including the peptides used in the experiment, supplemented with a list of common LC-MS/MS contaminants. Digestion specificity was set to unspecific and peptide variable modifications was set to allow Oxidation (M), the first search tolerance set to 20 ppm and the FDR was set to 1%.

EXAMPLES

Example 1: Deletion of an APX Gene Family by Targeted Mutagenesis

Herein describes how targeted mutagenesis of a family of antigen-presenting complex (APX) encoding genes was achieved to produce the first trait of an engineered antigen-presenting cell (eAPC). The said trait is the lack of surface expression of at least one member of the APX family.

In this example, the targeted APX comprised the three members of the major HLA class I family, HLA-A, HLA-B and HLA-C in the HEK293 cell line. HEK293 cells were derived from human embryonic kidney cells that showed endogenous surface expression of HLA-ABC. Cytogenetic analysis demonstrated that the cell line has a near triploid karyotype, therefore the HEK293 cells encoded three alleles of each HLA-A, HLA-B and HLA-C gene.

Targeted mutagenesis of the HLA-A, HLA-B and HLA-C genes was performed using an engineered CRISPR/Cas9 system, in which, Cas9 nuclease activity was targeted to the HLA-A, HLA-B and HLA-C loci by synthetic guide RNAs (gRNAs). 4 to 5 unique gRNAs were designed to target conserved nucleotide sequences for each HLA gene locus and the targeted sites were biased towards the start of the gene coding sequence as this was more likely to generate a null allele. The gRNAs efficiency to induce a mutation at their targeted loci was determined and the most efficient gRNAs were selected to generate the HLA-A, HLA-B and HLA-C null (HLA-ABC$^{null}$) HEK293 cell line.

Plasmid that encoded the optimal gRNAs targeting the HLA-A, HLA-B and HLA-C loci, together with a plasmid that encoded Cas9-P2 Å-GFP were transfected into HEK293 cells as described in the methods. Cells positive for Cas9-P2 Å-GFP plasmid uptake were FAC sorted based on GFP fluorescence, 2 days after transfection (FIG. 28a). The GFP sorted cells were further expanded for more than 5 days to allow sufficient time for gene editing events to occur, and in the case of a detrimental mutation, to lose expression of the residual endogenous HLAI protein. After this growth period, the cells were stained with a pan-HLA-ABC antibody, resulting in the identification of cells with reduced expressed HLA-ABC on their surface (FIG. 28b). The absence of pan-HLA-ABC antibody staining implied that each HLA-A, HLA-B and HLA-C allele was mutated. Individual HLA-ABC negative cells were sorted and expanded to represent a collection of monoclones.

HLA-ABC$^{null}$ monoclones were confirmed by lack of surface expression of HLA-ABC. It was demonstrated that a subset of monoclones lacked surface expression of HLA-ABC, of which three example monoclones, ACL-414, ACL-415 and ACL-416 are depicted in FIG. 29. Further genetic characterization of the monoclones that lacked HLAI surface expression was performed by determining that the cell lines possessed an underlying genetic mutation in all alleles of the HLA-A, HLA-B and HLA-C genes (FIG. 30). Genetic characterization was performed by PCR with primers that spanned the gRNA genomic target sites, for detection of amplicon size changes and/or were used as a template for sequencing. FIG. 30 shows a selection of HLA-ABC$^{null}$ monoclones that contained genetic deletion in the alleles of HLA-A, HLA-B and HLA-C genes detected by a shorter PCR amplicon compared to the amplicon size of the founding cell line (e.g. ACL-414).

In conclusion, the genetically modified HEK293 cell lines, including, ACL-414, ACL-415 and ACL-416, were demonstrated to lack surface expression of the HLA-ABC and therefore possessed the first trait of an engineered antigen-presenting cell (eAPC).

Example 2: Generation of an eAPC Containing Component B

Herein describes how Component B was stably integrated into the HLA-ABC$^{null}$ monoclone line ACL-414 to produce the second trait of an eAPC. The said second trait contained at least one genomic receiver site for integration of at least one ORF, wherein the genomic receiver site was a synthetic construct designed for recombinase mediated cassette exchange (RMCE).

In this example, the genomic integration site, component B, comprised of selected genetic elements. Two unique heterospecific recombinase sites, FRT and F3, which flanked an ORF that encoded the selection marker, blue fluorescent protein (BFP). Encoded 5' of the FRT site, was an EF1a promoter and 3' of the F3 site was a SV40 polyadenylation signal terminator. The benefit of positioning the non-coding cis-regulatory elements on the outside of the heterospecific recombinase sites was so they are not required in the matched genetic donor vector, component C. Therefore, after cellular delivery of the genetic donor vector, no transient expression of the encoded ORF would be observed. This made the selection of successful RMCE more reliable as the cellular expression of the ORF from the genetic donor vector would mostly likely occur only after correct integration into component B as it now contained the appropriate cis-regulator elements (see example 6).

To promote the stable genomic integration of component B into the genomic safe harbour locus, AAVS1, a plasmid was constructed, wherein; the DNA elements of component B were flanked with AAVS1 left and right homology arms. Each arm comprised of >500 bp of sequence homologous to the AAVS1 genomic locus.

Stable integration of component B was achieved through the process of homology directed recombination (HDR) at the genomic safe harbour locus, AAVS1. The ACL-414 cell line was transfected with plasmid that encoded the optimal gRNAs targeting the AAVS1 locus, plasmid that encoded Cas9-P2 Å-GFP and the plasmid that encoded component B genetic elements flanked by AAVS1 left and right homology arms. Cells positive for Cas9-P2 Å-GFP plasmid uptake were FAC sorted based on GFP fluorescence, 2 days after transfection (FIG. 31a). The GFP sorted cells were further expanded for greater than 7 days allowing sufficient time for HDR to occur and to lose transient expression of the selection marker, BFP. After this growth period, the cells were analysed on a FACS machine and individual BFP positive cells were sorted and expanded to represent a collection of monoclones (FIG. 31c).

Individual monoclone lines were selected as an eAPC on the basis of their maintained BFP expression and for a single integration of component B into the desired AAVS1 genomic location. Cell lines ACL-469 and ACL-470 represented monoclones with maintained BFP expression (FIGS. 32a and b). Genetic characterization was performed on DNA extracted from monoclones ACL-469 and ACL-470 and demonstrated that their genomes integrated component B, and that component B has been integrated into the AAVS1 site (FIG. 33). Confirmation of genomic integration was determined by the detection of a PCR amplicon of the expected size that utilized primers specific for the Component B (FIG. 33a). Confirmation that component B integrated into the AAVS1 site was determined by the detection of a PCR amplicon of the expected size that utilized primers designed against the AAVS1 genomic sequence distal to the region encoded by the homologous arms and a primer that is unique to the SV40 pA terminator encoded by component B (FIG. 33b). The copy-number of component B was determined by digital drop PCR, in which the number of component B and reference gene DNA molecules were measured and the ratio calculated (table 1). Monoclones ACL469 and ACL-470 contained a ratio of 1 component B molecule to 3 reference gene molecules. When factored in that the founding HEK293 cell line has a near triploid karyotype, this demonstrated a single integration of component B in ACL-469 and ACL470 cell lines.

In conclusion, the genetically modified ACL-469 and ACL-470 cell lines, were HLA-ABC$^{null}$ and contained a single copy of a synthetic genomic receiver site designed for RMCE and therefore demonstrated the creation of an eAPC with a single synthetic integration receiver site.

Example 3: Generation of an eAPC Containing Component B and Component D

Herein describes how Component B and Component D were stably integrated into the HLA-ABC$^{null}$ monoclone line ACL-414 to produce the second trait of an eAPC. The said second trait contains two genomic receiver sites for integration of at least one ORF, wherein the genomic receiver site was a synthetic construct designed for recombinase mediated cassette exchange (RMCE).

This example uses the same methods and components as described in example 2 but with the addition of a second genomic receiver site, Component D. Component D genetic elements comprised of two unique heterospecific recombinase sites, F14 and F15, which were different to component B. These sites flanked the ORF that encoded the selection marker, the red fluorescent protein (RFP). Encoded 5' of the F14 site was an EF1a promoter and 3' of the F15 site was a SV40 polyadenylation signal terminator. As in example 2, component D genetic elements were flanked with AAVS1 left and right homology arms, each comprised of >500 bp of sequence homologous to the AAVS1 genomic locus.

Component B and component D were integrated into the AAVS1 as described in example 2 but with the addition of the plasmid that encoded component D elements, to the transfection mix. Cells positive for Cas9-P2 Å-GFP plasmid uptake were FAC sorted based on GFP fluorescence, 2 days after transfection (FIG. 31a). The GFP sorted cells were further expanded for greater than 7 days, after which, the cells were analysed on a FACS machine and individual BFP and RFP positive cells were sorted and expanded to represents a collection of monoclones (FIG. 31b).

Individual monoclone lines were selected as an eAPC on the basis of their maintained BFP and RFP expression and for a single integration of component B and a single integration of component D into different AAVS1 alleles. Cell line ACL-472 was a representative monoclone with maintained BFP and RFP expression (FIG. 32c). As described in example 2, genetic characterization was performed on DNA extracted from monoclone ACL-472 and demonstrated that their genomes integrated component B and component D, and that both components integrated into the AAVS1 site (FIG. 33). The copy-number of both component B and D was determined by digital drop PCR, in which the number of component B, D and reference gene DNA molecules was measured and the ratio calculated. The monoclone ACL-472 contained a ratio of 2 component B and D molecules to 3 reference gene molecules (Table 2). When factored in that the founding HEK293 cell line has a near triploid karyotype, this demonstrated a single integration of component B and a single integration of component D into the ACL-472 cell line.

In conclusion, the genetically modified ACL-472 cell line, was HLA-ABC$^{null}$ and contained a single copies of the synthetic genomic receiver site component B and component D, designed for RMCE and therefore demonstrated the creation of an eAPC with two unique synthetic integration receiver sites.

Example 4: An eAPC-p Constructed in One Step with One Integration Couple Wherein Component C' Encoded a Single HLAI ORF Herein describes how an eAPC-p was constructed in one step with one integration couple, wherein, the genomic receiver site, component B, is a native genomic site and the genetic donor vector, component C', comprised a single ORF that encoded one analyte antigen-presenting complex (aAPX).

In this example, the eAPC was a genetically modified ARH-77 cell line, designated ACL-128, wherein, two families of APX, major HLA class I family and HLA class II, were mutated. The founding cell line, ARH-77, is a B lymphoblast derived from a plasma cell leukemia that showed strong HLA-A,B,C and HLA-DR,DP,DQ cell surface expression. Cytogenetic analysis demonstrated that the founding ARH-77 cell line has a near diploid karyotype, but also displayed a chromosome 6p21 deletion, the region encoding the HLA locus. DNA sequencing of the ARH-77 locus confirmed that ARH-77 encoded only a single allele of HLA-A, HLA-B and HLA-C and HLA-DRA, HLA-DRB, HLA-DQA, HLA-DQB, HLA-DPA and HLA-DPB gene families.

The HLA-ABC$^{null}$ and HLA-DR,DP,DQ$^{null}$ cell line ACL-128, was generated by CRISPR/cas9 targeted mutagenesis with gRNA targeting the HLA-A, HLA-B and HLA-C and HLA-DRA, HLA-DRB, HLA-DQA, HLA-DQB, HLA-DPA and HLA-DPB gene families using the method described in Example 1. Surface labeling with a pan-anti-HLA-ABC or pan-anti-HLA-DR,DP,DQ confirmed that ACL-128 lacked surface expression of both APX families, FIGS. 34b and 35 and FIG. 37b, respectively.

In this example, the genomic receiver site, component B, was the native AAVS1 genomic site, and the targeted integration was achieved through HDR. The genetic donor vector, component C, was matched to component B, by component C encoding the AAVS1 left and right homology arms, each comprised of >500 bp of sequence homologous to the AAVS1 genomic locus. Between the AAVS1 left and right homology arms, the plasmid encoded a CMV promoter and a SV40 terminator. The aAPX of interest was cloned between the promoter and the terminator, generating component C'. In this example, component C' comprised a single ORF that encoded one aAPX, the HLA-A*24:02 or HLA-B*-07:02, denoted component C'$^{HLA-A*24:02}$ and component C'$^{HLA-B*-07:02}$ respectively.

The process to construct an eAPC-p was via HDR induced integration of component C' into component B to produce component B'. The cell line ACL-128 was electroporated with plasmids that encoded the optimal gRNAs targeting the AAVS1 loci, Cas9-P2A-GFP and component C'. Cells positive for Cas9-P2A-GFP plasmid uptake were FAC sorted based on GFP fluorescence, 2 days after electroporation (FIG. 34a). The GFP sorted cells were further expanded for greater than 7 days allowing sufficient time for HDR to occur and lose transient expression of the aAPX. After this growth period, the cells were stained with a pan-HLA-ABC antibody, resulting in the identification of cells that gained expression of an analyte HLA on their surface (FIG. 34b). The presence of pan-HLA-ABC antibody staining implied that the analyte HLA ORF encoded in component C' had integrated into the genome. Individual HLA-ABC positive stained cells were sorted and expanded to represent a collection of eAPC-p monoclones.

Individual monoclone lines were selected as an eAPC-p on the basis of their maintained analyte HLA surface expression and the integration of the analyte ORF into the genomic receiver site, creating component B'. Cell lines ACL-321 and ACL-331 were representative monoclones with maintained analyte HLA surface expression of HLA-A*24:02 or HLA-B*-07:02 respectively (FIG. 35). Genetic characterization was performed on DNA extracted from selected monoclones ACL-321, ACL-327, ACL-331 and ACL-332 and demonstrated that their genomes integrated component C', and that the integration occurred in the AAVS1 genomic receiver site, generating component B' (FIG. 36). Confirmation of genomic integration was determined by the detection of a PCR amplicon of the expected size using primers specific to the Component C' (FIG. 36a). Presence of component B' was confirmed by the detection of a PCR amplicon of the expected size using primers designed against the AAVS1 genomic sequence distal to region encoded by the homologous arms and a primer unique to the SV40 pA terminator linked to the analyte HLA ORF (FIG. 36b).

In conclusion, the generation of the genetically modified ACL-321 and ACL-331 cell lines, which contained a copy of the aAPX HLA-A*24:02 or HLA-B*-07:02 ORF, respectively, within the genomic receiver site, component B', resulted in the said analyte aAPX to be the only major HLA class I member expressed on the cell surface. Therefore, this demonstrated the creation of two defined eAPC-p cell lines using the multicomponent system.

Example 5: An eAPC-p Constructed in One Step with One Integration Couple, Wherein Component C' Encoded a Paired HLAII ORF Herein describes how an eAPC-p was constructed in one step with one integration couple, wherein, the genomic receiver site, component B, was a native genomic site and the genetic donor vector, component C' comprised a single ORF that encoded two aAPX chains.

This example used eAPC, ACL-128, and component B, both of which are defined in example 4. However component C' comprised a single ORF that encoded an HLADRA*01:01 allele linked to an HLA-DRB1*01:01 allele by a viral self-cleaving peptide element, or HLA-DPA1*01:03 allele linked to an HLA-DPB1*04:01 allele by a viral self-cleaving peptide element, denoted component $C'^{HLA-DRA*01:01/HLA-DRB1*01:01}$ and component $C'^{HLA-DPA1*01:03/HLA-DPB1*04:01}$ respectively. The viral self-cleaving peptide element encoded a peptide sequence, that when transcribed resulted in self-cleavage of the synthesized peptide and produced two polypeptides defining each HLA chain.

Within example 4, described the process to construct an eAPC-p with the exception that identification of cells that gained expression of an analyte HLA on their surface were assessed by cell surface labelling with a pan-anti-HLA-DR, DP,DQ antibody (FIG. 37). The presence of pan-anti-HLA-DR,DP,DQ antibody staining implied that the analyte HLA ORF encoded in component C' had integrated into the genome. Individual HLA-DR,DP,DQ positive stained cells were sorted and expanded to represent a collection of eAPC-p monoclones.

Figure 38:
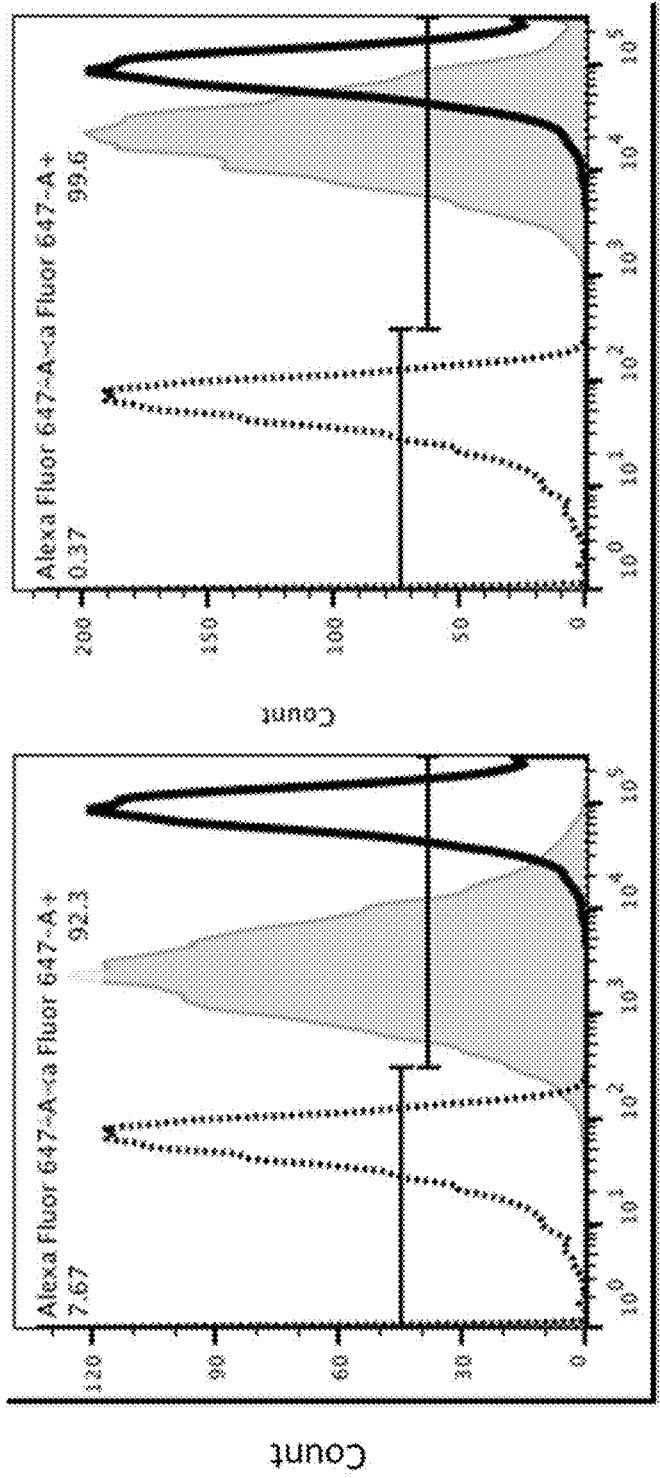

Individual monoclone lines were selected as an eAPC-p on the basis of their maintained analyte HLA surface expression and the integration of the analyte ORF into the genomic receiver site, creating component B' as described in example 4. Cell lines ACL-341 and ACL-350 were the representative monoclones with maintained analyte HLA surface expression of HLA-DRA*01:01/HLA-DRB1*01:01 or HLA-DPA1*01:03/HLA-DPB1*04:01 (FIG. 38).

In conclusion, the generation of the genetically modified ACL-341 and ACL-350 cell lines, which contained a copy of the aAPX HLA-DRA*01:01/HLA-DRB1*01:01 or HLA-DPA1*01:03/HLA-DPB1*04:01 ORF, respectively, within the genomic receiver site, component B', resulted in the said analyte aAPX to be the only major HLA class II member expressed on the cell surface. Therefore, this demonstrated the creation of two defined eAPC-p cell lines using the multicomponent system.

Example 6: An eAPC-p Constructed in One Step with One Integration Couple Wherein Component B was a Synthetic Construct Herein describes how an eAPC-p was constructed in one step with one integration couple, wherein, the genomic receiver site, component B, was a synthetic construct designed for RMCE genomic site and the genetic donor vector, component C' comprised a single ORF that encoded one aAPX.

In this example, the genomic integration site, component B, comprised of selected genetic elements. Two unique heterospecific recombinase sites, FRT and F3, which flanked the ORF that encoded the selection marker, blue fluorescent protein (BFP). Encoded 5' of the FRT site, was an EF1a promoter and 3' of the F3 site was a SV40 polyadenylation signal terminator. The genetic elements of component B, were integrated in the cell line ACL-128 by electroporation with the same plasmids as described in example 2. Individual monoclone lines were selected on the basis of their maintained BFP expression and were genetically characterised to contain a single integration of component B into the desired AAVS1 genomic location as described in example 2

(FIG. 39a). The resulting eAPC cell line, ACL-385, was HLA-ABC$^{null}$ and HLA-DR,DP,DQ$^{null}$ and contained a single copy of a synthetic genomic receiver site, component B, designed for RMCE The genetic donor vector, component C was matched to component B, as component C encoded the same heterospecific recombinase sites, FRT and F3. The aAPX ORF of interest, additionally encoded a kozak sequence just before the start codon, was cloned between the two heterospecific recombinase sites, and generated component C'. In this example, component C' comprised a single ORF that encoded one aAPX, the HLA-A*02:01, designated component $C'^{FRT:HLA-A*02:01:F3}$.

An eAPC-p was created through RMCE by electroporation of the cell line ACL-385 with plasmid that encoded the Tyr-recombinase, Flp, together with component $C'^{FRT:HLA-A*02:01:F3}$. 4-10 days after electroporation, individual cells positive for HLAI surface expression and negative/reduced for the fluorescent protein marker, BFP, encoded by component B selection marker, were sorted. Individual outgrown monoclone lines were selected on the basis of their maintained HLAI allele expression and loss of BFP florescence, which indicated that the expected RMCE occurred. To identify such monoclones, both phenotypic and genetic tests were performed. Firstly, all monoclone cell lines were screened for cell surface HLA-ABC expression and lack of BFP florescence (FIG. 39). Genomic DNA was extracted from such cell lines, e.g. ACL-421 and ACL422, and the integration of component C' into component B that generated component B' was confirmed by the detection of a PCR product specific to component B' (FIG. 40).

In conclusion, the generation of the genetically modified ACL-421 and ACL-422 cell lines, which contained a copy of the aAPX HLA-A*02:01 ORF, respectively, within the synthetic genomic receiver site, component B', resulted in the said analyte aAPX to be the only major HLA class I member expressed on the cell surface. Therefore, this demonstrated the creation of two defined eAPC-p cell lines using the multicomponent system.

Example 7: An eAPC-pa Constructed in Two Steps with Two Integration Couples

Herein describes how an eAPC-pa was constructed in two steps. Step 1, wherein the genomic receiver site, component B, was the native genomic site and the genetic donor vector, component C' comprised a single ORF that encoded one aAPX. Step 2 the genomic receiver site, component D, was a second native genomic site and the genetic donor vector, component E' comprised a single ORF that encoded one analyte antigen molecule (aAM).

In this example, step 1 was performed, wherein, the eAPC was ACL-128, the genomic receiver site, component B, was the mutated HLA-A allele genomic site, designated HLA-A$^{null}$, and the targeted integration was achieved through HDR. The genetic donor vector, component C was matched to component B, by the component C encoding the HLA-A$^{null}$ left and right homology arms, each comprised of >500 bp of sequence homologous to the HLA-A$^{null}$ genomic locus. Between the HLA-A$^{null}$ left and right homology arms, the plasmid encoded a CMV promoter and SV40 terminator. The aAPX of interest was cloned between the promoter and terminator, generating component C'. In this example, component C' comprised a single ORF that encoded one aAPX, the HLA-A*02:01 or HLA-B*-35:01, denoted component $C'^{HLA-A*02:01}$ component $C'^{HLA-B*-35:01}$ respectively.

The integration of component C' into component B, and selection of monoclone eAPC-p cell lines was as described in example 4, with the exception that a gRNA targeting the HLA-A$^{null}$ genomic locus was used to promote HDR integration of component C' into component B. Monoclone eAPC-p ACL-191 and ACL-286 expressed HLA-A*02:01 or HLA-B*-35:01 on the cell surface, respectively (FIG. 41a).

In this example, step 2 was performed, wherein, the genomic receiver site, component D, was the native AAVS1 genomic site, and the targeted integration was achieved through HDR. The genetic donor vector, component E was matched to component D, by the component E that encoded the AAVS1 left and right homology arms, each comprised of >500 bp of sequence homologous to the AAVS1 genomic locus. Between the AAVS1 left and right homology arms, the plasmid encoded a CMV promoter and SV40 terminator. The aAM of interest was cloned between the promoter and terminator, generating Component E'. In this example, component E' comprised a single ORF that encoded the selection marker, GFP, linked to the aAM ORF, encoding hCMV-pp65, denoted component E'$^{GFP:2A:pp63}$. The viral self-cleaving peptide element encoded a peptide sequence, that when transcribed resulted in self-cleavage of the synthesized peptide and produced two polypeptides, GFP and the intracellular hCMV-pp65 protein.

The integration of component E' into component D, was as described in example 4. Individual monoclone lines, ACL-391 and ACL-395, were selected as an eAPC-pa on the basis of their maintained selection marker GFP expression (FIG. 41b).

In conclusion, the genetically modified ACL-391 and ACL-395 cell lines, which contained a copy of the aAPX HLA-A*02:01 or HLA-B*-35:01 ORF, respectively, within the genomic receiver site, component B', and aAM ORF pp65 within the genomic receiver site component D' were generated. These genetic modifications resulted in the said aAPX to be the only major HLA class I member expressed on the cell surface of a cell that also expressed the said aAM. Therefore, this demonstrated the creation of two defined eAPC-pa cell lines using the multicomponent system.

Example 8: An eACP-p Constructed in One Step Wherein Component C' Encoded a Single HLAI ORF Herein describes the conversion of an eAPC to an eAPC-p in one step, via a single integration couple event, to integrate a single HLAI ORF encoding analyte antigen-presenting complex (aAPX), and wherein the eAPC contains two synthetic genomic receiver sites Component B and Component D designed for RMCE based genomic integration. The created eAPC-p has one genomic receiver site occupied by the HLAI ORF (Component B'), while the remaining Component D is available for an additional integration couple event (FIG. 6).

This example used the eAPC generated in example 3 (ACL-402) containing Components B and D, wherein Component B comprises two unique heterospecific recombinase sites, F14 and F15, which flank the ORF that encodes the selection marker, red fluorescent protein (RFP). Encoded 5' of the F14 site is an EF1a promoter and 3' of the F15 site is a SV40 polyadenylation signal terminator. Component D comprises of two unique heterospecific recombinase sites, FRT and F3, flanking the ORF that encodes the selection marker, blue fluorescent protein (BFP). Encoded 5' of the FRT site, is an EF1a promoter and 3' of the F15 site is a SV40 polyadenylation signal terminator.

This example utilizes a Component C genetic donor vector, comprising of heterospecific recombinase sites, F14 and F15 and thus is matched to Component B. Two independent Component C' were generated from Component C, wherein one vector (V4.H.5) comprises of a Kozak sequence, start codon and aAPX ORF encoding HLA-A*02:01 between the F14/F15 sites, and wherein the second vector (V4.H.6) comprises a Kozak sequence, start codon and aAPX ORF encoding HLA-A*24:02 between the F14/F15 sites.

The eAPC (ACL-402) was independently combined with vector encoding expression of the RMCE recombinase enzyme (Flp, V4.1.8) and each Component C' of either V4.H.5 or V4.H.6 by electroporation. Cells were cultured for 4-10 days, whereupon cells were selected and sorted based on loss of the selection marker of integration, RFP, and gain of HLAI on the surface of the cell. Subsequently, individual outgrown monoclone lines were characterized, confirmed and selected on the basis of the gain of HLAI surface expression and the loss of the RFP fluorescence, which indicated that the expected conversion of Component B to B' had occurred. Selected eAPC-p monoclones ACL-900 (V4.H.5, HLA-A*02:01) and ACL-963 (V4.H.6, HLA-A*24:02) are negative for RFP compared to the parental ACL-402 cell line and maintain HLAI surface expression (FIG. 43a). Furthermore, both monoclones retain expression of the BFP selection marker of integration, indicating that Component D remains uncoupled and isolated from Component B integration couple events. To further characterize the eAPC-p monoclones, genomic DNA was extracted from the cells, and confirmation of the integration couple between Component C' and Component B, generating Component B', was conducted by detection of a PCR product specific to Component B' (FIG. 43b, Table 5 lists primers used for genotyping). The primers were designed to target a region adjacent to the genomic receiver site (primer ID 8.B.3), and a region within the integration couple event (primer ID 15.H.2). Amplification occurred only in cases of specific integration, while no product was generated from the control (ACL-3) or from off-target recombination.

In summary, this example demonstrates two specific examples of conversion of an eAPC to an eAPC-p, using the multicomponent system, wherein two different aAPX are individually delivered (Component C') and integrated into a single genomic receiver site (Component B) by RMCE genomic integration method, subsequently creating a limited library comprising two discrete eAPC-p. Furthermore, it was demonstrated that second genomic receiver site (Component D) was insulated and unaffected by the Component B/Component C' integration couple.

Example 9: An eAPC-Pa Constructed from eAPC-p in One Step, Wherein Component D' Encodes a Single Analyte Antigen Molecule (aAM) ORF The present example describes how multiple eAPC-pa are constructed from a parental eAPC-p (described in example 8) in parallel, wherein the genomic receiver site, Component D, is targeted for integration by a primed genetic donor vector, Component E', comprising of a single ORF that encodes an aAM.

In the present example, the parental eAPC-p line used was ACL-900, which expresses a single aAPX (HLA-A*02:01) that is integrated at Component B' (described in example 8). The eAPC-p Component D remains open and comprises of two unique heterospecific recombinase sites, FRT and F3, which flank the ORF that encodes the selection marker, blue fluorescent protein (BFP). Encoded 5' of the FRT site, is an EF1a promoter, and 3' of the F15 site is a SV40 polyadenylation signal terminator. The genetic donor vector, Component E was used in this example and comprises of two heterospecific recombinase sites, F14 and F15, thus being matched to Component D. In this example, the Component E was further primed with one aAM ORF of interest selected from HCMVpp28 (V9.E.6), HCMVpp52 (V9.E.7), or HCMVpp65 (V9.E.8), which also each encode a C-terminal c-myc tag. Furthermore, each Component E' further comprises of Kozak sequence and start codon immediately 5' of the aAM ORF. Thus, a small discrete library of Component E' was created, comprising of three vectors.

The eAPC-p (ACL-900, example 8) was independently combined with a vector encoding expression of the RMCE recombinase enzyme (Flp, V4.1.8) and each Component E' of either V9.E.6, V9.E.7, or V9.E.8 by electroporation. Cells were incubated for 4-10 days to allow for the integration couple to occur, whereupon, individual eAPC-pa were selected and single cell sorted (monoclones) based on diminished signal of the selection marker of integration BFP, encoded by Component D (FIG. 44a). Subsequently, the individual outgrown monoclone eAPC-pa, ACL-1219 (pp28), ACL-1227 (pp52) and ACL-1233 (pp65), were characterized, confirmed and selected on the basis of the loss of BFP expression and maintained surface expression of HLAI (aAPX at Component B') (FIG. 44b), which indicated that the expected conversion of Component D to D' had occurred. Furthermore, the maintained surface expression of the aAPX indicated that Component B' was unaffected and isolated from the integration couple event between Component D and Component E'. To further characterize the selected eAPC-pa monoclones, genomic DNA was extracted, and confirmation of the integration couple between Component E' and Component D, generating Component D' was conducted by detection of a polymerase chain reaction (PCR) amplicon product specific to Component D'. In FIG. 44c two monoclones representing each of the three eAPC-pa are shown wherein amplicon products of the expected size for aAM ORF pp28 (0.8 kb), pp52 (1.5 kb) and pp65 (1.9 kb) are observed, further confirming that the expected integration event has occurred.

In summary, this example demonstrates three specific examples of conversion of an eAPC-p to an eAPC-pa, using the multicomponent system, wherein three different aAM are individually delivered (Component E') and integrated into a single genomic receiver site (Component D) by RMCE genomic integration method, subsequently creating a small library of three discrete eAPC-pa carrying three different aAM ORF. Furthermore, it was demonstrated that the loaded second genomic receiver site (Component B') was insulated and unaffected by the Component D/Component E' integration couple.

Example 10: Shotgun Integration of Multiple Analyte Antigen Molecule ORF into eAPC-p to Create a Pooled eAPC-Pa Library in a Single Step Herein describes how a pool of primed Component E vectors (Component E') collectively encoding multiple aAM ORF (HCMVpp28, HCMVpp52 and HCMVpp65) were integrated in a single step into the parental eAPC-p (described in example 8) to create a pooled eAPC-pa library, wherein each individual cell integrates a single random analyte antigen ORF derived from the original pool of vectors, at Component D', such that each eAPC-pa expresses a single random aAM, but collectively the pooled library of eAPC-pa represents all of aAM ORF encoded in the original pooled library of vectors. This method of creating a pool of eAPC-pa each expressing a single random ORF from a pool of vectors is referred to as shotgun integration.

In this example, the parental eAPC-p line used was ACL-905 expressing an aAPX (HLA-A*02:01) on the cell surface (the construction of the cell line is described in example 8), Component D and Component E' were as described in example 9. In this example, the individual Component E' vectors of example 9, V9.E.6, V9.E.7, and V9.E.8, comprising of aAM ORFs encoding HCMVpp28, HCMVpp52 and HCMVpp65, respectively, were mixed together in a 1:1:1 molar ratio to create a vector pool. The eAPC-p (ACL-905) was combined with the vector pool and a vector encoding expression of the RMCE recombinase enzyme (Flp, V4.1.8) by electroporation. Cells were incubated for 4-10 days, whereupon, cells were bulk sorted on the basis of having diminished signal for the selection marker of integration, BFP, encoded by Component D (FIG. 45a) generating the pooled cell population ACL-1050 (FIG. 45b).

To confirm that the eAPC-pa pool ACL-1050 was comprised of a mixture of eAPC-pa each encoding one of HCMVpp28, HCMVpp52 or HCMVpp65 at Component D', individual cells were single cell sorted from the polyclonal population and 12 were selected at random for genetic characterisation. Amplification of the Component D' was conducted using primers that span each aAM (table 5, FIG. 45c). In FIG. 45c, the amplicons generated for the 12 cells are presented, with controls, wherein for all 12 cells a single amplicon product consistent with the expected size for one of the aAM ORF, pp28 (0.8 kb), pp52 (1.5 kb) and pp65 (1.9 kb) is observed. Furthermore, each aAM ORF is identified at least once indicating that the eAPC-pa pool is comprised of a mixture eAPC-pa wherein each eAPC-pa in the pool has integrated a single random aAM ORF from the original pool of three vectors.

In conclusion, this example demonstrates the use of the multicomponent system for conversion of an eAPC-p into a pooled library of eAPC-pa in a single step, by combining the eAPC-p with a pooled library of three vectors encoding three different analyte antigen molecules (Component E') and utilizing a RMCE based shotgun integration approach. Furthermore, this example demonstrates that each eAPC-pa within the generated pool of eAPC-pa has integrated a single random aAM ORF from the original vector pool by an integration couple event between Component D and Component E', and that all three aAM ORF are represented within the generated pooled eAPC-pa library.

Example 11: Demonstration of Two eAPC:T Systems for eAPC-Pa Induced Antigen-Specific Outgrowth of Primary CD8 Cells The present example describes the compilation and use of two different eAPC:T systems, wherein the first system is comprised of an eAPC-p, an exogenously provided aAM (to create an aAPX: aAM presented by the eAPC-p), and analyte primary T-cells (analyte TC). The second system is comprised of an eAPC-pa presenting an aAPX: aAM, and analyte primary T-cells (analyte TC). The eAPC:T systems were used to identify and select analyte TC bearing a TCR that enables a response to analyte antigen (aAPX:aAM), via detection of proliferation and outgrowth of specific analyte TC.

In this example, an induced outgrowth of antigen-specific CD8+ T cells from a CD8+ T cell population was monitored, wherein the aAPX is HLA-A*02:01 (HLA class I) and the aAM is peptide NLVPMVATV. In the system comprised of eAPC-p the aAM is provided exogeneously, and in the system comprised of the eAPC-pa the aAM is natively processed from the integrated analyte antigen ORF (HCMVpp65). The cell line used are eAPC-p (ACL-191) and eAPC-pa (ACL-390), being described in examples 8 and 9, respectively. The analyte TC, CD8+ T cells, were isolated from a healthy blood donor that was known to have CD8+ T cells specific for the NLVPMVATV peptide as described in materials and methods.

In the first eAPC:T system, the eAPC-p (ACL-191) were pulsed with an exogenous NLVPMVATV (SEQ ID NO: 3) peptide at a peptide concentration of 1 µM for 4 hours as described in materials and methods. The eAPC:T system was then compiled by combing the pulsed eAPC-p cells with analyte TC (bulk sorted CD8+ T cells), and co-cultured under standard conditions. After 9 days of co-culture the cells were analysed for cells that formed co-operative complexes between analyte antigen and analyte TCR, by specific staining with CMV-A.0201-NLVP tetramer (aAPX:aAM as a soluble reagent) to detect outgrowth of antigen-specific T-cells by flow cytometry. Comparison was made to eAPC:T systems comprising unpulsed ACL-191 cells (no aAM), or pulsed HLA null ACL-128 (no aAPX) cells or unpulsed HLA null ACL-128 cells (no aAPX:aAM). Significant outgrowth of analyte TC (CD8+ T cells) that are confirmed specific for the NLVPMVATV (SEQ ID NO: 3) peptide by HLA-A*02:01-NLVP tetramer staining are only observed in the eAPC:T system comprising eAPC-p cells pulsed with NLVPMVATV (FIG. 46 *a*).

The second eAPC:T system was compiled by combining the eAPC-pa (ACL-390) cells with the analyte TC (bulk sorted CD8+ T cells) and co-cultured under standard conditions (see material and methods). As with the first system, co-cultured cells were harvested and analysed for cells that were induced by analyte antigen and analyte TCR, by specific staining with CMV-A.0201-NLVP tetramer (aAPX: aAM as a soluble reagent). FIG. 46*b* demonstrates antigen-specific outgrowth of primary CD8+ T cells co-cultured with eAPC-pa (ACL-390) cells with stable expression of the pp65 ORF (aAM) and aAPX (HLA-A*02:01), and thus present an aAPX:aAM. Comparison was made to two other eAPC:T systems with eAPC-p (ACL-191) cells without stable expression of the pp65 ORF and to HLA null ACL-128 cells. Outgrowth of CD8+ T cells specific for the aAPX:aAM present by eAPC-pa were identified by CMV-A.0201-NLVP tetramer staining only in the eAPC:T system with eAPC-pa (ACL-390)

In summary, this example demonstrated use of eAPC-p and eAPC-pa cells in compiled eAPC-T systems that can selectively outgrow analyte TC (CD8+ T-cells) for identification and selection of analyte TC bearing analyte TCR enable T-cell stimulation by the presented analyte antigen (aAPX:aAM). Furthermore, the two eAPC:T systems demonstrated the use of different forms of aAPX:aAM wherein one system the aAM is provided exogenously and in the second system the aAM is provided from the expressed integrated analyte antigen ORF of eAPC-pa through processing by the native cellular machinery.

Example 12: Demonstration of an eAPC:T System for eAPC-Pa Induced Antigen-Specific Outgrowth of Primary CD4 Cells The present example describes the compilation and use of an eAPC:T systems, wherein the system is comprised of an eAPC-p, an exogenously provided aAM (to create an aAPX: aAM presented by the eAPC-p), and analyte primary T-cells (analyte TC). The eAPC:T system was used to identify and select analyte TC bearing a TCR that enables a response to analyte antigen (aAPX:aAM) and analyte TCR by detection of proliferation and outgrowth of specific analyte TC.

In this example, an induced outgrowth of antigen-specific CD4+ T cells from a CD4+ T cell population by a specific aAPX:AM, wherein the aAPX is HLA-DRB1*01:01 (HLA class II) and the aAM is peptide PKYVKQNTLKLAT (SEQ ID NO: 1), provided exogenously. The cell line used was eAPC-p (ACL-341) constructed in a similar manner as described in examples 8 and 9. The analyte TC, CD4+ T cells, were isolated from a healthy blood donor that was known to have CD4+ T cells specific for the PKYVKQNTLKLAT peptide as described in materials and methods section.

In this example, the eAPC-p (ACL-341) were pulsed with an exogenous PKYVKQNTLKLAT (SEQ ID NO: 1) peptide at a peptide concentration of 1 µM for 2 hours as described in materials and methods section. The eAPC:T system was compiled by combing the pulsed eAPC-p cells with the analyte TC (bulk sorted CD4+ T cells), and co-cultured under standard conditions. After 7 days of co-culture the cells were analyzed for cells that were induced by the presented aAPX:aAM, by specific staining with INFL-DRB1*01:01-PKYV tetramer (aAPX:aAM as a soluble reagent) to detect outgrowth of antigen-specific T-cells by flow cytometry. Comparison was made to an eAPC:T system comprising unpulsed ACL-341 cells (aAPX:CM). Significant outgrowth of analyte TC (CD4+ T cells) that are confirmed specific for the PKYVKQNTLKLAT (SEQ ID NO: 1) peptide by CMV-A.0201-NLVP tetramer staining are only observed in the eAPC:T system comprising eAPC-p cells pulsed with PKYVKQNTLKLAT (FIG. 47)

In conclusion, this example demonstrated use of eAPC-p of HLA class II basis compiled into eAPC:T systems that can selectively outgrow analyte TC (CD4+ T-cells) for identification and selection of analyte TC bearing analyte TCR that form co-operative complexes with the presented analyte antigen (aAPX:aAM).

Example 13: Demonstration of an eAPC:T for eAPC-Pa Induced Antigen-Specific Cytotoxic Action by Co-Cultured Primary CD8 Cells The present example describes the compilation and use of two different eAPC:T systems, wherein the first system is comprised of an eAPC-p, an exogenously provided aAM (to create an aAPX: aAM presented by the eAPC-p), and analyte primary T-cells (analyte TC). The second system is comprised of an eAPC-pa presenting an aAPX: aAM, and analyte primary T-cells (analyte TC). The eAPC:T systems were used to confirm specificity of analyte TC for presented analyte antigen (aAPX:aAM) by detection of cytotoxic action against the eAPC-p or -pa by analyte TC.

In this example, cytotoxic action of antigen-specific CD8+ T cells from a CD8+ T cell population forming co-operative complexes between the analyte TCR and aAPX:AM is demonstrated, wherein the aAPX is HLA-A*02:01 (HLA class I) and the aAM is peptide NLVPMVATV (SEQ ID NO: 3). In the system comprised of eAPC-p the aAM is provide exogenously, and in the system comprised of the eAPC-pa the aAM is natively processed from the integrated analyte antigen ORF (HCMVpp65). The cell lines used are eAPC-p (ACL-191) and eAPC-pa (ACL-390) described in examples 8 and 9. The analyte TC, CD8+ T cells, were isolated from a healthy blood donor that was known to have CD8+ T cells specific for the NLVPMVATV peptide as described in materials and methods section.

In the first eAPC:T system, the eAPC-p (ACL-191) were pulsed with an exogenous NLVPMVATV peptide at a peptide concentration of 1 μM for 2 hours as described in materials and methods section. The eAPC:T system was then compiled by combing the pulsed eAPC-p cells with the analyte TC (bulk sorted CD8+ T cells), and co-cultured under standard conditions. Co-culture the cells were analysed for co-operative complexes between analyte antigen and analyte TCR, by assessing the killing of eAPC-p cells by AnnexinV and PI staining and flow cytometry. Comparison was made to eAPC:T systems comprising pulsed HLA null ACL-128 cells (no aAPX) or unpulsed HLA null ACL-128 cells (no aAPX:aAM). Significant cytotoxic action by the analyte TC (CD8+ T cells) is confirmed only in the eAPC:T system comprising eAPC-p cells pulsed with NLVPMVATV (FIG. 48 a).

The second eAPC:T system was compiled by combining the eAPC-pa (ACL-390) cells with the analyte TC (bulk sorted CD8+ T cells), and co-cultured under standard conditions. As with the first system, co-cultured cells were harvested and analysed for co-operative complexes between analyte antigen and analyte TCR, by assessing the killing of eAPC-pa cells by AnnexinV and PI staining and flow cytometry. FIG. 48b demonstrates antigen-specific cytotoxic action of primary CD8+ T cells co-cultured with eAPC-pa (ACL-390) cells with stable expression of the pp65 ORF (aAM, Component D') and aAPX (HLA-A*02:01, Component B'), and thus presenting an aAPX:aAM. Comparison was made to two other eAPC:T systems with eAPC-p (ACL-191) cells without stable expression of the pp65 ORF (no aAM) and to HLA null ACL-128 cells (no aAPX:aAM). Antigen-specific cytotoxic action of CD8+ T cells specific for the aAPX:aAM present by eAPC-pa was observed only in the eAPC:T system with eAPC-pa (ACL-390).

In conclusion, this example demonstrated use of eAPC-p and eAPC-pa cells in compiled eAPC-T systems that can selectively induce cytotoxic action by analyte TC (CD8+ T-cells) for identification and selection of analyte TC bearing analyte TCR that form cooperative complexes with the presented analyte antigen (aAPX:aAM). Furthermore, the two eAPC:T systems demonstrated the use of different forms of aAPX:aAM wherein one system the aAM is provided exogenously and in the second system the aAM is provided from the expressed integrated analyte antigen ORF of eAPC-pa through processing by the native cellular machinery.

Example 14: Identification of aAM Loaded into eAPC-p Via Mass Spectrometry

The present example describes the use of eAPC-p administered with exogeneous analyte antigen molecules (aAM), wherein the aAPX:aAM complexes are subsequently capture by metal affinity chromatography and the aAM cargo identified by mass-spectrometry. Thereby identifying the aAPX:aAM context of the aAM, i.e. HLA-restricted presentation of antigenic peptides.

This example uses eAPC-p cell lines from example 8, wherein the eAPC-p have an integrated aAPX at Component B', ACL-900 (HLA-A*02:01) and ACL-963 (HLA-A*24:02). The aAPX ORF also encoded a C-terminal 6xHistidine tag for capture by metal affinity chromatography. The eAPC-p were combined with an exogenous aAM, being pulsed for 2 hours at a concentration of 1 μM, wherein four discrete pulses were conducted, consisting of one of the following aAM as peptides; NLVPMVATV (APD-2, SEQ ID NO: 3), NLGPMAAGV (APD-21, SEQ ID NO: 4), or VYALPLKML (APD-11, SEQ ID NO: 5), or no peptide.

After pulsing eAPC-p were harvested, lysed and the aAPX:aAM were subsequently captured by metal affinity chromatopraphy as described in the material and methods. Once captured peptides (aAM and CM), were isolated from the aAPX but acid washing and filtration. Subsequently, the peptide fraction was subjected to liquid extraction and removal of the organic phase, followed by solid phase extraction and submission to mass spectrometry for identification of the peptide fraction.

FIG. 49 presents a table summarizing mass spectrometry results of the different eAPC-p/aAM pulsing combinations. The results identify that the peptide NLVPMVATV binds and forms a complex with aAPX HLA-A*02:01, and VYALPLKML complexes with aAPX HLA-A*24:01, whereas all other combinations of aAPX:aAM indicated that no detectable aAPX:aM complex was formed. These results are in accordance with the known peptide-HLA binding affinities of the three peptides.

In conclusion, this example demonstrated that eAPC-p can be used to identify the selective binding of aAM to aAPX by capture of the aAPX:aAM and subsequent release and enrichment of aAM for identification by mass spectrometry. This therefore demonstrates that eAPC-p can be used to determine the HLA-restricted presentation of analyte antigenic molecules.

SEQUENCE LISTING

```
<110> Genovie AB

<120> An Engineered Multi-component System for
      Identification and Characterisation of
      T-cellreceptors and T-cell antigens

<130> P018243PCT1

<160> 72

<170> BiSSAP 1.3

<210> 1
<223> Analyte Antigenic Molecule

<210> 2
<223> Analyte Antigenic Molecule

<210> 3
<223> Analyte Antigenic Molecule, APD-2

<210> 4
<223> Analyte Antigenic Molecule, APD-21

<210> 5
<223> Analyte Antigenic Molecule, APD-11

<210> 6
<223> V1.A.4 pcDNA3.1_GFP

<210> 7
<223> SpCas9-2A-GFP Vector V1.A.8

<210> 8
<223> pMA-SV40pA vector V1.C.2

<210> 9
<223> HLA-A 02:01 6xHis + Exon2/3-HA-L + R vector
      V1.C.6
```

-continued

<210> 10
<223> HLA-B 35:01 6xHis + Exon2/3-HA-L + R vector V1.C.9

<210> 11
<223> AAVS1-S_A24_6xH vector V1.F.8

<210> 12
<223> AAVS1-L_B07_6xH vector V1.F.10

<210> 13
<223> AAVS1-I_GFP_HCMVpp65_WT vector V1.G.10

<210> 14
<223> AAVS1-I_GFP_HCMVpp65 ANET vector V1.G.9

<210> 15
<223> AAVS1-I_GFP_HCMVpp65 AIN vector V1.H.1

<210> 16
<223> AAVS1_DRA_Flag-DRB1_6xHis vector V1.I.5

<210> 17
<223> AAVS1_DPA1_Flag-DPB1_6xHis vector V1.I.7

<210> 18
<223> HLA-A-sg-sp-opti1 vector V2.A.1

<210> 19
<223> HLA-B-sg-sp-3 vector V2.A.7

<210> 20
<223> HLA-C-sg-sp-4 vector V2.B.3

<210> 21
<223> HLA-A-ex2-3_sg-sp-opti_1 vector V2.I.10

<210> 22
<223> HLA-A-ex2-3_sg-sp-opti_2 vector V2.J.1

<210> 23
<223> AAVS1_sg-sp-opti_3 vector V2.J.6

<210> 24
<223> AAVS_Efla-intron_F14_RFPnls_F15 vector V4.B.2

<210> 25
<223> AAVS_Efla-intron_FRT_BFPnls_F3 vector V4.B.3

<210> 26
<223> pMA_FRT_HLA-A*02:01-6xHis_F3 vector V4.D.2

<210> 27
<223> pMA_F14_HLA-A*02:01-6xHis_F15 vector V4.H.5

<210> 28
<223> pMA_F14_HLA-A*24:02-6xHis_F15 vector V4.H.6

<210> 29
<223> pMA_F14_HLA-B*07:02-6xHis_F15 vector V4.H.7

<210> 30
<223> pMA_F14_HLA-B*35:01-6xHis_F15 vector V4.H.8

<210> 31
<223> CMVpro_FLP_Sv40pA_V2 vector V4.I.8

<210> 32
<223> FRT_HCMVpp28-3xMYC_F3 vector V9.E.6

<210> 33
<223> FRT_HCMVpp52-3xMYC_F3 vector V9.E.7

<210> 34
<223> FRT_HCMVpp52-3xMYC_F3 vector V9.E.8

<210> 35
<223> pMA-sv40_OE_F1 primer 1.C.2

<210> 36
<223> pMA-sv40_OE_R1 primer 1.C.3

<210> 37
<223> HLA-A-GT-Rg3 primer 4.A.3 1

<210> 38
<223> HLA-A-GT-Fg2 primer 4.A.4

<210> 39
<223> HLA-B-GT-Fg2 primer 4.A.7

<210> 40
<223> HLA-B-GT-Rg2 primer 4.B.1

<210> 41
<223> HLA-C-GT-Fg2 primer 4.B.5

<210> 42
<223> HLA-A-02_GT_Rg4 primer 4.I.9

<210> 43
<223> HLA-A-Exon3_HA-RE-BglII_F1 primer 6.I.9

<210> 44
<223> HLA-C-04-GT-Rg1 primer 8.A.1

<210> 45
<223> CMV-pA-HLA-Ex3_Probe_F1 primer 8.B.2

<210> 46
<223> CMV-pro_GT_R1 primer 9.C.3

<210> 47
<223> sv40pA_GT_F1 primer 9.C.4

<210> 48
<223> AAVS1_GT_F1 primer 9.C.5

<210> 49
<223> AAVS1_GT_F3 primer 9.C.7

<210> 50
<223> AAVS1_GT_F4 primer 9.C.8

<210> 51
<223> AAVS1_GT_R2 primer 9.C.10

<210> 52
<223> AAVS1_GT_R3 primer 9.D.1

<210> 53
<223> AAVS1_GT_R4 primer 9.D.2

<210> 54
<223> HLA-A-intron4_GT_R1 primer 9.D.6

<210> 55
<223> sv40pA-GT primer 9.D.7

<210> 56
<223> sv40pA-AAVS1-probe-FAM-F1 primer 9.J.2

<210> 57
<223> TRAC_TCRA-ex1_R1 primer 10.A.9

<210> 58
<223> TRAC_TCRA-promoter_F1 primer 10.A.10

<210> 59
<223> TRAC_probe(HEX) primer 10.B.6

<210> 60
<223> Pan-HLA_GT_F1 primer 8.B.3

<210> 61
<223> SV40pA_GT_R1 primer 15.H.2

<210> 62
<223> 3xMyc_OE_R1 primer 10.C.4

-continued

<210> 63
<223> CtermCysLink_OE_R1 primer 10.D.1

<210> 64
<223> Ef1a_intron_GT_F2 primer 15.H.4

<210> 65
<223> HCMVpp65_GT_F2ddPCR primer/probe 21.I.1

<210> 66
<223> HCMVpp28_GT_F1 ddPCR primer/probe 21.I.2

<210> 67
<223> HCMVpp52_GT_F1 ddPCR primer/probe 21.I.3

<210> 68
<223> Myc-Tag_GT_R1 ddPCR primer/probe 20.H.10

<210> 69
<223> Linker-Myc_Probe_Fam ddPCR primer/probe 20.H.9

<210> 70
<223> TRAC-TCRA-ex1-F1 ddPCR primer/probe 10.A.9

<210> 71
<223> TRAC-TCRA-ex1-F1 ddPCR primer/probe

<210> 72
<223> TRAC-probe (HEX) ddPCR primer/probe

LIST OF ABBREVIATIONS aAPX Analyte antigen-presenting complex
aAM Analyte antigenic molecule
APC Antigen-presenting cell
APX Antigen-presenting complex
BFP Blue fluorescent protein
CAR-T CAR T-cell
CM Cargo molecules
CRISPR Clustered Regularly Interspaced Short Palindromic Repeats
gRNA Cas9 guide RNA
CAR Chimeric antigen receptor
CDR Complementarity-determining regions
C-region Constant region
CMV Cytomegalovirus
DAMPS Danger associated molecular patterns
DC Dendritic cells
DNA Deoxyribonucleic acid
D-region Diversity region
eAPC Engineered antigen-presenting cell
eAPC-p Engineered antigen-presenting cell that present an analyte antigen-presenting complex
eAPC-pa Engineered antigen-presenting cell that presents an analyte antigen-presenting complex and analyte antigenic molecule
eAPC-a Engineered antigen-presenting cell expressing an analyte antigenic molecule
eAPC:T eAPC:TCR system, wherein analyte eAPC are combined with analyte TCR
FACS Fluorescence-activated cell sorting
GEM T-cells Germ line-encoded mycolyl-reactive T-cells
GFP Green fluorescent protein
HLAI HLA class I
HLAII HLA class II
HDR Homology directed recombination
HLA Human leukocyte antigen
IgSF Immunoglobulin superfamily
IRES Internal ribosome entry site
iNK T-cells Invariant natural killer T-cells
J-region Joining region
MACS Magnetic-activated cell sorting
MAGE Melanoma associated antigen
MAIT Mucosal-associated invariant T
NCBP Non-cell based particles
ORF Open reading frame
PAMPS Pathogen-associated molecular patterns
PCR Polymerase chain reaction
RMCE Recombinase mediated cassette exchange
RFP Red fluorescent protein
DNA Ribonucleic acid
SH2 Src homology 2
T-cells T lymphocytes
TC TCR or TCR mimic affinity reagent presenting cells
TCR T-cell Receptor
TRA TCR alpha
TRB TCR beta
TRD TCR delta
TCRsp TCR surface proteins in complex with CD3
TALEN Transcription activator-like effector nucleases
TRG TRCgamma
TAA Tumour-associated-antigens
V-region Variable region
β2M β2-microglobulin
ZAP-70 ζ-chain-associated protein of 70 kDa

Definitions

A pair of complementary TCR chains: two TCR chains wherein the translated proteins are capable of forming a TCRsp on the surface of a TCR presenting cell Affinity: Kinetic or equilibrium parameter of an interaction between two or more molecules or proteins Affinity reagent: Any reagent designed with specific affinity for an analyte. Often used in the context of affinity for HLA-antigen complex Allele: Variant form of a given gene AM: Analyte antigenic molecule. Generally, a protein but could also be a metabolite that is expressed by a cell from their genomic DNA and/or a specific introduced genetic sequence. The AM is expressed in the cell and a fragment can then be presented on the cell surface by an APX as cargo or on its own. Either as cargo or not, the AM can then be the target of T-cell receptor bearing cells or related affinity reagents.

Amplicon: a piece of DNA or RNA that is the source and/or product of artificial amplification using various methods including PCR.

Analyte: an entity that is of interest to be identified and/or measured and/or queried in the combined system Analyte TC: analyte cell presenting on the surface an analyte TCR, wherein the cell may be a primary T-cell, recombinant T-cell or an engineered TCR presenting cell.

Analyte TCR: a TCRsp or TCR-mimic affinity reagent provided in the form of a soluble reagent, immobilised reagent, presented by an NCBP or presented on the surface of a cell.

Antigen: any molecule that may be engaged by a TCR and results in a signal being transduced within the T-cell, often presented by an antigen-presenting complex Analyte antigen: collectively the eAPC:T system representing any entity presenting an antigen for analytical determination Antibody: Affinity molecule that is expressed by specialized cells of the immune system called B-cells and that contains of two chains. B-cells express a very large and very diverse repertoire of antibodies that do generally not bind self proteins but can bind and neutralize pathogens or toxins that would threaten the host. Natural or artificially engineered antibodies are often used as affinity reagents.

APC: Antigen-presenting cell. A cell bearing on the surface of the cell an AM, APX, APX APX: Antigen-presenting complex. A protein that is expressed and presented on the cell surface by nucleated cells from genes/ORF encoding genomic DNA and/or a specific introduced genetic sequence. The APX presents a cargo, being either a peptide or other metabolite molecules.

C-Region: Constant region. One of the gene segments that is used to assemble the T-cell receptor. The c-region is a distinct segment that rather than driving diversity of the TCR, defines its general function in the immune system.

Cargo-loading machinery: Cellular set of proteins that generate and load cargo molecules on APX from proteins or other presented molecules found in the cell.

CDR: complementarity-determining regions. Short sequences on the antigen-facing end of TCRs and antibodies that perform most of the target binding function. Each antibody and TCR contains six CDRs and they are generally the most variable part of the molecules allowing detection of a large number of diverse target molecules.

CM: Cargo molecules. peptide or metabolite that is presented by an antigen-presenting complex for example a HLA I or HLA II. The CM can be expressed by the cell intrinsically from the genomic DNA, introduced into the culture medium or expressed from a specifically introduced genetic sequence.

Copy-number: The whole number occurrence of a defined sequence encoded within the genome of a cell Cytogenetic: The study of inheritance in relation to the structure and function of chromosomes, i.e. determine the karyotype of a cell Cytotoxic/Cytotoxicity: Process in which a T-cells releases factors that directly and specifically damage a target cell.

D-region: Diversity region. One of the gene segments that is used to assemble the T-cell receptor. Each individual has a large number of different variations of these regions making it possible for each individual to arm T-cells with a very large variety of different TCR.

DNA: Desoxyribonucleic acid. Chemical name of the molecule that forms genetic material encoding genes and proteins eAPC:TCR system: eTPC:T, the system in which analyte eAPC are combined with analyte TCR to obtain primary and terminal outputs Endogenous: Substance that originated from within a cell Engineered Cell: A cell whereby the genome has been engineered through genetic modification modified.

Eukaryotic conditional regulatory element: A DNA sequence that can influence the activity of a promoter, which may be induced or repressed under defined conditions Eukaryotic Promoter: A DNA sequence that encodes a RNA polymerase binding site and response elements The sequence of the promoter region controls the binding of the RNA polymerase and transcription factors, therefore promoters play a large role in determining where and when your gene of interest will be expressed.

Eukaryotic terminator/Signal terminator: A DNA sequence that are recognized by protein factors that are associated with the RNA polymerase and which trigger the termination process of transcription. It also encodes the poly-A signal FACS/Flow Cytometry: Fluorescence-activated cell sorting. Analytical technique by which individual cells can be analyzed for the expression of specific cell surface and intracellular markers. A variation of that technique, cell sorting, allows cells that carry a defined set of markers to be retrieved for further analysis.

Family of APX: A set of several similar genes that encode functionally related proteins, which constitute an antigen pressing complex Fluorescent (protein) marker: Molecule that has specific extinction and emission characteristics and can be detected by Microscopy, FACS and related techniques.

Genetic Donor vector: A genetic based vector for delivery of genetic material to the genomic receiver site Genomic Receiver Site: A site within the genome for targeted integration of donor genetic material encoded within a Genetic Donor Vector.

Heterospecific recombinase sites: A DNA sequence that is recognized by a recombinase enzyme to promote the crossover of two DNA molecules HLA I: Human Leukocyte Antigen class I. A gene that is expressed in humans in all nucleated cells and exported to the cell surface where it presents as cargo short fragments, peptides, of internal proteins to T-cell receptors. As such it presents fragments of potential ongoing infections along with intrinsic proteins. The HLA I can additionally present as cargo peptides that are added to the culture medium, generated from proteins expressed form introduced genetic elements or generated from proteins that are taken up by the cell. HLA class I genes are polymorphic meaning that different individuals are likely to have variation in the same gene leading to a variation in presentation. Related to HLA class II.

HLA II: Human Leukocyte Antigen Class II. A gene that is expressed in humans in specific cells that are coordinating and helping the adaptive immune response for example dendritic cells. Related to HLA class I. HLA class II proteins are exported to the cell surface where they present as cargo short fragments, peptides, of external proteins to T-cell receptors. As such it presents fragments of potential ongoing infections along with intrinsic proteins. The HLA II can additionally present as cargo peptides that are added to the culture medium, generated from proteins expressed form introduced genetic elements or generated from proteins that are taken up by the cell. HLA class II genes are polymorphic meaning that different individuals are likely to have variation in the same gene leading to a variation in presentation.

Homologous arms: A stretch of DNA that has near identical sequence identity to a complement homologous arm and therefore promote the exchange of two DNA molecules by the cellular process, homology directed repair.

Immune surveillance: Process in which the immune system detects and becomes activated by infections, malignancies or other potentially pathogenic alterations.

Insulator: A DNA sequence that prevents a gene from being influenced by the activation or repression of nearby genes. Insulators also prevent the spread of heterochromatin from a silenced gene to an actively transcribed gene.

Integration: The physical ligation of a DNA sequence into a chromosome of a cell Integration couple: A paired genetic donor vector and genomic receiver site Internal ribosome entry site (IRES): A DNA sequence that once transcribed encodes a RNA element that allows the initiation of translation in a cap-independent manner J-region: Joining region. One of the gene segments that is used to assemble the T-cell receptor. Each individual has a large number of different variations of these regions making it possible for each individual to arm T-cells with a very large variety of different TCR.

Karyotype: The chromosome composition of a cell

Kozak Sequence: Short sequence required for the efficient initiation of translation Major HLA class I: a Family of APX that comprise of the genes HLA-A, HLA-B and HLA-C Matched: When two components encode genetic elements that direct and restrict the interaction between the complemented components Meganuclease recognition site: A DNA sequence that is recognized by a endodeoxyribonuclease, commonly referred to as a meganuclease Metabolite: A molecule created or altered through metabolic pathways of the cell Mobile genetic element: A DNA sequence that can permit the integration of DNA with the activity of transposases enzymes Monoclone cell line: A defined group of cells produced from a single ancestral cell by repeated cellular replication Native: a entity that is naturally occurring to the cell Non-coding gene: A non protein coding DNA sequence that is transcribed into functional non-coding RNA molecules ORF: Open reading frame. Stretch of genetic material that encodes a translation frame for synthesis of a protein (polypeptide) by the ribosome Paracrine: Signalling through soluble factors that directly act on neighboring cells.

PCR: Polymerase chain reaction in which a specific target DNA molecule is exponentially amplified Peptide: short string of amino acids between 6-30 amino acids in length Phenotypic analysis: Analysis of the observable characteristics of a cell.

Polymorphic: Present in different forms in individuals of the same species through the presence of different alleles of the same gene.

Polypeptide: Protein consisting of a stretch of peptides, forming a three-dimensional structure.

Primary Outputs: eAPC cells, analyte TC cells, NCBP or other analyte TCR forms from which the terminal outputs can be derived and/or determined from Primer: Short DNA sequence that allows specific recognition of a target DNA sequence for example during a PCR.

Promoter: Regulatory DNA element for the controlled initiation of gene expression Selectable marker: A DNA sequence that confers a trait suitable for artificial selection methods Shotgun Integration: The process whereby a library of vectors is introduced to a population of cells, whereby only a single copy of any given vector insert may be integrated to the genome of each single cell. Used to refer to pooled vector integration to a given cell population via an integration couple Slice acceptor site: A DNA sequence at the 3' end of the intron AM, APX CM or affinity reagent for interaction with cells with TCRsp on the surface, or TCRsp based reagents Slice donor site: A DNA sequence at the 5' end of the intron Synthetic: an entity that is artificially generated and introduced to a cell T-cell: T lymphocyte. White blood cell that expresses a T-cell receptor on its surface. Selected by the immune system to not react with the own body but have the potential to recognize infections and malignancies as well as reject grafts from most members of the same species.

TCR: T-cell Receptor. Affinity molecule expressed by a subgroup of lymphocytes called T-lymphocytes.

TCR-mimic affinity reagent: A protein or molecule that can interact and bind with an analyte antigen in mimicry to that of a natural TCRsp TCRsp: A pair of complementary TCR chains that express as surface proteins in complex with CD3 or a pair of complementary TCR chains expressed as proteins in the form of a soluble reagent, an immobilised reagent or present by NCBP.

Terminal Outputs: analyte antigen and TCR sequences, in the form of AM, APX, APX:CM, APX:AM, TCRsp or TCR-mimic affinity reagents TRA: TCR alpha encoding locus. One of the four different locus encoding genes that can form a VDJ recombined TCR chain. Translated TCR alpha chain proteins typically pair with translated TCR beta chain proteins to form alpha/beta TCRsp.

TRB: TCR beta encoding locus. One of the four different locus encoding genes that can form a VDJ recombined TCR chain. Translated TCR beta chain proteins typically pair with TCR alpha chain proteins to form alpha/beta TCRsp.

TRD: TCR delta encoding locus. One of the four different locus encoding genes that can form a VDJ recombined TCR chain. Translated TCR delta chain proteins typically pair with translated TCR gamma chain proteins to form gamma/delta TCRsp.

TRG: TCR gamma encoding locus. One of the four different locus encoding genes that can form a VDJ recombined TCR chain. Translated TCR gamma chain proteins typically pair with translate TCR delta chain proteins to form gamma/delta TCRsp.

V-region: Variable region. One of the gene segments that is used to assemble the T-cell receptor. Each individual has a large number of different variations of these regions making it possible for each individual to arm T-cells with a very large variety of different TCR.

The invention is further described in the following items:

Items

1. A multicomponent system wherein a first component is an engineered antigen-presenting cell (eAPC) designated component A and a second component is a genetic donor vector, designated component C, for delivery of one or more ORFs encoding an analyte antigen-presenting complex (aAPX) and/or an analyte antigenic molecule (aAM).

2. A multicomponent system according to item 1 wherein the component A
   a. Lacks endogenous surface expression of at least one family of aAPX and/or aAM and
   b. Contains at least one genomic integration site, designated component B, for integration of at least one ORF encoding at least aAPX and/or aAM.
3. A multicomponent system according to item 1 or 2 wherein component C is matched to component B, and wherein the component C is designed to deliver
   a. A single ORF encoding at least one aAPX and/or aAM and/or
   b. Two or more ORF encoding at least one aAPX and/or aAM
   and wherein a and/or b optionally encodes a selection marker of integration, such that said ORF(s) can be stably integrated into the B genomic receiver site and the aAPX and/or aAM are expressed.
4. A multicomponent system according to any of the preceding items, comprised of an eAPC, designated component A, and a genetic donor vector, designated component C for delivery of one or more ORFs encoding an aAPX and/or aAM,
   wherein
   component A
   a. Lacks endogenous surface expression of at least one family of aAPX and/or aAM and
   b. Contains at least one genomic integration site, designated component B, for integration of at least one ORF encoding at least one aAPX and/or aAM
   and component C is matched to the component B, and wherein component C is designed to deliver
   c. A single ORF encoding at least one aAPX and/or aAM or
   d. Two or more ORF encoding at least one aAPX and/or aAM
   and wherein c and/or d optionally encodes a selection marker of integration such that said ORF(s) can be stably integrated into the B genomic receiver site and the aAPX and/or aAM are expressed.
5. A multicomponent system according to any of the preceding items, wherein the component A comprises a further component, which is designated D, a genomic integration site for integration of a one or more ORF encoding at least one aAPX and/or aAM.
6. A multicomponent system according to item 5, wherein a further component designated E is a genetic vector matched to D, wherein the component E is designed to deliver
   a. A single ORF encoding at least one aAPX and/or aAM or
   b. Two or more ORF encoding at least one aAPX and/or aAM
   and wherein a and/or b optionally encodes a selection marker of integration such that said ORF(s) can be stably integrated into the D genomic receiver site and the aAPX and/or aAM are expressed.
7. A multicomponent system according to any of the preceding items wherein one or more additional genomic receiver site and matching genetic donor vector is added as additional components of the system.
8. A multicomponent system according to any of the preceding items wherein the genomic receiver site B and/or D is included and is selected from
   a. A synthetic construct designed for recombinase mediated cassette exchange (RMCE)
   b. A synthetic construct designed for site directed homologous recombination
   c. A native genomic site for site directed homologous recombination.
9. A multicomponent system according to any of the preceding items wherein the component A, expresses T-cell co-stimulation receptors.
10. A multicomponent system according to item 9 wherein the component A, expresses T-cell co-stimulation receptors CD80 and/or CD83 and/or CD86.
11. A multicomponent system according to any of the preceding items wherein component A, when provided with genetic material encoding one or more ORF encoding at least one or more aAPX, such that the aAPX is expressed on the surface of the cell, and can be loaded with a cargo molecule (CM), designated aAPX:CM.
12. A multicomponent system according to item 11 wherein the aAPX can be loaded with a CM via native processing and cargo-loading machinery.
13. A multicomponent system according to item 11 or 12 wherein the aAPX can be loaded with an aAM as CM, designated aAPX:aAM.
14. A multicomponent system according to any of the preceding items wherein the aAPX may be any of the following
   a. One or more members of HLA class I
   b. One or more members of HLA class
   c. On or more non-HLA antigen-presenting complex
   d. Or a combination a, b and/or c.
15. A multicomponent system according to any of the preceding items wherein the aAM is selected from
   a. a polypeptide or complex of polypeptides provided as analyte antigen
   b. a peptide derived from a polypeptide provided as analyte antigen
   c. a peptide provided as analyte antigen
   d. a metabolite provided as analyte antigen
   e. a polypeptide or complex of polypeptides translated from the analyte antigenic molecule ORF(s)
   f. a peptide derived from a polypeptide translated from the analyte antigenic molecule ORF(s)
   g. a peptide derived from altering the component A proteome
   h. a polypeptide derived from altering the component A proteome
   i. a metabolite derived from altering the component A metabolome
   and/or a combination thereof.
16. A multicomponent system according to any of the preceding items wherein the component B and/or D is included and comprises of at least one of the following genetic elements
   a. Heterospecific recombinase sites
   b. Homologous arms
   c. Eukaryotic promoter
   d. Eukaryotic conditional regulatory element
   e. Eukaryotic terminator
   f. Selection marker
   g. Splice acceptor site
   h. Splice donor site
   i. Non-protein coding gene
   j. Insulator
   k. Mobile genetic element
   l. Meganuclease recognition site
   m. Internal ribosome entry site (IRES)
   n. viral self-cleaving peptide element
   o. Akozak consensussequence 17. A multicomponent system according to any of preceding items wherein the component C and/or E is included and comprises of at least one of the following genetic elements
    a. Heterospecific recombinase sites
    b. Homologous arms
    c. Eukaryotic promoter
    d. Eukaryotic conditional regulatory element
    e. Eukaryotic terminator
    f. Selection marker
    g. Selection marker of integration
    h. Splice acceptor site
    i. Splice donor site
    j. Non-protein coding gene
    k. Insulator
    l. Mobile genetic element
    m. Meganuclease recognition site
    n. Internal ribosome entry site (IRES)
    o. viral self-cleaving peptide element
    p. An antibiotic resistance cassette
    q. A bacterial origin of replication
    r. A yeast origin of replication
    s. A cloning site
    t. A Kozak consensus sequence
18. A multicomponent system according to any of the preceding items, wherein the component B and/or D is included and is for RMCE integration of a single ORF and comprises:
    a. A Eukaryotic promoter
    b. A pair of heterospecific recombinase sites
    c. A Kozak consensus sequence
    d. A selection marker
    e. A Eukaryotic terminator.
19. A multicomponent system according any of the preceding items, wherein the component B and/or D is included and is for RMCE integration of two or more ORF comprises the following genetic elements:
    a. A Eukaryotic promoter
    b. A pair of heterospecific recombinase sites
    c. Two or more Kozak consensus sequences
    d. A selection marker
    e. A Eukaryotic terminator
    f. A second Eukaryotic promoter
    g. A second selection marker
    h. A second Eukaryotic terminator
20. A multicomponent system according to any of the preceding items wherein component C and/or E is present is for RMCE integration of a single ORF and comprises the following genetic elements:
    a. A pair of heterospecific recombinase sites
    b. A Kozak consensus sequence
    c. An antibiotic resistance cassette
    d. A bacterial origin of replication
    e. A cloning site for introduction of a single ORF encoding one or more aAPX and/or aAM and/or selection marker of integration.
21. A multicomponent system according to any of the preceding items wherein component C and/or E is present and is for RMCE integration of a two or more ORF and comprises of the following:
    a. A pair of heterospecific recombinase sites
    b. Two or more Kozak consensus sequences
    c. An antibiotic resistance cassette
    d. A bacterial or yeast origin of replication
    e. A cloning site for introduction of two or more ORF, with eukaryotic terminators, encoding one or more aAPX and/or aAM and/or selection marker of integration.
22. A multicomponent system according to any of the preceding items wherein component C and/or E is combined with at least one ORF encoding at least one aAPX and/or aAM to obtain component C' and/or E'.
23. A multicomponent system according to item 22 wherein the combination is performed multiple times to obtain a library of component C' and/or E'.
24. A multicomponent system according to any of items 22 or 23 wherein one or more component C' and/or E' is combined with component A, to integrate one or more aAPX ORF(s) encoded in component C' and/or E', into components B and/or D, to obtain a cell, designated eAPC-p, wherein components B and/or D become components B' and/or D' such that the eAPC-p expresses an aAPX on the cell surface.
25. A multicomponent system according to any of items 22 or 23 wherein one or more component C' and/or E' is combined with component A, to integrate one or more aAM ORF(s) encoded in component C' and/or E', into components B and/or D, to obtain a cell, designated eAPC-a, wherein components B and/or D become components B' and/or D' such that the eAPC-a expresses an aAM on the cell surface or intracellularly.
26. A multicomponent system according to any of items 22 or 23 wherein one or more component C' and/or E' is combined with component A, to integrate one or more aAPX ORF(s) and/or one or more aAM encoded in component C' and/or E', into components B and/or D, to obtain a cell, designated eAPC-pa, wherein components B and/or D becomes components B' and/or D' such that the eAPC-pa expresses an aAPX and aAM and/or an aAPX:aAM.
27. A multicomponent system according to any of items 24 wherein one or more component C' or E' is combined with an eAPC-p, to integrate one or more aAM ORF(s) encoded in component C' or E', into components B or D, to obtain a cell, designated an eAPC-pa, wherein components B or D becomes components B' or D' such that it expresses an aAPX and aAM and/or an aAPX:aAM.
28. A multicomponent system according to any of items 25 wherein one or more component C' or E' is combined with an eAPC-a, to integrate one or more aAPX ORF(s) encoded in component C' or E', into components B or D, to obtain a cell, designated an eAPC-pa, wherein components B or D becomes components B' or D' such that it expresses an aAPX and aAM and/or an aAPX:aAM.
29. A method for preparing an eAPC-p as defined in item 24 the method comprising
    a. Combining component A, with at least one of component C' and/or E', wherein the one or more component C' and/or E' encode one or more aAPX, and combining with integration factors and at least one of
    b. Selecting for loss of genomic receiver site selection marker(s)
    c. Selecting for gain of a surface expression of one or more aAPX
    d. Selecting for gain of one or more of a selection marker of integration.
30. A method according to item 29 wherein b, c and d are included.
31. A method according to item 29 or 30 wherein the one or more component C' and/or E' encodes a single aAPX in step a of item 29.

32. A method according to item 31 wherein the method is conducted multiple times wherein each time step a of item 29 is performed using a unique aAPX, such that a unique eAPC-p is obtained, to obtain a library of discrete and defined eAPC-p.
33. A method according to item 29 or 30 wherein the one or more component C' and/or E' encodes a mixed pool of two or more unique aAPX in step a of item 29, to obtain a library, wherein the library is comprised of a mixed population of eAPC-p, wherein each eAPC-p expresses a single aAPX from the pool used in step a of item 29.
34. A method for preparing an eAPC-a as defined in item 25 the method comprising
   a. Combining component A, with at least one of component C' and/or E', wherein the one or more component C' and/or E' encode one or more aAM, and combining with integration factors and at least one of
   b. Selecting for loss of genomic receiver site selection marker(s)
   c. Selecting for gain of expression of one or more aAM
   d. Selecting for gain of one or more of a selection marker of integration.
35. A method according to item 34 wherein b and d are included.
36. A method according to item 34 or 35 wherein the one or more component C' and/or E' encodes a single aAM in step a of item 34.
37. A method according to item 36 wherein the method is conducted multiple times wherein each time step a of item 34 is performed using a unique aAM, such that a unique eAPC-a is obtained, to obtain a library of discrete and defined eAPC-a.
38. A method according to item 34 or 35 wherein the one or more component C' and/or E' encodes a mixed pool of two or more unique aAM in step a of item 34, to obtain a library, wherein the library is comprised of a mixed population of eAPC-a wherein each eAPC-a expresses a single aAM from the pool used in step a of item 34.
39. A method for preparing an eAPC-pa as defined in item 28 the method comprising
   a. Combining eAPC-a, with at least one of component C' or E', wherein one or more component C' or E' encode one or more aAPX ORF, and combining with integration factors and at least one of
   b. Selecting for loss of genomic receiver site selection marker(s)
   c. Selecting for gain of a surface expression of one or more aAPX
   d. Selecting for gain of one or more of a selection marker of integration.
40. A method according to item 39 wherein b, c and d are included.
41. A method according to item 39 or 40 wherein the one or more component C' or E' encodes a single aAPX in step a of item 39.
42. A method according to item 41 wherein the method is conducted multiple times wherein each time step a of item 39 is performed using a unique aAPX, such that a unique eAPC-pa is obtained, to obtain a library of discrete and defined eAPC-pa.
43. A method according to item 39 or 40 wherein the one or more component C' or E' encodes a mixed pool of two or more unique aAPX in step a of item 39, to obtain a library, wherein the library is comprised of a mixed population of eAPC-pa, wherein each eAPC-pa expresses a single aAPX from the pool used in step a of item 39.
44. A method for preparing an eAPC-pa as defined in item 27 the method comprising
   a. Combining eAPC-p, with at least one of component C' or E', wherein the one or more component C' or E' encode one or more aAM ORF, and combining with integration factors and at least one of
   b. Selecting for loss of genomic receiver site selection marker(s)
   c. Selecting for gain of expression of one or more aAM
   d. Selecting for gain of one or more of a selection marker of integration.
45. A method according to item 44 wherein b and d are included.
46. A method according to item 44 or 45 wherein the one or more component C' or E' encodes a single aAM in step a of item 44.
47. A method according to item 46 wherein the method is conducted multiple times wherein each time step a of item 44 is performed using a unique aAM, such that a unique eAPC-pa is obtained, to obtain a library of discrete and defined eAPC-pa.
48. A method according to item 44 or 45 wherein the one or more component C' or E' encodes a mixed pool of two or more unique aAM in step a of item 44, to obtain a library, wherein the library is comprised of a mixed population of eAPC-pa, wherein each eAPC-pa expresses a single aAM from the pool used in step a of item 44.
49. A method for preparing an eAPC-pa as defined in item 26 the method comprising
   a. Combining eAPC, with at least one of component C' or E', wherein the one or more component C' and/or E' encode one or more aAM ORF and one or more aAPX ORF, and combining with integration factors and at least one of
   b. Selecting for loss of genomic receiver site selection marker(s)
   c. Selecting for gain of expression of one or more aAM and/or surface expression one or more aAPX
   d. Selecting for gain of one or more of a selection marker of integration.
50. A method according to item 49 wherein b, c and d are included.
51. A method according to item 49 or 50 wherein the one or more component C' and/or E' encodes a single aAM and a single aAPX in step a of item 49.
52. A method according to item 51 wherein the method is conducted multiple times wherein each time step a of item 49 is performed using at least one of a unique aAM and/or a unique aAPX, such that a unique eAPC-pa is obtained, to obtain a library of discrete and defined eAPC-pa.
53. A method according to item 49 or 50 wherein the one or more component C' and/or E' encodes a mixed pool of two or more unique aAM and/or two or more unique aAPX in step a of item 49, to obtain a library, wherein the library is comprised of a mixed population of eAPC-pa, wherein each eAPC-pa expresses a single aAM and a single aAPX from the pool used in step a of item 49.
54. A analyte eAPC, obtained from the multicomponent system according to any of the preceding items for use in characterisation of
   a. specificity of the expressed analyte antigen to an analyte affinity reagent and/or
   b. affinity of the expressed analyte antigen to an analyte affinity reagent
   c. a signal response of one or more analyte cell expressing an analyte TCR (analyte TC) to the expressed analyte antigen wherein the analyte antigen is selected from an aAPX: aAM and/or aAM and/or aAPX and/or aAPX:CM and wherein the analyte eAPC is selected from an eAPCp and/or an eAPC-a and/or an eAPC-pa.

55. A method for selecting one or more analyte eAPC from an input analyte eAPC or a library of analyte eAPC, to obtain one or more analyte eAPC that binds to one or more analyte TCR wherein the method comprises
    a. Combining one or more analyte eAPC with one or analyte TCR, resulting in a contact between an analyte antigen presented by the analyte eAPC with analyte TCR
    b. Measuring a formation, if any, of a complex between one or more analyte antigen with one or more analyte TCR and/or
    c. Measuring a signal response, if any, of one or more analyte eAPC, induced by the formation of a complex between the analyte antigen with one or more analyte TCR and/or
    d. Measuring a signal response, if any, of one or more analyte TC, induced by the formation of a complex between the analyte antigen with one or more analyte TCR expressed by one or more analyte TC and
    e. Selecting one or more analyte eAPC from step b wherein the selection is made by a positive and/or negative measurement
    wherein the analyte antigen is selected from an aAPX: aAM and/or aAM and/or aAPX and/or aAPX:CM and wherein the analyte eAPC is selected from an eAPC-p and/or an eAPC-a and/or an eAPC-pa and wherein the analyte TCR is a pair of TCR chains or TCR-mimic affinity reagent, in the form of at least one of the following, a soluble reagent, an immobilised reagent, presented by a non-cell based particle (NCBP), presented on the surface of a cell (TC), wherein a cell can be selected from a primary T-cell and/or a recombinant T-cell and/or an engineered cell.
56. A method according to item 55 wherein the selection step e is performed by single cell sorting and/or cell sorting to a pool.
57. A method according to item 56 wherein the sorting is followed by expansion of the sorted single cell.
58. A method according to item 56 wherein the sorting is followed by expansion of the sorted pool of cells
59. A method according to any of items 56 to 58 further comprising a step of sequencing component B' and/or component D' of the sorted and/or expanded cell(s).
60. A method according to item 59 wherein the sequencing step is preceded by the following
    a. Extracting of genomic DNA and/or
    b. Extracting of component B' and/or component D' RNA transcript and/or
    c. Amplifying by a PCR and/or a RT-PCR the DNA and/or RNA transcript of component B' and/or component D'.
61. A method according to item 59 or 60 wherein the sequencing step is destructive to the cell and wherein the sequencing information obtained is used for preparing the analyte eAPC selected in step e of item 55.
62. A method according to any of items 55, 56, 57, 58, 61 wherein the selected analyte eAPC is subjected to an affinity analysis to determine the affinity of the analyte antigen to an analyte TCR wherein the method further comprises
    a. Labelling the selected analyte eAPC(s) with the analyte TCR at a range of concentrations
    b. Conducting FACS analysis on the labelled analyte eAPC of step a
    c. Determining the intensity of fluorescent labelling of the analyte eAPC over the range of concentrations of analyte affinity reagent
    d. Calculating the affinity of the analyte antigen to the analyte TCR.
63. A method according to item 62 wherein step b to c is performed with a labelled reference, and step d is calculating the affinity using the ratio of the analyte affinity reagent fluorescence intensity to the reference fluorescence intensity.
64. A method according to item 63 wherein the labelled reference is selected from
    a. The analyte eAPC labelled with an affinity reagent to the analyte antigen
    b. a cell or particle presenting a labelled reference analyte antigen.
65. A method according to any of items 55, 56, 57, 58, 61 wherein the selected analyte eAPC is subjected to characterisation of a signal response wherein the method further comprises
    a. Determining a native signalling response and/or
    b. Determining a synthetic signalling response.
66. A method according to item 65 wherein the induced signal response is determined by detecting an increase or decrease in one or more of the following
    a. a secreted biomolecule
    b. a secreted chemical
    c. an intracellular biomolecule
    d. an intracellular chemical
    e. a surface expressed biomolecule
    f. a cytotoxic action of an analyte TC upon the analyte eAPC
    g. a paracrine action of an analyte TC upon the analyte eAPC such that a signal response is induced in the analyte eAPC and is determined by detecting an increase or decrease any of a to e
    h. a proliferation of an analyte TC
    i. an immunological synapse formation between an analyte TC and the analyte eAPC
    compared to the non-induced signal response state.
67. A method for selecting one or more analyte TCR from an input analyte TCR or a library of analyte TCR, wherein the analyte TCR binds to one or more analyte eAPC, to obtain the sequence of one or more pairs of TCR chains encoded in the analyte TCR, and/or to obtain the analyte TCR, wherein the method comprises
    a. Combining one or more analyte eAPC with one or more analyte TCR resulting in a contact between an analyte antigen presented by the analyte eAPC with one or analyte TCR and
    b. Measuring a formation, if any, of a complex between the analyte antigen with one or more analyte TCR and/or
    c. Measuring a signal response, if any, of one or more analyte TC, induced by the formation of a complex between the analyte antigen with one or more TCR expressed by one or more analyte TC and/or
    d. Measuring a signal response, if any, of one or more analyte eAPC, induced by the formation of a complex between the analyte antigen with one or more analyte TCR and
    e. Selecting one or more analyte TCR from step b, c and/or d wherein the selection is made by a positive and/or negative measurement
    wherein the analyte antigen is selected from an aAPX: aAM and/or aAM and/or aAPX and/or aAPX:CM and wherein the analyte eAPC is selected from an eAPCp and/or an eAPC-a and/or an eAPC-pa and wherein the analyte TCR is a pair of TCR chains or TCR-mimic affinity reagent, in the form of at least one of the following, a soluble reagent, an immobilised reagent, presented by a non-cell based particle (NCBP), presented on the surface of a cell (TC), wherein a cell can be selected from a primary T-cell and/or a recombinant T-cell and/or an engineered cell 68. A method according item 67 wherein the selection step e is performed by single cell sorting and/or cell sorting to a pool.

69. A method according to item 68 wherein the sorting is followed by expansion of the sorted single cell.

70. A method according to item 68 wherein the sorting is followed by expansion of the sorted pool of cells.

71. A method according to any of items 67 to 70 further comprising a step of sequencing the analyte TCR chains of the sorted and/or expanded cell(s).

72. A method according to item 71 wherein the sequencing step is preceded by the following
    a. Extracting of genomic DNA and/or
    b. Extracting of analyte TCR chains RNA transcript and/or
    c. Amplifying by a PCR and/or a RT-PCR of the DNA and/or RNA transcript of the analyte TCR chains.

73. A method according to any of items 67, 68, 69, 70 wherein the selected analyte TC is subjected to characterisation of the signal response wherein the method further comprises
    a. Determining a native signalling response and/or
    b. Determining a synthetic signalling response 74. A method according to item 73 wherein the induced signal response is determined by detecting an increase or decrease in one or more of the following
    a. a secreted biomolecule
    b. a secreted chemical
    c. an intracellular biomolecule
    d. an intracellular chemical
    e. a surface expressed biomolecule
    f. a cytotoxic action of the analyte TC upon an analyte eAPC
    g. a paracrine action of the analyte TC upon an analyte eAPC such that a signal response is induced in an analyte eAPC and is determined by detecting an increase or decrease any of a to e
    h. a proliferation of the analyte TC
    i. an immunological synapse between the analyte TC and an analyte eAPC compared to the non-induced signal response state.

75. A method to select and identify an aAM cargo or a CM cargo, wherein the cargo is a metabolite and/or a peptide, that is loaded in an aAPX of an analyte eAPC wherein the method comprises
    a. isolating an aAPX:aAM or an aAPX:CM or the cargo aM or the cargo CM and
    b. identifying the loaded cargo.

76. A method according to item 75 wherein step b comprises subjecting the isolated aAPX:aAM or an aAPX:CM to one or more
    a. Mass-spectroscopy analysis
    b. Peptide sequencing analysis.

77. A pair of TCR chain sequences or library of pairs of TCR chain sequences selected by the method as defined in items 67 to 74 for use in at least one of the following
    a. diagnostics
    b. medicine
    c. cosmetics
    d. research and development.

78. An antigenic molecule and/or ORF encoding said antigenic molecule, or libraries thereof selected by the method as defined in items 55 to 66 or 75, 76 for use in at least one of the following
    a. diagnostics
    b. medicine
    c. cosmetics
    d. research and development.

79. A antigen-presenting complex loaded with an antigenic molecule as cargo and/or ORF(s) encoding said complex, or libraries thereof selected by the method as defined in items 55 to 66 or 75, 76 for use in at least one of the following
    a. diagnostics
    b. medicine
    c. cosmetics
    d. research and development.

80. An eAPC, or library of eAPC selected by the method as defined in items 55 to 66 for use in at least one of the following
    a. diagnostics
    b. medicine
    c. cosmetics
    d. research and development.

81. A cell expressing a TCR on the surface of the cell in complex with CD3, or library of thereof selected by the method as defined in items 67 to 74 for use in at least one of the following
    a. diagnostics
    b. medicine
    c. cosmetics
    d. research and development.

82. A multicomponent system according to any of items 1-28 for use in at least one of the following
    a. diagnostics
    b. medicine
    c. cosmetics
    d. research and development.

83. A TCR-mimic affinity reagent sequence(s) or library of TCR-mimic affinity reagent sequences selected by the method as defined in items 67 to 74 for use in at least one of the following
    a. diagnostics
    b. medicine
    c. cosmetics
    d. research and development.

84. A NCBP bearing a TCR pair or TCR-mimic affinity reagent or library of NCBP bearing a TCR pair or TCR-mimic affinity reagent selected by the method as defined in items 67 to 74 for use in at least one of the following
    a. diagnostics
    b. medicine
    c. cosmetics

SEQUENCE LISTING

<160> NUMBER OF SEQ ID NOS: 72

<210> SEQ ID NO 1
<211> LENGTH: 13
<212> TYPE: PRT
<213> ORGANISM: Homo sapiens
<220> FEATURE:
<223> OTHER INFORMATION: Analyte Antigenic Molecule

<400> SEQUENCE: 1

Pro Lys Tyr Val Lys Gln Asn Thr Leu Lys Leu Ala Thr
1               5                   10

<210> SEQ ID NO 2
<211> LENGTH: 4
<212> TYPE: PRT
<213> ORGANISM: Homo sapiens
<220> FEATURE:
<223> OTHER INFORMATION: Analyte Antigenic Molecule

<400> SEQUENCE: 2

Pro Lys Tyr Val
1

<210> SEQ ID NO 3
<211> LENGTH: 17
<212> TYPE: PRT
<213> ORGANISM: Homo sapiens
<220> FEATURE:
<223> OTHER INFORMATION: Analyte Antigenic Molecule, APD-2

<400> SEQUENCE: 3

Asn Leu Val Pro Met Val Ala Thr Asn Leu Val Pro Met Val Ala Thr
1               5                   10                  15

Val

<210> SEQ ID NO 4
<211> LENGTH: 9
<212> TYPE: PRT
<213> ORGANISM: Homo sapiens
<220> FEATURE:
<223> OTHER INFORMATION: Analyte Antigenic Molecule, APD-21

<400> SEQUENCE: 4

Asn Leu Gly Pro Met Ala Ala Gly Val
1               5

<210> SEQ ID NO 5
<211> LENGTH: 9
<212> TYPE: PRT
<213> ORGANISM: Homo sapiens
<220> FEATURE:
<223> OTHER INFORMATION: Analyte Antigenic Molecule, APD-11

<400> SEQUENCE: 5

Val Tyr Ala Leu Pro Leu Lys Met Leu
1               5

<210> SEQ ID NO 6
<211> LENGTH: 6071
<212> TYPE: DNA
<213> ORGANISM: Artificial Sequence
<220> FEATURE:
<223> OTHER INFORMATION: V1.A.4 pcDNA3.1_GFP

<400> SEQUENCE: 6

| | |
|---|---|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttgcg atgtacgggc cagatatacg cgttgacatt | 240 |
| gattattgac tagttattaa tagtaatcaa ttacgggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttggta ccgccaccat ggaatccgat gagtctggcc tgcccgccat | 960 |
| ggaaatcgag tgcagaatca ccggcaccct gaacggcgtg gaatttgagc tcgtgggcgg | 1020 |
| aggcgagggc acacctgaac agggcagaat gaccaacaag atgaagtcca ccaaggggc | 1080 |
| cctgaccttc agccctacc tgctgtctca cgtgatgggc tacggcttct accacttcgg | 1140 |
| cacctacccc agcggctacg agaacccttt cctgcacgcc atcaacaacg gcggctacac | 1200 |
| caacacccgg atcgagaagt acgaggacgg cggcgtgctg cacgtgtcct tcagctacag | 1260 |
| atacgaggcc ggcagagtga tcggcgactt caaagtgatg ggcaccggat tccccgagga | 1320 |
| cagcgtgatc ttcaccgaca agatcatccg gtccaacgcc accgtggaac atctgcaccc | 1380 |
| catgggcgac aacgacctgg acggcagctt caccagaacc ttctccctgc gggatggcgg | 1440 |
| ctactacagc agcgtggtgg acagccacat gcacttcaag agcgccatcc accccagcat | 1500 |
| cctccagaac ggcggaccca tgttcgcctt cagacgggtg aagaggacc acagcaacac | 1560 |
| cgagctgggc atcgtggaat accagcacgc cttcaagacc cccgatgccg atgccggcga | 1620 |
| ggaatgagtc gagtctagag ggcccgttta aacccgctga tcagcctcga ctgtgccttc | 1680 |
| tagttgccag ccatctgttg tttgcccctc cccgtgcct tccttgaccc tggaaggtgc | 1740 |
| cactcccact gtcctttcct aataaaatga ggaaattgca tcgcattgtc tgagtaggtg | 1800 |
| tcattctatt ctgggggtg gggtgggca ggacagcaag ggggaggatt gggaagacaa | 1860 |
| tagcaggcat gctggggatg cggtgggctc tatggcttct gaggcggaaa gaaccagctg | 1920 |
| gggctctagg gggtatcccc acgcgccctg tagcggcgca ttaagcgcgg cgggtgtggt | 1980 |
| ggttacgcgc agcgtgaccg ctacacttgc cagcgcccta gcgcccgctc ctttcgcttt | 2040 |
| cttcccttcc tttctcgcca cgttcgccgg cttccccgt caagctctaa atcggggct | 2100 |
| cccctttaggg ttccgattta gtgctttacg gcacctcgac cccaaaaaac ttgattaggg | 2160 |
| tgatggttca cgtagtgggc catcgccctg atagacggtt tttcgccctt tgacgttgga | 2220 |
| gtccacgttc tttaatagtg gactcttgtt ccaaactgga acaacactca accctatctc | 2280 |
| ggtctattct tttgatttat aagggatttt gccgatttcg gcctattggt taaaaaatga | 2340 |
| gctgatttaa caaaaattta acgcgaatta attctgtgga atgtgtgtca gttagggtgt | 2400 |

```
ggaaagtccc caggctcccc agcaggcaga agtatgcaaa gcatgcatct caattagtca      2460
gcaaccaggt gtggaaagtc cccaggctcc ccagcaggca gaagtatgca aagcatgcat      2520
ctcaattagt cagcaaccat agtcccgccc ctaactccgc ccatcccgcc cctaactccg      2580
cccagttccg cccattctcc gccccatggc tgactaattt tttttattta tgcagaggcc      2640
gaggccgcct ctgcctctga gctattccag aagtagtgag gaggcttttt tggaggccta      2700
ggcttttgca aaaagctccc gggagcttgt atatccattt tcggatctga tcaagagaca      2760
ggatgaggat cgtttcgcat gattgaacaa gatggattgc acgcaggttc tccggccgct      2820
tgggtggaga ggctattcgg ctatgactgg gcacaacaga caatcggctg ctctgatgcc      2880
gccgtgttcc ggctgtcagc gcaggggcgc ccggttcttt tgtcaagac cgacctgtcc       2940 ggtgccctga atgaactgca ggacgaggca gcgcggctat cgtggctggc cacgacgggc      3000
gttccttgcg cagctgtgct cgacgttgtc actgaagcgg gaagggactg gctgctattg      3060
ggcgaagtgc cggggcagga tctcctgtca tctcaccttg ctcctgccga aaagtatcc       3120 atcatggctg atgcaatgcg gcggctgcat acgcttgatc cggctacctg cccattcgac      3180
caccaagcga acatcgcat cgagcgagca cgtactcgga tggaagccgg tcttgtcgat       3240
caggatgatc tggacgaaga gcatcagggg ctcgcgccag ccgaactgtt cgccaggctc      3300
aaggcgcgca tgcccgacgg cgaggatctc gtcgtgaccc atggcgatgc ctgcttgccg      3360
aatatcatgg tggaaaatgg ccgcttttct ggattcatcg actgtggccg gctgggtgtg      3420
gcggaccgct atcaggacat agcgttggct acccgtgata ttgctgaaga gcttggcggc      3480
gaatgggctg accgcttcct cgtgctttac ggtatcgccg ctcccgattc gcagcgcatc      3540
gccttctatc gccttcttga cgagttcttc tgagcgggac tctggggttc gaaatgaccg      3600
accaagcgac gcccaacctg ccatcacgag atttcgattc caccgccgcc ttctatgaaa      3660
ggttgggctt cggaatcgtt ttccgggacg ccggctggat gatcctccag cgcgggatc       3720 tcatgctgga gttcttcgcc cacccaact tgtttattgc agcttataat ggttacaaat        3780
aaagcaatag catcacaaat ttcacaaata aagcattttt ttcactgcat tctagttgtg      3840
gtttgtccaa actcatcaat gtatcttatc atgtctgtat accgtcgacc tctagctaga     3900
gcttggcgta atcatggtca tagctgtttc ctgtgtgaaa ttgttatccg ctcacaattc      3960
cacacaacat acgagccgga agcataaagt gtaaagcctg gggtgcctaa tgagtgagct      4020
aactcacatt aattgcgttg cgctcactgc ccgctttcca gtcgggaaac ctgtcgtgcc      4080
agctgcatta atgaatcggc caacgcgcgg ggagaggcgg tttgcgtatt gggcgctctt      4140
ccgcttcctc gctcactgac tcgctgcgct cggtcgttcg gctgcggcga gcggtatcag      4200
ctcactcaaa ggcggtaata cggttatcca cagaatcagg ggataacgca ggaaagaaca     4260
tgtgagcaaa aggccagcaa aaggccagga accgtaaaaa ggccgcgttg ctggcgtttt      4320
tccataggct ccgcccccct gacgagcatc acaaaaatcg acgctcaagt cagaggtggc      4380
gaaacccgac aggactataa agataccagg cgtttccccc tggaagctcc ctcgtgcgct      4440
ctcctgttcc gaccctgccg cttaccggat acctgtccgc ctttctccct tcgggaagcg      4500
tggcgctttc tcatagctca cgctgtaggt atctcagttc ggtgtaggtc gttcgctcca      4560
agctgggctg tgtgcacgaa ccccccgttc agcccgaccg ctgcgcctta tccggtaact      4620
atcgtcttga gtccaacccg gtaagacacg acttatcgcc actggcagca gccactggta      4680
acaggattag cagagcgagg tatgtaggcg gtgctacaga gttcttgaag tggtggccta      4740
```

```
actacggcta cactagaaga acagtatttg gtatctgcgc tctgctgaag ccagttacct    4800
tcggaaaaag agttggtagc tcttgatccg gcaaacaaac caccgctggt agcggttttt    4860
ttgtttgcaa gcagcagatt acgcgcagaa aaaaggatc tcaagaagat cctttgatct     4920
tttctacggg gtctgacgct cagtggaacg aaaactcacg ttaagggatt ttggtcatga    4980
gattatcaaa aaggatcttc acctagatcc ttttaaatta aaaatgaagt tttaaatcaa    5040
tctaaagtat atatgagtaa acttggtctg acagttacca atgcttaatc agtgaggcac    5100
ctatctcagc gatctgtcta tttcgttcat ccatagttgc ctgactcccc gtcgtgtaga    5160
taactacgat acgggagggc ttaccatctg gccccagtgc tgcaatgata ccgcgagacc    5220
cacgctcacc ggctccagat ttatcagcaa taaaccagcc agccggaagg gccgagcgca    5280
gaagtggtcc tgcaacttta tccgcctcca tccagtctat taattgttgc cgggaagcta    5340
gagtaagtag ttcgccagtt aatagtttgc gcaacgttgt tgccattgct acaggcatcg    5400
tggtgtcacg ctcgtcgttt ggtatggctt cattcagctc cggttcccaa cgatcaaggc    5460
gagttacatg atcccccatg ttgtgcaaaa aagcggttag ctccttcggt cctccgatcg    5520
ttgtcagaag taagttggcc gcagtgttat cactcatggt tatggcagca ctgcataatt    5580
ctcttactgt catgccatcc gtaagatgct tttctgtgac tggtgagtac tcaaccaagt    5640
cattctgaga atagtgtatg cggcgaccga gttgctcttg cccggcgtca atacgggata    5700
ataccgcgcc acatagcaga actttaaaag tgctcatcat tggaaaacgt tcttcggggc    5760
gaaaactctc aaggatctta ccgctgttga tccagttc gatgtaaccc actcgtgcac     5820
ccaactgatc ttcagcatct tttactttca ccagcgtttc tgggtgagca aaaacaggaa    5880
ggcaaaatgc cgcaaaaaag ggaataaggg cgacacggaa atgttgaata ctcatactct    5940
tcctttttca atattattga agcatttatc agggttattg tctcatgagc ggatacatat    6000
ttgaatgtat ttagaaaaat aaacaaatag gggttccgcg cacatttccc cgaaaagtgc    6060
cacctgacgt c                                                         6071
```

<210> SEQ ID NO 7
<211> LENGTH: 10428
<212> TYPE: DNA
<213> ORGANISM: Artificial Sequence
<220> FEATURE:
<223> OTHER INFORMATION: SpCas9-2A-GFP Vector V1.A.8

<400> SEQUENCE: 7

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
```

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgccaccat ggactataag gaccacgacg gagactacaa    960
ggatcatgat attgattaca aagacgatga cgataagatg gccccaaaga agaagcggaa   1020
ggtcggtatc cacggagtcc cagcagccga caagaagtac agcatcggcc tggacatcgg   1080
caccaactct gtgggctggg ccgtgatcac cgacgagtac aaggtgccca gcaagaaatt   1140
caaggtgctg ggcaacaccg accggcacag catcaagaag aacctgatcg gagccctgct   1200
gttcgacagc ggcgaaacag ccgaggccac ccggctgaag agaaccgcca gaagaagata   1260
caccagacga aagaaccgga tctgctatct gcaagagatc ttcagcaacg agatggccaa   1320
ggtggacgac agcttcttcc acagactgga agagtccttc ctggtggaag aggataagaa   1380
gcacgagcgg cacccatct tcggcaacat cgtggacgag gtggcctacc acgagaagta   1440
ccccaccatc taccacctga gaaagaaact ggtggacagc accgacaagg ccgacctgcg   1500
gctgatctat ctggccctgg cccacatgat caagttccgg ggccacttcc tgatcgaggg   1560
cgacctgaac cccgacaaca gcgacgtgga caagctgttc atccagctgg tgcagaccta   1620
caaccagctg ttcgaggaaa acccccatcaa cgccagcggc gtggacgcca aggccatcct   1680
gtctgccaga ctgagcaaga gcagacggct ggaaaatctg atcgcccagc tgcccggcga   1740
gaagaagaat ggcctgttcg gaaacctgat tgccctgagc ctgggcctga cccccaactt   1800
caagagcaac ttcgacctgg ccgaggatgc caaactgcag ctgagcaagg acacctacga   1860
cgacgacctg gacaacctgc tggcccagat cggcgaccag tacgccgacc tgtttctggc   1920
cgccaagaac ctgtccgacg ccatcctgct gagcgacatc ctgagagtga acaccgagat   1980
caccaaggcc cccctgagcg cctctatgat caagagatac gacgagcacc accaggacct   2040
gaccctgctg aaagctctcg tgcggcagca gctgcctgag aagtacaaag atttttctt   2100 cgaccagagc aagaacggct acgccggcta cattgacggc ggagccagcc aggaagagtt   2160
ctacaagttc atcaagccca tcctggaaaa gatggacggc accgaggaac tgctcgtgaa   2220
gctgaacaga gaggacctgc tgcggaagca gcggaccttc gacaacggca gcatccccca   2280
ccagatccac ctgggagagc tgcacgccat tctgcggcgg caggaagatt tttacccatt   2340
cctgaaggac aaccgggaaa agatcgagaa gatcctgacc ttccgcatcc cctactacgt   2400
gggccctctg gccaggggaa acagcagatt cgcctggatg accagaaaga gcgaggaaac   2460
catcaccccc tggaacttcg aggaagtggt ggacaagggc gcttccgccc agagcttcat   2520
cgagcggatg accaacttcg ataagaacct gcccaacgag aaggtgctgc caagcacag   2580 cctgctgtac gagtacttca ccgtgtataa cgagctgacc aaagtgaaat acgtgaccga   2640
gggaatgaga aagcccgcct tcctgagcgg cgagcagaaa aaggccatcg tggacctgct   2700
gttcaagacc aaccggaaag tgaccgtgaa gcagctgaaa gaggactact tcaagaaaat   2760
cgagtgcttc gactccgtgg aaatctccgg cgtggaagat cggttcaacg cctccctggg   2820
cacataccac gatctgctga aaattatcaa ggacaaggac ttcctggaca atgaggaaaa   2880
cgaggacatt ctggaagata tcgtgctgac cctgacactg tttgaggaca gagagatgat   2940
cgaggaacgg ctgaaaacct atgcccacct gttcgacgac aaagtgatga agcagctgaa   3000
gcggcggaga tacaccggct ggggcaggct gagccggaag ctgatcaacg gcatccggga   3060
```

| | |
|---|---|
| caagcagtcc ggcaagacaa tcctggattt cctgaagtcc gacggcttcg ccaacagaaa | 3120 |
| cttcatgcag ctgatccacg acgacagcct gaccttaaa gaggacatcc agaaagccca | 3180 |
| ggtgtccggc cagggcgata gcctgcacga gcacattgcc aatctggccg gcagccccgc | 3240 |
| cattaagaag ggcatcctgc agacagtgaa ggtggtggac gagctcgtga aagtgatggg | 3300 |
| ccggcacaag cccgagaaca tcgtgatcga aatggccaga gagaaccaga ccacccagaa | 3360 |
| gggacagaag aacagccgcg agagaatgaa gcggatcgaa gagggcatca agagctgggg | 3420 |
| cagccagatc ctgaaagaac ccccgtgga aaacacccag ctgcagaacg agaagctgta | 3480 |
| cctgtactac ctgcagaatg gcgggatat gtacgtggac caggaactgg acatcaaccg | 3540 |
| gctgtccgac tacgatgtgg accatatcgt gcctcagagc tttctgaagg acgactccat | 3600 |
| cgacaacaag gtgctgacca gaagcgacaa gaaccgggc aagagcgaca acgtgccctc | 3660 |
| cgaagaggtc gtgaagaaga tgaagaacta ctggcggcag ctgctgaacg ccaagctgat | 3720 |
| tacccagaga aagttcgaca atctgaccaa ggccgagaga ggcggcctga gcgaactgga | 3780 |
| taaggccggc ttcatcaaga acagctggt ggaaacccgg cagatcacaa agcacgtggc | 3840 |
| acagatcctg gactcccgga tgaacactaa gtacgacgag aatgacaagc tgatccggga | 3900 |
| agtgaaagtg atcaccctga gtccaagct ggtgtccgat ttccggaagg atttccagtt | 3960 |
| ttacaaagtg cgcgagatca caactacca ccacgcccac gacgcctacc tgaacgccgt | 4020 |
| cgtgggaacc gccctgatca aaaagtaccc taagctggaa agcgagttcg tgtacgcgga | 4080 |
| ctacaaggtg tacgacgtgc ggaagatgat cgccaagagc gagcaggaaa tcggcaaggc | 4140 |
| taccgccaag tacttcttct acagcaacat catgaacttt ttcaagaccg agattaccct | 4200 |
| ggccaacggc gagatccgga agcggcctct gatcgagaca aacggcgaaa ccggggagat | 4260 |
| cgtgtgggat aagggccggg attttgccac cgtgcgaaa gtgctgagca tgccccaagt | 4320 |
| gaatatcgtg aaaagaccg aggtgcagac aggcggcttc agcaaagagt ctatcctgcc | 4380 |
| caagaggaac agcgataagc tgatcgccag aaagaaggac tgggaccta agaagtacgg | 4440 |
| cggcttcgac agccccaccg tggcctattc tgtgctggtg gtggccaaag tggaaaaggg | 4500 |
| caagtccaag aaactgaaga gtgtgaaaga gctgctgggg atcaccatca tggaaagaag | 4560 |
| cagcttcgag aagaatccca tcgactttct ggaagccaag ggctacaaag aagtgaaaaa | 4620 |
| ggacctgatc atcaagctgc ctaagtactc cctgttcgag ctggaaaacg ccgaagag | 4680 |
| aatgctggcc tctgccggcg aactgcagaa gggaaacgaa ctggccctgc cctccaaata | 4740 |
| tgtgaacttc ctgtacctgg ccagccacta tgagaagctg aagggctccc ccgaggataa | 4800 |
| tgagcagaaa cagctgtttg tggaacagca caagcactac ctggacgaga tcatcgagca | 4860 |
| gatcagcgag ttctccaaga gagtgatcct ggccgacgct aatctggaca aagtgctgtc | 4920 |
| cgcctacaac aagcaccggg ataagcccat cagagagcag gccgagaata tcatccacct | 4980 |
| gtttaccctg accaatctgg agccccctgc cgccttcaag tactttgaca ccaccatcga | 5040 |
| ccggaagagg tacaccagca ccaaagaggt gctggacgcc accctgatcc accagagcat | 5100 |
| caccggcctg tacgagacac ggatcgacct gtctcagctg ggaggcgaca aaaggccggc | 5160 |
| ggccacgaaa aaggccggcc aggcaaaaaa gaaaaaggaa ttcggcagtg agagggcag | 5220 |
| aggaagtctg ctaacatgcg gtgacgtcga ggagaatcct ggcccagtga gcaagggcga | 5280 |
| ggagctgttc accggggtgg tgcccatcct ggtcgagctg gacggcgacg taaacggcca | 5340 |
| caagttcagc gtgtccggcg agggcgaggg cgatgccacc tacggcaagc tgaccctgaa | 5400 |
| gttcatctgc accaccggca agctgcccgt gccctggccc accctcgtga ccaccctgac | 5460 |

```
ctacggcgtg cagtgcttca gccgctaccc cgaccacatg aagcagcacg acttcttcaa    5520
gtccgccatg cccgaaggct acgtccagga gcgcaccatc ttcttcaagg acgacggcaa    5580
ctacaagacc cgcgccgagg tgaagttcga gggcgacacc ctggtgaacc gcatcgagct    5640
gaagggcatc gacttcaagg aggacggcaa catcctgggg cacaagctgg agtacaacta    5700
caacagccac aacgtctata tcatggccga caagcagaag aacggcatca aggtgaactt    5760
caagatccgc cacaacatcg aggacggcag cgtgcagctc gccgaccact accagcagaa    5820
cacccccatc ggcgacggcc ccgtgctgct gcccgacaac cactacctga gcacccagtc    5880
cgccctgagc aaagacccca acgagaagcg cgatcacatg gtcctgctgg agttcgtgac    5940
cgccgccggg atcactctcg gcatggacga gctgtacaag gaattctaac gctagagggc    6000
ccgtttaaac ccgctgatca gcctcgactg tgccttctag ttgccagcca tctgttgttt    6060
gcccctcccc cgtgccttcc ttgaccctgg aaggtgccac tcccactgtc ctttcctaat    6120
aaaatgagga attgcatcg cattgtctga gtaggtgtca ttctattctg ggggtgggg     6180
tggggcagga cagcaagggg gaggattggg aagacaatag caggcatgct ggggatgcgg    6240
tgggctctat ggcttctgag gcggaaagaa ccagctgggg ctctaggggg tatccccacg    6300
cgccctgtag cggcgcatta agcgcggcgg gtgtggtggt tacgcgcagc gtgaccgcta    6360
cacttgccag cgccctagcg cccgctcctt tcgctttctt cccttccttt ctcgccacgt    6420
tcgccggctt tccccgtcaa gctctaaatc ggggggctccc tttagggttc cgatttagtg    6480
ctttacggca cctcgacccc aaaaaacttg attagggtga tggttcacgt agtgggccat    6540
cgccctgata cacggttttt cgccctttga cgttggagtc cacgttcttt aatagtggac    6600
tcttgttcca aactggaaca cactcaacc ctatctcggt ctattctttt gatttataag    6660
ggattttgcc gatttcggcc tattggttaa aaaatgagct gatttaacaa aaatttaacg    6720
cgaattaatt ctgtggaatg tgtgtcagtt agggtgtgga aagtccccag gctccccagc    6780
aggcagaagt atgcaaagca tgcatctcaa ttagtcagca accaggtgtg gaaagtcccc    6840
aggctcccca gcaggcagaa gtatgcaaag catgcatctc aattagtcag caaccatagt    6900
cccgccccta actccgccca tcccgcccct aactccgccc agttccgccc attctccgcc    6960
ccatggctga ctaattttt ttatttatgc agaggccgag gccgcctctg cctctgagct    7020
attccagaag tagtgaggag gctttttgg aggcctaggc ttttgcaaaa agctcccggg    7080
agcttgtata tccattttcg gatctgatca agagacagga tgaggatcgt ttcgcatgat    7140
tgaacaagat ggattgcacg caggttctcc ggccgcttgg gtggagaggc tattcggcta    7200
tgactgggca acagacaa tcggctgctc tgatgccgcc gtgttccggc tgtcagcgca    7260
ggggcgcccg gttcttttg tcaagaccga cctgtccggt gccctgaatg aactgcagga    7320
cgaggcagcg cggctatcgt ggctggccac gacgggcgtt ccttgcgcag ctgtgctcga    7380
cgttgtcact gaagcgggaa gggactggct gctattgggc gaagtgccgg ggcaggatct    7440
cctgtcatct caccttgctc ctgccgagaa agtatccatc atggctgatg caatgcggcg    7500
gctgcatacg cttgatccgg ctacctgccc attcgaccac caagcgaaac atcgcatcga    7560
gcgagcacgt actcggatgg aagccggtct tgtcgatcag gatgatctgg acgaagagca    7620
tcaggggctc gcgccagccg aactgttcgc caggctcaag gcgcgcatgc ccgacggcga    7680
ggatctcgtc gtgacccatg gcgatgcctg cttgccgaat atcatggtgg aaaatggccg    7740
cttttctgga ttcatcgact gtggccggct gggtgtggcg gaccgctatc aggacatagc    7800
```

```
gttggctacc cgtgatattg ctgaagagct tggcggcgaa tgggctgacc gcttcctcgt   7860
gctttacggt atcgccgctc ccgattcgca gcgcatcgcc ttctatcgcc ttcttgacga   7920
gttcttctga gcgggactct ggggttcgaa atgaccgacc aagcgacgcc caacctgcca   7980
tcacgagatt tcgattccac cgccgccttc tatgaaaggt tgggcttcgg aatcgttttc   8040
cgggacgccg gctggatgat cctccagcgc ggggatctca tgctggagtt cttcgcccac   8100
cccaacttgt ttattgcagc ttataatggt tacaaataaa gcaatagcat cacaaatttc   8160
acaaataaag catttttttc actgcattct agttgtggtt tgtccaaact catcaatgta   8220
tcttatcatg tctgtatacc gtcgacctct agctagagct tggcgtaatc atggtcatag   8280
ctgtttcctg tgtgaaattg ttatccgctc acaattccac acaacatacg agccggaagc   8340
ataaagtgta aagcctgggg tgcctaatga gtgagctaac tcacattaat tgcgttgcgc   8400
tcactgcccg ctttccagtc gggaaacctg tcgtgccagc tgcattaatg aatcggccaa   8460
cgcgcgggga gaggcggttt gcgtattggg cgctcttccg cttcctcgct cactgactcg   8520
ctgcgctcgg tcgttcggct gcggcgagcg gtatcagctc actcaaaggc ggtaatacgg   8580
ttatccacag aatcagggga taacgcagga agaacatgt gagcaaaagg ccagcaaaag   8640
gccaggaacc gtaaaaaggc cgcgttgctg gcgttttttcc ataggctccg ccccctgac   8700
gagcatcaca aaaatcgacg ctcaagtcag aggtggcgaa acccgacagg actataaaga   8760
taccaggcgt ttccccctgg aagctccctc gtgcgctctc ctgttccgac cctgccgctt   8820
accggatacc tgtccgcctt tctcccttcg ggaagcgtgg cgctttctca tagctcacgc   8880
tgtaggtatc tcagttcggt gtaggtcgtt cgctccaagc tgggctgtgt gcacgaaccc   8940
cccgttcagc ccgaccgctg cgccttatcc ggtaactatc gtcttgagtc aacccggta   9000
agacacgact tatcgccact ggcagcagcc actggtaaca ggattagcag agcgaggtat   9060
gtaggcggtg ctacagagtt cttgaagtgg tggcctaact acggctacac tagaagaaca   9120
gtatttggta tctgcgctct gctgaagcca gttaccttcg aaaaagagt tggtagctct   9180
tgatccggca aacaaaccac cgctggtagc ggttttttg tttgcaagca gcagattacg   9240
cgcagaaaaa aaggatctca agaagatcct ttgatctttt ctacgggtc tgacgctcag   9300
tggaacgaaa actcacgtta agggatttg gtcatgagat tatcaaaaag gatcttcacc   9360
tagatccttt taaattaaaa atgaagtttt aaatcaatct aaagtatata tgagtaaact   9420
tggtctgaca gttaccaatg cttaatcagt gaggcaccta tctcagcgat ctgtctattt   9480
cgttcatcca tagttgcctg actccccgtc gtgtagataa ctacgatacg ggagggctta   9540
ccatctggcc ccagtgctgc aatgataccg cgagacccac gctcaccggc tccagattta   9600
tcagcaataa accagccagc cggaagggcc gagcgcagaa gtggtcctgc aactttatcc   9660
gcctccatcc agtctattaa ttgttgccgg gaagctagag taagtagttc gccagttaat   9720
agtttgcgca acgttgttgc cattgctaca ggcatcgtgg tgtcacgctc gtcgtttggt   9780
atggcttcat tcagctccgg ttcccaacga tcaaggcgag ttacatgatc ccccatgttg   9840
tgcaaaaaag cggttagctc cttcggtcct ccgatcgttg tcagaagtaa gttggccgca   9900
gtgttatcac tcatggttat ggcagcactg cataattctc ttactgtcat gccatccgta   9960
agatgctttt ctgtgactgg tgagtactca accaagtcat tctgagaata gtgtatgcgg  10020
cgaccgagtt gctcttgccc ggcgtcaata cgggataata ccgcgccaca tagcagaact  10080
ttaaaagtgc tcatcattgg aaaacgttct tcggggcgaa aactctcaag gatcttaccg  10140
ctgttgagat ccagttcgat gtaacccact cgtgcaccca actgatcttc agcatctttt  10200
```

```
acttctcacca gcgtttctgg gtgagcaaaa acaggaaggc aaaatgccgc aaaaaaggga    10260
ataagggcga cacggaaatg ttgaatactc atactcttcc tttttcaata ttattgaagc    10320
atttatcagg gttattgtct catgagcgga tacatatttg aatgtattta gaaaaataaa    10380
caaatagggg ttccgcgcac atttccccga aaagtgccac ctgacgtc                 10428
```

<210> SEQ ID NO 8
<211> LENGTH: 2508
<212> TYPE: DNA
<213> ORGANISM: Artificial Sequence
<220> FEATURE:
<223> OTHER INFORMATION: pMA-SV40pA vector V1.C.2

<400> SEQUENCE: 8

```
ctaaattgta agcgttaata ttttgttaaa attcgcgtta aattttttgtt aaatcagctc      60 attttttaac caataggccg aaatcggcaa aatcccttat aaatcaaaag aatagaccga     120
gatagggttg agtggccgct acagggcgct cccattcgcc attcaggctg cgcaactgtt     180
gggaagggcg tttcggtgcg ggcctcttcg ctattacgcc agctggcgaa aggggggatgt    240 gctgcaaggc gattaagttg ggtaacgcca gggttttccc agtcacgacg ttgtaaaacg     300
acggccagtg agcgcgacgt aatacgactc actatagggc gaattggcgg aaggccgtca    360
aggccgcatg aattgttgtt gttaacttgt ttattgcagc ttataatggt tacaaataaa     420
gcaatagcat cacaaatttc acaaataaag cattttttttc actgcattct agttgtggtt    480
tgtccaaact catcaatgta tcttatcatg tctggatctg cggatccaat ctcgagctgg    540
gcctcatggg ccttccgctc actgcccgct ttccagtcgg gaaacctgtc gtgccagctg    600
cattaacatg gtcatagctg tttccttgcg tattgggcgc tctccgcttc ctcgctcact    660
gactcgctgc gctcggtcgt tcgggtaaag cctggggtgc ctaatgagca aaaggccagc    720
aaaaggccag gaaccgtaaa aaggccgcgt tgctggcgtt tttccatagg ctccgccccc    780
ctgacgagca tcacaaaaat cgacgctcaa gtcagaggtg gcgaaacccg acaggactat    840
aaagatacca ggcgtttccc cctggaagct ccctcgtgcg ctctcctgtt ccgaccctgc    900
cgcttaccgg atacctgtcc gcctttctcc cttcgggaag cgtggcgctt tctcatagct    960
cacgctgtag gtatctcagt tcggtgtagg tcgttcgctc caagctgggc tgtgtgcacg   1020
aaccccccgt tcagcccgac cgctgcgcct tatccggtaa ctatcgtctt gagtccaacc   1080
cggtaagaca cgacttatcg ccactggcag cagccactgg taacaggatt agcagagcga   1140
ggtatgtagg cggtgctaca gagttcttga agtggtggcc taactacggc tacactagaa   1200
gaacagtatt tggtatctgc gctctgctga agccagttac cttcggaaaa agagttggta   1260
gctcttgatc cggcaaacaa accaccgctg gtagcggtgt ttttttgttt tgcaagcagc   1320
agattacgcg cagaaaaaaa ggatctcaag aagatccttt gatcttttct acggggtctg   1380
acgctcagtg gaacgaaaac tcacgttaag ggattttggt catgagatta tcaaaaagga   1440
tcttcaccta gatcctttta aattaaaaat gaagttttaa atcaatctaa agtatatatg   1500
agtaaacttg gtctgacagt taccaatgct taatcagtga ggcacctatc tcagcgatct   1560
gtctatttcg ttcatccata gttgcctgac tccccgtcgt gtagataact acgatacggg   1620
agggcttacc atctggcccc agtgctgcaa tgataccgcg agaaccacgc tcaccggctc   1680
cagatttatc agcaataaac cagccagccg aagggccga gcgcagaagt ggtcctgcaa   1740
ctttatccgc ctccatccag tctattaatt gttgccggga agctagagta agtagttcgc   1800
```

-continued

| | |
|---|---|
| cagttaatag tttgcgcaac gttgttgcca ttgctacagg catcgtggtg tcacgctcgt | 1860 |
| cgtttggtat ggcttcattc agctccggtt cccaacgatc aaggcgagtt acatgatccc | 1920 |
| ccatgttgtg caaaaaagcg gttagctcct tcggtcctcc gatcgttgtc agaagtaagt | 1980 |
| tggccgcagt gttatcactc atggttatgg cagcactgca taattctctt actgtcatgc | 2040 |
| catccgtaag atgctttttct gtgactggtg agtactcaac caagtcattc tgagaatagt | 2100 |
| gtatgcggcg accgagttgc tcttgcccgg cgtcaatacg ggataatacc gcgccacata | 2160 |
| gcagaacttt aaaagtgctc atcattggaa aacgttcttc ggggcgaaaa ctctcaagga | 2220 |
| tcttaccgct gttgagatcc agttcgatgt aacccactcg tgcacccaac tgatcttcag | 2280 |
| catcttttac tttcaccagc gtttctgggt gagcaaaaac aggaaggcaa aatgccgcaa | 2340 |
| aaaagggaat aagggcgaca cggaaatgtt gaatactcat actcttcctt tttcaatatt | 2400 |
| attgaagcat ttatcagggt tattgtctca tgagcggata catatttgaa tgtatttaga | 2460 |
| aaaataaaca aataggggtt ccgcgcacat ttccccgaaa agtgccac | 2508 |

<210> SEQ ID NO 9
<211> LENGTH: 4341
<212> TYPE: DNA
<213> ORGANISM: Artificial Sequence
<220> FEATURE:
<223> OTHER INFORMATION: HLA-A 02:01 6xHis + Exon2/3-HA-L+R vector V1.C.6

<400> SEQUENCE: 9

| | |
|---|---|
| ctaaattgta agcgttaata ttttgttaaa attcgcgtta aattttttgtt aaatcagctc | 60 |
| attttttaac caataggccg aaatcggcaa aatcccttat aaatcaaaag aatagaccga | 120 |
| gatagggttg agtggccgct acagggcgct cccattcgcc attcaggctg cgcaactgtt | 180 |
| gggaagggcg tttcggtgcg ggcctcttcg ctattacgcc agctggcgaa aggggggatgt | 240 |
| gctgcaaggc gattaagttg ggtaacgcca gggttttccc agtcacgacg ttgtaaaacg | 300 |
| acggccagtg agcgcgacgt aatacgactc actatagggc gaattggcgg aaggccgtca | 360 |
| aggccgcatg aattcgctac cggtatagta atcaattacg ggtcattag ttcatagccc | 420 |
| atatatggag ttccgcgtta cataacttac ggtaaatggc ccgcctggct gaccgcccaa | 480 |
| cgacccccgc ccattgacgt caataatgac gtatgttccc atagtaacgc caatagggac | 540 |
| tttccattga cgtcaatggg tggagtattt acggtaaact gcccacttgg cagtacatca | 600 |
| agtgtatcat atgccaagta cgccccctat tgacgtcaat gacggtaaat ggcccgcctg | 660 |
| gcattatgcc cagtacatga ccttatggga ctttcctact tggcagtaca tctacgtatt | 720 |
| agtcatcgct attaccatgg tgatgcggtt ttggcagtac atcaatgggc gtggatagcg | 780 |
| gtttgactca cggggatttc caagtctcca ccccattgac gtcaatggga gtttgttttg | 840 |
| gcaccaaaat caacgggact ttccaaaatg tcgtaacaac tccgccccat tgacgcaaat | 900 |
| gggcggtagg cgtgtacggt gggaggtcta tataagcaga gctggtttag tgaaccgtca | 960 |
| gatcaggtac catggccgtc atggcgcccc gaaccctcgt cctgctactc tcgggggctc | 1020 |
| tggccctgac ccagacctgg gcgggctctc actccatgag gtatttcttc acatccgtgt | 1080 |
| ctcggccagg acgcggagag ccacgcttca tcgcagtggg ctacgtggac gacacgcagt | 1140 |
| tcgtgcggtt cgacagcgac gccgcgagcc agaggatgga gccgcgggcg ccgtggatag | 1200 |
| agcaggaggg tccggagtat tgggacggga gacacggaa agtgaaggcc cactcacaga | 1260 |
| ctcaccgagt ggacctgggg accctgcgcg gctactacaa ccagagcgag gccggttctc | 1320 |

```
acaccgtcca gaggatgtat ggctgcgacg tggggtcgga ctggcgcttc ctccgcggat    1380
accaccagta cgcctacgac ggcaaggatt acatcgccct gaaagaggac ctgcgctctt    1440
ggaccgcggc ggacatggca gctcagacca ccaagcacaa gtgggaggcg gcccatgtgg    1500
cggagcagtt gagagcctac ctggagggca cgtgcgtgga gtggctccgc agatacctgg    1560
agaacgggaa ggagacgctg cagcgcacgg acgcccccaa aacgcatatg actcaccacg    1620
ctgtctctga ccatgaagcc accctgaggt gctgggccct gagcttctac cctgcgagaa    1680
tcacactgac ctggcagcgg gatggggagg accagaccca ggacacggag ctcgtggaga    1740
ccaggcctgc aggggatgga accttccaga agtgggcggc tgtggtggtg ccttctggac    1800
aggagcagag atacacctgc catgtgcagc atgagggttt gcccaagccc ctcaccctga    1860
gatgggagcc gtcttcccag cccaccatcc ccatcgtggg catcattgct ggcctggttc    1920
tctttggagc tgtgatcact ggagctgtgg tcgctgctgt gatgtggagg aggaagagct    1980
cagatagaaa aggagggagc tactctcagg ctgcaagcag tgacagtgcc cagggctctg    2040
atgtgtctct cacagcttgt aaagtgcccg ggcatcatca ccatcaccac tgactatagt    2100
cgtctagacc tgatcataat caagccatat cacatctgta gaggtttact tgctttaaaa    2160
aacctccaca cctcccctg aacctgaaac ataaaatgaa tgcaattgtt gttgttaact    2220
tgtttattgc agcttataat ggttacaaat aaagcaatag catcacaaat ttcacaaata    2280
aagcattttt ttcactgcat tctagttgtg gtttgtccaa actcatcaat gtatcttatc    2340
atgtctggat ctgcggatcc aatctcgagc tgggcctcat gggccttccg ctcactgccc    2400
gctttccagt cgggaaacct gtcgtgccag ctgcattaac atggtcatag ctgtttcctt    2460
gcgtattggg cgctctccgc ttcctcgctc actgactcgc tgcgctcggt cgttcgggta    2520
aagcctgggg tgcctaatga gcaaaaggcc agcaaaaggc caggaaccgt aaaaaggccg    2580
cgttgctggc gttttttccat aggctccgcc cccctgacga gcatcacaaa aatcgacgct    2640
caagtcagag gtggcgaaac ccgacaggac tataaagata ccaggcgttt ccccctggaa    2700
gctccctcgt gcgctctcct gttccgaccc tgccgcttac cggatacctg tccgcctttc    2760
tcccttcggg aagcgtggcg ctttctcata gctcacgctg taggtatctc agttcggtgt    2820
aggtcgttcg ctccaagctg ggctgtgtgc acgaaccccc cgttcagccc gaccgctgcg    2880
ccttatccgg taactatcgt cttgagtcca acccggtaag acacgactta tcgccactgg    2940
cagcagccac tggtaacagg attagcagag cgaggtatgt aggcggtgct acagagttct    3000
tgaagtggtg gcctaactac ggctacacta gaagaacagt atttggtatc tgcgctctgc    3060
tgaagccagt taccttcgga aaaagagttg gtagctcttg atccggcaaa caaaccaccg    3120
ctggtagcgg tggtttttt gtttgcaagc agcagattac gcgcagaaaa aaaggatctc    3180
aagaagatcc tttgatcttt tctacggggt ctgacgctca gtggaacgaa aactcacgtt    3240
aagggatttt ggtcatgaga ttatcaaaaa ggatcttcac ctagatcctt ttaaattaaa    3300
aatgaagttt taaatcaatc taaagtatat atgagtaaac ttggtctgac agttaccaat    3360
gcttaatcag tgaggcacct atctcagcga tctgtctatt tcgttcatcc atagttgcct    3420
gactccccgt cgtgtagata actacgatac ggggaggctt accatctggc cccagtgctg    3480
caatgatacc gcgagaacca cgctcaccgg ctccagattt atcagcaata aaccagccag    3540
ccggaagggc cgagcgcaga agtggtcctg caactttatc cgcctccatc cagtctatta    3600
attgttgccg ggaagctaga gtaagtagtt cgccagttaa tagtttgcgc aacgttgttg    3660
ccattgctac aggcatcgtg gtgtcacgct cgtcgtttgg tatggcttca ttcagctccg    3720
```

```
gttcccaacg atcaaggcga gttacatgat cccccatgtt gtgcaaaaaa gcggttagct    3780
ccttcggtcc tccgatcgtt gtcagaagta agttggccgc agtgttatca ctcatggtta    3840
tggcagcact gcataattct cttactgtca tgccatccgt aagatgcttt tctgtgactg    3900
gtgagtactc aaccaagtca ttctgagaat agtgtatgcg cgaccgagt tgctcttgcc     3960 cggcgtcaat acgggataat accgcgccac atagcagaac tttaaaagtg ctcatcattg    4020
gaaaacgttc ttcggggcga aaactctcaa ggatcttacc gctgttgaga tccagttcga    4080
tgtaacccac tcgtgcaccc aactgatctt cagcatcttt tactttcacc agcgtttctg    4140
ggtgagcaaa acaggaagg caaaatgccg caaaaaggg aataagggcg acacggaaat       4200
gttgaatact catactcttc cttttcaat attattgaag catttatcag ggttattgtc      4260
tcatgagcgg atacatattt gaatgtattt agaaaaataa acaaataggg gttccgcgca    4320
catttccccg aaaagtgcca c                                              4341

<210> SEQ ID NO 10
<211> LENGTH: 4332
<212> TYPE: DNA
<213> ORGANISM: Artificial Sequence
<220> FEATURE:
<223> OTHER INFORMATION: HLA-B 35:01 6xHis + Exon2/3-HA-L+R vector
      V1.C.9

<400> SEQUENCE: 10
ctaaattgta agcgttaata ttttgttaaa attcgcgtta aattttgtt aaatcagctc       60 attttttaac caataggccg aaatcggcaa atcccttat aaatcaaaag aatagaccga     120
gatagggttg agtggccgct acagggcgct cccattcgcc attcaggctg cgcaactgtt    180
gggaagggcg tttcggtgcg ggcctcttcg ctattacgcc agctggcgaa aggggggatgt   240 gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccgcatg aattcgctac cggtatagta atcaattacg gggtcattag ttcatagccc    420
atatatggag ttccgcgtta cataacttac ggtaaatggc ccgcctggct gaccgcccaa    480
cgacccccgc ccattgacgt caataatgac gtatgttccc atagtaacgc caatagggac    540
tttccattga cgtcaatggg tggagtattt acggtaaact gcccacttgg cagtacatca    600
agtgtatcat atgccaagta cgccccctat tgacgtcaat gacggtaaat ggcccgcctg    660
gcattatgcc cagtacatga ccttatggga ctttcctact tggcagtaca tctacgtatt    720
agtcatcgct attaccatgg tgatgcggtt ttggcagtac atcaatgggc gtggatagcg    780
gtttgactca cggggatttc caagtctcca ccccattgac gtcaatggga gtttgtttg     840 gcaccaaaat caacgggact ttccaaaatg tcgtaacaac tccgccccat tgacgcaaat    900
gggcggtagg cgtgtacggt gggaggtcta tataagcaga ctggtttag tgaaccgtca     960 gatcaggtac catgcgggtc acggcgcccc gaaccgtcct cctgctgctc tgggggcag    1020 tggccctgac cgagacctgg gccggctccc actccatgag gtatttctac accgccatgt   1080
cccggccagg acgcggagag ccacgcttca tcgcagtggg ctacgtggac gacacccagt   1140
tcgtgaggtt cgacagcgac gccgcgagtc gaggacgga gcctcgggcg ccatggatag    1200
agcaggaggg gccggagtat tgggaccgga acacacagat cttcaagacc aacacacaga   1260
cttaccgaga gagcctgcgg aacctgcgcg gctactacaa ccagagcgag gccgggtctc   1320
acatcatcca gaggatgtat ggctgcgacc tggggcccga cggcgcctc ctccgcgggc    1380
```

```
atgaccagtc cgcctacgac ggcaaggatt acatcgccct gaacgaggac ctgagctcct    1440
ggaccgcggc ggacaccgcg gctcagatca cccagcgcaa gtgggaggcg gcccgtgtgg    1500
cggagcagct gagagcctac ctggagggcc tgtgcgtgga gtggctccgc agatacctgg    1560
agaacgggaa ggagactctt cagcgcgcag atcctccaaa gacacacgtg acccaccacc    1620
ccgtctctga ccatgaggcc accctgaggt gctgggccct gggcttctac cctgcggaga    1680
tcacactgac ctggcagcgg gatggcgagg accaaactca ggacactgag cttgtggaga    1740
ccagaccagc aggagataga accttccaga agtgggcagc tgtggtggtg ccttctggag    1800
aagagcagag atacacatgc catgtacagc atgaggggct gccgaagccc ctcaccctga    1860
gatgggagcc atcttcccag tccaccatcc ccatcgtggg cattgttgct ggcctggctg    1920
tcctagcagt tgtggtcatc ggagctgtgg tcgctactgt gatgtgtagg aggaagagct    1980
caggtggaaa aggagggagc tactctcagg ctgcgtccag cgacagtgcc cagggctctg    2040
atgtgtctct cacagctccc ggcatcatc accatcacca ctgactatag tcgtctagac    2100
ctgatcataa tcaagccata tcacatctgt agaggtttac ttgctttaaa aaacctccac    2160
acctccccct gaacctgaaa cataaaatga atgcaattgt tgttgttaac ttgtttattg    2220
cagcttataa tggttacaaa taaagcaata gcatcacaaa tttcacaaat aaagcatttt    2280
tttcactgca ttctagttgt ggtttgtcca aactcatcaa tgtatcttat catgtctgga    2340
tctgcggatc caatctcgag ctgggcctca tgggccttcc gctcactgcc cgctttccag    2400
tcgggaaacc tgtcgtgcca gctgcattaa catggtcata gctgtttcct gcgtattgg    2460 gcgctctccg cttcctcgct cactgactcg ctgcgctcgg tcgttcgggt aaagcctggg    2520
gtgcctaatg agcaaaaggc cagcaaaagg ccaggaaccg taaaaaggcc gcgttgctgg    2580 cgttttttcca taggctccgc cccctgacg agcatcacaa aaatcgacgc tcaagtcaga    2640
ggtggcgaaa cccgacagga ctataaagat accaggcgtt tcccctgga agctccctcg    2700 tgcgctctcc tgttccgacc ctgccgctta ccggatacct gtccgccttt ctcccttcgg    2760
gaagcgtggc gctttctcat agctcacgct gtaggtatct cagttcggtg taggtcgttc    2820
gctccaagct gggctgtgtg cacgaacccc ccgttcagcc cgaccgctgc gccttatccg    2880
gtaactatcg tcttgagtcc aacccggtaa gacacgactt atcgccactg gcagcagcca    2940
ctggtaacag gattagcaga gcgaggtatg taggcggtgc tacagagttc ttgaagtggt    3000
ggcctaacta cggctacact agaagaacag tatttggtat ctgcgctctg ctgaagccag    3060
ttaccttcgg aaaaagagtt ggtagctctt gatccggcaa acaaaccacc gctggtagcg    3120
gtggtttttt tgtttgcaag cagcagatta cgcgcagaaa aaaaggatct caagaagatc    3180
ctttgatctt ttctacgggg tctgacgctc agtggaacga aaactcacgt taagggattt    3240
tggtcatgag attatcaaaa aggatcttca cctagatcct tttaaattaa aaatgaagtt    3300
ttaaatcaat ctaaagtata tatgagtaaa cttggtctga cagttaccaa tgcttaatca    3360
gtgaggcacc tatctcagcg atctgtctat ttcgttcatc catagttgcc tgactccccg    3420
tcgtgtagat aactacgata cgggagggct taccatctgg ccccagtgct gcaatgatac    3480
cgcgagaacc acgctcaccg gctccagatt tatcagcaat aaaccagcca gccggaaggg    3540
ccgagcgcag aagtggtcct gcaactttat ccgcctccat ccagtctatt aattgttgcc    3600
gggaagctag agtaagtagt tcgccagtta atagtttgcg caacgttgtt gccattgcta    3660
caggcatcgt ggtgtcacgc tcgtcgtttg gtatggcttc attcagctcc ggttcccaac    3720
```

| | |
|---|---:|
| gatcaaggcg agttacatga tcccccatgt tgtgcaaaaa agcggttagc tccttcggtc | 3780 |
| ctccgatcgt tgtcagaagt aagttggccg cagtgttatc actcatggtt atggcagcac | 3840 |
| tgcataattc tcttactgtc atgccatccg taagatgctt ttctgtgact ggtgagtact | 3900 |
| caaccaagtc attctgagaa tagtgtatgc ggcgaccgag ttgctcttgc ccggcgtcaa | 3960 |
| tacgggataa taccgcgcca catagcagaa ctttaaaagt gctcatcatt ggaaaacgtt | 4020 |
| cttcggggcg aaaactctca aggatcttac cgctgttgag atccagttcg atgtaaccca | 4080 |
| ctcgtgcacc caactgatct tcagcatctt ttactttcac cagcgtttct gggtgagcaa | 4140 |
| aaacaggaag gcaaaatgcc gcaaaaaagg gaataagggc gacacggaaa tgttgaatac | 4200 |
| tcatactctt cctttttcaa tattattgaa gcatttatca gggttattgt ctcatgagcg | 4260 |
| gatacatatt tgaatgtatt tagaaaaata aacaataggg gttccgcgc acatttcccc | 4320 |
| gaaaagtgcc ac | 4332 |

<210> SEQ ID NO 11
<211> LENGTH: 5520
<212> TYPE: DNA
<213> ORGANISM: Artificial Sequence
<220> FEATURE:
<223> OTHER INFORMATION: AAVS1-S_A24_6xH vector V1.F.8

<400> SEQUENCE: 11

| | |
|---|---:|
| ctaaattgta agcgttaata tttgttaaa attcgcgtta aattttgtt aaatcagctc | 60 |
| atttttaac caataggccg aaatcggcaa atcccttat aaatcaaaag aatagaccga | 120 |
| gatagggttg agtggccgct acagggcgct cccattcgcc attcaggctg cgcaactgtt | 180 |
| gggaagggcg tttcggtgcg ggcctcttcg ctattacgcc agctggcgaa aggggggatgt | 240 |
| gctgcaaggc gattaagttg ggtaacgcca gggttttccc agtcacgacg ttgtaaaacg | 300 |
| acggccagtg agcgcgacgt aatacgactc actatagggc gaattggcgg aaggccgtca | 360 |
| aggccgcatg aattgctgcc caaggatgct cttttccggag cacttccttc tcggcgctgc | 420 |
| accacgtgat gtcctctgag cggatcctcc ccgtgtctgg gtcctctccg ggcatctctc | 480 |
| ctccctcacc caaccccatg ccgtgttcac tcgctgggtt ccctttttcct tctccttctg | 540 |
| gggcctgtgc catctctcgt ttcttaggat ggccttctcc gacggatgtc tcccttgcgt | 600 |
| cccgcctccc cttcttgtag gcctgcatca tcaccgtttt tctggacaac cccaaagtac | 660 |
| cccgtctccc tggcttagca cctctccatc ctcttgcttt ctttgcctgg caccccgtt | 720 |
| ctcctgtgga ttcgggtcac ctctcactcc tttcatttgg gcagctcccc tacccccctt | 780 |
| acctctctag tctgtgctag ctcttccagc ccctgtcat ggcatcttcc aggggtccga | 840 |
| gagctcagct agtcttcttc ctccaacccg ggccctatgt ccacttcagg acagcatgtt | 900 |
| tgctgcctcc agggatcctg tgtccccgag ctgggaccac cttatattcc cagggccggt | 960 |
| taatgtggct ctggttctgg gtactttat ctgtcccctc caccggtata gtaatcaatt | 1020 |
| acggggtcat tagttcatag cccatatatg gagttccgcg ttacataact tacggtaaat | 1080 |
| ggcccgcctg gctgaccgcc caacgacccc cgcccattga cgtcaataat gacgtatgtt | 1140 |
| cccatagtaa cgccaatagg gactttccat tgacgtcaat gggtggagta tttacgtaa | 1200 |
| actgcccact tggcagtaca tcaagtgtat catatgccaa gtacgccccc tattgacgtc | 1260 |
| aatgacggta aatggcccgc ctggcattat gcccagtaca tgaccttatg gactttcct | 1320 |
| acttggcagt acatctacgt attagtcatc gctattacca tggtgatgcg gttttggcag | 1380 |
| tacatcaatg ggcgtggata gcggtttgac tcacggggat ttccaagtct ccaccccatt | 1440 |

```
gacgtcaatg ggagtttgtt ttggcaccaa aatcaacggg actttccaaa atgtcgtaac    1500
aactccgccc cattgacgca aatgggcggt aggcgtgtac ggtgggaggt ctatataagc    1560
agagctggtt tagtgaaccg tcagatcagg taccatggcc gtcatggcgc cccgaaccct    1620
cgtcctgcta ctctcggggg ccctggccct gacccagacc tgggcaggct cccactccat    1680
gaggtatttc tccacatccg tgtctcggcc aggacgcgga gagccacgct tcatcgccgt    1740
gggctacgtg gacgacacgc agttcgtgcg gttcgacagc gacgccgcga gccagaggat    1800
ggagccgcgg gcgccgtgga tagagcagga ggggccggag tattgggacg aggagacagg    1860
gaaagtgaag gcccactcac agactgaccg agagaacctg cggatcgcgc tccgctacta    1920
caaccagagc gaggccggtt ctcacaccct ccagatgatg tttggctgcg acgtggggtc    1980
ggacgggcgc ttcctccgcg gataccacca gtacgcctac gacggcaagg attacatcgc    2040
cctgaaagag gacctgcgct cttggaccgc ggcggacatg gcggctcaga tcaccaagcg    2100
caagtgggag gcgccccatg tggcggagca gcagagagcc tacctggagg cacgtgcgt    2160 ggacgggctc cgcagatacc tggagaacgg gaaggagacg ctgcagcgca cggaccccc    2220 caagacacat atgacccacc accccatctc tgaccatgag gccactctga gatgctgggc    2280
cctgggcttc taccctgcgg agatcacact gacctggcag cgggatgggg aggaccagac    2340
ccaggacacg gagcttgtgg agaccaggcc tgcaggggat ggaaccttcc agaagtgggc    2400
agctgtggtg gttccttctg gagaggagca gagatacacc tgccatgtgc agcatgaggg    2460
tctgcccaag cccctcaccc tgagatggga gccatcttcc cagcccaccg tccccatcgt    2520
gggcatcatt gctggcctgg ttctccttgg agctgtgatc actggagctg tggtcgctgc    2580
tgtgatgtgg aggaggaaca gctcagatag aaaaggaggg agctactctc aggctgcaag    2640
cagtgacagt gcccagggct ctgatgtgtc tctcacagct tgtaaagtgc ccgggcatca    2700
tcaccatcac cactgactat agtcgtctag acctgatcat aatcaagcca tatcacatct    2760
gtagaggttt acttgcttta aaaaacctcc acacctcccc ctgaacctga aacataaaat    2820
gaatgcaatt gttgttgtta acttgtttat tgcagcttat aatggttaca ataaagcaa    2880 tagcatcaca aatttcacaa ataaagcatt tttttcactg cattctagtt gtggtttgtc    2940
caaactcatc aatgtatctt atcatgtctg gatctgcgga tcaggattgg tgacagaaaa    3000 gccccccatcc ttaggcctcc tccttcctag tctcctgata ttcgtctaac ccccacctcc    3060
tgttaggcag attccttatc tggtgacaca ccccattttc tggagccat ctctctcctt    3120 gccagaacct ctaaggtttg cttacgatgg agccagagag gatcctggga gggagacttg    3180
gcagggggtg ggagggaagg gggggatgcg tgacctgccc ggttctcagt ggccaccctg    3240
cgctaccctc tcccagaacc tgagctgctc tgacgcggct gtctggtgcg tttcactgat    3300
cctggtgctg cagcttcctt acacttccca agaggagaag cagtttggaa aaacaaaatc    3360
agaataagtt ggtcctgagt tctaactttg gctcttcacc tttctagccc caatttata    3420 ttgttcctcc gtgcgtcagt tttacctgtg agataaggcc agtagccacc cccgtcctgg    3480
cagggctgtg gtgaggaggg gggtgtccgt gtggaaaact ccctttgtga gatggtgcg    3540 tcctcgagct gggcctcatg ggccttccgc tcactgcccg ctttccagtc gggaaacctg    3600
tcgtgccagc tgcattaaca tggtcatagc tgtttccttg cgtattgggc gctctccgct    3660
tcctcgctca ctgactcgct gcgctcggtc gttcgggtaa agcctggggt gcctaatgag    3720
caaaaggcca gcaaaaggcc aggaaccgta aaaaggccgc gttgctggcg ttttccata    3780
```

| | |
|---|---|
| ggctccgccc ccctgacgag catcacaaaa atcgacgctc aagtcagagg tggcgaaacc | 3840 |
| cgacaggact ataaagatac caggcgtttc ccccctggaag ctccctcgtg cgctctcctg | 3900 |
| ttccgaccct gccgcttacc ggatacctgt ccgcctttct cccttcggga agcgtggcgc | 3960 |
| tttctcatag ctcacgctgt aggtatctca gttcggtgta ggtcgttcgc tccaagctgg | 4020 |
| gctgtgtgca cgaaccccccc gttcagcccg accgctgcgc cttatccggt aactatcgtc | 4080 |
| ttgagtccaa cccggtaaga cacgacttat cgccactggc agcagccact ggtaacagga | 4140 |
| ttagcagagc gaggtatgta ggcggtgcta cagagttctt gaagtggtgg cctaactacg | 4200 |
| gctacactag aagaacagta tttggtatct gcgctctgct gaagccagtt accttcggaa | 4260 |
| aaagagttgg tagctcttga tccggcaaac aaaccaccgc tggtagcggt ggtttttttg | 4320 |
| tttgcaagca gcagattacg cgcagaaaaa aaggatctca agaagatcct ttgatctttt | 4380 |
| ctacggggtc tgacgctcag tggaacgaaa actcacgtta agggattttg gtcatgagat | 4440 |
| tatcaaaaag gatcttcacc tagatccttt taaattaaaa atgaagtttt aaatcaatct | 4500 |
| aaagtatata tgagtaaact tggtctgaca gttaccaatg cttaatcagt gaggcaccta | 4560 |
| tctcagcgat ctgtctattt cgttcatcca tagttgcctg actccccgtc gtgtagataa | 4620 |
| ctacgatacg ggagggctta ccatctggcc ccagtgctgc aatgataccg cgagaaccac | 4680 |
| gctcaccggc tccagattta tcagcaataa accagccagc cggaagggcc gagcgcagaa | 4740 |
| gtggtcctgc aactttatcc gcctccatcc agtctattaa ttgttgccgg gaagctagag | 4800 |
| taagtagttc gccagttaat agtttgcgca acgttgttgc cattgctaca ggcatcgtgg | 4860 |
| tgtcacgctc gtcgtttggt atggcttcat tcagctccgg ttcccaacga tcaaggcgag | 4920 |
| ttacatgatc ccccatgttg tgcaaaaaag cggttagctc cttcggtcct ccgatcgttg | 4980 |
| tcagaagtaa gttggccgca gtgttatcac tcatggttat ggcagcactg cataattctc | 5040 |
| ttactgtcat gccatccgta agatgctttt ctgtgactgg tgagtactca accaagtcat | 5100 |
| tctgagaata gtgtatgcgg cgaccgagtt gctcttgccc ggcgtcaata cgggataata | 5160 |
| ccgcgccaca tagcagaact ttaaaagtgc tcatcattgg aaaacgttct cggggcgaa | 5220 |
| aactctcaag gatcttaccg ctgttgagat ccagttcgat gtaacccact cgtgcaccca | 5280 |
| actgatcttc agcatctttt actttcacca gcgtttctgg gtgagcaaaa acaggaaggc | 5340 |
| aaaatgccgc aaaaaaggga ataagggcga cacggaaatg ttgaatactc atactcttcc | 5400 |
| tttttcaata ttattgaagc atttatcagg gttattgtct catgagcgga tacatatttg | 5460 |
| aatgtattta gaaaaataaa caaataggg ttccgcgcac atttccccga aaagtgccac | 5520 |

<210> SEQ ID NO 12
<211> LENGTH: 5733
<212> TYPE: DNA
<213> ORGANISM: Artificial Sequence
<220> FEATURE:
<223> OTHER INFORMATION: AAVS1-L_B07_6xH vector V1.F.10

<400> SEQUENCE: 12

| | |
|---|---|
| ctaaattgta agcgttaata tttgttaaa attttttgtt aaatcagctc | 60 |
| atttttaac caataggccg aaatcggcaa atcccttat aaatcaaaag aatagaccga | 120 |
| gatagggttg agtggccgct acagggcgct cccattcgcc attcaggctg cgcaactgtt | 180 |
| gggaagggcg tttcggtgcg ggcctcttcg ctattacgcc agctggcgaa aggggggatgt | 240 |
| gctgcaaggc gattaagttg ggtaacgcca gggttttccc agtcacgacg ttgtaaaacg | 300 |
| acggccagtg agcgcgacgt aatacgactc actatagggc gaattggcgg aaggccgtca | 360 |

```
aggccgcatg aattgagctc tactggcttc tgcgccgcct ctggcccact gtttcccctt    420
cccaggcagg tcctgctttc tctgacctgc attctctccc ctgggcctgt gccgctttct    480
gtctgcagct tgtggcctgg gtcacctcta cggctggccc agatccttcc ctgccgcctc    540
cttcaggttc cgtcttcctc cactccctct tccccttgct ctctgctgtg ttgctgccca    600
aggatgctct ttccggagca cttccttctc ggcgctgcac cacgtgatgt cctctgagcg    660
gatcctcccc gtgtctgggt cctctccggg catctctcct ccctcaccca accccatgcc    720
gtcttcactc gctgggttcc cttttccttc tccttctggg gcctgtgcca tctctcgttt    780
cttaggatgg ccttctccga cggatgtctc ccttgcgtcc cgcctcccct tcttgtaggc    840
ctgcatcatc accgtttttc tggacaaccc caaagtaccc cgtctccctg gctttagcca    900
cctctccatc ctcttgcttt ctttgcctgg acaccccgtt ctcctgtgga ttcgggtcac    960
ctctcactcc tttcatttgg gcagctcccc tacccccctt acctctctag tctgtgctag   1020
ctcttccagc cccctgtcat ggcatcttcc aggggtccga gagctcagct agtcttcttc   1080
ctccaacccg ggcccctatg tccacttcag acagcatgt ttgctgcctc cagggatcct    1140
gtgtccccga gctgggacca ccttatattc ccagggccgg ttaatgtggc tctggttctg   1200
ggtactttta tctgtcccct ccaccggtat agtaatcaat tacgggtca ttagttcata    1260 gcccatatat ggagttccgc gttacataac ttacggtaaa tggcccgcct ggctgaccgc   1320
ccaacgaccc ccgcccattg acgtcaataa tgacgtatgt tcccatagta acgccaatag   1380
ggactttcca ttgacgtcaa tgggtggagt atttacggta aactgcccac ttggcagtac   1440
atcaagtgta tcatatgcca agtacgcccc ctattgacgt caatgacggt aaatggcccg   1500
cctggcatta tgcccagtac atgaccttat gggactttcc tacttggcag tacatctacg   1560
tattagtcat cgctattacc atggtgatgc ggttttggca gtacatcaat gggcgtggat   1620
agcggtttga ctcacgggga tttccaagtc tccaccccat tgacgtcaat gggagtttgt   1680
tttggcacca aaatcaacgg gactttccaa aatgtcgtaa caactccgcc ccattgacgc   1740
aaatgggcgg taggcgtgta cggtgggagg tctatataag cagagctggt ttagtgaacc   1800
gtcagatcag gtaccatgct ggtcatggcg ccccgaaccg tcctcctgct gctctcggcg   1860
gccctggccc tgaccgagac ctgggccggc tcccactcca tgaggtattt ctacacctcc   1920
gtgtctcggc caggacgcgg agagccacgc ttcatctcag tgggctacgt ggacgacacc   1980
cagttcgtga ggttcgacag cgacgccgcg agtccgagag aggagccgcg ggcgccgtgg   2040
atagagcagg aggggccgga gtattgggac cggaacacac agatctacaa ggcccaggca   2100
cagactgacc gagagagcct gcggaacctg cgcggctact acaaccagag cgaggccggg   2160
tctcacaccc tccagagcat gtacggctgc gacgtggggc cggacgggcg cctcctccgc   2220
gggcatgacc agtacgccta cgacggcaag gattacatcg ccctgaacga ggacctgcgc   2280
tcctggaccg ccgcggacac ggcggctcag atcacccagc gcaagtggga ggcggcccgt   2340
gaggcggagc agcggagagc ctacctggag ggcgagtgcg tggagtggct ccgcagatac   2400
ctggagaacg ggaaggacaa acttgagcgc gcagaccctc aaagacaca cgtgaccca    2460 caccccatct ctgaccatga ggccaccctg aggtgctggg ccctgggttt ctaccctgcg   2520
gagatcacac tgacctggca gcgggatggc gaggaccaaa ctcaggacac tgagcttgtg   2580
gagaccagac cagcaggaga tagaaccttc cagaagtggg cagctgtggt ggtgccttct   2640
ggagaagagc agagatacac atgccatgta cagcatgagg ggctgccgaa gcccctcacc   2700
```

```
ctgagatggg agccgtcttc ccagtccacc gtccccatcg tgggcattgt tgctggcctg    2760
gctgtcctag cagttgtggt catcggagct gtggtcgctg ctgtgatgtg taggaggaag    2820
agttcaggtg gaaaaggagg gagctactct caggctgcgt gcagcgacag tgcccagggc    2880
tctgatgtgt ctctcacagc tcccgggcat catcaccatc accactgact atagtcgtct    2940
agacctgatc ataatcaagc catatcacat ctgtagaggt ttacttgctt taaaaaacct    3000
ccacacctcc ccctgaacct gaaacataaa atgaatgcaa ttgttgttgt taacttgttt    3060
attgcagctt ataatggtta caaataaagc aatagcatca caaatttcac aaataaagca    3120
tttttttcac tgcattctag ttgtggtttg tccaaactca tcaatgtatc ttatcatgtc    3180
tggatctgcg gatcaggatt ggtgacagaa aagccccatc cttaggcctc ctccttccta    3240
gtctcctgat attgggtcta accccccacct cctgttaggc agattcctta tctggtgaca    3300 caccccatt tcctggagcc atctctctcc ttgccagaac ctctaaggtt tgcttacgat    3360
ggagccagag aggatcctgg gagggagagc ttggcgggg gtgggaggga agggggggat    3420
gcgtgacctg cccggttctc agtggccacc ctgcgctacc ctctcccaga acctgagctg    3480
ctctgacgcg gctgtctggt gcgtttcact gatcctggtg ctgcagcttc cttacacttc    3540
ccaagaggag aagcagtttg gaaaaacaaa atcagaataa gttggtcctg agttctaact    3600
ttggctcttc accttttctag tccccaattt atattgttcc tccgtgcgtc agttttacct    3660
gtgagataag gccagtagcc agcccccgtcc tggcagggct gtggtgagga ggggggtgtc    3720
cgtgtggaaa actccctttg tgagaatggt gcgtcctcga gctgggcctc atgggccttc    3780
cgctcactgc ccgctttcca gtcgggaaac ctgtcgtgcc agctgcatta acatggtcat    3840 agctgttttcc ttgcgtattg ggcgctctcc gcttcctcgc tcactgactc gctgcgctcg    3900
gtcgttcggg taaagcctgg ggtgcctaat gagcaaaagg ccagcaaaag gccaggaacc    3960
gtaaaaaggc cgcgttgctg gcgttttttcc ataggctccg ccccctgac gagcatcaca    4020 aaaatcgacg ctcaagtcag aggtggcgaa acccgacagg actataaaga taccaggcgt    4080
ttccccctgg aagctccctc gtgcgctctc ctgttccgac cctgccgctt accggatacc    4140
tgtccgcctt tctcccttcg ggaagcgtgg cgctttctca tagctcacgc tgtaggtatc    4200
tcagttcggt gtaggtcgtt cgctccaagc tgggctgtgt gcacgaaccc cccgttcagc    4260
ccgaccgctg cgccttatcc ggtaactatc gtcttgagtc aacccggta agacacgact    4320 tatcgccact ggcagcagcc actggtaaca ggattagcag agcgaggtat gtaggcggtg    4380
ctacagagtt cttgaagtgg tggcctaact acggctacac tagaagaaca gtatttggta    4440
tctgcgctct gctgaagcca gttaccttcg gaaaaagagt tggtagctct tgatccggca    4500
aacaaaccac cgctggtagc ggtggttttt ttgtttgcaa gcagcagatt acgcgcagaa    4560
aaaaaggatc tcaagaagat cctttgatct tttctacggg gtctgacgct cagtggaacg    4620
aaaactcacg ttaagggatt ttggtcatga gattatcaaa aaggatcttc acctagatcc    4680
ttttaaatta aaaatgaagt tttaaatcaa tctaaagtat atatgagtaa acttggtctg    4740
acagttacca atgcttaatc agtgaggcac ctatctcagc gatctgtcta tttcgttcat    4800
ccatagttgc ctgactcccc gtcgtgtaga taactacgat acgggagggc ttaccatctg    4860
gccccagtgc tgcaatgata ccgcgagaac cacgctcacc ggctccagat ttatcagcaa    4920
taaaccagcc agccggaagg gccgagcgca gaagtggtcc tgcaacttta tccgcctcca    4980
tccagtctat taattgttgc cgggaagcta gagtaagtag ttcgccagtt aatagtttgc    5040
gcaacgttgt tgccattgct acaggcatcg tggtgtcacg ctcgtcgttt ggtatggctt    5100
```

| | |
|---|---|
| cattcagctc cggttcccaa cgatcaaggc gagttacatg atcccccatg ttgtgcaaaa | 5160 |
| aagcggttag ctccttcggt cctccgatcg ttgtcagaag taagttggcc gcagtgttat | 5220 |
| cactcatggt tatggcagca ctgcataatt ctcttactgt catgccatcc gtaagatgct | 5280 |
| tttctgtgac tggtgagtac tcaaccaagt cattctgaga atagtgtatg cggcgaccga | 5340 |
| gttgctcttg cccggcgtca atacgggata taccgcgcc acatagcaga actttaaaag | 5400 |
| tgctcatcat tggaaaacgt tcttcggggc gaaaactctc aaggatctta ccgctgttga | 5460 |
| gatccagttc gatgtaaccc actcgtgcac ccaactgatc ttcagcatct tttactttca | 5520 |
| ccagcgtttc tgggtgagca aaaacaggaa ggcaaaatgc cgcaaaaaag gaataagggg | 5580 |
| cgacacggaa atgttgaata ctcatactct tccttttca atattattga agcatttatc | 5640 |
| agggttattg tctcatgagc ggatacatat ttgaatgtat ttagaaaaat aaacaaatag | 5700 |
| gggttccgcg cacatttccc cgaaaagtgc cac | 5733 |

<210> SEQ ID NO 13
<211> LENGTH: 7062
<212> TYPE: DNA
<213> ORGANISM: Artificial Sequence
<220> FEATURE:
<223> OTHER INFORMATION: AAVS1-1_GFP_HCMVpp65_WT vector V1.G.10

<400> SEQUENCE: 13

| | |
|---|---|
| ctaaattgta agcgttaata ttttgttaaa attcgcgtta aattttgtt aaatcagctc | 60 |
| attttttaac caataggccg aaatcggcaa atcccttat aaatcaaaag aatagaccga | 120 |
| gatagggttg agtggccgct acagggcgct cccattcgcc attcaggctg cgcaactgtt | 180 |
| gggaagggcg tttcggtgcg ggcctcttcg ctattacgcc agctggcgaa agggggatgt | 240 |
| gctgcaaggc gattaagttg ggtaacgcca gggttttccc agtcacgacg ttgtaaaacg | 300 |
| acggccagtg agcgcgacgt aatacgactc actatagggc gaattggcgg aaggccgtca | 360 |
| aggccgcatg aattgagctc tactggcttc tgcgccgcct ctggcccact gtttccctt | 420 |
| cccaggcagg tcctgctttc tctgacctgc attctctccc ctgggcctgt gccgcttct | 480 |
| gtctgcagct tgtggcctgg gtcacctcta cggctggccc agatccttcc ctgccgcctc | 540 |
| cttcaggttc cgtcttcctc cactccctct tcccttgct ctctgctgtg ttgctgccca | 600 |
| aggatgctct ttccggagca cttccttctc ggcgctgcac cacgtgatgt cctctgagcg | 660 |
| gatcctcccc gtgtctgggt cctccgggg catctctcct ccctcaccca accccatgcc | 720 |
| gtcttcactc gctgggttcc cttttccttc tccttctggg gctgtgcca tctctcgttt | 780 |
| cttaggatgg ccttctccga cggatgtctc ccttgcgtcc cgcctccct tcttgtaggc | 840 |
| ctgcatcatc accgttttc tggacaaccc caaagtaccc cgtctccctg ctttagcca | 900 |
| cctctccatc ctcttgcttt ctttgcctgg acaccccgtt ctcctgtgga ttcgggtcac | 960 |
| ctctcactcc tttcatttgg gcagctccc tacccccctt acctctctag tctgtgctag | 1020 |
| ctcttccagc cccctgtcat ggcatcttcc aggggtccga gagctcagct agtcttcttc | 1080 |
| ctccaacccg ggcccctatg tccacttcag gacagcatgt ttgctgcctc cagggatcct | 1140 |
| gtgtccccga gctgggacca cccttatattc ccagggccgg ttaatgtggc tctggttctg | 1200 |
| ggtactttta tctgtcccct ccaccggtat agtaatcaat tacgggtca ttagttcata | 1260 |
| gcccatatat ggagttccgc gttacataac ttacggtaaa tggcccgcct ggctgaccgc | 1320 |
| ccaacgaccc ccgcccattg acgtcaataa tgacgtatgt tcccatagta acgccaatag | 1380 |

```
ggactttcca ttgacgtcaa tgggtggagt atttacggta aactgcccac ttggcagtac    1440
atcaagtgta tcatatgcca agtacgcccc ctattgacgt caatgacggt aaatggcccg    1500
cctggcatta tgcccagtac atgaccttat gggactttcc tacttggcag tacatctacg    1560
tattagtcat cgctattacc atggtgatgc ggttttggca gtacatcaat gggcgtggat    1620
agcggtttga ctcacgggga tttccaagtc tccacccat tgacgtcaat gggagtttgt     1680
tttggcacca aaatcaacgg gactttccaa aatgtcgtaa caactccgcc ccattgacgc    1740
aaatgggcgg taggcgtgta cggtgggagg tctatataag cagagctggt ttagtgaacc    1800
gtcagatcag gtaccgccac catggaatcc gatgagtctg gcctgcccgc catggaaatc    1860
gagtgcagaa tcaccggcac cctgaacggc gtggaatttg agctcgtggg cggaggcgag    1920
ggcacacctg aacagggcag aatgaccaac aagatgaagt ccaccaaggg ggccctgacc    1980
ttcagcccct acctgctgtc tcacgtgatg ggctacggct ctaccactt cggcacctac     2040 cccagcggct acgagaaccc tttcctgcac gccatcaaca cggcggcta caccaacacc     2100 cggatcgaga agtacgagga cggcggcgtg ctgcacgtgt ccttcagcta cagatacgag    2160
gccggcagag tgatcggcga cttcaaagtg atgggcaccg gattccccga ggacagcgtg    2220
atcttcaccg acaagatcat ccggtccaac gccaccgtgg aacatctgca ccccatgggc    2280
gacaacgacc tggacggcag cttcaccaga accttctccc tgcgggatgg cggctactac    2340
agcagcgtgg tggacagcca catgcacttc aagagcgcca tccacccag catcctccag     2400 aacggcggac ccatgttcgc cttcagacgg gtggaagagg accacagcaa caccgagctg    2460
ggcatcgtgg aataccagca cgccttcaag accccgatg ccgatgccgg cgaggaaggc     2520
agtggagagg gcagaggaag tctgctaaca tgtggtgacg tcgaggagaa tcctggccca    2580
atggagtcgc gcggtcgccg ttgtcccgaa atgatatccg tactgggtcc catttcgggg    2640
cacgtgctga agccgtgtt tagtcgcggc gatacgccgg tgctgccgca cgagacgcga     2700
ctcctgcaga cgggtatcca cgtacgcgtg agccagccct cgctgatctt ggtatcgcag    2760
tacacgcccg actcgacgcc atgccaccgc ggcgacaatc agctgcaggt gcagcacacg    2820
tactttacgg gcagcgaggt ggagaacgtg tcggtcaacg tgcacaaccc cacgggccga    2880
agcatctgcc ccagccagga gcccatgtcg atctatgtgt acgcgctgcc gctcaagatg    2940
ctgaacatcc ccagcatcaa cgtgcaccac tacccgtcgg cggccgagcg caaacaccga    3000
cacctgcccg tagctgacgc tgtgattcac gcgtcgggca agcagatgtg gcaggcgcgt    3060
ctcacggtct cgggactggc ctggacgcgt cagcagaacc agtggaaaga gcccgacgtc    3120
tactacacgt cagcgttcgt gtttcccacc aaggacgtgg cactgcggca cgtggtgtgc    3180
gcgcacgagc tggtttgctc catggagaac acgcgcgcaa ccaagatgca ggtgataggt    3240
gaccagtacg tcaaggtgta cctggagtcc ttctgcgagg acgtgccctc cggcaagctc    3300
tttatgcacg tcacgctggg ctctgacgtg gaagaggacc tgacgatgac ccgcaacccg    3360
caacccttca tgcgcccca cgagcgcaac ggctttacgg tgttgtgtcc caaaaatatg    3420
ataatcaaac cgggcaagat ctcgcacatc atgctggatg tggcttttac ctcacacgag    3480
cattttgggc tgctgtgtcc caagagcatc ccgggcctga gcatctcagg taacctgttg    3540
atgaacgggc agcagatctt cctggaggta caagccatac gcgagaccgt ggaactgcgt    3600
cagtacgatc ccgtggctgc gctcttcttt ttcgatatcg acttgctgct gcagcgcggg    3660
cctcagtaca gcgagcaccc caccttcacc agccagtatc gcatccaggg caagcttgag    3720
taccgacaca cctgggaccg gcacgacgag ggtgccgccc agggcgacga cgacgtctgg    3780
```

```
accagcggat cggactccga cgaagaactc gtaaccaccg agcgcaagac gcccgcgtc    3840 accggcggcg gcgccatggc gggcgcctcc acttccgcgg gccgcaaacg caaatcagca    3900
tcctcggcga cggcgtgcac gtcgggcgtt atgacacgcg gccgccttaa ggccgagtcc    3960
accgtcgcgc ccgaagagga caccgacgag gattccgaca cgaaatccaa caatccggcc    4020
gtgttcacct ggccgccctg gcaggccggc atcctggccc gcaacctggt gcccatggtg    4080
gctacggttc agggtcagaa tctgaagtac caggagttct tctgggacgc caacgacatc    4140
taccgcatct tcgccgaatt ggaaggcgta tggcagcccg ctgcgcaacc caaacgtcgc    4200
cgccaccgga agacgccttg ccccgggcca tgcatcgcct cgacgcccaa aaagcaccga    4260
ggttgatcta gacctgatca taatcaagcc atatcacatc tgtagaggtt tacttgcttt    4320
aaaaaacctc cacacctccc cctgaacctg aaacataaaa tgaatgcaat tgttgttgtt    4380
aacttgttta ttgcagctta taatggttac aaataaagca atagcatcac aaatttcaca    4440
aataaagcat ttttttcact gcattctagt tgtggtttgt ccaaactcat caatgtatct    4500
tatcatgtct ggatctgcgg atcaggattg gtgacagaaa agccccatcc ttaggcctcc    4560
tccttcctag tctcctgata ttgggtctaa ccccccacctc ctgttaggca gattccttat    4620
ctggtgacac accccccattt cctggagcca tctctctcct tgccagaacc tctaaggttt    4680
gcttacgatg gagccagaga ggatcctggg agggagagct tggcagggg tgggagggaa    4740 ggggggatg cgtgacctgc ccggttctca gtggccaccc tgcgctaccc tctcccagaa    4800
cctgagctgc tctgacgcgg ctgtctggtg cgtttcactg atcctggtgc tgcagcttcc    4860
ttacacttcc caagaggaga agcagtttgg aaaaacaaaa tcagaataag ttggtcctga    4920
gttctaactt tggctcttca cctttctagt ccccaattta tattgttcct ccgtgcgtca    4980
gttttacctg tgagataagg ccagtagcca gccccgtcct ggcagggctg tggtgaggag    5040 ggggggtgtcc gtgtggaaaa ctcccctttgt gagaatggtg cgtcctcgag ctgggcctca    5100
tgggccttcc gctcactgcc cgcttccag tcgggaaacc tgtcgtgcca gctgcattaa    5160
catggtcata gctgtttcct tgcgtattgg gcgctctccg cttcctcgct cactgactcg    5220
ctgcgctcgg tcgttcgggt aaagcctggg gtgcctaatg agcaaaaggc cagcaaaagg    5280
ccaggaaccg taaaaaggcc gcgttgctgg cgttttttcca taggctccgc ccccctgacg    5340
agcatcacaa aaatcgacgc tcaagtcaga ggtggcgaaa cccgacagga ctataaagat    5400
accaggcgtt tccccctgga agctccctcg tgcgctctcc tgttccgacc ctgccgctta    5460
ccggatacct gtccgccttt ctcccttcgg gaagcgtggc gctttctcat agctcacgct    5520
gtaggtatct cagttcggtg taggtcgttc gctccaagct gggctgtgtg cacgaacccc    5580
ccgttcagcc cgaccgctgc gccttatccg gtaactatcg tcttgagtcc aacccggtaa    5640
gacacgactt atcgccactg gcagcagcca ctggtaacag gattagcaga gcgaggtatg    5700
taggcggtgc tacagagttc ttgaagtggt ggcctaacta cggctacact agaagaacag    5760
tatttggtat ctgcgctctg ctgaagccag ttaccttcgg aaaaagagtt ggtagctctt    5820
gatccggcaa acaaaccacc gctggtagcg gtggtttttt tgtttgcaag cagcagatta    5880
cgcgcagaaa aaaaggatct caagaagatc ctttgatctt ttctacgggg tctgacgctc    5940
agtggaacga aaactcacgt taagggattt tggtcatgag attatcaaaa aggatcttca    6000
cctagatcct tttaaattaa aaatgaagtt ttaaatcaat ctaaagtata tatgagtaaa    6060
cttggtctga cagttaccaa tgcttaatca gtgaggcacc tatctcagcg atctgtctat    6120
```

```
ttcgttcatc catagttgcc tgactcccg tcgtgtagat aactacgata cgggagggct    6180
taccatctgg ccccagtgct gcaatgatac cgcgagaacc acgctcaccg gctccagatt    6240
tatcagcaat aaaccagcca gccggaaggg ccgagcgcag aagtggtcct gcaactttat    6300
ccgcctccat ccagtctatt aattgttgcc gggaagctag agtaagtagt tcgccagtta    6360
atagtttgcg caacgttgtt gccattgcta caggcatcgt ggtgtcacgc tcgtcgtttg    6420
gtatggcttc attcagctcc ggttcccaac gatcaaggcg agttacatga tcccccatgt    6480
tgtgcaaaaa agcggttagc tccttcggtc ctccgatcgt tgtcagaagt aagttggccg    6540
cagtgttatc actcatggtt atggcagcac tgcataattc tcttactgtc atgccatccg    6600
taagatgctt ttctgtgact ggtgagtact caaccaagtc attctgagaa tagtgtatgc    6660
ggcgaccgag ttgctcttgc ccggcgtcaa tacgggataa taccgcgcca catagcagaa    6720
ctttaaaagt gctcatcatt ggaaaacgtt cttcggggcg aaaactctca aggatcttac    6780
cgctgttgag atccagttcg atgtaaccca ctcgtgcacc caactgatct tcagcatctt    6840
ttactttcac cagcgtttct gggtgagcaa aaacaggaag gcaaaatgcc gcaaaaaagg    6900
gaataagggc gacacggaaa tgttgaatac tcatactctt cctttttcaa tattattgaa    6960
gcatttatca gggttattgt ctcatgagcg gatacatatt tgaatgtatt tagaaaaata    7020
aacaaatagg ggttccgcgc acatttcccc gaaaagtgcc ac                       7062
```

<210> SEQ ID NO 14
<211> LENGTH: 7062
<212> TYPE: DNA
<213> ORGANISM: Artificial Sequence
<220> FEATURE:
<223> OTHER INFORMATION: AAVS1-1_GFP_HCMVpp65 ANET vector V1.G.9

<400> SEQUENCE: 14

```
ctaaattgta agcgttaata ttttgttaaa attcgcgtta aattttgtt aaatcagctc      60 attttttaac caataggccg aaatcggcaa aatcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa aggggggatgt    240 gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccgcatg aattgagctc tactggcttc tgcgccgcct ctggcccact gtttcccctt    420
cccaggcagg tcctgctttc tctgacctgc attctctccc ctgggcctgt gccgctttct    480
gtctgcagct tgtggcctgg gtcacctcta cggctggccc agatccttcc ctgccgcctc    540
cttcaggttc cgtcttcctc cactccctct tccccttgct ctctgctgtg ttgctgccca    600
aggatgctct ttccggagca cttccttctc ggcgctgcac cacgtgatgt cctctgagcg    660
gatcctcccc gtgtctgggt cctctccggg catctctcct ccctcaccca acccccatgcc    720 gtcttcactc gctgggttcc cttttccttc tccttctggg gcctgtgcca tctctcgttt    780
cttaggatgg ccttctccga cggatgtctc ccttgcgtcc cgcctcccct tcttgtaggc    840
ctgcatcatc accgtttttc tggacaaccc caaagtaccc cgtctccctg ctttagccaa    900
cctctccatc ctcttgcttt ctttgcctgg acaccccgtt ctcctgtgga ttcgggtcac    960
ctctcactcc tttcatttgg gcagctcccc tacccccctt acctctctag tctgtgctag   1020
ctcttccagc cccctgtcat ggcatcttcc aggggtccga gagctcagct agtcttcttc   1080
ctccaacccg ggcccctatg tccacttcag gacagcatgt ttgctgcctc cagggatcct   1140
```

```
gtgtccccga gctgggacca ccttatattc ccagggccgg ttaatgtggc tctggttctg      1200 ggtacttttta tctgtcccct ccaccggtat agtaatcaat tacggggtca ttagttcata     1260
gcccatatat ggagttccgc gttacataac ttacggtaaa tggcccgcct ggctgaccgc     1320
ccaacgaccc ccgcccattg acgtcaataa tgacgtatgt tcccatagta acgccaatag     1380
ggactttcca ttgacgtcaa tgggtggagt atttacggta aactgcccac ttggcagtac     1440
atcaagtgta tcatatgcca gtacgcccc ctattgacgt caatgacggt aaatggcccg      1500
cctggcatta tgcccagtac atgaccttat gggactttcc tacttggcag tacatctacg     1560
tattagtcat cgctattacc atggtgatgc ggttttggca gtacatcaat gggcgtggat     1620
agcggtttga ctcacgggga tttccaagtc tccaccccat tgacgtcaat gggagtttgt     1680
tttggcacca aaatcaacgg gactttccaa aatgtcgtaa caactccgcc ccattgacgc     1740
aaatgggcgg taggcgtgta cggtgggagg tctatataag cagagctggt ttagtgaacc     1800
gtcagatcag gtaccgccac catggaatcc gatgagtctg gcctgcccgc catggaaatc     1860
gagtgcagaa tcaccggcac cctgaacggc gtggaatttg agctcgtggg cggaggcgag     1920
ggcacacctg aacagggcag aatgaccaac aagatgaagt ccaccaaggg ggccctgacc     1980
ttcagcccct acctgctgtc tcacgtgatg ggctacggct ctaccactt cggcacctac     2040 cccagcggct acgagaaccc tttcctgcac gccatcaaca cggcggcta caccaacacc     2100 cggatcgaga agtacgagga cggcggcgtg ctgcacgtgt ccttcagcta cagatacgag     2160
gccggcagag tgatcggcga cttcaaagtg atgggcaccg gattcccga ggacagcgtg     2220 atcttcaccg acaagatcat ccggtccaac gccaccgtgg aacatctgca ccccatgggc     2280
gacaacgacc tggacggcag cttcaccaga accttctccc tgcgggatgg cggctactac     2340
agcagcgtgg tggacagcca catgcacttc aagagcgcca tccaccccag catcctccag     2400
aacggcggac ccatgttcgc cttcagacgg gtggaagagg accacagcaa caccgagctg     2460
ggcatcgtgg aataccagca cgccttcaag accccgatg ccgatgccgg cgaggaaggc     2520
agtggagagg gcagaggaag tctgctaaca tgtggtgacg tcgaggagaa tcctggccca     2580
atggagtcgc gcggtcgccg ttgtcccgaa atgatatccg tactgggtcc catttcgggg     2640
cacgtgctga agccgtgtt tagtcgcggc gatacgccgg tgctgccgca cgagacgcga     2700
ctcctgcaga cgggtatcca cgtacgcgtg agccagccct cgctgatctt ggtatcgcag     2760
tacacgcccg actcgacgcc atgccaccgc ggcgacaatc agctgcaggt gcagcacacg     2820
tactttacgg gcagcgaggt ggagaacgtg tcggtcaacg tgcacaaccc cacggggcga     2880
agcatctgcc ccagccagga gcccatgtcg atctatgtgt acgcgctgcc gctcaagatg     2940
ctgaacatcc ccagcgctaa cgaaacccac tacccgtcgg cggccgagcg caaacaccga     3000
cacctgcccg tagctgacgc tgtgattcac gcgtcgggca agcagatgtg gcaggcgcgt     3060
ctcacggtct cggactggc ctggacgcgt cagcagaacc agtggaaaga gcccgacgtc     3120
tactacacgt cagcgttcgt gtttcccacc aaggacgtgg cactgcggca cgtggtgtgc     3180
gcgcacgagc tggttttgctc catggagaac acgcgcgcaa ccaagatgca ggtgataggt     3240
gaccagtacg tcaaggtgta cctggagtcc ttctgcgagg acgtgccctc cggcaagctc     3300
tttatgcacg tcacgctggg ctctgacgtg aagaggacc tgacgatgac ccgcaacccg     3360
caacccttca tgcgccccca cgagcgcaac ggctttacgg tgttgtgtcc caaaaatatg     3420
ataatcaaac cgggcaagat ctcgcacatc atgctggatg tggctttac ctcacacgag     3480
```

```
cattttgggc tgctgtgtcc caagagcatc ccgggcctga gcatctcagg taacctgttg   3540
atgaacgggc agcagatctt cctggaggta caagccatac gcgagaccgt ggaactgcgt   3600
cagtacgatc ccgtggctgc gctcttcttt ttcgatatcg acttgctgct gcagcgcggg   3660
cctcagtaca gcgagcaccc caccttcacc agccagtatc gcatccaggg caagcttgag   3720
taccgacaca cctgggaccg gcacgacgag ggtgccgccc agggcgacga cgacgtctgg   3780
accagcggat cggactccga cgaagaactc gtaaccaccg agcgcaagac gccccgcgtc   3840
accggcggcg gcgccatggc gggcgcctcc acttccgcgg gccgcaaacg caaatcagca   3900
tcctcggcga cggcgtgcac gtcgggcgtt atgacacgcg gccgccttaa ggccgagtcc   3960
accgtcgcgc ccgaagagga caccgacgag gattccgaca acgaaatcca caatccggcc   4020
gtgttcacct ggccgccctg gcaggccggc atcctggccc gcaacctggt gcccatggtg   4080
gctacggttc agggtcagaa tctgaagtac caggagttct ctgggacgc caacgacatc    4140 taccgcatct tcgccgaatt ggaaggcgta tggcagcccg ctgcgcaacc caaacgtcgc   4200
cgccaccggc aagacgcctt gcccgggcca tgcatcgcct cgacgccaa aaagcaccga    4260 ggttgatcta gacctgatca taatcaagcc atatcacatc tgtagaggtt tacttgcttt   4320
aaaaaacctc cacacctccc cctgaacctg aaacataaaa tgaatgcaat tgttgttgtt   4380
aacttgttta ttgcagctta taatggttac aaataaagca atagcatcac aaatttcaca   4440
aataaagcat ttttttcact gcattctagt tgtggtttgt ccaaactcat caatgtatct   4500
tatcatgtct ggatctgcgg atcaggattg gtgacagaaa agccccatcc ttaggcctcc   4560
tccttcctag tctcctgata ttgggtctaa ccccacctc ctgttaggca gattccttat     4620
ctggtgacac accccatttt cctggagcca tctctctcct tgccagaacc tctaaggttt   4680
gcttacgatg gagccagaga ggatcctggg agggagagct tggcagggg tgggagggaa    4740 gggggggatg cgtgacctgc ccggttctca gtggccaccc tgcgctaccc tctcccagaa   4800
cctgagctgc tctgacgcgg ctgtctggtg cgtttcactg atcctggtgc tgcagcttcc   4860
ttacacttcc caagaggaga agcagtttgg aaaaacaaaa tcagaataag ttggtcctga   4920
gttctaactt tggctcttca cctttctagt ccccaattta tattgttcct ccgtgcgtca   4980
gttttacctg tgagataagg ccagtagcca gccccgtcct ggcagggctg tggtgaggag   5040
gggggtgtcc gtgtggaaaa ctcccttttgt gagaatggtg cgtcctcgag ctgggcctca   5100
tgggccttcc gctcactgcc cgctttccag tcgggaaacc tgtcgtgcca gctgcattaa   5160
catggtcata gctgtttcct tgcgtattgg gcgctctccg cttcctcgct cactgactcg   5220
ctgcgctcgg tcgttcgggt aaagcctggg gtgcctaatg agcaaaaggc cagcaaaagg   5280
ccaggaaccg taaaaaggcc gcgttgctgg cgttttttcca taggctccgc cccctgacg   5340 agcatcacaa aaatcgacgc tcaagtcaga ggtggcgaaa cccgacagga ctataaagat   5400
accaggcgtt tccccctgga agctccctcg tgcgctctcc tgttccgacc ctgccgctta   5460
ccggatacct gtccgccttt ctcccttcgg gaagcgtggc gctttctcat agctcacgct   5520
gtaggtatct cagttcggtg taggtcgttc gctccaagct gggctgtgtg cacgaacccc   5580
ccgttcagcc cgaccgctgc gccttatccg gtaactatcg tcttgagtcc aacccggtaa   5640
gacacgactt atcgccactg gcagcagcca ctggtaacag gattagcaga gcgaggtatg   5700
taggcggtgc tacagagttc ttgaagtggt ggcctaacta cggctacact agaagaacag   5760
tatttggtat ctgcgctctg ctgaagccag ttaccttcgg aaaaagagtt ggtagctctt   5820
gatccggcaa acaaaccacc gctggtagcg gtggtttttt tgtttgcaag cagcagatta   5880
```

```
cgcgcagaaa aaaaggatct caagaagatc ctttgatctt ttctacgggg tctgacgctc    5940
agtggaacga aaactcacgt taagggattt tggtcatgag attatcaaaa aggatcttca    6000
cctagatcct tttaaattaa aaatgaagtt ttaaatcaat ctaaagtata tatgagtaaa    6060
cttggtctga cagttaccaa tgcttaatca gtgaggcacc tatctcagcg atctgtctat    6120
ttcgttcatc catagttgcc tgactccccg tcgtgtagat aactacgata cgggagggct    6180
taccatctgg ccccagtgct gcaatgatac cgcgagaacc acgctcaccg gctccagatt    6240
tatcagcaat aaaccagcca gccggaaggg ccgagcgcag aagtggtcct gcaactttat    6300
ccgcctccat ccagtctatt aattgttgcc gggaagctag agtaagtagt tcgccagtta    6360
atagtttgcg caacgttgtt gccattgcta caggcatcgt ggtgtcacgc tcgtcgtttg    6420
gtatggcttc attcagctcc ggttcccaac gatcaaggcg agttacatga tcccccatgt    6480
tgtgcaaaaa agcggttagc tccttcggtc ctccgatcgt tgtcagaagt aagttggccg    6540
cagtgttatc actcatggtt atggcagcac tgcataattc tcttactgtc atgccatccg    6600
taagatgctt ttctgtgact ggtgagtact caaccaagtc attctgagaa tagtgtatgc    6660
ggcgaccgag ttgctcttgc ccggcgtcaa tacgggataa taccgcgcca catagcagaa    6720
ctttaaaagt gctcatcatt ggaaaacgtt cttcggggcg aaaactctca aggatcttac    6780
cgctgttgag atccagttcg atgtaaccca ctcgtgcacc caactgatct tcagcatctt    6840
ttactttcac cagcgtttct gggtgagcaa aaacaggaag gcaaaatgcc gcaaaaaagg    6900
gaataagggc gacacggaaa tgttaatac tcatactctt cctttttcaa tattattgaa    6960
gcatttatca gggttattgt ctcatgagcg gatacatatt tgaatgtatt tagaaaaata    7020
aacaaatagg ggttccgcgc acatttcccc gaaaagtgcc ac                      7062

<210> SEQ ID NO 15
<211> LENGTH: 7062
<212> TYPE: DNA
<213> ORGANISM: Artificial Sequence
<220> FEATURE:
<223> OTHER INFORMATION: AAVS1-1_GFP_HCMVpp65 AIN vector V1.H.1

<400> SEQUENCE: 15
ctaaattgta agcgttaata ttttgttaaa attcgcgtta aatttttgtt aaatcagctc      60
attttttaac caataggccg aaatcggcaa aatcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccgcatg aattgagctc tactggcttc tgcgccgcct ctggcccact gtttcccctt    420
cccaggcagg tcctgctttc tctgacctgc attctctccc ctgggcctgt gccgctttct    480
gtctgcagct tgtggcctgg gtcacctcta cggctggccc agatccttcc ctgccgcctc    540
cttcaggttc cgtcttcctc cactccctct tccccttgct ctctgctgtg ttgctgccca    600
aggatgctct ttccggagca cttccttctc ggcgctgcac cacgtgatgt cctctgagcg    660
gatcctcccc gtgtctgggt cctctccggg catctctcct ccctcaccca accccatgcc    720
gtcttcactc gctgggttcc cttttccttc tccttctggg gcctgtgcca tctctcgttt    780
cttaggatgg ccttctccga cggatgtctc ccttgcgtcc cgcctcccct tcttgtaggc    840
```

```
ctgcatcatc accgtttttc tggacaaccc caaagtaccc cgtctccctg gctttagcca    900
cctctccatc ctcttgcttt ctttgcctgg acacccgtt  ctcctgtgga ttcgggtcac    960
ctctcactcc tttcatttgg gcagctcccc tacccccctt acctctctag tctgtgctag   1020
ctcttccagc cccctgtcat ggcatcttcc aggggtccga gagctcagct agtcttcttc   1080
ctccaacccg ggcccctatg tccacttcag acagcatgt  ttgctgcctc cagggatcct   1140
gtgtccccga gctgggacca ccttatattc ccagggccgg ttaatgtggc tctggttctg   1200
ggtactttta tctgtcccct ccaccggtat agtaatcaat tacgggtca  ttagttcata   1260
gcccatatat ggagttccgc gttacataac ttacggtaaa tggcccgcct ggctgaccgc   1320
ccaacgaccc ccgcccattg acgtcaataa tgacgtatgt tcccatagta acgccaatag   1380
ggactttcca ttgacgtcaa tgggtggagt atttacggta aactgcccac ttggcagtac   1440
atcaagtgta tcatatgcca agtacgcccc ctattgacgt caatgacggt aaatggcccg   1500
cctggcatta tgcccagtac atgaccttat gggactttcc tacttggcag tacatctacg   1560
tattagtcat cgctattacc atggtgatgc ggttttggca gtacatcaat gggcgtggat   1620
agcggtttga ctcacgggga tttccaagtc tccacccat  tgacgtcaat gggagtttgt   1680
tttggcacca aaatcaacgg gactttccaa aatgtcgtaa caactccgcc ccattgacgc   1740
aaatgggcgg taggcgtgta cggtgggagg tctatataag cagagctggt ttagtgaacc   1800
gtcagatcag gtaccgccac catggaatcc gatgagtctg gcctgcccgc catgaaatc   1860
gagtgcagaa tcaccggcac cctgaacggc gtggaatttg agctcgtggg cggaggcgag   1920
ggcacacctg aacagggcag aatgaccaac aagatgaagt ccaccaaggg ggccctgacc   1980
ttcagcccct acctgctgtc tcacgtgatg ggctacggct tctaccactt cggcacctac   2040
cccagcggct acgagaaccc tttcctgcac gccatcaaca cggcggcta  caccaacacc   2100
cggatcgaga agtacgagga cggcggcgtg ctgcacgtgt ccttcagcta cagatacgag   2160
gccggcagag tgatcggcga cttcaaagtg atgggcaccg gattcccga  ggacagcgtg   2220
atcttcaccg acaagatcat ccggtccaac gccaccgtgg aacatctgca ccccatgggc   2280
gacaacgacc tggacggcag cttcaccaga accttctccc tgcgggatgg cggctactac   2340
agcagcgtgg tggacagcca catgcacttc aagagcgcca tccaccccag catcctccag   2400
aacgcggac  ccatgttcgc cttcagacgg gtggaagagg accacagcaa caccgagctg   2460
ggcatcgtgg aataccagca cgccttcaag acccccgatg ccgatgccgg cgaggaaggc   2520
agtggagagg gcagaggaag tctgctaaca tgtggtgacg tcgaggagaa tcctggccca   2580
atggagtcgc gcggtcgccg ttgtcccgaa atgatatccg tactgggtcc catttcgggg   2640
cacgtgctga agccgtgtt  tagtcgcggc gatacgccgg tgctgccgca cgagacgcga   2700
ctcctgcaga cgggtatcca cgtacgcgtg agccagccct cgctgatctt ggtatcgcag   2760
tacacgcccg actcgacgcc atgccaccgc ggcgacaatc agctgcaggt gcagcacacg   2820
tactttacgg gcagcgaggt ggagaacgtg tcggtcaacg tgcacaaccc cacggggcga   2880
agcatctgcc ccagccagga gcccatgtcg atctatgtgt acgcgctgcc gctcaagatg   2940
ctgaacatcc ccagcatcaa cgtgcaccac tacccgtcgg cggccgagcg caaacaccga   3000
cacctgcccg tagctgacgc tgtgattcac gcgtcgggca agcagatgtg gcaggcgcgt   3060
ctcacggtct cgggactggc ctggacgcgt cagcagaacc agtggaaaga gcccgacgtc   3120
tactacacgt cagcgttcgt gtttcccacc aaggacgtgg cactgcgcca cgtggtgtgc   3180
gcgcacgagc tggtttgctc catggagaac acgcgcgcaa ccaagatgca ggtgataggt   3240
```

```
gaccagtacg tcaaggtgta cctggagtcc ttctgcgagg acgtgccctc cggcaagctc   3300
tttatgcacg tcacgctggg ctctgacgtg aagaggacc tgacgatgac ccgcaacccg    3360
caacccttca tgcgccccca cgagcgcaac ggctttacgg tgttgtgtcc caaaaatatg   3420
ataatcaaac cgggcaagat ctcgcacatc atgctggatg tggcttttac ctcacacgag   3480
cattttgggc tgctgtgtcc caagagcatc ccgggcctga gcatctcagg taacctgttg   3540
atgaacgggc agcagatctt cctggaggta caagccatac gcgagaccgt ggaactgcgt   3600
cagtacgatc ccgtggctgc gctcttcttt ttcgatatcg acttgctgct gcagcgcggg   3660
cctcagtaca gcgagcaccc caccttcacc agccagtatc gcatccaggg caagcttgag   3720
taccgacaca cctgggaccg gcacgacgag ggtgccgccc agggcgacga cgacgtctgg   3780
accagcggat cggactccga cgaagaactc gtaaccaccg agcgcaagac gccccgcgtc   3840
accggcggcg gcgccatggc gggcgcctcc acttccgcgg gccgcaaacg caaatcagca   3900
tcctcggcga cggcgtgcac gtcgggcgtt atgacacgcg gccgccttaa ggccgagtcc   3960
accgtcgcgc ccgaagagga caccgacgag gattccgaca acgaaatcca caatccggcc   4020
gtgttcacct ggccgccctg gcaggccggc atcctggccc gcaacctggt ggcaattaat   4080
gctacggttc agggtcagaa tctgaagtac caggagttct tctgggacgc caacgacatc   4140
taccgcatct tcgccgaatt ggaaggcgta tggcagcccg ctgcgcaacc caaacgtcgc   4200
cgccaccggc aagacgcctt gccgcgggcca tgcatcgcct cgacgcccaa aaagcaccga   4260
ggttgatcta gacctgatca taatcaagcc atatcacatc tgtagaggtt tacttgcttt   4320
aaaaaacctc cacacctccc cctgaacctg aaacataaaa tgaatgcaat tgttgttgtt   4380
aacttgttta ttgcagctta taatggttac aaataaagca atagcatcac aaatttcaca   4440
aataaagcat ttttttcact gcattctagt tgtggtttgt ccaaactcat caatgtatct   4500
tatcatgtct ggatctgcgg atcaggattg gtgacagaaa agccccatcc ttaggcctcc   4560
tccttcctag tctcctgata ttgggtctaa ccccccacctc ctgttaggca gattccttat   4620
ctggtgacac accccccattt cctgagcca tctctctcct tgccagaacc tctaaggttt   4680
gcttacgatg gagccagaga ggatcctggg agggagagct tggcaggggg tgggagggaa   4740
gggggggatg cgtgacctgc ccggttctca gtggccaccc tgcgctaccc tctcccagaa   4800
cctgagctgc tctgacgcgg ctgtctggtg cgtttcactg atcctggtgc tgcagcttcc   4860
ttacacttcc caagaggaga agcagtttgg aaaacaaaa tcagaataag ttggtcctga    4920
gttctaactt tggctcttca cctttctagt ccccaattta tattgttcct ccgtgcgtca   4980
gtttttacctg tgagataagg ccagtagcca gccccgtcct ggcagggctg tggtgaggag   5040
gggggtgtcc gtgtggaaaa ctcccttttgt gagaatggtg cgtcctcgag ctgggcctca   5100
tgggccttcc gctcactgcc cgctttccag tcgggaaacc tgtcgtgcca gctgcattaa   5160
catggtcata gctgtttcct tgcgtattgg gcgctctccg cttcctcgct cactgactcg   5220
ctgcgctcgg tcgttcgggt aaagcctggg gtgcctaatg agcaaaaggc cagcaaaagg   5280
ccaggaaccg taaaaaggcc gcgttgctgg cgttttttcca taggctccgc ccccctgacg   5340
agcatcacaa aaatcgacgc tcaagtcaga ggtggcgaaa cccgacagga ctataaagat   5400
accaggcgtt tccccctgga agctccctcg tgcgctctcc tgttccgacc ctgccgctta   5460
ccggatacct gtccgccttt ctcccttcgg gaagcgtggc gctttctcat agctcacgct   5520
gtaggtatct cagttcggtg taggtcgttc gctccaagct gggctgtgtg cacgaaccc    5580
```

```
ccgttcagcc cgaccgctgc gccttatccg gtaactatcg tcttgagtcc aacccggtaa    5640
gacacgactt atcgccactg gcagcagcca ctggtaacag gattagcaga gcgaggtatg    5700
taggcggtgc tacagagttc ttgaagtggt ggcctaacta cggctacact agaagaacag    5760
tatttggtat ctgcgctctg ctgaagccag ttaccttcgg aaaaagagtt ggtagctctt    5820
gatccggcaa acaaaccacc gctggtagcg gtggtttttt tgtttgcaag cagcagatta    5880
cgcgcagaaa aaaaggatct caagaagatc ctttgatctt ttctacgggg tctgacgctc    5940
agtggaacga aaactcacgt taagggattt tggtcatgag attatcaaaa aggatcttca    6000
cctagatcct tttaaattaa aaatgaagtt ttaaatcaat ctaaagtata tatgagtaaa    6060
cttggtctga cagttaccaa tgcttaatca gtgaggcacc tatctcagcg atctgtctat    6120
ttcgttcatc catagttgcc tgactccccg tcgtgtagat aactacgata cgggagggct    6180
taccatctgg ccccagtgct gcaatgatac cgcgagaacc acgctcaccg gctccagatt    6240
tatcagcaat aaaccagcca gccggaaggg ccgagcgcag aagtggtcct gcaactttat    6300
ccgcctccat ccagtctatt aattgttgcc gggaagctag agtaagtagt tcgccagtta    6360
atagtttgcg caacgttgtt gccattgcta caggcatcgt ggtgtcacgc tcgtcgtttg    6420
gtatggcttc attcagctcc ggttcccaac gatcaaggcg agttacatga tcccccatgt    6480
tgtgcaaaaa agcggttagc tccttcggtc ctccgatcgt tgtcagaagt aagttggccg    6540
cagtgttatc actcatggtt atggcagcac tgcataattc tcttactgtc atgccatccg    6600
taagatgctt ttctgtgact ggtgagtact caaccaagtc attctgagaa tagtgtatgc    6660
ggcgaccgag ttgctcttgc ccggcgtcaa tacgggataa taccgcgcca catagcagaa    6720
ctttaaaagt gctcatcatt ggaaaacgtt cttcggggcg aaaactctca aggatcttac    6780
cgctgttgag atccagttcg atgtaaccca ctcgtgcacc caactgatct tcagcatctt    6840
ttactttcac cagcgtttct gggtgagcaa aaacaggaag gcaaaatgcc gcaaaaaagg    6900
gaataagggc gacacggaaa tgttgaatac tcatactctt cctttttcaa tattattgaa    6960
gcatttatca gggttattgt ctcatgagcg gatacatatt tgaatgtatt tagaaaaata    7020
aacaaatagg ggttccgcgc acatttcccc gaaaagtgcc ac                      7062
```

<210> SEQ ID NO 16
<211> LENGTH: 6348
<212> TYPE: DNA
<213> ORGANISM: Artificial Sequence
<220> FEATURE:
<223> OTHER INFORMATION: AAVS1_DRA_Flag-DRB1_6xHis vector V1.I.5

<400> SEQUENCE: 16

```
ctaaattgta agcgttaata ttttgttaaa attcgcgtta aatttttgtt aaatcagctc      60
attttttaac caataggccg aaatcggcaa aatcccttat aaatcaaaag aatagaccga     120
gatagggttg agtggccgct acagggcgct cccattcgcc attcaggctg cgcaactgtt     180
gggaagggcg tttcggtgcg ggcctcttcg ctattacgcc agctggcgaa aggggatgt      240 gctgcaaggc gattaagttg ggtaacgcca gggttttccc agtcacgacg ttgtaaaacg     300
acggccagtg agcgcgacgt aatacgactc actatagggc gaattggcgg aaggccgtca    360
aggccgcatg aattgagctc tactggcttc tgcgccgcct ctggcccact gtttcccctt    420
cccaggcagg tcctgctttc tctgacctgc attctctccc ctgggcctgt gccgctttct    480
gtctgcagct tgtggcctgg gtcacctcta cggctggccc agatccttcc ctgccgcctc    540
cttcaggttc cgtcttcctc cactccctct tcccccttgct ctctgctgtg ttgctgccca    600
```

```
aggatgctct tccggagca cttccttctc ggcgctgcac cacgtgatgt cctctgagcg    660
gatcctcccc gtgtctgggt cctctccggg catctctcct ccctcaccca acccatgcc    720 gtcttcactc gctgggttcc cttttccttc tccttctggg gcctgtgcca tctctcgttt    780
cttaggatgg ccttctccga cggatgtctc ccttgcgtcc cgcctcccct tcttgtaggc    840
ctgcatcatc accgttttc tggacaaccc caaagtaccc cgtctccctg ctttagcca      900 cctctccatc ctcttgcttt ctttgcctgg acacccgtt ctcctgtgga ttcgggtcac     960
ctctcactcc tttcatttgg gcagctcccc tacccccctt acctctctag tctgtgctag   1020
ctcttccagc ccctgtcat ggcatcttcc aggggtccga gagctcagct agtcttcttc   1080
ctccaacccg ggcccctatg tccacttcag gacagcatgt tgctgcctc cagggatcct    1140 gtgtccccga gctgggacca ccttatattc ccagggccgg ttaatgtggc tctggttctg    1200
ggtactttta tctgtcccct ccaccggtat agtaatcaat tacgggtca ttagttcata    1260 gcccatatat ggagttccgc gttacataac ttacggtaaa tggcccgcct ggctgaccgc    1320
ccaacgaccc ccgcccattg acgtcaataa tgacgtatgt tcccatagta acgccaatag    1380
ggactttcca ttgacgtcaa tgggtggagt atttacggta aactgcccac ttggcagtac    1440
atcaagtgta tcatatgcca agtacgcccc ctattgacgt caatgacggt aaatggcccg    1500
cctggcatta tgcccagtac atgaccttat gggactttcc tacttggcag tacatctacg    1560
tattagtcat cgctattacc atggtgatgc ggttttggca gtacatcaat gggcgtggat    1620
agcggtttga ctcacgggga tttccaagtc tccaccccat tgacgtcaat gggagtttgt    1680
tttggcacca aaatcaacgg gactttccaa aatgtcgtaa caactccgcc ccattgacgc    1740
aaatgggcgg taggcgtgta cggtgggagg tctatataag cagagctggt ttagtgaacc    1800
gtcagatcag gtaccatggc cataagtgga gtccctgtgc taggattttt catcatagct    1860
gtgctgatga gcgctcagga atcatgggct atcaaagaag aacatgtgat catccaggcc    1920
gagttctatc tgaatcctga ccaatcaggc gagtttatgt ttgactttga tggtgatgag    1980
attttccatg tggatatggc aaagaaggag acggtctggc ggcttgaaga atttggacga    2040
tttgccagct ttgaggctca aggtgcattg ccaacatag ctgtggacaa agccaacctg    2100
gaaatcatga caaagcgctc caactatact ccgatcacca atgtacctcc agaggtaact    2160
gtgctcacga acagccctgt ggaactgaga gagcccaacg tcctcatctg tttcatcgac    2220
aagttcaccc caccagtggt caatgtcacg tggcttcgaa atggaaaacc tgtcaccaca    2280
ggagtgtcag agacagtctt tctgcccagg gaagatcacc ttttccgcaa gttccactat    2340
ctccccttcc tgccctcaac tgaggacgtt tacgactgca gggtggagca ctggggcttg    2400
gatgagcctc ttctcaagca ctgggagttt gatgctccaa gccctctccc agagactaca    2460
gagaacgtgg tgtgtgccct gggcctgact gtgggtctgg tgggcatcat tattgggacc    2520
atcttcatca tcaagggagt gcgcaaaagc aatgcagcag aacgcagagg acctctgccc    2580
gggatggact ataaggacca cgacggagac tacaaggatc atgatattga ttacaaagac    2640
gatgacgata agggatccgg agccacgaac ttctctctgt taaagcaagc aggagacgtg    2700
gaagagaacc ctggtcctat ggtgtgtctg aagctccctg gaggctcctg catgacagcg    2760
ctgacagtga cactgatggt gctgagctcc ccactggctt tggctgggga cacccgacca    2820
cgttccttgt ggcagcttaa gttcgaatgt catttcttca atgggacgga gagagtgcgg    2880
ttgctggaaa gatgcatcta taaccaagag gagtccgtgc gcttcgacag cgacgtgggg    2940
```

```
gagtaccggg ctgtgacgga gctgggaagg cctgatgccg agtactggaa cagccagaag    3000
gacctcctgg agcagaggag agccgctgtg acacctact gcagacacaa ctacggggtt      3060
ggtgagagct tcacagtgca gcggcgagtt gagcctaagg tgactgtgta tccttcaaag    3120
acccagcccc tgcagcacca caacctcctg gtctgctctg tgagtggttt ctatccaggc    3180
agcattgaag tcaggtggtt ccggaacggc caggaagaga aggctggggt ggtgtccaca    3240
ggcctgatcc agaatggaga ttggaccttc cagaccctgg tgatgctgga aacagttcct    3300
cggagtggag aggtttacac ctgccaagtg gagcacccaa gtgtgacgag ccctctcaca    3360
gtggaatgga gagcacggtc tgaatctgca cagagcaaga tgctgagtgg agtcgggggc    3420
ttcgtgctgg gcctgctctt ccttggggcc gggctgttca tctacttcag gaatcagaaa    3480
ggacactctg gacttcagcc aacaggattc ctgagcccg gcatcatca ccatcaccac      3540 tgactatagt cgtctagacc tgatcataat caagccatat cacatctgta gaggtttact    3600
tgctttaaaa aacctccaca cctcccctg aacctgaaac ataaaatgaa tgcaattgtt     3660
gttgttaact tgtttattgc agcttataat ggttacaaat aaagcaatag catcacaaat    3720
ttcacaaata aagcattttt ttcactgcat tctagttgtg gtttgtccaa actcatcaat    3780
gtatcttatc atgtctggat ctgcggatca ggattggtga cagaaaagcc ccatccttag    3840
gcctcctcct tcctagtctc ctgatattgg gtctaacccc cacctcctgt taggcagatt    3900
ccttatctgg tgacacaccc ccatttcctg gagccatctc tctccttgcc agaacctcta    3960
aggtttgctt acgatggagc cagagaggat cctgggaggg agagcttggc agggggtggg    4020
agggaagggg gggatgcgtg acctgcccgg ttctcagtgg ccaccctgcg ctaccctctc    4080
ccagaacctg agctgctctg acgcggctgt ctggtgcgtt tcactgatcc tggtgctgca    4140
gcttccttac acttcccaag aggagaagca gtttggaaaa acaaaatcag aataagttgg    4200
tcctgagttc taactttggc tcttcacctt tctagtcccc aatttatatt gttcctccgt    4260
gcgtcagttt tacctgtgag ataaggccag tagccagccc cgtcctggca gggctgtggt    4320
gaggaggggg gtgtccgtgt ggaaaactcc ctttgtgaga atggtgcgtc ctcgagctgg    4380
gcctcatggg ccttccgctc actgcccgct ttccagtcgg gaaacctgtc gtgccagctg    4440
cattaacatg gtcatagctg tttccttgcg tattgggcgc tctccgcttc ctcgctcact    4500
gactcgctgc gctcggtcgt tcgggtaaag cctggggtgc ctaatgagca aaaggccagc    4560
aaaaggccag gaaccgtaaa aaggccgcgt tgctggcgtt tttccatagg ctccgccccc    4620
ctgacgagca tcacaaaaat cgacgctcaa gtcagaggtg gcgaaacccg acaggactat    4680
aaagatacca ggcgtttccc cctggaagct ccctcgtgcg ctctcctgtt ccgaccctgc    4740
cgcttaccgg atacctgtcc gcctttctcc cttcgggaag cgtggcgctt tctcatagct    4800
cacgctgtag gtatctcagt tcggtgtagg tcgttcgctc caagctgggc tgtgtgcacg    4860
aaccccccgt tcagcccgac cgctgcgcct tatccggtaa ctatcgtctt gagtccaacc    4920
cggtaagaca cgacttatcg ccactggcag cagccactgg taacaggatt agcagagcga    4980
ggtatgtagg cggtgctaca gagttcttga agtggtggcc taactacggc tacactagaa    5040
gaacagtatt tggtatctgc gctctgctga agccagttac cttcggaaaa agagttggta    5100
gctcttgatc cggcaaacaa accaccgctg gtagcggtgg ttttttgtt tgcaagcagc    5160 agattacgcg cagaaaaaaa ggatctcaag aagatccttt gatcttttct acggggtctg    5220
acgctcagtg gaacgaaaac tcacgttaag ggattttggt catgagatta tcaaaaagga    5280
tcttcaccta gatcctttta aattaaaaat gaagttttaa atcaatctaa agtatatatg    5340
```

```
agtaaacttg gtctgacagt taccaatgct taatcagtga ggcacctatc tcagcgatct   5400
gtctatttcg ttcatccata gttgcctgac tccccgtcgt gtagataact acgatacggg   5460
agggcttacc atctggcccc agtgctgcaa tgataccgcg agaaccacgc tcaccggctc   5520
cagatttatc agcaataaac cagccagccg aagggccga gcgcagaagt ggtcctgcaa   5580
ctttatccgc ctccatccag tctattaatt gttgccggga agctagagta agtagttcgc   5640
cagttaatag tttgcgcaac gttgttgcca ttgctacagg catcgtggtg tcacgctcgt   5700
cgtttggtat ggcttcattc agctccggtt cccaacgatc aaggcgagtt acatgatccc   5760
ccatgttgtg caaaaaagcg gttagctcct tcggtcctcc gatcgttgtc agaagtaagt   5820
tggccgcagt gttatcactc atggttatgg cagcactgca taattctctt actgtcatgc   5880
catccgtaag atgcttttct gtgactggtg agtactcaac caagtcattc tgagaatagt   5940
gtatgcggcg accgagttgc tcttgcccgg cgtcaatacg ggataatacc gcgccacata   6000
gcagaacttt aaaagtgctc atcattggaa aacgttcttc ggggcgaaaa ctctcaagga   6060
tcttaccgct gttgagatcc agttcgatgt aacccactcg tgcacccaac tgatcttcag   6120
catcttttac tttcaccagc gtttctgggt gagcaaaaac aggaaggcaa aatgccgcaa   6180
aaaagggaat aagggcgaca cggaaatgtt gaatactcat actcttcctt tttcaatatt   6240
attgaagcat ttatcagggt tattgtctca tgagcggata catatttgaa tgtatttaga   6300
aaaataaaca ataggggtt ccgcgcacat ttccccgaaa agtgccac              6348
```

<210> SEQ ID NO 17
<211> LENGTH: 6342
<212> TYPE: DNA
<213> ORGANISM: Artificial Sequence
<220> FEATURE:
<223> OTHER INFORMATION: AAVS1_DPA1_Flag-DPB1_6xHis vector V1.I.7

<400> SEQUENCE: 17

```
ctaaattgta agcgttaata ttttgttaaa attcgcgtta aattttttgtt aaatcagctc     60 attttttaac caataggccg aaatcggcaa atcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa aggggatgt    240 gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccgcatt aattgagctc tactggcttc tgcgccgcct ctggcccact gtttcccctt    420
cccaggcagg tcctgctttc tctgacctgc attctctccc ctgggcctgt gccgctttct    480
gtctgcagct tgtggcctgg gtcacctcta cggctggccc agatccttcc ctgccgcctc    540
cttcaggttc cgtcttcctc cactccctct tcccccttgct ctctgctgtg ttgctgccca    600
aggatgctct ttccggagca cttccttctc ggcgctgcac cacgtgatgt cctctgagcg    660
gatcctcccc gtgtctgggt cctctccggg catctctcct ccctcaccca accccatgcc    720
gtcttcactc gctgggttcc cttttccttc tccttctggg gctgtgcca tctctcgttt    780 cttaggatgg ccttctccga cggatgtctc ccttgcgtcc cgcctcccct tcttgtaggc    840
ctgcatcatc accgtttttc tggacaaccc caaagtaccc cgtctccctg gctttagcca    900
cctctccatc ctcttgcttt ctttgcctgg acacccgtt ctcctgtgga ttcgggtcac    960
ctctcactcc tttcatttgg gcagctcccc taccccccctt acctctctag tctgtgctag   1020
```

```
ctcttccagc cccctgtcat ggcatcttcc aggggtccga gagctcagct agtcttcttc    1080
ctccaacccg ggcccctatg tccacttcag gacagcatgt ttgctgcctc cagggatcct    1140
gtgtccccga gctgggacca ccttatattc ccagggccgg ttaatgtggc tctggttctg    1200
ggtactttta tctgtcccct ccaccggtat agtaatcaat tacggggtca ttagttcata    1260
gcccatatat ggagttccgc gttacataac ttacggtaaa tggcccgcct ggctgaccgc    1320
ccaacgaccc ccgcccattg acgtcaataa tgacgtatgt tcccatagta acgccaatag    1380
ggactttcca ttgacgtcaa tgggtggagt atttacggta aactgcccac ttggcagtac    1440
atcaagtgta tcatatgcca agtacgcccc ctattgacgt caatgacggt aaatggcccg    1500
cctggcatta tgcccagtac atgaccttat gggactttcc tacttggcag tacatctacg    1560
tattagtcat cgctattacc atggtgatgc ggttttggca gtacatcaat gggcgtggat    1620
agcggtttga ctcacgggga tttccaagtc tccaccccat tgacgtcaat gggagtttgt    1680
tttggcacca aaatcaacgg gactttccaa aatgtcgtaa caactccgcc ccattgacgc    1740
aaatgggcgg taggcgtgta cggtgggagg tctatataag cagagctggt ttagtgaacc    1800
gtcagatcag gtaccatgcg ccctgaggac agaatgttcc atatcagagc tgtgatcttg    1860
agagccctct ccttggcttt cctgctgagt ctccgaggag ctggggccat caaggcggac    1920
catgtgtcaa cttatgccgc gtttgtacag acgcatagac caacagggga gtttatgttt    1980
gaatttgatg aagatgagat gttctatgtg atctggaca agaaggagac cgtctggcat    2040
ctggaggagt ttggccaagc cttttccttt gaggctcagg gcgggctggc taacattgct    2100
atattgaaca caacttgaa taccttgatc cagcgttcca accacactca ggccaccaac    2160
gatcccctg aggtgaccgt gtttcccaag gagcctgtgg agctgggcca gcccaacacc    2220
ctcatctgcc acattgacaa gttcttccca ccagtgctca cgtcacgtg gctgtgcaac    2280
ggggagctgg tcactgaggg tgtcgctgag agcctcttcc tgcccagaac agattacagc    2340
ttccacaagt tccattacct gaccttgtg ccctcagcag aggacttcta tgactgcagg    2400
gtggagcact ggggcttgga ccagccgctc ctcaagcact gggaggccca agagccaatc    2460
cagatgcctg agacaacgga gactgtgctc tgtgccctgg gcctggtgct gggcctagtc    2520
ggcatcatcg tgggcaccgt cctcatcata aagtctctgc gttctggcca tgaccctaga    2580
gcccagggaa ccctgcccgg gatggactat aaggaccacg acggagacta caaggatcat    2640
gatattgatt acaaagacga tgacgataag ggatccggag ccacgaactt ctctctgtta    2700
aagcaagcag gagacgtgga agagaacccc tggtcctatg tggttctgca ggtttctgcg    2760
gcccccccga cagtggctct gacggcgtta ctgatggtgc tgctcacatc tgtggtccag    2820
ggcagggcca ctccagagaa ttacctttc caggacgc aggaatgcta cgcgtttaat    2880
gggacacagc gcttcctgga gagatacatc tacaaccggg aggagttcgc gcgcttcgac    2940
agcgacgtgg gggagttccg ggcggtgacg gagctgggc ggcctgctgc ggagtactgg    3000
aacagccaga aggacatcct ggaggagaag cgggcagtgc cggacaggat gtgcagacac    3060
aactacgagc tgggcgggcc catgacctg cagcgccgag tccagcctag ggtgaatgtt    3120
tccccctcca agaagggcc cttgcagcac acaacctgc ttgtctgcca cgtgacggat    3180
ttctacccag gcagcattca agtccgatgg ttcctgaatg gacaggagga acagctggg    3240
gtcgtgtcca ccaacctgat ccgtaatgga gactggacct tccagatcct ggtgatgctg    3300
gaaatgaccc cccagcaggg agatgtctac acctgccaag tggagcacac cagcctggat    3360
agtcctgtca ccgtggagtg gaaggcacag tctgattctg cccggagtaa gacattgacg    3420
```

```
ggagctgggg gcttcgtgct ggggctcatc atctgtggag tgggcatctt catgcacagg    3480
aggagcaaga aagttcaacg aggatctgca cccgggcatc atcaccatca ccactgacta    3540
tagtcgtcta gacctgatca taatcaagcc atatcacatc tgtagaggtt tacttgcttt    3600
aaaaaacctc cacacctccc cctgaacctg aaacataaaa tgaatgcaat tgttgttgtt    3660
aacttgttta ttgcagctta taatggttac aaataaagca atagcatcac aaatttcaca    3720
aataaagcat tttttcact gcattctagt tgtggtttgt ccaaactcat caatgtatct    3780
tatcatgtct ggatctgcgg atcaggattg gtgacagaaa agccccatcc ttaggcctcc    3840
tccttcctag tctcctgata ttgggtctaa ccccccacctc ctgttaggca gattccttat    3900
ctggtgacac accccccattt cctggagcca tctctctcct tgccagaacc tctaaggttt    3960
gcttacgatg gagccagaga ggatcctggg agggagagct tggcaggggg tgggagggaa    4020 ggggggatg cgtgacctgc ccggttctca gtggccaccc tgcgctaccc tctcccagaa    4080
cctgagctgc tctgacgcgg ctgtctggtg cgtttcactg atcctggtgc tgcagcttcc    4140
ttacacttcc caagaggaga agcagtttgg aaaaacaaaa tcagaataag ttggtcctga    4200
gttctaactt tggctcttca cctttctagt ccccaattta tattgttcct ccgtgcgtca    4260
gttttacctg tgagataagg ccagtagcca gccccgtcct ggcagggctg tggtgaggag    4320 ggggtgtcc gtgtggaaaa ctcccttgt gagaatggtg cgtcctcgag ctgggcctca    4380
tgggccttcc gctcactgcc cgctttccag tcgggaaacc tgtcgtgcca gctgcattaa    4440
catggtcata gctgttccct tgcgtattgg gcgctctccg cttcctcgct cactgactcg    4500
ctgcgctcgg tcgttcgggt aaagcctggg gtgcctaatg agcaaaaggc cagcaaaagg    4560
ccaggaaccg taaaaaggcc gcgttgctgg cgttttcca taggctccgc cccctgacg    4620 agcatcacaa aaatcgacgc tcaagtcaga ggtggcgaaa cccgacagga ctataaagat    4680
accaggcgtt ccccctgga agctccctcg tgcgctctcc tgttccgacc ctgccgctta    4740
ccggatacct gtccgccttt ctcccttcgg gaagcgtggc gctttctcat agctcacgct    4800
gtaggtatct cagttcggtg taggtcgttc gctccaagct gggctgtgtg cacgaacccc    4860
ccgttcagcc cgaccgctgc gccttatccg gtaactatcg tcttgagtcc aacccggtaa    4920
gacacgactt atcgccactg gcagcagcca ctggtaacag gattagcaga gcgaggtatg    4980
taggcggtgc tacagagttc ttgaagtggt ggcctaacta cggctacact agaagaacag    5040
tatttggtat ctgcgctctg ctgaagccag ttaccttcgg aaaaagagtt ggtagctctt    5100
gatccggcaa acaaaccacc gctggtagcg gtggttttt tgtttgcaag cagcagatta    5160
cgcgcagaaa aaaaggatct caagaagatc ctttgatctt ttctacgggg tctgacgctc    5220
agtggaacga aaactcacgt taagggattt tggtcatgag attatcaaaa aggatcttca    5280
cctagatcct tttaaattaa aaatgaagtt ttaaatcaat ctaaagtata tatgagtaaa    5340
cttggtctga cagttaccaa tgcttaatca gtgaggcacc tatctcagcg atctgtctat    5400
ttcgttcatc catagttgcc tgactccccg tcgtgtagat aactacgata cgggagggct    5460
taccatctgg ccccagtgct gcaatgatac cgcgagaacc acgctcaccg gctccagatt    5520
tatcagcaat aaaccagcca gccggaaggg ccgagcgcag aagtggtcct gcaactttat    5580
ccgcctccat ccagtctatt aattgttgcc gggaagctag agtaagtagt tcgccagtta    5640
atagtttgcg caacgttgtt gccattgcta caggcatcgt ggtgtcacgc tcgtcgtttg    5700
gtatggcttc attcagctcc ggttcccaac gatcaaggcg agttacatga tcccccatgt    5760
```

| | |
|---|---|
| tgtgcaaaaa agcggttagc tccttcggtc ctccgatcgt tgtcagaagt aagttggccg | 5820 |
| cagtgttatc actcatggtt atggcagcac tgcataattc tcttactgtc atgccatccg | 5880 |
| taagatgctt ttctgtgact ggtgagtact caaccaagtc attctgagaa tagtgtatgc | 5940 |
| ggcgaccgag ttgctcttgc ccggcgtcaa tacgggataa taccgcgcca catagcagaa | 6000 |
| ctttaaaagt gctcatcatt ggaaaacgtt cttcggggcg aaaactctca aggatcttac | 6060 |
| cgctgttgag atccagttcg atgtaaccca ctcgtgcacc caactgatct tcagcatctt | 6120 |
| ttactttcac cagcgtttct gggtgagcaa aaacaggaag gcaaaatgcc gcaaaaaagg | 6180 |
| gaataagggc gacacggaaa tgttaatac tcatactctt cctttttcaa tattattgaa | 6240 |
| gcatttatca gggttattgt ctcatgagcg gatacatatt tgaatgtatt tagaaaaata | 6300 |
| aacaaatagg ggttccgcgc acatttcccc gaaaagtgcc ac | 6342 |

<210> SEQ ID NO 18
<211> LENGTH: 2762
<212> TYPE: DNA
<213> ORGANISM: Artificial Sequence
<220> FEATURE:
<223> OTHER INFORMATION: HLA-A-sg-sp-opti1 vector V2.A.1

<400> SEQUENCE: 18

| | |
|---|---|
| ctaaattgta agcgttaata tttgttaaa attcgcgtta aattttgtt aaatcagctc | 60 |
| attttttaac caataggccg aaatcggcaa aatcccttat aaatcaaaag aatagaccga | 120 |
| gatagggttg agtggccgct acagggcgct cccattcgcc attcaggctg cgcaactgtt | 180 |
| gggaagggcg tttcggtgcg ggcctcttcg ctattacgcc agctggcgaa aggggggatgt | 240 |
| gctgcaaggc gattaagttg gtaacgcca gggttttccc agtcacgacg ttgtaaaacg | 300 |
| acggccagtg agcgcgacgt aatacgactc actatagggc gaattggcgg aaggccgtca | 360 |
| aggccgcatg gatccaaggt cgggcaggaa gagggcctat ttcccatgat tccttcatat | 420 |
| ttgcatatac gatacaaggc tgttagagag ataattagaa ttaatttgac tgtaaacaca | 480 |
| aagatattag tacaaaatac gtgacgtaga agtaataat ttcttgggta gtttgcagtt | 540 |
| ttaaaattat gttttaaaat ggactatcat atgcttaccg taacttgaaa gtatttcgat | 600 |
| ttcttggctt tatatatctt gtggaaagga cgaaacaccg agggttcggg gcgccatgag | 660 |
| tttaagagct atgctggaaa cagcatagca agtttaaata aggctagtcc gttatcaact | 720 |
| tgaaaaagtg gcaccgagtc ggtgcttttt ttcagacatc catagatcta gctcgagttt | 780 |
| tttttctaga ctgggcctca tgggccttcc gctcactgcc cgctttccag tcgggaaacc | 840 |
| tgtcgtgcca gctgcattaa catggtcata gctgtttcct tgcgtattgg gcgctctccg | 900 |
| cttcctcgct cactgactcg ctgcgctcgg tcgttcgggt aaagcctggg gtgcctaatg | 960 |
| agcaaaaggc cagcaaaagg ccaggaaccg taaaaaggcc gcgttgctgg cgttttttcca | 1020 |
| taggctccgc cccctgacg agcatcacaa aaatcgacgc tcaagtcaga ggtggcgaaa | 1080 |
| cccgacagga ctataaagat accaggcgtt tcccctgga agctccctcg tgcgctctcc | 1140 |
| tgttccgacc ctgccgctta ccggatacct gtccgccttt ctcccttcgg aagcgtggc | 1200 |
| gctttctcat agctcacgct gtaggtatct cagttcggtg taggtcgttc gctccaagct | 1260 |
| gggctgtgtg cacgaaccc cgttcagcc cgaccgctgc gccttatccg gtaactatcg | 1320 |
| tcttgagtcc aacccggtaa gacacgactt atcgccactg gcagcagcca ctggtaacag | 1380 |
| gattagcaga gcgaggtatg taggcggtgc tacagagttc ttgaagtggt ggcctaacta | 1440 |
| cggctacact agaagaacag tatttggtat ctgcgctctg ctgaagccag ttaccttcgg | 1500 |

```
aaaaagagtt ggtagctctt gatccggcaa acaaaccacc gctggtagcg gtggtttttt    1560
tgtttgcaag cagcagatta cgcgcagaaa aaaggatct caagaagatc ctttgatctt    1620
ttctacgggg tctgacgctc agtggaacga aaactcacgt taagggattt tggtcatgag    1680
attatcaaaa aggatcttca cctagatcct tttaaattaa aaatgaagtt ttaaatcaat    1740
ctaaagtata tatgagtaaa cttggtctga cagttaccaa tgcttaatca gtgaggcacc    1800
tatctcagcg atctgtctat ttcgttcatc catagttgcc tgactccccg tcgtgtagat    1860
aactacgata cgggagggct taccatctgg ccccagtgct gcaatgatac cgcgagaacc    1920
acgctcaccg gctccagatt tatcagcaat aaaccagcca gccggaaggg ccgagcgcag    1980
aagtggtcct gcaactttat ccgcctccat ccagtctatt aattgttgcc gggaagctag    2040
agtaagtagt tcgccagtta atagtttgcg caacgttgtt gccattgcta caggcatcgt    2100
ggtgtcacgc tcgtcgtttg gtatggcttc attcagctcc ggttcccaac gatcaaggcg    2160
agttacatga tcccccatgt tgtgcaaaaa agcggttagc tccttcggtc ctccgatcgt    2220
tgtcagaagt aagttggccg cagtgttatc actcatggtt atggcagcac tgcataattc    2280
tcttactgtc atgccatccg taagatgctt ttctgtgact ggtgagtact caaccaagtc    2340
attctgagaa tagtgtatgc ggcgaccgag ttgctcttgc ccggcgtcaa tacgggataa    2400
taccgcgcca catagcagaa ctttaaaagt gctcatcatt ggaaaacgtt cttggggcg    2460 aaaactctca aggatcttac cgctgttgag atccagttcg atgtaaccca ctcgtgcacc    2520
caactgatct tcagcatctt ttactttcac cagcgtttct gggtgagcaa aaacaggaag    2580
gcaaaatgcc gcaaaaaagg gaataagggc gacacggaaa tgttgaatac tcatactctt    2640
cctttttcaa tattattgaa gcatttatca gggttattgt ctcatgagcg gatacatatt    2700
tgaatgtatt tagaaaaata aacaaatagg ggttccgcgc acatttcccc gaaaagtgcc    2760
ac                                                                  2762

<210> SEQ ID NO 19
<211> LENGTH: 2762
<212> TYPE: DNA
<213> ORGANISM: Artificial Sequence
<220> FEATURE:
<223> OTHER INFORMATION: HLA-B-sg-sp-3 vector V2.A.7

<400> SEQUENCE: 19
ctaaattgta agcgttaata tttgttaaa attcgcgtta aattttgtt aaatcagctc      60 atttttaac caataggccg aaatcggcaa aatcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa aggggggatgt   240 gctgcaaggc gattaagttg gtaacgcca gggttttccc agtcacgacg ttgtaaaacg    300
acggccagtg agcgcgacgt aatacgactc actataggc gaattggcgg aaggccgtca    360
aggccgcatg gatccaaggt cgggcaggaa gagggcctat ttcccatgat tccttcatat    420
ttgcatatac gatacaaggc tgttagagag ataattagaa ttaatttgac tgtaaacaca    480
aagatattag tacaaaatac gtgacgtaga aagtaataat ttcttgggta gtttgcagtt    540
ttaaaattat gttttaaaat ggactatcat atgcttaccg taacttgaaa gtatttcgat    600
ttcttggctt tatatatctt gtggaaagga cgaaacaccg tagaaatacc tcatggagtg    660
tttaagagct atgctggaaa cagcatagca agtttaaata aggctagtcc gttatcaact    720
```

```
tgaaaaagtg gcaccgagtc ggtgcttttt ttcagacatc catagatcta gctcgagttt    780
tttttctaga ctgggcctca tgggccttcc gctcactgcc cgctttccag tcgggaaacc    840
tgtcgtgcca gctgcattaa catggtcata gctgtttcct tgcgtattgg gcgctctccg    900
cttcctcgct cactgactcg ctgcgctcgg tcgttcgggt aaagcctggg gtgcctaatg    960
agcaaaaggc cagcaaaagg ccaggaaccg taaaaaggcc gcgttgctgg cgttttccca   1020
taggctccgc cccctgacg agcatcacaa aaatcgacgc tcaagtcaga ggtggcgaaa   1080
cccgacagga ctataaagat accaggcgtt tcccctgga agctccctcg tgcgctctcc   1140
tgttccgacc ctgccgctta ccggatacct gtccgccttt ctcccttcgg aagcgtggc   1200
gctttctcat agctcacgct gtaggtatct cagttcggtg taggtcgttc gctccaagct   1260
gggctgtgtg cacgaacccc ccgttcagcc cgaccgctgc gccttatccg gtaactatcg   1320
tcttgagtcc aacccggtaa gacacgactt atcgccactg gcagcagcca ctggtaacag   1380
gattagcaga gcgaggtatg taggcggtgc tacagagttc ttgaagtggt ggcctaacta   1440
cggctacact agaagaacag tatttggtat ctgcgctctg ctgaagccag ttaccttcgg   1500
aaaaagagtt ggtagctctt gatccggcaa acaaaccacc gctggtagcg gtggtttttt   1560
tgtttgcaag cagcagatta cgcgcagaaa aaaggatct caagaagatc ctttgatctt   1620
ttctacgggg tctgacgctc agtggaacga aaactcacgt taagggattt tggtcatgag   1680
attatcaaaa aggatcttca cctagatcct tttaaattaa aaatgaagtt ttaaatcaat   1740
ctaaagtata tatgagtaaa cttggtctga cagttaccaa tgcttaatca gtgaggcacc   1800
tatctcagcg atctgtctat ttcgttcatc catagttgcc tgactccccg tcgtgtagat   1860
aactacgata cgggagggct taccatctgg ccccagtgct gcaatgatac cgcgagaacc   1920
acgctcaccg gctccagatt tatcagcaat aaaccagcca gccggaaggg ccgagcgcag   1980
aagtggtcct gcaactttat ccgcctccat ccagtctatt aattgttgcc gggaagctag   2040
agtaagtagt tcgccagtta atagtttgcg caacgttgtt gccattgcta caggcatcgt   2100
ggtgtcacgc tcgtcgtttg gtatggcttc attcagctcc ggttcccaac gatcaaggcg   2160
agttacatga tcccccatgt tgtgcaaaaa agcggttagc tccttcggtc ctccgatcgt   2220
tgtcagaagt aagttggccg cagtgttatc actcatggtt atggcagcac tgcataattc   2280
tcttactgtc atgccatccg taagatgctt ttctgtgact ggtgagtact caaccaagtc   2340
attctgagaa tagtgtatgc ggcgaccgag ttgctcttgc ccggcgtcaa tacgggataa   2400
taccgcgcca catagcagaa ctttaaaagt gctcatcatt ggaaaacgtt cttcggggcg   2460
aaaactctca aggatcttac cgctgttgag atccagttcg atgtaaccca ctcgtgcacc   2520
caactgatct tcagcatctt ttactttcac cagcgtttct gggtgagcaa aaacaggaag   2580
gcaaaatgcc gcaaaaaagg aataagggc gacacggaaa tgttgaatac tcatactctt   2640
cctttttcaa tattattgaa gcatttatca gggttattgt ctcatgagcg gatacatatt   2700
tgaatgtatt tagaaaaata acaaataggg gttccgcgc acatttcccc gaaaagtgcc   2760
ac                                                                 2762
```

<210> SEQ ID NO 20
<211> LENGTH: 2762
<212> TYPE: DNA
<213> ORGANISM: Artificial Sequence
<220> FEATURE:
<223> OTHER INFORMATION: HLA-C-sg-sp-4 vector V2.B.3

<400> SEQUENCE: 20

```
ctaaattgta agcgttaata ttttgttaaa attcgcgtta aatttttgtt aaatcagctc      60
attttttaac caataggccg aaatcggcaa aatcccttat aaatcaaaag aatagaccga     120 gataggttg agtggccgct acagggcgct cccattcgcc attcaggctg cgcaactgtt     180
gggaagggcg tttcggtgcg ggcctcttcg ctattacgcc agctggcgaa aggggggatgt     240 gctgcaaggc gattaagttg ggtaacgcca gggttttccc agtcacgacg ttgtaaaacg     300
acggccagtg agcgcgacgt aatacgactc actatagggc gaattggcgg aaggccgtca     360
aggccgcatg gatccaaggt cgggcaggaa gagggcctat ttcccatgat tccttcatat     420
ttgcatatac gatacaaggc tgttagagag ataattagaa ttaatttgac tgtaaacaca     480
aagatattag tacaaaatac gtgacgtaga aagtaataat ttcttgggta gtttgcagtt     540
ttaaaattat gttttaaaat ggactatcat atgcttaccg taacttgaaa gtatttcgat     600
ttcttggctt tatatatctt gtggaaagga cgaaacaccg gggccggagt attgggaccg     660
tttaagagct atgctggaaa cagcatagca agtttaaata aggctagtcc gttatcaact     720
tgaaaaagtg gcaccgagtc ggtgcttttt ttcagacatc catagatcta gctcgagttt     780
tttttctaga ctgggcctca tgggccttcc gctcactgcc cgctttccag tcgggaaacc     840
tgtcgtgcca gctgcattaa catggtcata gctgtttcct tgcgtattgg gcgctctccg     900
cttcctcgct cactgactcg ctgcgctcgg tcgttcgggt aaagcctggg gtgcctaatg     960
agcaaaaggc cagcaaaagg ccaggaaccg taaaaaggcc gcgttgctgg cgttttttcca    1020 taggctccgc ccccctgacg agcatcacaa aaatcgacgc tcaagtcaga ggtggcgaaa    1080
cccgacagga ctataaagat accaggcgtt tccccctgga agctccctcg tgcgctctcc    1140
tgttccgacc ctgccgctta ccggatacct gtccgccttt ctcccttcgg gaagcgtggc    1200
gctttctcat agctcacgct gtaggtatct cagttcggtg taggtcgttc gctccaagct    1260
gggctgtgtg cacgaacccc ccgttcagcc cgaccgctgc gccttatccg gtaactatcg    1320
tcttgagtcc aacccggtaa gacacgactt atcgccactg gcagcagcca ctggtaacag    1380
gattagcaga gcgaggtatg taggcggtgc tacagagttc ttgaagtggt ggcctaacta    1440
cggctacact agaagaacag tatttggtat ctgcgctctg ctgaagccag ttaccttcgg    1500
aaaaagagtt ggtagctctt gatccggcaa acaaaccacc gctggtagcg gtggtttttt    1560
tgtttgcaag cagcagatta cgcgcagaaa aaaaggatct caagaagatc ctttgatctt    1620
ttctacgggg tctgacgctc agtggaacga aaactcacgt taagggattt tggtcatgag    1680
attatcaaaa aggatcttca cctagatcct ttttaaatta aaatgaagtt ttaaatcaat    1740
ctaaagtata tatgagtaaa cttggtctga cagttaccaa tgcttaatca gtgaggcacc    1800
tatctcagcg atctgtctat ttcgttcatc catagttgcc tgactccccg tcgtgtagat    1860
aactacgata cgggagggct taccatctgg ccccagtgct gcaatgatac cgcgagaacc    1920
acgctcaccg gctccagatt tatcagcaat aaaccagcca gccggaaggg ccgagcgcag    1980
aagtggtcct gcaactttat ccgcctccat ccagtctatt aattgttgcc gggaagctag    2040
agtaagtagt tcgccagtta atagtttgcg caacgttgtt gccattgcta caggcatcgt    2100
ggtgtcacgc tcgtcgtttg gtatggcttc attcagctcc ggttcccaac gatcaaggcg    2160
agttacatga tcccccatgt tgtgcaaaaa agcggttagc tccttcggtc ctccgatcgt    2220
tgtcagaagt aagttggccg cagtgttatc actcatggtt atggcagcac tgcataattc    2280
tcttactgtc atgccatccg taagatgctt ttctgtgact ggtgagtact caaccaagtc    2340
```

```
attctgagaa tagtgtatgc ggcgaccgag ttgctcttgc ccggcgtcaa tacgggataa    2400
taccgcgcca catagcagaa ctttaaaagt gctcatcatt ggaaaacgtt cttcggggcg    2460
aaaactctca aggatcttac cgctgttgag atccagttcg atgtaaccca ctcgtgcacc    2520
caactgatct tcagcatctt ttactttcac cagcgtttct gggtgagcaa aacaggaag    2580 gcaaaatgcc gcaaaaaagg gaataagggc gacacggaaa tgttgaatac tcatactctt    2640 ccttttcaa tattattgaa gcatttatca gggttattgt ctcatgagcg gatacatatt    2700
tgaatgtatt tagaaaaata acaaataggg gttccgcgc acatttcccc gaaaagtgcc    2760
ac                                                                   2762
```

<210> SEQ ID NO 21
<211> LENGTH: 2762
<212> TYPE: DNA
<213> ORGANISM: Artificial Sequence
<220> FEATURE:
<223> OTHER INFORMATION: HLA-A-ex2-3_sg-sp-opti_1 vector V2.I.10

<400> SEQUENCE: 21

```
ctaaattgta agcgttaata ttttgttaaa attcgcgtta aatttttgtt aaatcagctc      60
attttttaac caataggccg aaatcggcaa aatcccttat aaatcaaaag aatagaccga     120
gatagggttg agtggccgct acagggcgct cccattcgcc attcaggctg cgcaactgtt     180
gggaagggcg tttcggtgcg ggcctcttcg ctattacgcc agctggcgaa aggggggatgt    240 gctgcaaggc gattaagttg ggtaacgcca gggttttccc agtcacgacg ttgtaaaacg     300
acggccagtg agcgcgacgt aatacgactc actatagggc gaattggcgg aaggccgtca    360
aggccgcatg gatccaaggt cgggcaggaa gagggcctat ttcccatgat tccttcatat    420
ttgcatatac gatacaaggc tgttagagag ataattagaa ttaatttgac tgtaaacaca    480
aagatattag tacaaaatac gtgacgtaga agtaataat ttcttgggta gtttgcagtt     540
ttaaaattat gttttaaaat ggactatcat atgcttaccg taacttgaaa gtatttcgat    600
ttcttggctt tatatatctt gtggaaagga cgaaacaccg tccccaggct ctcactgaag    660
tttaagagct atgctggaaa cagcatagca agtttaaata aggctagtcc gttatcaact    720
tgaaaaagtg gcaccgagtc ggtgcttttt ttcagacatc catagatcta gctcgagttt    780
tttttctaga ctgggcctca tgggccttcc gctcactgcc cgctttccag tcgggaaacc    840
tgtcgtgcca gctgcattaa catggtcata gctgtttcct tgcgtattgg gcgctctccg    900
cttcctcgct cactgactcg ctgcgctcgg tcgttcgggt aaagcctggg gtgcctaatg    960
agcaaaaggc cagcaaaagg ccaggaaccg taaaaaggcc gcgttgctgg cgttttttcca   1020 taggctccgc ccccctgacg agcatcacaa aaatcgacgc tcaagtcaga ggtggcgaaa   1080
cccgacagga ctataaagat accaggcgtt tcccctgga agctccctcg tgcgctctcc    1140
tgttccgacc ctgccgctta ccggatacct gtccgccttt ctcccttcgg gaagcgtggc    1200
gctttctcat agctcacgct gtaggtatct cagttcggtg taggtcgttc gctccaagct    1260
gggctgtgtg cacgaacccc ccgttcagcc cgaccgctgc gccttatccg gtaactatcg    1320
tcttgagtcc aacccggtaa gacacgactt atcgccactg gcagcagcca ctggtaacag    1380
gattagcaga gcgaggtatg taggcggtgc tacagagttc ttgaagtggt ggcctaacta   1440
cggctacact agaagaacag tatttggtat ctgcgctctg ctgaagccag ttaccttcgg    1500
aaaaagagtt ggtagctctt gatccggcaa acaaaccacc gctggtagcg gtggtttttt   1560
tgtttgcaag cagcagatta cgcgcagaaa aaaaggatct caagaagatc ctttgatctt    1620
```

```
ttctacgggg tctgacgctc agtggaacga aaactcacgt taagggattt tggtcatgag    1680
attatcaaaa aggatcttca cctagatcct tttaaattaa aaatgaagtt ttaaatcaat    1740
ctaaagtata tatgagtaaa cttggtctga cagttaccaa tgcttaatca gtgaggcacc    1800
tatctcagcg atctgtctat ttcgttcatc catagttgcc tgactccccg tcgtgtagat    1860
aactacgata cgggagggct taccatctgg ccccagtgct gcaatgatac cgcgagaacc    1920
acgctcaccg gctccagatt tatcagcaat aaaccagcca gccggaaggg ccgagcgcag    1980
aagtggtcct gcaactttat ccgcctccat ccagtctatt aattgttgcc gggaagctag    2040
agtaagtagt tcgccagtta atagtttgcg caacgttgtt gccattgcta caggcatcgt    2100
ggtgtcacgc tcgtcgtttg gtatggcttc attcagctcc ggttcccaac gatcaaggcg    2160
agttacatga tcccccatgt tgtgcaaaaa agcggttagc tccttcggtc ctccgatcgt    2220
tgtcagaagt aagttggccg cagtgttatc actcatggtt atggcagcac tgcataattc    2280
tcttactgtc atgccatccg taagatgctt ttctgtgact ggtgagtact caaccaagtc    2340
attctgagaa tagtgtatgc ggcgaccgag ttgctcttgc ccggcgtcaa tacgggataa    2400
taccgcgcca catagcagaa ctttaaaagt gctcatcatt ggaaaacgtt cttcggggcg    2460
aaaactctca aggatcttac cgctgttgag atccagttcg atgtaaccca ctcgtgcacc    2520
caactgatct tcagcatctt ttactttcac cagcgtttct gggtgagcaa aaacaggaag    2580
gcaaaatgcc gcaaaaaagg gaataagggc gacacggaaa tgttgaatac tcatactctt    2640
cctttttcaa tattattgaa gcatttatca gggttattgt ctcatgagcg gatacatatt    2700
tgaatgtatt tagaaaaata aacaaatagg ggttccgcgc acatttcccc gaaaagtgcc    2760
ac                                                                    2762
```

<210> SEQ ID NO 22
<211> LENGTH: 2763
<212> TYPE: DNA
<213> ORGANISM: Artificial Sequence
<220> FEATURE:
<223> OTHER INFORMATION: HLA-A-ex2-3_sg-sp-opti_2 vector V2.J.1

<400> SEQUENCE: 22

```
ctaaattgta agcgttaata ttttgttaaa attcgcgtta aattttttgtt aaatcagctc      60 attttttaac caataggccg aaatcggcaa aatcccttat aaatcaaaag aatagaccga     120
gatagggttg agtggccgct acagggcgct cccattcgcc attcaggctg cgcaactgtt     180
gggaagggcg tttcggtgcg ggcctcttcg ctattacgcc agctggcgaa aggggggatgt    240 gctgcaaggc gattaagttg ggtaacgcca gggttttccc agtcacgacg ttgtaaaacg     300
acggccagtg agcgcgacgt aatacgactc actatagggc gaattggcgg aaggccgtca    360
aggccgcatg gatccaaggt cgggcaggaa gagggcctat ttcccatgat tccttcatat    420
ttgcatatac gatacaaggc tgttagagag ataattagaa ttaatttgac tgtaaacaca    480
aagatattag tacaaaatac gtgacgtaga agtaataatt tcttgggta gtttgcagtt     540 ttaaaattat gttttaaaat ggactatcat atgcttaccg taacttgaaa gtatttcgat    600
ttcttggctt tatatatctt gtggaaagga cgaaacaccg caggctctca ctgaacggga    660
gtttaagagc tatgctggaa acagcatagc aagtttaaat aaggctagtc cgttatcaac    720
ttgaaaaagt ggcaccgagt cggtgctttt tttcagacat ccatagatct agctcgagtt    780
ttttttctag actgggcctc atgggccttc cgctcactgc ccgctttcca gtcgggaaac    840
```

```
ctgtcgtgcc agctgcatta acatggtcat agctgtttcc ttgcgtattg ggcgctctcc    900
gcttcctcgc tcactgactc gctgcgctcg gtcgttcggg taaagcctgg ggtgcctaat    960
gagcaaaagg ccagcaaaag gccaggaacc gtaaaaaggc cgcgttgctg gcgttttcc    1020
ataggctccg cccccctgac gagcatcaca aaaatcgacg ctcaagtcag aggtggcgaa   1080
acccgacagg actataaaga taccaggcgt ttccccctgg aagctccctc gtgcgctctc   1140
ctgttccgac cctgccgctt accggatacc tgtccgcctt tctcccttcg ggaagcgtgg   1200
cgctttctca tagctcacgc tgtaggtatc tcagttcggt gtaggtcgtt cgctccaagc   1260
tgggctgtgt gcacgaaccc cccgttcagc ccgaccgctg cgccttatcc ggtaactatc   1320
gtcttgagtc caacccggta agacacgact tatcgccact ggcagcagcc actggtaaca   1380
ggattagcag agcgaggtat gtaggcggtg ctacagagtt cttgaagtgg tggcctaact   1440
acggctacac tagaagaaca gtatttggta tctgcgctct gctgaagcca gttaccttcg   1500
gaaaaagagt tggtagctct tgatccggca acaaaccac cgctggtagc ggtggttttt    1560
ttgtttgcaa gcagcagatt acgcgcagaa aaaaaggatc tcaagaagat cctttgatct   1620
tttctacggg gtctgacgct cagtggaacg aaaactcacg ttaagggatt ttggtcatga   1680
gattatcaaa aaggatcttc acctagatcc ttttaaatta aaaatgaagt tttaaatcaa   1740
tctaaagtat atatgagtaa acttggtctg acagttacca atgcttaatc agtgaggcac   1800
ctatctcagc gatctgtcta tttcgttcat ccatagttgc ctgactcccc gtcgtgtaga   1860
taactacgat acgggagggc ttaccatctg gccccagtgc tgcaatgata ccgcgagaac   1920
cacgctcacc ggctccagat ttatcagcaa taaaccagcc agccggaagg gccgagcgca   1980
gaagtggtcc tgcaacttta tccgcctcca tccagtctat taattgttgc cgggaagcta   2040
gagtaagtag ttcgccagtt aatagtttgc gcaacgttgt tgccattgct acaggcatcg   2100
tggtgtcacg ctcgtcgttt ggtatggctt cattcagctc cggttcccaa cgatcaaggc   2160
gagttacatg atcccccatg ttgtgcaaaa aagcggttag ctccttcggt cctccgatcg   2220
ttgtcagaag taagttggcc gcagtgttat cactcatggt tatggcagca ctgcataatt   2280
ctcttactgt catgccatcc gtaagatgct tttctgtgac tggtgagtac tcaaccaagt   2340
cattctgaga atagtgtatg cggcgaccga gttgctcttg cccggcgtca atacgggata   2400
ataccgcgcc acatagcaga actttaaaag tgctcatcat tggaaaacgt tcttcggggc   2460
gaaaactctc aaggatctta ccgctgttga tccagttc gatgtaaccc actcgtgcac   2520
ccaactgatc ttcagcatct tttactttca ccagcgtttc tgggtgagca aaaacaggaa   2580
ggcaaaatgc cgcaaaaaag ggaataaggg cgacacggaa atgttgaata ctcatactct   2640
tcctttttca atattattga agcatttatc agggttattg tctcatgagc ggatacatat   2700
ttgaatgtat ttagaaaaat aaacaaatag gggttccgcg cacatttccc cgaaaagtgc   2760
cac                                                                 2763
```

<210> SEQ ID NO 23
<211> LENGTH: 2762
<212> TYPE: DNA
<213> ORGANISM: Artificial Sequence
<220> FEATURE:
<223> OTHER INFORMATION: AAVSI_sg-sp-opti_3 vector V2.J.6

<400> SEQUENCE: 23

```
ctaaattgta agcgttaata ttttgttaaa attcgcgtta aatttttgtt aaatcagctc     60
attttttaac caataggccg aaatcggcaa aatcccttat aaatcaaaag aatagaccga    120
```

-continued

```
gatagggttg agtggccgct acagggcgct cccattcgcc attcaggctg cgcaactgtt    180
gggaagggcg tttcggtgcg ggcctcttcg ctattacgcc agctggcgaa aggggggatgt   240 gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccgcatg gatccaaggt cgggcaggaa gagggcctat ttcccatgat tccttcatat    420
ttgcatatac gatacaaggc tgttagagag ataattagaa ttaatttgac tgtaaacaca    480
aagatattag tacaaaatac gtgacgtaga aagtaataat ttcttgggta gtttgcagtt    540
ttaaaattat gttttaaaat ggactatcat atgcttaccg taacttgaaa gtatttcgat    600
ttcttggctt tatatatctt gtggaaagga cgaaacaccg tcaccaatcc tgtccctagg    660
tttaagagct atgctggaaa cagcatagca agtttaaata aggctagtcc gttatcaact    720
tgaaaaagtg gcaccgagtc ggtgcttttt ttcagacatc catagatcta gctcgagttt    780 ttttctaga ctgggcctca tgggccttcc gctcactgcc cgctttccag tcgggaaacc    840
tgtcgtgcca gctgcattaa catggtcata gctgtttcct tgcgtattgg gcgctctccg    900
cttcctcgct cactgactcg ctgcgctcgg tcgttcgggt aaagcctggg gtgcctaatg    960
agcaaaaggc cagcaaaagg ccaggaaccg taaaaaggcc gcgttgctgg cgttttttcca   1020 taggctccgc cccctgacg agcatcacaa aaatcgacgc tcaagtcaga ggtggcgaaa    1080
cccgacagga ctataaagat accaggcgtt tccccctgga agctccctcg tgcgctctcc    1140
tgttccgacc ctgccgctta ccggatacct gtccgccttt ctcccttcgg gaagcgtggc    1200
gctttctcat agctcacgct gtaggtatct cagttcggtg taggtcgttc gctccaagct    1260
gggctgtgtg cacgaacccc ccgttcagcc cgaccgctgc gccttatccg gtaactatcg    1320
tcttgagtcc aacccggtaa gacacgactt atcgccactg gcagcagcca ctggtaacag    1380
gattagcaga gcgaggtatg taggcggtgc tacagagttc ttgaagtggt ggcctaacta    1440
cggctacact agaagaacag tatttggtat ctgcgctctg ctgaagccag ttaccttcgg    1500
aaaaagagtt ggtagctctt gatccggcaa acaaaccacc gctggtagcg gtggtttttt    1560
tgtttgcaag cagcagatta cgcgcagaaa aaaaggatct caagaagatc ctttgatctt    1620
ttctacgggg tctgacgctc agtggaacga aaactcacgt taagggattt tggtcatgag    1680
attatcaaaa aggatcttca cctagatcct tttaaattaa aaatgaagtt ttaaatcaat    1740
ctaaagtata tatgagtaaa cttggtctga cagttaccaa tgcttaatca gtgaggcacc    1800
tatctcagcg atctgtctat ttcgttcatc catagttgcc tgactccccg tcgtgtagat    1860
aactacgata cgggagggct taccatctgg ccccagtgct gcaatgatac cgcgagaacc    1920
acgctcaccg gctccagatt tatcagcaat aaaccagcca gccggaaggg ccgagcgcag    1980
aagtggtcct gcaactttat ccgcctccat ccagtctatt aattgttgcc gggaagctag    2040
agtaagtagt tcgccagtta atagtttgcg caacgttgtt gccattgcta caggcatcgt    2100
ggtgtcacgc tcgtcgtttg gtatggcttc attcagctcc ggttcccaac gatcaaggcg    2160
agttacatga tcccccatgt tgtgcaaaaa agcggttagc tccttcggtc ctccgatcgt    2220
tgtcagaagt aagttggccg cagtgttatc actcatggtt atggcagcac tgcataattc    2280
tcttactgtc atgccatccg taagatgctt ttctgtgact ggtgagtact caaccaagtc    2340
attctgagaa tagtgtatgc ggcgaccgag ttgctcttgc ccggcgtcaa tacgggataa    2400
taccgcgcca catagcagaa ctttaaaagt gctcatcatt ggaaaacgtt cttcggggcg    2460
```

```
aaaactctca aggatcttac cgctgttgag atccagttcg atgtaaccca ctcgtgcacc    2520
caactgatct tcagcatctt ttactttcac cagcgtttct gggtgagcaa aaacaggaag    2580
gcaaaatgcc gcaaaaaagg aataagggc gacacggaaa tgttgaatac tcatactctt    2640 ccttttcaa tattattgaa gcatttatca gggttattgt ctcatgagcg gatacatatt    2700
tgaatgtatt tagaaaaata acaaatagg ggttccgcgc acatttcccc gaaaagtgcc    2760
ac                                                                   2762
```

<210> SEQ ID NO 24
<211> LENGTH: 6125
<212> TYPE: DNA
<213> ORGANISM: Artificial Sequence
<220> FEATURE:
<223> OTHER INFORMATION: AAVS_Efla-intron_F14_RFPnls_F15 vector V4.B.2

<400> SEQUENCE: 24

```
ctaaattgta agcgttaata ttttgttaaa attcgcgtta aatttttgtt aaatcagctc      60 atttttaac caataggccg aaatcggcaa atcccttat aaatcaaaag aatagaccga     120
gatagggttg agtggccgct acagggcgct cccattcgcc attcaggctg cgcaactgtt     180
gggaagggcg tttcggtgcg ggcctcttcg ctattacgcc agctggcgaa aggggggatgt    240 gctgcaaggc gattaagttg ggtaacgcca gggttttccc agtcacgacg ttgtaaaacg     300
acggccagtg agcgcgacgt aatacgactc actataggc gaattggcgg aaggccgtca     360
aggccgcatg aattgagctc tactggcttc tgcgccgcct ctggcccact gtttcccctt     420
cccaggcagg tcctgctttc tctgacctgc attctctccc ctgggcctgt gccgctttct     480
gtctgcagct tgtggcctgg gtcacctcta cggctggccc agatccttcc ctgccgcctc     540
cttcaggttc cgtcttcctc cactccctct tccccttgct ctctgctgtg ttgctgccca     600
aggatgctct ttccggagca cttccttctc ggcgctgcac cacgtgatgt cctctgagcg     660
gatcctcccc gtgtctgggt cctctccggg catctctcct ccctcaccca accccatgcc     720
gtcttcactc gctgggttcc cttttccttc tccttctggg gcctgtgcca tctctcgttt     780
cttaggatgg ccttctccga cggatgtctc ccttgcgtcc cgcctcccct tcttgtaggc     840
ctgcatcatc accgtttttc tggacaaccc caaagtaccc cgtctccctg gctttagcca     900
cctctccatc ctcttgcttt cttgcctgg acacccgtt ctcctgtgga ttcgggtcac     960
ctctcactcc tttcatttgg gcagctcccc tacccccctt acctctctag tctgtgctag    1020
ctcttccagc ccctgtcat ggcatcttcc aggggtccga gagctcagct agtcttcttc    1080
ctccaacccg ggcccctatg tccacttcag acagcatgt tgctgcctc cagggatcct    1140 gtgtccccga gctgggacca ccttatattc ccagggccgg ttaatgtggc tctggttctg    1200
ggtactttta tctgtcccct ccaccgggtg gctccggtgc ccgtcagtgg gcagagcgca    1260
catcgcccac agtccccgag aagttggggg gaggggtcgg caattgaacc ggtgcctaga    1320
gaaggtggcg cggggtaaac tgggaaagtg atgtcgtgta ctggctccgc cttttttccg    1380
agggtggggg agaaccgtat ataagtgcag tagtcgccgt gaacgttctt tttcgcaacg    1440
ggtttgccgc cagaacacag gtaagtgccg tgtgtggttc ccgcgggcct ggcctcttta    1500
cgggttatgg cccttgcgtg ccttgaatta cttccactgg ctgcagtacg tgattcttga    1560
tcccgagctt cgggttggaa gtgggtggga gagttcgagg ccttgcgctt aaggagcccc    1620
ttcgcctcgt gcttgagttg aggcctggcc tgggcgctgg ggccgccgcg tgcgaatctg    1680
gtggcacctt cgcgcctgtc tcgctgcttt cgataagtct ctagccattt aaaattttg    1740
```

```
atgacctgct gcgacgcttt ttttctggca agatagtctt gtaaatgcgg gccaagatct    1800
gcacactggt atttcggttt ttggggccgc gggcggcgac ggggcccgtg cgtcccagcg    1860
cacatgttcg gcgaggcggg gcctgcgagc gcggccaccg agaatcggac ggggtagtc     1920
tcaagctggc cggcctgctc tggtgcctgg cctcgcgccg ccgtgtatcg ccccgccctg    1980
ggcggcaagg ctggcccggt cggcaccagt tgcgtgagcg gaaagatggc cgcttcccgg    2040
ccctgctgca gggagctcaa aatgaggac gcggcgctcg ggagagcggg cgggtgagtc     2100
acccacacaa aggaaaaggg cctttccgtc ctcagccgtc gcttcatgtg actccacgga    2160
gtaccgggcg ccgtccaggc acctcgatta gttctcgagc ttttggagta cgtcgtcttt    2220
aggttggggg gaggggtttt atgcgatgga gtttccccac actgagtggg tggagactga    2280
agttaggcca gcttggcact tgatgtaatt ctccttggaa tttgcccttt ttgagtttgg    2340
atcttggttc attctcaagc ctcagacagt ggttcaaagt tttttcttc catttcaggt     2400
gtcgtgactg gtaccggaag ttcctattcc gaagttccta ttctatcaga agtataggaa    2460
cttcgtaccg agaccatggc cccaaagaag aagcggaagg tcggtatcca cggagtccca    2520
gcagccatga gcgagctgat caaagaaaac atgcacatga agctgtacat ggaaggcacc    2580
gtgaacaacc accacttcaa gtgcaccagc gagggcgagg gcaagcctta cgagggcacc    2640
cagaccatga agatcaaggt ggtggaaggc ggccctctgc ccttcgcctt tgatatcctg    2700
gccaccagct ttatgtacgg cagcaaggcc ttcatcaacc acacccaggg catccccgat    2760
ttcttcaagc agagcttccc cgagggcttc acctgggagc ggatcaccac atacgaggac    2820
ggcggagtgc tgaccgccac ccaggatacc agcttccaga acggctgcat catctacaac    2880
gtgaagatta acggcgtgaa tttccccagc aacggcccg tgatgcagaa gaaaaccaga     2940
ggctgggagg ccaacaccga tgctgtac cctgccgatg gcggcctgag aggccattct      3000
cagatggccc tgaaactcgt gggcggaggc tacctgcact gctccttcaa gaccaccta     3060
agaagcaaga agcccgccaa gaacctgaag atgcccggct tccacttcgt ggaccaccgg    3120
ctggaacgga tcaaagaggc cgacaaagaa acctacgtgg aacagcacga gatggccgtg    3180
gccaagtact gcgacctgcc tagcaagctg ggccacagaa aaaggccggc ggccacgaaa    3240
aaggccggcc aggcaaaaaa gaaaaagtga ggtctctcta ggaagttcct attccgaagt    3300
tcctattctt ataggagtat aggaacttct ctagacctga tcataatcaa gccatatcac    3360
atctgtagag gtttacttgc tttaaaaaac ctccacacct cccctgaac ctgaaacata     3420
aaatgaatgc aattgttgtt gttaacttgt ttattgcagc ttataatggt tacaaataaa    3480
gcaatagcat cacaaatttc acaaataaag cattttttc actgcattct agttgtggtt     3540
tgtccaaact catcaatgta tcttatcatg tctggatctg cggatcagga ttggtgacag    3600
aaaagcccca tccttaggcc tcctccttcc tagtctcctg atattgggtc taaccccac     3660
ctcctgttag gcagattcct tatctggtga cacaccccca tttcctggag ccatctctct    3720
ccttgccaga acctctaagg tttgcttacg atggagccag agaggatcct gggagggaga    3780
gcttggcagg gggtgggagg aagggggggg atgcgtgacc tgcccggttc tcagtggcca    3840
ccctgcgcta ccctctccca gaacctgagc tgctctgacg cggctgtctg gtgcgtttca    3900
ctgatcctgg tgctgcagct tccttacact tcccaagagg agaagcagtt tggaaaaaca    3960
aaatcagaat aagttggtcc tgagttctaa ctttggctct tcacctttct agtccccaat    4020
ttatattgtt cctccgtgcg tcagttttac ctgtgagata aggccagtag ccagcccgt     4080
```

```
cctggcaggg ctgtggtgag gagggggtg tccgtgtgga aaactccctt tgtgagaatg   4140
gtgcgtcctc gagctgggcc tcatgggcct tccgctcact gcccgctttc cagtcgggaa   4200
acctgtcgtg ccagctgcat aacatggtc atagctgttt ccttgcgtat tgggcgctct   4260
ccgcttcctc gctcactgac tcgctgcgct cggtcgttcg ggtaaagcct ggggtgccta   4320
atgagcaaaa ggccagcaaa aggccaggaa ccgtaaaaag gccgcgttgc tggcgttttt   4380
ccataggctc cgcccccctg acgagcatca aaaaatcga cgctcaagtc agaggtggcg   4440
aaacccgaca ggactataaa gataccaggc gtttccccct ggaagctccc tcgtgcgctc   4500
tcctgttccg accctgccgc ttaccggata cctgtccgcc tttctccctt cgggaagcgt   4560
ggcgctttct catagctcac gctgtaggta tctcagttcg gtgtaggtcg ttcgctccaa   4620
gctgggctgt gtgcacgaac ccccgttca gcccgaccgc tgcgccttat ccggtaacta   4680
tcgtcttgag tccaacccgg taagacacga cttatcgcca ctggcagcag ccactggtaa   4740
caggattagc agagcgaggt atgtaggcgg tgctacagag ttcttgaagt ggtggcctaa   4800
ctacggctac actagaagaa cagtatttgg tatctgcgct ctgctgaagc cagttacctt   4860
cggaaaaaga gttggtagct cttgatccgg caaacaaacc accgctggta gcggtggttt   4920
ttttgtttgc aagcagcaga ttacgcgcag aaaaaaagga tctcaagaag atcctttgat   4980
cttttctacg gggtctgacg ctcagtggaa cgaaaactca cgttaaggga ttttggtcat   5040
gagattatca aaaaggatct tcacctagat ccttttaaat taaaaatgaa gttttaaatc   5100
aatctaaagt atatatgagt aaacttggtc tgacagttac caatgcttaa tcagtgaggc   5160
acctatctca gcgatctgtc tatttcgttc atccatagtt gcctgactcc ccgtcgtgta   5220
gataactacg atacgggagg gcttaccatc tggccccagt gctgcaatga taccgcgaga   5280
accacgctca ccggctccag atttatcagc aataaaccag ccagccggaa gggccgagcg   5340
cagaagtggt cctgcaactt tatccgcctc catccagtct attaattgtt gccgggaagc   5400
tagagtaagt agttcgccag ttaatagttt gcgcaacgtt gttgccattg ctacaggcat   5460
cgtggtgtca cgctcgtcgt ttggtatggc ttcattcagc tccggttccc aacgatcaag   5520
gcgagttaca tgatccccca tgttgtgcaa aaaagcggtt agctccttcg gtcctccgat   5580
cgttgtcaga agtaagttgg ccgcagtgtt atcactcatg gttatggcag cactgcataa   5640
ttctcttact gtcatgccat ccgtaagatg cttttctgtg actggtgagt actcaaccaa   5700
gtcattctga gaatagtgta tgcggcgacc gagttgctct tgcccggcgt caatacggga   5760
taataccgcg ccacatagca gaactttaaa agtgctcatc attggaaaac gttcttcggg   5820
gcgaaaactc tcaaggatct taccgctgtt gagatccagt tcgatgtaac ccactcgtgc   5880
acccaactga tcttcagcat cttttacttt caccagcgtt tctgggtgag caaaaacagg   5940
aaggcaaaat gccgcaaaaa agggaataag ggcgacacgg aaatgttgaa tactcatact   6000
cttcctttt caatattatt gaagcattta tcagggttat tgtctcatga gcggatacat   6060
atttgaatgt atttagaaaa ataaacaaat aggggttccg cgcacatttc cccgaaaagt   6120
gccac                                                              6125
```

<210> SEQ ID NO 25
<211> LENGTH: 6131
<212> TYPE: DNA
<213> ORGANISM: Artificial Sequence
<220> FEATURE:
<223> OTHER INFORMATION: AAVS_Ef1a-intron_FRT_BFPnls_F3 vector V4.B.3

<400> SEQUENCE: 25

```
ctaaattgta agcgttaata ttttgttaaa attcgcgtta aatttttgtt aaatcagctc      60
atttttttaac caataggccg aaatcggcaa atcccttat aaatcaaaag aatagaccga     120
gataggttg agtggccgct acagggcgct cccattcgcc attcaggctg cgcaactgtt     180
gggaagggcg tttcggtgcg ggcctcttcg ctattacgcc agctggcgaa agggggatgt     240
gctgcaaggc gattaagttg ggtaacgcca gggttttccc agtcacgacg ttgtaaaacg     300
acggccagtg agcgcgacgt aatacgactc actatagggc gaattggcgg aaggccgtca     360
aggccgcatg aattgagctc tactggcttc tgcgccgcct ctggcccact gtttcccctt     420
cccaggcagg tcctgctttc tctgacctgc attctctccc ctgggcctgt gccgctttct     480
gtctgcagct tgtggcctgg gtcacctcta cggctggccc agatccttcc ctgccgcctc     540
cttcaggttc cgtcttcctc cactccctct tcccctttgct ctgctgtg ttgctgccca     600
aggatgctct ttccggagca cttccttctc ggcgctgcac cacgtgatgt cctctgagcg     660
gatcctcccc gtgtctgggt cctctccggg catctctcct ccctcaccca acccatgcc     720
gtcttcactc gctgggttcc cttttccttc tccttctggg gcctgtgcca tctctcgttt     780
cttaggatgg ccttctccga cggatgtctc ccttgcgtcc cgcctcccct tcttgtaggc     840
ctgcatcatc accgtttttc tggacaaccc caaagtaccc cgtctccctg ctttagcca     900
cctctccatc ctcttgcttt cttttgcctgg acacccgtt ctcctgtgga ttcgggtcac     960
ctctcactcc tttcatttgg gcagctcccc taccccctt acctctctag tctgtgctag    1020
ctcttccagc cccctgtcat ggcatcttcc agggtccga gagctcagct agtcttcttc    1080
ctccaaccccg ggcccctatg tccacttcag gacagcatgt ttgctgcctc cagggatcct    1140
gtgtccccga gctgggacca ccttatattc ccagggccgg ttaatgtggc tctggttctg    1200
ggtacttta tctgtcccct ccaccgggtg gctccggtgc ccgtcagtgg gcagagcgca    1260
catcgcccac agtccccgag aagttggggg gaggggtcgg caattgaacc ggtgcctaga    1320
gaaggtggcg cggggtaaac tgggaaagtg atgtcgtgta ctgctccgc ctttttcccg    1380
agggtgggg agaaccgtat ataagtgcag tagtcgccgt gaacgttctt tttcgcaacg    1440
ggtttgccgc cagaacacag gtaagtgccg tgtgtggttc ccgcgggcct ggcctcttta    1500
cgggttatgg cccttgcgtg ccttgaatta cttccactgg ctgcagtacg tgattcttga    1560
tcccgagctt cgggttggaa gtgggtggga gagttcgagg ccttgcgctt aaggagcccc    1620
ttcgcctcgt gcttgagttg aggcctggcc tgggcgctgg ggccgccgcg tgcgaatctg    1680
gtggcacctt cgcgcctgtc tcgctgcttt cgataagtct ctagccattt aaaattttg    1740
atgacctgct gcgacgcttt ttttctggca agatagtctt gtaaatgcgg gccaagatct    1800
gcacactggt atttcggttt ttggggccgc gggcggcgac ggggcccgtg cgtcccagcg    1860
cacatgttcg gcgaggcggg gcctgcgagc gcggccaccg agaatcggac ggggggtagtc    1920
tcaagctggc cggcctgctc tggtgcctgg cctcgcgccg ccgtgtatcg ccccgccctg    1980
ggcggcaagg ctggcccggt cggcaccagt tgcgtgagcg gaaagatggc cgcttcccgg    2040
ccctgctgca gggagctcaa aatggaggac gcggcgctcg ggagagcggg cgggtgagtc    2100
acccacacaa aggaaaaggg cctttccgtc ctcagccgtc gcttcatgtg actccacgga    2160
gtaccgggcg ccgtccaggc acctcgatta gttctcgagc ttttggagta cgtcgtcttt    2220
aggttggggg gaggggtttt atgcgatgga gtttccccac actgagtggg tggagactga    2280
agttaggcca gcttggcact tgatgtaatt ctccttggaa tttgcccttt ttgagtttgg    2340
```

| | |
|---|---|
| atcttggttc attctcaagc ctcagacagt ggttcaaagt tttttcttc catttcaggt | 2400 |
| gtcgtgactg gtaccggaag ttcctattcc gaagttccta ttctctagaa agtataggaa | 2460 |
| cttcgtaccg agaccatggc cccaagaag aagcggaagg tcggtatcca cggagtccca | 2520 |
| gcagccatga gcgagctgat taaggagaac atgcacatga agctgtacat ggagggcacc | 2580 |
| gtggacaacc atcacttcaa gtgcacatcc gagggcgaag gcaagcccta cgagggcacc | 2640 |
| cagaccatga gaatcaaggt ggtcgagggc ggcctctcc ccttcgcctt cgacatcctg | 2700 |
| gctactagct tcctctacgg cagcaagacc ttcatcaacc acacccaggg catccccgac | 2760 |
| ttcttcaagc agtccttccc tgagggcttc acatgggaga gagtcaccac atacgaggac | 2820 |
| gggggcgtgc tgaccgctac ccaggacacc agcctccagg acggctgcct catctacaac | 2880 |
| gtcaagatca gaggggtgaa tttcacatcc aacggccctg tgatgcagaa gaaaacactc | 2940 |
| ggctgggagg ccttcaccga gacgctgtac cccgctgacg gcggcctgga aggcagaaac | 3000 |
| gacatggccc tgaagctcgt gggcgggagc catctgatcg caaacatcaa gaccacatat | 3060 |
| agatccaaga aacccgctaa gaacctcaag atgcctggcg tctactatgt ggactacaga | 3120 |
| ctggaaagaa tcaaggaggc caacaacgag acatacgtcg agcagcacga ggtggcagtg | 3180 |
| gccagatact gcgacctccc tagcaaactg gggcacaagc ttaataaaag gccggcggcc | 3240 |
| acgaaaaagg ccggccaggc aaaaaagaaa aagtaaggtc tctctaggaa gttcctattc | 3300 |
| cgaagttcct attcttcaaa tagtatagga acttctctag acctgatcat aatcaagcca | 3360 |
| tatcacatct gtagaggttt acttgcttta aaaaacctcc cacctccc ctgaacctga | 3420 |
| aacataaaat gaatgcaatt gttgttgtta acttgtttat tgcagcttat aatggttaca | 3480 |
| aataaagcaa tagcatcaca aatttcacaa ataaagcatt tttttcactg cattctagtt | 3540 |
| gtggtttgtc caaactcatc aatgtatctt atcatgtctg gatctgcgga tcaggattgg | 3600 |
| tgacagaaaa gccccatcct taggcctcct ccttcctagt ctcctgatat gggtctaac | 3660 |
| ccccacctcc tgttaggcag attccttatc tggtgacaca cccccatttc ctggagccat | 3720 |
| ctctctcctt gccagaacct ctaaggtttg cttacgatgg agccagagag atcctggga | 3780 |
| gggagagctt ggcaggggt gggagggaag gggggatgc gtgacctgcc cggttctcag | 3840 |
| tggccaccct gcgctaccct ctcccagaac ctgagctgct ctgacgcggc tgtctggtgc | 3900 |
| gtttcactga tcctggtgct gcagcttcct tacacttccc aagaggagaa gcagtttgga | 3960 |
| aaaacaaaat cagaataagt tggtcctgag ttctaacttt ggctcttcac ctttctagtc | 4020 |
| cccaatttat attgttcctc cgtgcgtcag ttttacctgt gagataaggc cagtagccag | 4080 |
| ccccgtcctg gcagggctgt ggtgaggagg ggggtgtccg tgtggaaaac tccctttgtg | 4140 |
| agaatggtgc gtcctcgagc tgggcctcat gggccttccg ctcactgccc gctttccagt | 4200 |
| cgggaaacct gtcgtgccag ctgcattaac atggtcatag ctgtttcctt gcgtattggg | 4260 |
| cgctctccgc ttcctcgctc actgactcgc tgcgctcggt cgttcgggta agcctgggg | 4320 |
| tgcctaatga gcaaaaggcc agcaaaaggc caggaaccgt aaaaaggccg cgttgctggc | 4380 |
| gtttttccat aggctccgcc cccctgacga gcatcacaaa aatcgacgct caagtcagag | 4440 |
| gtggcgaaac ccgacaggac tataaagata ccaggcgttt ccccctggaa gctccctcgt | 4500 |
| gcgctctcct gttccgaccc tgccgcttac cggatacctg tccgcctttc tcccttcggg | 4560 |
| aagcgtggcg ctttctcata gctcacgctg taggtatctc agttcggtgt aggtcgttcg | 4620 |
| ctccaagctg ggctgtgtgc acgaaccccc cgttcagccc gaccgctgcg ccttatccgg | 4680 |
| taactatcgt cttgagtcca acccggtaag acacgactta tcgccactgg cagcagccac | 4740 |

```
tggtaacagg attagcagag cgaggtatgt aggcggtgct acagagttct gaagtggtg      4800 gcctaactac ggctacacta aagaacagt atttggtatc tgcgctctgc tgaagccagt      4860
taccttcgga aaagagttg gtagctcttg atccggcaaa caaaccaccg ctggtagcgg      4920
tggttttttt gtttgcaagc agcagattac gcgcagaaaa aaaggatctc aagaagatcc      4980
tttgatcttt tctacggggt ctgacgctca gtggaacgaa aactcacgtt aagggatttt      5040
ggtcatgaga ttatcaaaaa ggatcttcac ctagatcctt ttaaattaaa aatgaagttt      5100
taaatcaatc taaagtatat atgagtaaac ttggtctgac agttaccaat gcttaatcag      5160
tgaggcacct atctcagcga tctgtctatt tcgttcatcc atagttgcct gactccccgt      5220
cgtgtagata actacgatac gggagggctt accatctggc cccagtgctg caatgatacc      5280
gcgagaacca cgctcaccgg ctccagattt atcagcaata aaccagccag ccggaagggc      5340
cgagcgcaga agtggtcctg caactttatc cgcctccatc cagtctatta attgttgccg      5400
ggaagctaga gtaagtagtt cgccagttaa tagtttgcgc aacgttgttg ccattgctac      5460
aggcatcgtg gtgtcacgct cgtcgtttgg tatggcttca ttcagctccg gttcccaacg      5520
atcaaggcga gttacatgat cccccatgtt gtgcaaaaaa gcggttagct ccttcggtcc      5580
tccgatcgtt gtcagaagta agttggccgc agtgttatca ctcatggtta tggcagcact      5640
gcataattct cttactgtca tgccatccgt aagatgcttt tctgtgactg gtgagtactc      5700
aaccaagtca ttctgagaat agtgtatgcg gcgaccgagt tgctcttgcc cggcgtcaat      5760
acgggataat accgcgccac atagcagaac tttaaaagtg ctcatcattg gaaaacgttc      5820
ttcggggcga aaactctcaa ggatcttacc gctgttgaga tccagttcga tgtaacccac      5880
tcgtgcaccc aactgatctt cagcatcttt tactttcacc agcgtttctg gtgagcaaa       5940 aacaggaagg caaaatgccg caaaaaaggg aataagggcg acacggaaat gttgaatact      6000
catactcttc ctttttcaat attattgaag catttatcag ggttattgtc tcatgagcgg      6060
atacatattt gaatgtattt agaaaaataa acaaataggg gttccgcgca catttccccg      6120
aaaagtgcca c                                                          6131
```

<210> SEQ ID NO 26
<211> LENGTH: 3602
<212> TYPE: DNA
<213> ORGANISM: Artificial Sequence
<220> FEATURE:
<223> OTHER INFORMATION: pMA_FRT_HLA-A*02:01-6xHis_F3 vector V4.D.2

<400> SEQUENCE: 26

```
ctaaattgta agcgttaata ttttgttaaa attcgcgtta aatttttgtt aaatcagctc       60
attttttaac caataggccg aaatcggcaa aatcccttat aaatcaaaag aatagaccga      120
gatagggttg agtggccgct acagggcgct cccattcgcc attcaggctg cgcaactgtt      180
gggaagggcg tttcggtgcg ggcctcttcg ctattacgcc agctggcgaa agggggatgt      240
gctgcaaggc gattaagttg ggtaacgcca gggttttccc agtcacgacg ttgtaaaacg      300
acggccagtg agcgcgacgt aatacgactc actatagggc gaattggcgg aaggccgtca      360
aggccgcatg aattcgctac cggaagttc ctattccgaa gttcctattc tctagaaagt      420
ataggaactt caggtaccat ggccgtcatg gcgccccgaa ccctcgtcct gctactctcg      480
ggggctctgg ccctgaccca gacctgggcg gctctcact ccatgaggta tttcttcaca      540
tccgtgtctc ggccaggacg cggagagcca cgcttcatcg cagtgggcta cgtggacgac      600
```

```
acgcagttcg tgcggttcga cagcgacgcc gcgagccaga ggatggagcc gcgggcgccg    660
tggatagagc aggagggtcc ggagtattgg gacggggaga cacggaaagt gaaggcccac    720
tcacagactc accgagtgga cctggggacc ctgcgcggct actacaacca gagcgaggcc    780
ggttctcaca ccgtccagag gatgtatggc tgcgacgtgg ggtcggactg gcgcttcctc    840
cgcggatacc accagtacgc ctacgacggc aaggattaca tcgccctgaa agaggacctg    900
cgctcttgga ccgcggcgga catggcagct cagaccacca agcacaagtg ggaggcggcc    960
catgtggcgg agcagttgag agcctacctg gagggcacgt gcgtggagtg gctccgcaga    1020
tacctggaga cgggaagga gacgctgcag cgcacggacg cccccaaaac gcatatgact    1080
caccacgctg tctctgacca tgaagccacc ctgaggtgct gggccctgag cttctaccct    1140
gcggagatca cactgacctg gcagcgggat ggggaggacc agacccagga cacggagctc    1200
gtggagacca ggcctgcagg ggatggaacc ttccagaagt gggcggctgt ggtggtgcct    1260
tctggacagg agcagagata cacctgccat gtgcagcatg agggtttgcc caagcccctc    1320
accctgagat gggagccgtc ttcccagccc accatcccca tcgtgggcat cattgctggc    1380
ctggttctct ttggagctgt gatcactgga gctgtggtcg ctgctgtgat gtggaggagg    1440
aagagctcag atagaaaagg agggagctac tctcaggctg caagcagtga cagtgcccag    1500
ggctctgatg tgtctctcac agcttgtaaa gtgcccgggc atcatcacca tcaccactga    1560
ctatagtcgt ctagacgaag ttcctattcc gaagttccta ttcttcaaat agtataggaa    1620
cttcctcgag ctgggcctca tgggccttcc gctcactgcc cgctttccag tcgggaaacc    1680
tgtcgtgcca gctgcattaa catggtcata gctgtttcct tgcgtattgg gcgctctccg    1740
cttcctcgct cactgactcg ctgcgctcgg tcgttcgggt aaagcctggg gtgcctaatg    1800
agcaaaaggc cagcaaaagg ccaggaaccg taaaaaggcc gcgttgctgg cgttttccca    1860
taggctccgc ccccctgacg agcatcacaa aaatcgacgc tcaagtcaga ggtggcgaaa    1920
cccgacagga ctataaagat accaggcgtt ccccctgga agctccctcg tgcgctctcc    1980
tgttccgacc ctgccgctta ccggatacct gtccgccttt ctcccttcgg gaagcgtggc    2040
gctttctcat agctcacgct gtaggtatct cagttcggtg taggtcgttc gctccaagct    2100
gggctgtgtg cacgaacccc ccgttcagcc cgaccgctgc gccttatccg gtaactatcg    2160
tcttgagtcc aacccggtaa gacacgactt atcgccactg gcagcagcca ctggtaacag    2220
gattagcaga gcgaggtatg taggcggtgc tacagagttc ttgaagtggt ggcctaacta    2280
cggctacact agaagaacag tatttggtat ctgcgctctg ctgaagccag ttaccttcgg    2340
aaaaagagtt ggtagctctt gatccggcaa acaaaccacc gctggtagcg tggtttttt    2400 tgtttgcaag cagcagatta cgcgcagaaa aaaaggatct caagaagatc ctttgatctt    2460
ttctacgggg tctgacgctc agtggaacga aaactcacgt taagggattt tggtcatgag    2520
attatcaaaa aggatcttca cctagatcct tttaaattaa aaatgaagtt ttaaatcaat    2580
ctaaagtata tatgagtaaa cttggtctga cagttaccaa tgcttaatca gtgaggcacc    2640
tatctcagcg atctgtctat ttcgttcatc catagttgcc tgactccccg tcgtgtagat    2700
aactacgata cgggagggct taccatctgg ccccagtgct gcaatgatac cgcgagaacc    2760
acgctcaccg gctccagatt tatcagcaat aaaccagcca gccggaaggg ccgagcgcag    2820
aagtggtcct gcaactttat ccgcctccat ccagtctatt aattgttgcc gggaagctag    2880
agtaagtagt tcgccagtta atagtttgcg caacgttgtt gccattgcta caggcatcgt    2940
ggtgtcacgc tcgtcgtttg gtatggcttc attcagctcc ggttcccaac gatcaaggcg    3000
```

| | |
|---|---|
| agttacatga tcccccatgt tgtgcaaaaa agcggttagc tccttcggtc ctccgatcgt | 3060 |
| tgtcagaagt aagttggccg cagtgttatc actcatggtt atggcagcac tgcataattc | 3120 |
| tcttactgtc atgccatccg taagatgctt ttctgtgact ggtgagtact caaccaagtc | 3180 |
| attctgagaa tagtgtatgc ggcgaccgag ttgctcttgc ccggcgtcaa tacgggataa | 3240 |
| taccgcgcca catagcagaa ctttaaaagt gctcatcatt ggaaaacgtt cttcggggcg | 3300 |
| aaaactctca aggatcttac cgctgttgag atccagttcg atgtaaccca ctcgtgcacc | 3360 |
| caactgatct tcagcatctt ttactttcac cagcgtttct gggtgagcaa aacaggaag | 3420 |
| gcaaaatgcc gcaaaaaagg aataagggc gacacgaaaa tgttgaatac tcatactctt | 3480 |
| cctttttcaa tattattgaa gcatttatca gggttattgt ctcatgagcg gatacatatt | 3540 |
| tgaatgtatt tagaaaaata acaaataggg gttccgcgc acatttcccc gaaaagtgcc | 3600 |
| ac | 3602 |

<210> SEQ ID NO 27
<211> LENGTH: 3602
<212> TYPE: DNA
<213> ORGANISM: Artificial Sequence
<220> FEATURE:
<223> OTHER INFORMATION: pMA_F14_HLA-A*02:01-6xHis_F15 vector V4.H.5

<400> SEQUENCE: 27

| | |
|---|---|
| ctaaattgta agcgttaata ttttgttaaa attcgcgtta aattttgtt aaatcagctc | 60 |
| attttttaac caataggccg aaatcggcaa aatcccttat aaatcaaaag aatagaccga | 120 |
| gatagggttg agtggccgct acagggcgct cccattcgcc attcaggctg cgcaactgtt | 180 |
| gggaagggcg tttcggtgcg ggcctcttcg ctattacgcc agctggcgaa agggggatgt | 240 |
| gctgcaaggc gattaagttg ggtaacgcca gggttttccc agtcacgacg ttgtaaaacg | 300 |
| acggccagtg agcgcgacgt aatacgactc actatagggc gaattggcgg aaggccgtca | 360 |
| aggccgcatg aattcgctac cgggaagttc ctattccgaa gttcctattc tatcagaagt | 420 |
| ataggaactt cagtgtacc atggccgtcatg gcgccccgaa ccctcgtcct gctactctcg | 480 |
| ggggctctgg ccctgaccca gacctgggcg ggctctcact ccatgaggta tttcttcaca | 540 |
| tccgtgtctc ggccaggacg cggagagcca cgcttcatcg cagtgggcta cgtggacgac | 600 |
| acgcagttcg tgcggttcga cagcgacgcc gcgagccaga ggatggagcc gcgggcgccg | 660 |
| tggatagagc aggagggtcc ggagtattgg gacggggaga cacggaaagt gaaggcccac | 720 |
| tcacagactg accgagtgga cctggggacc ctgcgcggct actacaacca gagcgaggcc | 780 |
| ggttctcaca ccgtccagag gatgtatggc tgcgacgtgg ggtcggactg gcgcttcctc | 840 |
| cgcggatacc accagtacgc ctacgacggc aaggattaca tcgccctgaa agaggacctg | 900 |
| cgctcttgga ccgcggcgga catggcagct cagaccacca agcacaagtg ggaggcggcc | 960 |
| catgtggcgg agcagttgag agcctacctg gagggcacgt gcgtggagtg gctccgcaga | 1020 |
| tacctggaga acgggaagga gacgctgcag cgcacggacg cccccaaaac gcatatgact | 1080 |
| caccacgctg tctctgacca tgaagccacc ctgaggtgct gggccctgag cttctacccct | 1140 |
| gcggagatca cactgacctg gcagcgggat ggggaggacc agacccagga cacggagctc | 1200 |
| gtggagacca ggcctgcagg ggatggaacc ttccagaagt gggcggctgt ggtggtgcct | 1260 |
| tctggacagg agcagagata cacctgccat gtgcagcatg agggtttgcc caagccctc | 1320 |
| accctgagat gggagccgtc ttcccagccc accatcccca tcgtgggcat cattgctggc | 1380 |

```
ctggttctct ttggagctgt gatcactgga gctgtggtcg ctgctgtgat gtggaggagg    1440
aagagctcag atagaaaagg agggagctac tctcaggctg caagcagtga cagtgcccag    1500
ggctctgatg tgtctctcac agcttgtaaa gtgcccgggc atcatcacca tcaccactga    1560
ctatagtcgt ctagacgaag ttcctattcc gaagttccta ttcttatagg agtataggaa    1620
cttcctcgag ctgggcctca tgggccttcc gctcactgcc cgctttccag tcgggaaacc    1680
tgtcgtgcca gctgcattaa catggtcata gctgtttcct tgcgtattgg gcgctctccg    1740
cttcctcgct cactgactcg ctgcgctcgg tcgttcgggt aaagcctggg gtgcctaatg    1800
agcaaaaggc cagcaaaagg ccaggaaccg taaaaaggcc gcgttgctgg cgttttccca    1860
taggctccgc cccctgacg agcatcacaa aaatcgacgc tcaagtcaga ggtggcgaaa    1920
cccgacagga ctataaagat accaggcgtt tccccctgga agctccctcg tgcgctctcc    1980
tgttccgacc ctgccgctta ccggatacct gtccgccttt ctcccttcgg gaagcgtggc    2040
gctttctcat agctcacgct gtaggtatct cagttcggtg taggtcgttc gctccaagct    2100
gggctgtgtg cacgaacccc ccgttcagcc cgaccgctgc gccttatccg gtaactatcg    2160
tcttgagtcc aacccggtaa gacacgactt atcgccactg gcagcagcca ctggtaacag    2220
gattagcaga gcgaggtatg taggcggtgc tacagagttc ttgaagtggt ggcctaacta    2280
cggctacact agaagaacag tatttggtat ctgcgctctg ctgaagccag ttaccttcgg    2340
aaaaagagtt ggtagctctt gatccggcaa acaaaccacc gctggtagcg gtggtttttt    2400
tgtttgcaag cagcagatta cgcgcagaaa aaaggatctc aagaagatc ctttgatctt    2460 ttctacgggg tctgacgctc agtggaacga aaactcacgt taagggattt tggtcatgag    2520
attatcaaaa aggatcttca cctagatcct tttaaattaa aaatgaagtt ttaaatcaat    2580
ctaaagtata tatgagtaaa cttggtctga cagttaccaa tgcttaatca gtgaggcacc    2640
tatctcagcg atctgtctat ttcgttcatc catagttgcc tgactccccg tcgtgtagat    2700
aactacgata cgggagggct taccatctgg ccccagtgct gcaatgatac cgcgagaacc    2760
acgctcaccg gctccagatt tatcagcaat aaaccagcca gccggaaggg ccgagcgcag    2820
aagtggtcct gcaactttat ccgcctccat ccagtctatt aattgttgcc gggaagctag    2880
agtaagtagt tcgccagtta atagtttgcg caacgttgtt gccattgcta caggcatcgt    2940
ggtgtcacgc tcgtcgtttg gtatggcttc attcagctcc ggttcccaac gatcaaggcg    3000
agttacatga tcccccatgt tgtgcaaaaa agcggttagc tccttcggtc ctccgatcgt    3060
tgtcagaagt aagttggccg cagtgttatc actcatggtt atggcagcac tgcataattc    3120
tcttactgtc atgccatccg taagatgctt ttctgtgact ggtgagtact caaccaagtc    3180
attctgagaa tagtgtatgc ggcgaccgag ttgctcttgc ccggcgtcaa tacgggataa    3240
taccgcgcca catagcagaa ctttaaaagt gctcatcatt ggaaaacgtt cttcggggcg    3300
aaaactctca aggatcttac cgctgttgag atccagttcg atgtaaccca ctcgtgcacc    3360
caactgatct tcagcatctt ttactttcac cagcgtttct gggtgagcaa aaacaggaag    3420
gcaaaatgcc gcaaaaaagg gaataagggc gacacggaaa tgttgaatac tcatactctt    3480 ccttttcaa tattattgaa gcatttatca gggttattgt ctcatgagcg gatacatatt    3540
tgaatgtatt tagaaaaata aacaaatagg ggttccgcgc acatttcccc gaaaagtgcc    3600
ac                                                                   3602

<210> SEQ ID NO 28
<211> LENGTH: 3602
```

<212> TYPE: DNA
<213> ORGANISM: Artificial Sequence
<220> FEATURE:
<223> OTHER INFORMATION: pMA_F14_HLA-A*24:02-6xHis_F15 vector V4.H.6

<400> SEQUENCE: 28

| | | | | | |
|---|---|---|---|---|---|
| ctaaattgta | agcgttaata | ttttgttaaa | attcgcgtta | aattttttgtt | aaatcagctc | 60 |
| attttttaac | caataggccg | aaatcggcaa | aatcccttat | aaatcaaaag | aatagaccga | 120 |
| gatagggttg | agtggccgct | acagggcgct | cccattcgcc | attcaggctg | cgcaactgtt | 180 |
| gggaagggcg | tttcggtgcg | ggcctcttcg | ctattacgcc | agctggcgaa | aggggggatgt | 240 |
| gctgcaaggc | gattaagttg | ggtaacgcca | gggttttccc | agtcacgacg | ttgtaaaacg | 300 |
| acggccagtg | agcgcgacgt | aatacgactc | actatagggc | gaattggcgg | aaggccgtca | 360 |
| aggccgcatg | aattcgctac | cgggaagttc | ctattccgaa | gttcctattc | tatcagaagt | 420 |
| ataggaactt | caggtaccat | ggccgtcatg | gcgccccgaa | ccctcgtcct | gctactctcg | 480 |
| ggggccctgg | ccctgaccca | gacctgggca | ggctcccact | ccatgaggta | tttctccaca | 540 |
| tccgtgtctc | ggccaggacg | cggagagcca | cgcttcatcg | ccgtgggcta | cgtggacgac | 600 |
| acgcagttcg | tgcggttcga | cagcgacgcc | gcgagccaga | ggatgsgagcc | gcgggcgccg | 660 |
| tggatagagc | aggagggggcc | ggagtattgg | gacgaggaga | cagggaaagt | gaaggcccac | 720 |
| tcacagactg | accgagagaa | cctgcggatc | gcgctccgct | actacaacca | gagcgaggcc | 780 |
| ggttctcaca | ccctccagat | gatgtttggc | tgcgacgtgg | ggtcggacgg | gcgcttcctc | 840 |
| cgcggatacc | accagtacgc | ctacgacggc | aaggattaca | tcgccctgaa | agaggacctg | 900 |
| cgctcttgga | ccgcggcgga | catggcggct | cagatcacca | agcgcaagtg | ggaggcggcc | 960 |
| catgtggcgg | agcagcagag | agcctacctg | gagggcacgt | gcgtggacgg | gctccgcaga | 1020 |
| tacctggaga | acgggaagga | gacgctgcag | cgcacggacc | cccccaagac | acatatgacc | 1080 |
| caccacccca | tctctgacca | tgaggccact | ctgagatgct | gggccctggg | cttctaccct | 1140 |
| gcggagatca | cactgacctg | gcagcgggat | ggggaggacc | agacccagga | cacggagctt | 1200 |
| gtggagacca | ggcctgcagg | ggatggaacc | ttccagaagt | gggcagctgt | ggtggttcct | 1260 |
| tctggagagg | agcagagata | cacctgccat | gtgcagcatg | agggtctgcc | caagcccctc | 1320 |
| accctgagat | gggagccatc | ttcccagccc | accgtcccca | tcgtgggcat | cattgctggc | 1380 |
| ctggttctcc | ttggagctgt | gatcactgga | gctgtggtcg | ctgctgtgat | gtggaggagg | 1440 |
| aacagctcag | atagaaaagg | agggagctac | tctcaggctg | caagcagtga | cagtgcccag | 1500 |
| ggctctgatg | tgtctctcac | agcttgtaaa | gtgcccgggc | atcatcacca | tcaccactga | 1560 |
| ctatagtcgt | ctagacgaag | ttcctattcc | gaagttccta | ttcttatagg | agtataggaa | 1620 |
| cttcctcgag | ctgggcctca | tgggccttcc | gctcactgcc | cgctttccag | tcgggaaacc | 1680 |
| tgtcgtgcca | gctgcattaa | catggtcata | gctgtttcct | tgcgtattgg | gcgctctccg | 1740 |
| cttcctcgct | cactgactcg | ctgcgctcgg | tcgttcgggt | aaagcctggg | gtgcctaatg | 1800 |
| agcaaaaggc | cagcaaaagg | ccaggaaccg | taaaaaggcc | gcgttgctgg | cgttttttcca | 1860 |
| taggctccgc | cccccctgacg | agcatcacaa | aaatcgacgc | tcaagtcaga | ggtggcgaaa | 1920 |
| cccgacagga | ctataaagat | accaggcgtt | tccccctgga | agctccctcg | tgcgctctcc | 1980 |
| tgttccgacc | ctgccgctta | ccggatacct | gtccgccttt | ctcccttcgg | gaagcgtggc | 2040 |
| gctttctcat | agctcacgct | gtaggtatct | cagttcggtg | taggtcgttc | gctccaagct | 2100 |
| gggctgtgtg | cacgaacccc | ccgttcagcc | cgaccgctgc | gccttatccg | gtaactatcg | 2160 |

```
tcttgagtcc aacccggtaa gacacgactt atcgccactg gcagcagcca ctggtaacag    2220
gattagcaga gcgaggtatg taggcggtgc tacagagttc ttgaagtggt ggcctaacta    2280
cggctacact agaagaacag tatttggtat ctgcgctctg ctgaagccag ttaccttcgg    2340
aaaaagagtt ggtagctctt gatccggcaa acaaaccacc gctggtagcg gtggtttttt    2400
tgtttgcaag cagcagatta cgcgcagaaa aaaggatct caagaagatc ctttgatctt    2460
ttctacgggg tctgacgctc agtggaacga aaactcacgt taagggattt tggtcatgag    2520
attatcaaaa aggatcttca cctagatcct tttaaattaa aaatgaagtt ttaaatcaat    2580
ctaaagtata tatgagtaaa cttggtctga cagttaccaa tgcttaatca gtgaggcacc    2640
tatctcagcg atctgtctat ttcgttcatc catagttgcc tgactccccg tcgtgtagat    2700
aactacgata cgggagggct taccatctgg ccccagtgct gcaatgatac cgcgagaacc    2760
acgctcaccg gctccagatt tatcagcaat aaaccagcca gccggaaggg ccgagcgcag    2820
aagtggtcct gcaactttat ccgcctccat ccagtctatt aattgttgcc gggaagctag    2880
agtaagtagt tcgccagtta atagtttgcg caacgttgtt gccattgcta caggcatcgt    2940
ggtgtcacgc tcgtcgtttg gtatggcttc attcagctcc ggttcccaac gatcaaggcg    3000
agttacatga tcccccatgt tgtgcaaaaa agcggttagc tccttcggtc ctccgatcgt    3060
tgtcagaagt aagttggccg cagtgttatc actcatggtt atggcagcac tgcataattc    3120
tcttactgtc atgccatccg taagatgctt ttctgtgact ggtgagtact caaccaagtc    3180
attctgagaa tagtgtatgc ggcgaccgag ttgctcttgc ccggcgtcaa tacgggataa    3240
taccgcgcca catagcagaa ctttaaaagt gctcatcatt ggaaaacgtt cttcggggcg    3300
aaaactctca aggatcttac cgctgttgag atccagttcg atgtaaccca ctcgtgcacc    3360
caactgatct tcagcatctt ttactttcac cagcgtttct gggtgagcaa aaacaggaag    3420
gcaaaatgcc gcaaaaaagg gaataagggc gacacggaaa tgttgaatac tcatactctt    3480
cctttttcaa tattattgaa gcatttatca gggttattgt ctcatgagcg gatacatatt    3540
tgaatgtatt tagaaaaata acaaataggg gttccgcgc acatttcccc gaaaagtgcc    3600
ac                                                                   3602

<210> SEQ ID NO 29
<211> LENGTH: 3593
<212> TYPE: DNA
<213> ORGANISM: Artificial Sequence
<220> FEATURE:
<223> OTHER INFORMATION: pMA_F14_HLA-B*07:02-6xHis_F15 vector V4.H.7

<400> SEQUENCE: 29
ctaaattgta agcgttaata ttttgttaaa attcgcgtta aatttttgtt aaatcagctc      60
attttttaac caataggccg aaatcggcaa aatcccttat aaatcaaaag aatagaccga     120
gatagggttg agtggccgct acagggcgct cccattcgcc attcaggctg cgcaactgtt     180
gggaagggcg tttcggtgcg ggcctcttcg ctattacgcc agctggcgaa aggggggatgt     240
gctgcaaggc gattaagttg ggtaacgcca gggttttccc agtcacgacg ttgtaaaacg     300
acggccagtg agcgcgacgt aatacgactc actataggc gaattggcgg aaggccgtca     360
aggccgcatg aattcgctac cgggaagttc ctattccgaa gttcctattc tatcagaagt     420
ataggaactt caggtaccat gctggtcatg cgccccgaa ccgtcctcct gctgctctcg     480
gcggccctgg ccctgaccga gacctgggcc ggctcccact ccatgaggta tttctacacc     540
tccgtgtctc ggccaggacg cggagagcca cgcttcatct cagtgggcta cgtggacgac     600
```

```
acccagttcg tgaggttcga cagcgacgcc gcgagtccga gagaggagcc gcgggcgccg    660
tggatagagc aggaggggcc ggagtattgg gaccggaaca cacagatcta caaggcccag    720
gcacagactg accgagagag cctgcggaac ctgcgcggct actacaacca gagcgaggcc    780
gggtctcaca ccctccagag catgtacggc tgcgacgtgg ggccgacgg cgcctcctc     840 cgcgggcatg accagtacgc ctacgacggc aaggattaca tcgccctgaa cgaggacctg    900
cgctcctgga ccgccgcgga cacggcggct cagatcaccc agcgcaagtg ggaggcggcc    960
cgtgaggcgg agcagcggag agcctacctg gagggcgagt gcgtggagtg gctccgcaga   1020
tacctggaga acgggaagga caaacttgag cgcgcagacc ctccaaagac acacgtgacc   1080
caccacccca tctctgacca tgaggccacc ctgaggtgct gggccctggg tttctaccct   1140
gcggagatca cactgacctg gcagcgggat ggcgaggacc aaaactcagga cactgagctt   1200 gtggagacca gaccagcagg agatagaacc ttccagaagt gggcagctgt ggtggtgcct   1260
tctggagaag agcagagata cacatgccat gtacagcatg aggggctgcc gaagcccctc   1320
accctgagat gggagccgtc ttcccagtcc accgtcccca tcgtgggcat tgttgctggc   1380
ctggctgtcc tagcagttgt ggtcatcgga gctgtggtcg ctgctgtgat tgtaggagg    1440 aagagttcag gtgaaaagg agggagctac tctcaggctg cgtgcagcga cagtgcccag   1500
ggctctgatg tgtctctcac agctcccggg catcatcacc atcacctg actatagtcg    1560 tctagacgaa gttcctattc cgaagttcct attcttatag gagtatagga acttcctcga   1620
gctgggcctc atgggccttc cgctcactgc ccgctttcca gtcgggaaac ctgtcgtgcc   1680
agctgcatta acatggtcat agctgtttcc ttgcgtattg ggcgctctcc gcttcctcgc   1740
tcactgactc gctgcgctcg gtcgttcggg taaagcctgg ggtgcctaat gagcaaaagg   1800
ccagcaaaag gccaggaacc gtaaaaaggc cgcgttgctg gcgttttcc ataggctccg   1860 cccccctgac gagcatcaca aaaatcgacg ctcaagtcag aggtggcgaa acccgacagg   1920
actataaaga taccaggcgt ttccccctgg aagctccctc gtgcgctctc ctgttccgac   1980
cctgccgctt accggatacc tgtccgcctt tctcccttcg ggaagcgtgg cgctttctca   2040
tagctcacgc tgtaggtatc tcagttcggt gtaggtcgtt cgctccaagc tgggctgtgt   2100
gcacgaaccc cccgttcagc ccgaccgctg cgccttatcc ggtaactatc gtcttgagtc   2160
caacccggta agacacgact tatcgccact ggcagcagcc actggtaaca ggattagcag   2220
agcgaggtat gtaggcggtg ctacagagtt cttgaagtgg tggcctaact acggctacac   2280
tagaagaaca gtatttggta tctgcgctct gctgaagcca gttaccttcg aaaaagagt    2340 tggtagctct tgatccggca aacaaaccac cgctggtagc ggtggttttt tgtttgcaa    2400 gcagcagatt acgcgcagaa aaaaggatc tcaagaagat cctttgatct tttctacggg    2460
gtctgacgct cagtggaacg aaaactcacg ttaagggatt ttggtcatga gattatcaaa   2520
aaggatcttc acctagatcc ttttaaatta aaaatgaagt tttaaatcaa tctaaagtat   2580
atatgagtaa acttggtctg acagttacca atgcttaatc agtgaggcac ctatctcagc   2640
gatctgtcta tttcgttcat ccatagttgc ctgactcccc gtcgtgtaga taactacgat   2700
acgggagggc ttaccatctg gccccagtgc tgcaatgata ccgcgagaac cacgctcacc   2760
ggctccagat ttatcagcaa taaaccagcc agccggaagg gccgagcgca gaagtggtcc   2820
tgcaacttta tccgcctcca tccagtctat taattgttgc cgggaagcta gagtaagtag   2880
ttcgccagtt aatagtttgc gcaacgttgt tgccattgct acaggcatcg tggtgtcacg   2940
```

```
ctcgtcgttt ggtatggctt cattcagctc cggttcccaa cgatcaaggc gagttacatg    3000
atcccccatg ttgtgcaaaa aagcggttag ctccttcggt cctccgatcg ttgtcagaag    3060
taagttggcc gcagtgttat cactcatggt tatggcagca ctgcataatt ctcttactgt    3120
catgccatcc gtaagatgct tttctgtgac tggtgagtac tcaaccaagt cattctgaga    3180
atagtgtatg cggcgaccga gttgctcttg cccggcgtca atacgggata ataccgcgcc    3240
acatagcaga actttaaaag tgctcatcat tggaaaacgt tcttcgggc gaaaactctc    3300 aaggatctta ccgctgttga tccagttc gatgtaaccc actcgtgcac ccaactgatc    3360
ttcagcatct tttactttca ccagcgtttc tgggtgagca aaaacaggaa ggcaaaatgc    3420
cgcaaaaaag gaataaggg cgacacggaa atgttgaata ctcatactct ccttttttca    3480
atattattga agcatttatc agggttattg tctcatgagc ggatacatat ttgaatgtat    3540
ttagaaaaat aaacaaatag gggttccgcg cacatttccc cgaaaagtgc cac          3593
```

<210> SEQ ID NO 30
<211> LENGTH: 3593
<212> TYPE: DNA
<213> ORGANISM: Artificial Sequence
<220> FEATURE:
<223> OTHER INFORMATION: pMA_F14_HLA-B*35:01-6xHis_F15 vector V4.H.8

<400> SEQUENCE: 30

```
ctaaattgta agcgttaata ttttgttaaa attcgcgtta aattttttgtt aaatcagctc     60 atttttttaac caataggccg aaatcggcaa aatcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa aggggggatgt    240 gctgcaaggc gattaagttg gtaacgcca gggttttccc agtcacgacg ttgtaaaacg    300
acggccagtg agcgcgacgt aatacgactc actatagggc gaattggcgg aaggccgtca    360
aggccgcatg aattcgctac cgggaagttc ctattccgaa gttcctattc tatcagaagt    420
ataggaactt caggtaccat gcgggtcacg gcgccccgaa ccgtcctcct gctgctctgg    480
ggggcagtgg ccctgaccga gacctgggcc ggctcccact ccatgaggta tttctacacc    540
gccatgtccc ggccaggacg cggagagcca cgcttcatcg cagtgggcta cgtggacgac    600
acccagttcg tgaggttcga cagcgacgcc gcgagtccga ggacggagcc tcgggcgcca    660
tggatagagc aggaggggcc ggagtattgg gaccggaaca cacagatctt caagaccaac    720
acacagactt accgagagag cctgcggaac ctgcgcggct actacaacca gagcgaggcc    780
gggtctcaca tcatccagag gatgtatggc tgcgacctgg ggcccgacgg gcgcctcctc    840
cgcgggcatg accagtccgc ctacgacggc aaggattaca tcgccctgaa cgaggacctg    900
agctcctgga ccgcggcgga caccgcggct cagatcaccc agcgcaagtg ggaggcggcc    960
cgtgtggcgg agcagctgag agcctacctg gagggcctgt gcgtggagtg gctccgcaga   1020
tacctggaga cgggaagga gactcttcag gcgcagatc ctccaaagac acacgtgacc    1080
caccaccccg tctctgacca tgaggccacc ctgaggtgct gggccctggg cttctaccct   1140
gcggagatca cactgacctg gcagcgggat ggcgaggacc aaactcagga cactgagctt   1200
gtggagacca gaccagcagg agatagaacc ttccagaagt gggcagctgt ggtggtgcct   1260
tctggagaag agcagagata cacatgccat gtacagcatg agggggctgcc gaagcccctc   1320 accctgagat gggagccatc ttcccagtcc accatcccca tcgtgggcat tgttgctggc   1380
ctggctgtcc tagcagttgt ggtcatcgga gctgtggtcg ctactgtgat gtgtaggagg   1440
```

```
aagagctcag gtggaaaagg agggagctac tctcaggctg cgtccagcga cagtgcccag    1500
ggctctgatg tgtctctcac agctcccggg catcatcacc atcaccactg actatagtcg    1560
tctagacgaa gttcctattc cgaagttcct attcttatag gagtatagga acttcctcga    1620
gctgggcctc atgggccttc cgctcactgc ccgctttcca gtcgggaaac ctgtcgtgcc    1680
agctgcatta acatggtcat agctgttttcc ttgcgtattg ggcgctctcc gcttcctcgc    1740
tcactgactc gctgcgctcg gtcgttcggg taaagcctgg ggtgcctaat gagcaaaagg    1800
ccagcaaaag gccaggaacc gtaaaaaggc cgcgttgctg gcgttttttcc ataggctccg    1860 cccccctgac gagcatcaca aaaatcgacg ctcaagtcag aggtggcgaa acccgacagg    1920
actataaaga taccaggcgt ttccccctgg aagctccctc gtgcgctctc ctgttccgac    1980
cctgccgctt accggatacc tgtccgcctt tctcccttcg ggaagcgtgg cgctttctca    2040
tagctcacgc tgtaggtatc tcagttcggt gtaggtcgtt cgctccaagc tgggctgtgt    2100
gcacgaaccc cccgttcagc ccgaccgctg cgccttatcc ggtaactatc gtcttgagtc    2160
caacccggta agacacgact tatcgccact ggcagcagcc actggtaaca ggattagcag    2220
agcgaggtat gtaggcggtg ctacagagtt cttgaagtgg tggcctaact acggctacac    2280
tagaagaaca gtatttggta tctgcgctct gctgaagcca gttaccttcg gaaaaagagt    2340
tggtagctct tgatccggca acaaaccac cgctggtagc ggtggttttt ttgtttgcaa    2400
gcagcagatt acgcgcagaa aaaaggatc tcaagaagat cctttgatct tttctacggg    2460
gtctgacgct cagtggaacg aaaactcacg ttaagggatt ttggtcatga gattatcaaa    2520
aaggatcttc acctagatcc ttttaaatta aaaatgaagt tttaaatcaa tctaaagtat    2580
atatgagtaa acttggtctg acagttacca atgcttaatc agtgaggcac ctatctcagc    2640
gatctgtcta tttcgttcat ccatagttgc ctgactcccc gtcgtgtaga taactacgat    2700
acgggagggc ttaccatctg gccccagtgc tgcaatgata ccgcgagaac cacgctcacc    2760
ggctccagat ttatcagcaa taaaccagcc agccggaagg gccgagcgca gaagtggtcc    2820
tgcaacttta tccgcctcca tccagtctat taattgttgc cgggaagcta gagtaagtag    2880
ttcgccagtt aatagtttgc gcaacgttgt tgccattgct acaggcatcg tggtgtcacg    2940
ctcgtcgttt ggtatggctt cattcagctc cggttcccaa cgatcaaggc gagttacatg    3000
atcccccatg ttgtgcaaaa aagcggttag ctccttcggt cctccgatcg ttgtcagaag    3060
taagttggcc gcagtgttat cactcatggt tatggcagca ctgcataatt ctcttactgt    3120
catgccatcc gtaagatgct tttctgtgac tggtgagtac tcaaccaagt cattctgaga    3180
atagtgtatg cggcgaccga gttgctcttg cccggcgtca atacgggata ataccgcgcc    3240
acatagcaga actttaaaag tgctcatcat tggaaaacgt tcttcgggc gaaaactctc    3300 aaggatctta ccgctgttga tccagttc gatgtaaccc actcgtgcac ccaactgatc    3360
ttcagcatct tttactttca ccagcgtttc tgggtgagca aaaacaggaa ggcaaaatgc    3420
cgcaaaaaag ggaataaggg cgacacggaa atgttgaata ctcatactct ccttttttca    3480
atattattga agcatttatc agggttattg tctcatgagc ggatacatat ttgaatgtat    3540
ttagaaaaat aaacaaatag gggttccgcg cacatttccc cgaaaagtgc cac          3593
```

<210> SEQ ID NO 31
<211> LENGTH: 4542
<212> TYPE: DNA
<213> ORGANISM: Artificial Sequence
<220> FEATURE:

<223> OTHER INFORMATION: CMVpro_FLP_Sv40pA_V2 vector V4.1.8

<400> SEQUENCE: 31

```
ctaaattgta agcgttaata ttttgttaaa attcgcgtta aattttttgtt aaatcagctc      60
attttttaac caataggccg aaatcggcaa atcccttat aaatcaaaag aatagaccga      120
gatagggttg agtggccgct acagggcgct cccattcgcc attcaggctg cgcaactgtt    180
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccgcatg aattcgctac cggtatagta atcaattacg gggtcattag ttcatagccc    420
atatatggag ttccgcgtta cataacttac ggtaaatggc ccgcctggct gaccgcccaa    480
cgacccccgc ccattgacgt caataatgac gtatgttccc atagtaacgc caatagggac    540
tttccattga cgtcaatggg tggagtattt acggtaaact gcccacttgg cagtacatca    600
agtgtatcat atgccaagta cgccccctat tgacgtcaat gacggtaaat ggcccgcctg    660
gcattatgcc cagtacatga ccttatggga ctttcctact tggcagtaca tctacgtatt    720
agtcatcgct attaccatgg tgatgcggtt ttggcagtac atcaatgggc gtggatagcg    780
gtttgactca cggggatttc caagtctcca ccccattgac gtcaatggga gtttgttttg    840
gcaccaaaat caacgggact ttccaaaatg tcgtaacaac tccgccccat tgacgcaaat    900
gggcggtagg cgtgtacggt gggaggtcta taagcaga gctggtttag tgaaccgtca     960
gatcaggtac catggccccc aagaaaaagc ggaaagtggg catccacggc gtgccagctg   1020
caggcggctc tatgagccag ttcgacatcc tgtgcaagac cccacctaag gtgctcgtgc   1080
ggcagttcgt ggaaagattc gagaggccta gcggcgagaa gatcgcctct tgtgctgccg   1140
agctgaccta cctgtgctgg atgatcaccc acaacggcac cgccatcaag cgggccacct   1200
tcatgagcta caataccatc atcagcaaca gcctgagctt cgacatcgtg aacaagagcc   1260
tgcagttcaa gtacaagacc cagaaggcca ccatcctgga agccagcctg aagaaactga   1320
tccccgcctg ggagttttacc atcatcccat acaatggcca gaaacatcag agcgacatta   1380
ccgatatcgt gtccagcctc cagctgcagt tcgagagtag cgaagaagcc gacaagggca   1440
acagccacag caagaagatg ctgaaggccc tgctgagcga gggcgagagc atctgggaga   1500
tcacagagaa gatcctgaac agcttcgagt acaccagccg gttcaccaag accaagaccc   1560
tgtaccagtt cctgttcctg gccaccttta tcaactgcgg ccggttctcc gacatcaaga   1620
acgtggaccc caagagcttc aagctggtgc agaacaagta cctgggcgtg atcattcagt   1680
gcctcgtgac cgagacaaag accagcgtgt cccggcacat ctactttttc agcgccagag   1740
gccggatcga ccccctggtg tacctggacg agttcctgag aaacagcgag cccgtgctga   1800
agagagtgaa ccggaccggc aacagcagct ccaacaagca ggaataccag ctgctgaagg   1860
acaacctcgt gcggtcctac aacaaggccc tgaagaaaaa cgcccctac cccatcttcg    1920
ccattaagaa cggccccaag tcccacatcg gccggcacct gatgaccagc tttctgagca   1980
tgaagggcct gacagagctg accaacgtcg tgggcaattg gagcgacaag agggcctctg   2040
ccgtggccag aaccacctac acccaccaga tcacagccat ccccgaccac tacttcgccc   2100
tggtgtctcg gtactacgcc tacgacccca tcagcaaaga gatgatcgcc ctgaaggacg   2160
agacaaaccc catcgaggaa tggcagcaca tcgagcagct gaagggcagc gccgagggca   2220
gcatcagata ccctgcctgg aacggcatca tctcccagga agtgctggac tacctgagca   2280
```

-continued

```
gctacatcaa ccggcggatc tgatctagac ctgatcataa tcaagccata tcacatctgt    2340
agaggtttac ttgctttaaa aaacctccac acctccccct gaacctgaaa cataaaatga    2400
atgcaattgt tgttgttaac ttgtttattg cagcttataa tggttacaaa taaagcaata    2460
gcatcacaaa tttcacaaat aaagcatttt tttcactgca ttctagttgt ggtttgtcca    2520
aactcatcaa tgtatcttat catgtctgga tctgcggatc caatctcgag ctgggcctca    2580
tgggccttcc gctcactgcc cgctttccag tcgggaaacc tgtcgtgcca gctgcattaa    2640
catggtcata gctgtttcct tgcgtattgg gcgctctccg cttcctcgct cactgactcg    2700
ctgcgctcgg tcgttcgggt aaagcctggg gtgcctaatg agcaaaaggc cagcaaaagg    2760
ccaggaaccg taaaaaggcc gcgttgctgg cgttttttcca taggctccgc ccccctgacg    2820
agcatcacaa aaatcgacgc tcaagtcaga ggtggcgaaa cccgacagga ctataaagat    2880
accaggcgtt tccccctgga agctccctcg tgcgctctcc tgttccgacc ctgccgctta    2940
ccggatacct gtccgccttt ctcccttcgg aagcgtggc gctttctcat agctcacgct    3000
gtaggtatct cagttcggtg taggtcgttc gctccaagct gggctgtgtg cacgaacccc    3060
ccgttcagcc cgaccgctgc gccttatccg gtaactatcg tcttgagtcc aacccggtaa    3120
gacacgactt atcgccactg gcagcagcca ctggtaacag gattagcaga gcgaggtatg    3180
taggcggtgc tacagagttc ttgaagtggt ggcctaacta cggctacact agaagaacag    3240
tatttggtat ctgcgctctg ctgaagccag ttaccttcgg aaaaagagtt ggtagctctt    3300
gatccggcaa acaaaccacc gctggtagcg gtggtttttt tgtttgcaag cagcagatta    3360
cgcgcagaaa aaaggatct caagaagatc ctttgatctt ttctacgggg tctgacgctc    3420
agtggaacga aaactcacgt taagggattt tggtcatgag attatcaaaa aggatcttca    3480
cctagatcct tttaaattaa aaatgaagtt ttaaatcaat ctaaagtata tatgagtaaa    3540
cttggtctga cagttaccaa tgcttaatca gtgaggcacc tatctcagcg atctgtctat    3600
ttcgttcatc catagttgcc tgactccccg tcgtgtagat aactacgata cgggagggct    3660
taccatctgg ccccagtgct gcaatgatac cgcgagaacc acgctcaccg gctccagatt    3720
tatcagcaat aaaccagcca gccggaaggg ccgagcgcag aagtggtcct gcaactttat    3780
ccgcctccat ccagtctatt aattgttgcc gggaagctag agtaagtagt tcgccagtta    3840
atagtttgcg caacgttgtt gccattgcta caggcatcgt ggtgtcacgc tcgtcgtttg    3900
gtatggcttc attcagctcc ggttcccaac gatcaaggcg agttacatga tcccccatgt    3960
tgtgcaaaaa agcggttagc tccttcggtc ctccgatcgt tgtcagaagt aagttggccg    4020
cagtgttatc actcatggtt atggcagcac tgcataattc tcttactgtc atgccatccg    4080
taagatgctt ttctgtgact ggtgagtact caaccaagtc attctgagaa tagtgtatgc    4140
ggcgaccgag ttgctcttgc ccggcgtcaa tacgggataa taccgcgcca catagcagaa    4200
ctttaaaagt gctcatcatt ggaaaacgtt cttcggggcg aaaactctca aggatcttac    4260
cgctgttgag atccagttcg atgtaaccca ctcgtgcacc caactgatct tcagcatctt    4320
ttactttcac cagcgtttct gggtgagcaa aaacaggaag gcaaaatgcc gcaaaaaagg    4380
gaataagggc gacacggaaa tgttgaatac tcatactctt ccttttttcaa tattattgaa    4440 gcatttatca gggttattgt ctcatgagcg gatacatatt tgaatgtatt tagaaaaata    4500
aacaaatagg ggttccgcgc acatttcccc gaaaagtgcc ac                      4542
```

<210> SEQ ID NO 32

<211> LENGTH: 3172
<212> TYPE: DNA
<213> ORGANISM: Artificial Sequence
<220> FEATURE:
<223> OTHER INFORMATION: FRT_HCMVpp28-3xMYC_F3 vector V9.E.6

<400> SEQUENCE: 32

```
ggcggttcct ctacatccgg tggatctgga tctggagaac aaaagctcat ctctgaggag      60
gaccttgggg agcagaagct aatcagtgaa gaagacctcg gagagcagaa attgattagc     120
gaggaggatc tttaaagact aggcacgaag ttcctattcc gaagttccta ttctttcaaat    180
agtataggaa cttccgctct gaccagctgc attaacatgg tcatagctgt ttccttgcgt     240
attgggcgct ctccgcttcc tcgctcactg actcgctgcg ctcggtcgtt cgggtaaagc     300
ctggggtgcc taatgagcaa aaggccagca aaaggccagg aaccgtaaaa aggccgcgtt     360
gctggcgttt ttccataggc tccgccccc tgacgagcat cacaaaaatc gacgctcaag     420
tcagaggtgg cgaaacccga caggactata aagataccag gcgtttcccc ctggaagctc     480
cctcgtgcgc tctcctgttc cgaccctgcc gcttaccgga tacctgtccg cctttctccc    540
ttcgggaagc gtggcgcttt ctcatagctc acgctgtagg tatctcagtt cggtgtaggt     600
cgttcgctcc aagctgggct gtgtgcacga accccccgtt cagcccgacc gctgcgcctt    660
atccggtaac tatcgtcttg agtccaaccc ggtaagacac gacttatcgc cactggcagc     720
agccactggt aacaggatta gcagagcgag gtatgtaggc ggtgctacag agttcttgaa     780
gtggtggcct aactacggct acactagaag aacagtattt ggtatctgcg ctctgctgaa     840
gccagttacc ttcggaaaaa gagttggtag ctcttgatcc ggcaaacaaa ccaccgctgg     900
tagcggtggt ttttttgttt gcaagcagca gattacgcgc agaaaaaaag gatctcaaga    960
agatcctttg atcttttcta cggggtctga cgctcagtgg aacgaaaact cacgttaagg    1020
gattttggtc atgagattat caaaaaggat cttcacctag atcctttta attaaaaatg    1080
aagttttaaa tcaatctaaa gtatatatga gtaaacttgg tctgacagtt accaatgctt    1140
aatcagtgag gcacctatct cagcgatctg tctatttcgt tcatccatag ttgcctgact    1200
ccccgtcgtg tagataacta cgatacggga gggcttacca tctggcccca gtgctgcaat    1260
gataccgcga gaaccacgct caccggctcc agatttatca gcaataaacc agccagccgg    1320
aagggccgag cgcagaagtg gtcctgcaac tttatccgcc tccatccagt ctattaattg    1380
ttgccgggaa gctagagtaa gtagttcgcc agttaatagt ttgcgcaacg ttgttgccat    1440
tgctacaggc atcgtggtgt cacgctcgtc gtttggtatg gcttcattca gctccggttc    1500
ccaacgatca aggcgagtta catgatcccc catgttgtgc aaaaaagcgg ttagctcctt    1560
cggtcctccg atcgttgtca gaagtaagtt ggccgcagtg ttatcactca tggttatggc    1620
agcactgcat aattctctta ctgtcatgcc atccgtaaga tgcttttctg tgactggtga    1680
gtactcaacc aagtcattct gagaatagtg tatgcggcga ccgagttgct cttgcccggc    1740
gtcaatacgg gataataccg cgccacatag cagaacttta aaagtgctca tcattggaaa    1800
acgttcttcg gggcgaaaac tctcaaggat cttaccgctg ttgagatcca gttcgatgta    1860
acccactcgt gcacccaact gatcttcagc atcttttact ttcaccagcg tttctgggtg    1920
agcaaaaaca ggaaggcaaa atgccgcaaa aaagggaata agggcgacac ggaaatgttg    1980
aatactcata ctcttccttt ttcaatatta ttgaagcatt tatcagggtt attgtctcat    2040
gagcggatac atatttgaat gtatttagaa aaataaacaa ataggggttc cgcgcacatt    2100
tccccgaaaa gtgccaccta aattgtaagc gttaatattt tgttaaaatt cgcgttaaat    2160
```

```
ttttgttaaa tcagctcatt ttttaaccaa taggccgaaa tcggcaaaat cccttataaa    2220
tcaaaagaat agaccgagat agggttgagt ggccgctaca gggcgctccc attcgccatt    2280
caggctgcgc aactgttggg aagggcgttt cggtgcgggc ctcttcgcta ttacgccagc    2340
tggcgaaagg gggatgtgct gcaaggcgat taagttgggt aacgccaggg ttttcccagt    2400
cacgacgttg taaaacgacg gccagtgagc gcgacgtaat acgactcact ataggggcaa    2460
ttggcggaag gccgtcaagg ccgcatgaat tcgctaccgg gagttggtag gtaagtatca    2520
aggttacaag acaggtttaa ggaggaagtt cctattccga agttcctatt ctctagaaag    2580
tataggaact tcgactctca ccatgggtgc cgaactctgc aaacgaatat gttgtgagtt    2640
cggtaccacg tccggtgagc ccctgaaaga tgctctgggt cgccaggtgt ctctacgctc    2700
ctacgacaac atccctccga cttcctcctc ggacgaaggg gaggacgatg acgacgggga    2760
ggatgacgat aacgaggagc ggcaacagaa gctgcggctc tgcggtagtg gctgcggagg    2820
aaacgacagt agcagtggca gccaccgaga ggccacccac gacggcccta agaagaacgc    2880
tgtgcgctcg acgtttcgcg aggacaaggc tccgaaaccg agcaagcagt ccaagaagaa    2940
aaagaaaccc tcaaagcatc accaccatca gcaaagctcc attatgcagg agacggacga    3000
cttagacgaa gaggacacct caatttacct gtcccctccc cctgttccac cagttcaggt    3060
ggtggctaag cgactgccgc gtcccgacac acccaggact ccgcgccaga agaagatttc    3120
acaacgtcca cccacacccg ggaccaaaaa gcccgctgcc tccttgccct tt           3172
```

<210> SEQ ID NO 33
<211> LENGTH: 3900
<212> TYPE: DNA
<213> ORGANISM: Artificial Sequence
<220> FEATURE:
<223> OTHER INFORMATION: FRT_HCMVpp52-3xMYC_F3 vector V9.E.7

<400> SEQUENCE: 33

```
ggcggttcct ctacatccgg tggatctgga tctggagaac aaaagctcat ctctgaggag      60
gaccttgggg agcagaagct aatcagtgaa gaagacctcg gagagcagaa attgattagc     120
gaggaggatc tttaaagact aggcacgaag ttcctattcc gaagttccta ttcttcaaat     180
agtataggaa cttccgctct gaccagctgc attaacatgg tcatagctgt ttccttgcgt     240
attgggcgct ctccgcttcc tcgctcactg actcgctgcg ctcggtcgtt cgggtaaagc     300
ctggggtgcc taatgagcaa aaggccagca aaaggccagg aaccgtaaaa aggccgcgtt     360
gctggcgttt ttccataggc tccgcccccc tgacgagcat cacaaaaatc gacgctcaag     420
tcagaggtgg cgaaacccga caggactata aagataccag gcgtttcccc ctggaagctc     480
cctcgtgcgc tctcctgttc cgaccctgcc gcttaccgga tacctgtccg cctttctccc     540
ttcgggaagc gtggcgcttt ctcatagctc acgctgtagg tatctcagtt cggtgtaggt     600
cgttcgctcc aagctgggct gtgtgcacga accccccgtt cagcccgacc gctgcgcctt     660
atccggtaac tatcgtcttg agtccaaccc ggtaagacac gacttatcgc cactggcagc     720
agccactggt aacaggatta gcagagcgag gtatgtaggc ggtgctacag agttcttgaa     780
gtggtggcct aactacggct acactagaag aacagtattt ggtatctgcg ctctgctgaa     840
gccagttacc ttcggaaaaa gagttggtag ctccttgatc cggcaaacaa accaccgctgg    900 tagcggtggt ttttttgttt gcaagcagca gattacgcgc agaaaaaaag gatctcaaga     960
agatcctttg atcttttcta cggggtctga cgctcagtgg aacgaaaact cacgttaagg    1020
```

-continued

```
gattttggtc atgagattat caaaaaggat cttcacctag atccttttaa attaaaaatg   1080
aagttttaaa tcaatctaaa gtatatatga gtaaacttgg tctgacagtt accaatgctt   1140
aatcagtgag gcacctatct cagcgatctg tctatttcgt tcatccatag ttgcctgact   1200
ccccgtcgtg tagataacta cgatacggga gggcttacca tctggcccca gtgctgcaat   1260
gataccgcga gaaccacgct caccggctcc agatttatca gcaataaacc agccagccgg   1320
aagggccgag cgcagaagtg gtcctgcaac tttatccgcc tccatccagt ctattaattg   1380
ttgccgggaa gctagagtaa gtagttcgcc agttaatagt ttgcgcaacg ttgttgccat   1440
tgctacaggc atcgtggtgt cacgctcgtc gtttggtatg gcttcattca gctccggttc   1500
ccaacgatca aggcgagtta catgatcccc catgttgtgc aaaaaagcgg ttagctcctt   1560
cggtcctccg atcgttgtca gaagtaagtt ggccgcagtg ttatcactca tggttatggc   1620
agcactgcat aattctctta ctgtcatgcc atccgtaaga tgcttttctg tgactggtga   1680
gtactcaacc aagtcattct gagaatagtg tatgcggcga ccgagttgct cttgcccggc   1740
gtcaatacgg gataataccg cgccacatag cagaacttta aaagtgctca tcattggaaa   1800
acgttcttcg gggcgaaaac tctcaaggat cttaccgctg ttgagatcca gttcgatgta   1860
acccactcgt gcacccaact gatcttcagc atcttttact ttcaccagcg tttctgggtg   1920
agcaaaaaca ggaaggcaaa atgccgcaaa aagggaata agggcgacac ggaaatgttg   1980
aatactcata ctcttccttt ttcaatatta ttgaagcatt tatcagggtt attgtctcat   2040
gagcggatac atatttgaat gtatttagaa aaataaacaa ataggggttc cgcgcacatt   2100
tccccgaaaa gtgccaccta aattgtaagc gttaatattt tgttaaaatt cgcgttaaat   2160
ttttgttaaa tcagctcatt ttttaaccaa taggccgaaa tcggcaaaat cccttataaa   2220
tcaaaagaat agaccgagat agggttgagt ggccgctaca gggcgctccc attcgccatt   2280
caggctgcgc aactgttggg aagggcgttt cggtgcgggc ctcttcgcta ttacgccagc   2340
tggcgaaagg gggatgtgct gcaaggcgat taagttgggt aacgccaggg ttttcccagt   2400
cacgacgttg taaaacgacg gccagtgagc gcgacgtaat acgactcact atagggcgaa   2460
ttggcggaag gccgtcaagg ccgcatgaat tcgctaccgg gagttggtag gtaagtatca   2520
aggttacaag acaggtttaa ggaggaagtt cctattccga agttcctatt ctctagaaag   2580
tataggaact tcgactctac caccatggat cgcaagacgc gcctctcgga gccgccgacg   2640
ctggcgctgc ggctgaagcc gtacaagacg gctatccagc agctgcgatc tgtgatccgt   2700
gcgctcaagg agaacaccac ggttaccttc ttgcccacac cgtcgcttat cttgcaaacg   2760
gtacgcagtc actgcgtgtc aaagatcact tttaacagct catgcctcta catcactgac   2820
aagtcgtttc agcccaagac cattaacaat tccacgcctc tgctgggtaa cttcatgtac   2880
ctgacttcca gcaaggacct gaccaagttc tacgtgcagg acatctcgga cctgtcggcc   2940
aagatctcca tgtgcgcacc cgatttcaat atggagttca gctcggcctg cgtgcacggc   3000
caagacattg tgcgcgaaag cgagaattcg gccgtgcacg tggatctaga tttcggcgtg   3060
gtggccgacc tgcttaagtg gatcgggccg catacccgcg tcaagcgtaa cgtgaagaaa   3120
gcgccctgcc ctacgggcac cgtgcagatt ctggtgcacg ccggtccacc ggccatcaag   3180
ttcatcctga ccaacggcag cgagctggaa ttcacagcca ataaccgcgt cagtttccac   3240
ggcgtgaaaa acatgcgtat caacgtgcag ctgaagaact tctaccagac gctgctcaat   3300
tgcgccgtca ccaaactgcc gtgcacgttg cgtatagtta cggagcacga cacgctgttg   3360
tacgtggcca gccgcaacgg tctgttcgcc gtggagaatt ttctcaccga ggaacctttc   3420
```

| | |
|---|---|
| cagcgtggcg atcccttcga caagaattac gtcgggaaca gcggcaaatc gcgtggcgga | 3480 |
| ggcggtggta gcggcagcct ctcttcgctg gctaatgccg gcggtctgca cgacgacggt | 3540 |
| ccgggtctgg acaacgatat catgaacgag cccatgggtc tcggcggact gggaggtggc | 3600 |
| ggaggagggg gaggcaagaa gcacgaccgc ggaggtggcg gtggttccgg tacgcggaaa | 3660 |
| atgagcagcg gtggcggagg tggagatcac gaccacggtc tttcctccaa ggaaaaatac | 3720 |
| gagcagcaca gatcaccag ctacctgacg tccaaaggtg gatcgggagg aggggggtgga | 3780 |
| ggcggaggtg gaggtttgga tcgcaactcc ggcaattact caacgacgc gaaagaggag | 3840 |
| agcgacagcg aggattctgt aacgttcgag ttcgtcccta acaccaagaa gcaaaagtgc | 3900 |

<210> SEQ ID NO 34
<211> LENGTH: 4286
<212> TYPE: DNA
<213> ORGANISM: Artificial Sequence
<220> FEATURE:
<223> OTHER INFORMATION: FRT_HCMVpp52-3xMYC_F3 vector V9.E.8

<400> SEQUENCE: 34

| | |
|---|---|
| ggcggttcct ctacatccgg tggatctgga tctggagaac aaaagctcat ctctgaggag | 60 |
| gaccttgggg agcagaagct aatcagtgaa gaagacctcg gagagcagaa attgattagc | 120 |
| gaggaggatc tttaaagact aggcacgaag ttcctattcc gaagttccta ttcttcaaat | 180 |
| agtataggaa cttccgctct gaccagctgc attaacatgg tcatagctgt ttccttgcgt | 240 |
| attgggcgct ctccgcttcc tcgctcactg actcgctgcg ctcggtcgtt cgggtaaagc | 300 |
| ctggggtgcc taatgagcaa aaggccagca aaaggccagg aaccgtaaaa aggccgcgtt | 360 |
| gctggcgttt ttccataggc tccgcccccc tgacgagcat cacaaaaatc gacgctcaag | 420 |
| tcagaggtgg cgaaacccga caggactata aagataccag gcgtttcccc ctggaagctc | 480 |
| cctcgtgcgc tctcctgttc cgaccctgcc gcttaccgga tacctgtccg cctttctccc | 540 |
| ttcgggaagc gtggcgcttt ctcatagctc acgctgtagg tatctcagtt cggtgtaggt | 600 |
| cgttcgctcc aagctgggct gtgtgcacga accccccgtt cagcccgacc gctgcgcctt | 660 |
| atccggtaac tatcgtcttg agtccaaccc ggtaagacac gacttatcgc cactggcagc | 720 |
| agccactggt aacaggatta gcagagcgag gtatgtaggc ggtgctacag agttcttgaa | 780 |
| gtggtggcct aactacggct acactagaag aacagtattt ggtatctgcg ctctgctgaa | 840 |
| gccagttacc ttcggaaaaa gagttggtag ctcttgatcc ggcaaacaaa ccaccgctgg | 900 |
| tagcggtggt ttttttgttt gcaagcagca gattacgcgc agaaaaaaag gatctcaaga | 960 |
| agatcctttg atcttttcta cggggtctga cgctcagtgg aacgaaaact cacgttaagg | 1020 |
| gattttggtc atgagattat caaaaaggat cttcacctag atccttttaa attaaaaatg | 1080 |
| aagttttaaa tcaatctaaa gtatatatga gtaaacttgg tctgacagtt accaatgctt | 1140 |
| aatcagtgag gcacctatct cagcgatctg tctatttcgt tcatccatag ttgcctgact | 1200 |
| ccccgtcgtg tagataacta cgatacggga gggcttacca tctggcccca gtgctgcaat | 1260 |
| gataccgcga gaaccacgct caccggctcc agatttatca gcaataaacc agccagccgg | 1320 |
| aagggccgag cgcagaagtg gtcctgcaac tttatccgcc tccatccagt ctattaattg | 1380 |
| ttgccgggaa gctagagtaa gtagttcgcc agttaatagt ttgcgcaacg ttgttgccat | 1440 |
| tgctacaggc atcgtggtgt cacgctcgtc gtttggtatg gcttcattca gctccggttc | 1500 |
| ccaacgatca aggcgagtta catgatcccc catgttgtgc aaaaaagcgg ttagctcctt | 1560 |

```
cggtcctccg atcgttgtca gaagtaagtt ggccgcagtg ttatcactca tggttatggc      1620
agcactgcat aattctctta ctgtcatgcc atccgtaaga tgcttttctg tgactggtga      1680
gtactcaacc aagtcattct gagaatagtg tatgcggcga ccgagttgct cttgcccggc      1740
gtcaatacgg gataataccg cgccacatag cagaacttta aaagtgctca tcattggaaa      1800
acgttcttcg gggcgaaaac tctcaaggat cttaccgctg ttgagatcca gttcgatgta      1860
acccactcgt gcacccaact gatcttcagc atcttttact ttcaccagcg tttctgggtg      1920
agcaaaaaca ggaaggcaaa atgccgcaaa aaagggaata agggcgacac ggaaatgttg      1980
aatactcata ctcttccttt ttcaatatta ttgaagcatt tatcagggtt attgtctcat      2040
gagcggatac atatttgaat gtatttagaa aaataaacaa atagggggttc cgcgcacatt      2100 tccccgaaaa gtgccaccta aattgtaagc gttaatattt tgttaaaatt cgcgttaaat      2160
ttttgttaaa tcagctcatt ttttaaccaa taggccgaaa tcggcaaaat cccttataaa      2220
tcaaaagaat agaccgagat agggttgagt ggccgctaca gggcgctccc attcgccatt      2280
caggctgcgc aactgttggg aagggcgttt cggtgcgggc ctcttcgcta ttacgccagc      2340
tggcgaaagg gggatgtgct gcaaggcgat taagttgggt aacgccaggg ttttcccagt      2400
cacgacgttg taaaacgacg gccagtgagc gcgacgtaat acgactcact atagggcgaa      2460
ttggcggaag gccgtcaagg ccgcatgaat tcgctaccgg gagttggtag gtaagtatca      2520
aggttacaag acaggtttaa ggaggaagtt cctattccga agttcctatt ctctagaaag      2580
tataggaact tcgactctca ggtaccatgg agtcgcgcgg tcgccgttgt cccgaaatga      2640
tatccgtact gggtcccatt tcggggcacg tgctgaaagc cgtgtttagt cgcggcgata      2700
cgccggtgct gccgcacgag acgcgactcc tgcagacggg tatccacgta cgcgtgagcc      2760
agccctcgct gatcttggta tcgcagtaca cgcccgactc gacgccatgc caccgcggcg      2820
acaatcagct gcaggtgcag cacacgtact ttacgggcag cgaggtggag aacgtgtcgg      2880
tcaacgtgca caaccccacg ggccgaagca tctgccccag ccaggagccc atgtcgatct      2940
atgtgtacgc gctgccgctc aagatgctga acatccccag catcaacgtg caccactacc      3000
cgtcggcggc cgagcgcaaa caccgacacc tgcccgtagc tgacgctgtg attcacgcgt      3060
cgggcaagca gatgtggcag gcgcgtctca cggtctcggg actggcctgg acgcgtcagc      3120
agaaccagtg gaaagagccc gacgtctact acacgtcagc gttcgtgttt cccaccaagg      3180
acgtggcact gcggcacgtg gtgtgcgcgc acagctggt ttgctccatg gagaacacgc      3240
gcgcaaccaa gatgcaggtg ataggtgacc agtacgtcaa ggtgtacctg gagtccttct      3300
gcgaggacgt gccctccggc aagctcttta tgcacgtcac gctgggctct gacgtggaag      3360
aggacctgac gatgacccgc aacccgcaac ccttcatgcg cccccacgag cgcaacggct      3420
ttacggtgtt gtgtcccaaa aatatgataa tcaaaccggg caagatctcg cacatcatgc      3480
tggatgtggc ttttacctca cacgagcatt ttgggctgct gtgtcccaag agcatcccgg      3540
gcctgagcat ctcaggtaac ctgttgatga acggcagca gatcttcctg gaggtacaag      3600
ccatacgcga gaccgtggaa ctgcgtcagt acgatcccgt ggctgcgctc ttctttttcg      3660
atatcgactt gctgctgcag cgcgggcctc agtacagcga gcaccccacc ttcaccagcc      3720
agtatcgcat ccagggcaag cttgagtacc gacacacctg ggaccggcac gacgagggtg      3780
ccgcccaggg cgacgacgac gtctggacca gcggatcgga ctccgacgaa gaactcgtaa      3840
ccaccgagcg caagacgccc cgcgtcaccg gcggcggcgc catggcgggc gcctccactt      3900
ccgcgggccg caaacgcaaa tcagcatcct cggcgacggc gtgcacgtcg ggcgttatga      3960
```

```
cacgcggccg ccttaaggcc gagtccaccg tcgcgcccga agaggacacc gacgaggatt    4020
ccgacaacga aatccacaat ccggccgtgt tcacctggcc gccctggcag gccggcatcc    4080
tggcccgcaa cctggtgccc atggtggcta cggttcaggg tcagaatctg aagtaccagg    4140
agttcttctg ggacgccaac gacatctacc gcatcttcgc cgaattggaa ggcgtatggc    4200
agcccgctgc gcaacccaaa cgtcgccgcc accggcaaga cgccttgccc gggccatgca    4260
tcgcctcgac gcccaaaaag caccga                                         4286
```

<210> SEQ ID NO 35
<211> LENGTH: 25
<212> TYPE: DNA
<213> ORGANISM: Homo sapiens
<220> FEATURE:
<223> OTHER INFORMATION: pMA-sv40_OE_F1 primer 1.C.2

<400> SEQUENCE: 35
cctgatcata atcaagccat atcac                                          25

<210> SEQ ID NO 36
<211> LENGTH: 25
<212> TYPE: DNA
<213> ORGANISM: Homo sapiens
<220> FEATURE:
<223> OTHER INFORMATION: pMA-sv40_OE_R1 primer 1.C.3

<400> SEQUENCE: 36
gtgatatggc ttgattatga tcagg                                          25

<210> SEQ ID NO 37
<211> LENGTH: 20
<212> TYPE: DNA
<213> ORGANISM: Homo sapiens
<220> FEATURE:
<223> OTHER INFORMATION: HLA-A-GT-Rg3 primer 4.A.3 1

<400> SEQUENCE: 37
tcccgttctc caggtatctg                                                20

<210> SEQ ID NO 38
<211> LENGTH: 20
<212> TYPE: DNA
<213> ORGANISM: Homo sapiens
<220> FEATURE:
<223> OTHER INFORMATION: HLA-A-GT-Fg2 primer 4.A.4

<400> SEQUENCE: 38
gtgtcgggtt tccagagaag                                                20

<210> SEQ ID NO 39
<211> LENGTH: 20
<212> TYPE: DNA
<213> ORGANISM: Homo sapiens
<220> FEATURE:
<223> OTHER INFORMATION: HLA-B-GT-Fg2 primer 4.A.7

<400> SEQUENCE: 39
gggtcccagt tctaaagtcc                                                20

<210> SEQ ID NO 40
<211> LENGTH: 20
<212> TYPE: DNA
<213> ORGANISM: Homo sapiens
<220> FEATURE:

<223> OTHER INFORMATION: HLA-B-GT-Rg2 primer 4.B.1

<400> SEQUENCE: 40
ggggattttg gcctcaactg                                             20

<210> SEQ ID NO 41
<211> LENGTH: 21
<212> TYPE: DNA
<213> ORGANISM: Homo sapiens
<220> FEATURE:
<223> OTHER INFORMATION: HLA-C-GT-Fg2 primer 4.B.5

<400> SEQUENCE: 41
tcttcctgaa tactcatgac g                                           21

<210> SEQ ID NO 42
<211> LENGTH: 20
<212> TYPE: DNA
<213> ORGANISM: Homo sapiens
<220> FEATURE:
<223> OTHER INFORMATION: HLA-A-02_GT_Rg4 primer 4.I.9

<400> SEQUENCE: 42
ggagatctac aggcgatcag                                             20

<210> SEQ ID NO 43
<211> LENGTH: 28
<212> TYPE: DNA
<213> ORGANISM: Homo sapiens
<220> FEATURE:
<223> OTHER INFORMATION: HLA-A-Exon3_HA-RE-BglII_F1 primer 6.I.9

<400> SEQUENCE: 43
ggttagatct gggaaggaga cgctgcag                                    28

<210> SEQ ID NO 44
<211> LENGTH: 20
<212> TYPE: DNA
<213> ORGANISM: Homo sapiens
<220> FEATURE:
<223> OTHER INFORMATION: HLA-C-04-GT-Rg1 primer 8.A.1

<400> SEQUENCE: 44
gatcccattt tcctcccctc                                             20

<210> SEQ ID NO 45
<211> LENGTH: 27
<212> TYPE: DNA
<213> ORGANISM: Homo sapiens
<220> FEATURE:
<223> OTHER INFORMATION: CMV-pA-HLA-Ex3_Probe_F1 primer 8.B.2

<400> SEQUENCE: 45
atgtctggat ctgcggatca gcgcacg                                     27

<210> SEQ ID NO 46
<211> LENGTH: 21
<212> TYPE: DNA
<213> ORGANISM: Homo sapiens
<220> FEATURE:
<223> OTHER INFORMATION: CMV-pro_GT_R1 primer 9.C.3

<400> SEQUENCE: 46
atgggctatg aactaatgac c                                           21

```
<210> SEQ ID NO 47
<211> LENGTH: 21
<212> TYPE: DNA
<213> ORGANISM: Homo sapiens
<220> FEATURE:
<223> OTHER INFORMATION: sv40pA_GT_F1 primer 9.C.4

<400> SEQUENCE: 47
cattctagtt gtggtttgtc c                                         21

<210> SEQ ID NO 48
<211> LENGTH: 20
<212> TYPE: DNA
<213> ORGANISM: Homo sapiens
<220> FEATURE:
<223> OTHER INFORMATION: AAVS1_GT_F1 primer 9.C.5

<400> SEQUENCE: 48
cttacctctc tagtctgtgc                                           20

<210> SEQ ID NO 49
<211> LENGTH: 19
<212> TYPE: DNA
<213> ORGANISM: Homo sapiens
<220> FEATURE:
<223> OTHER INFORMATION: AAVS1_GT_F3 primer 9.C.7

<400> SEQUENCE: 49
ccattgtcac tttgcgctg                                            19

<210> SEQ ID NO 50
<211> LENGTH: 20
<212> TYPE: DNA
<213> ORGANISM: Homo sapiens
<220> FEATURE:
<223> OTHER INFORMATION: AAVS1_GT_F4 primer 9.C.8

<400> SEQUENCE: 50
tcctggactt tgtctccttc                                           20

<210> SEQ ID NO 51
<211> LENGTH: 20
<212> TYPE: DNA
<213> ORGANISM: Homo sapiens
<220> FEATURE:
<223> OTHER INFORMATION: AAVS1_GT_R2 primer 9.C.10

<400> SEQUENCE: 51
agagatggct ccaggaaatg                                           20

<210> SEQ ID NO 52
<211> LENGTH: 20
<212> TYPE: DNA
<213> ORGANISM: Homo sapiens
<220> FEATURE:
<223> OTHER INFORMATION: AAVS1_GT_R3 primer 9.D.1

<400> SEQUENCE: 52
aagagaaagg gagtagaggc                                           20

<210> SEQ ID NO 53
<211> LENGTH: 18
<212> TYPE: DNA
<213> ORGANISM: Homo sapiens
<220> FEATURE:
<223> OTHER INFORMATION: AAVS1_GT_R4 primer 9.D.2
```

```
<400> SEQUENCE: 53
cccgaagagt gagtttgc                                                 18

<210> SEQ ID NO 54
<211> LENGTH: 20
<212> TYPE: DNA
<213> ORGANISM: Homo sapiens
<220> FEATURE:
<223> OTHER INFORMATION: HLA-A-intron4_GT_R1 primer 9.D.6

<400> SEQUENCE: 54
gctaaaggtc agagaggctc                                               20

<210> SEQ ID NO 55
<211> LENGTH: 23
<212> TYPE: DNA
<213> ORGANISM: Homo sapiens
<220> FEATURE:
<223> OTHER INFORMATION: sv40pA-GT primer 9.D.7

<400> SEQUENCE: 55
ctgcattcta gttgtggttt gtc                                           23

<210> SEQ ID NO 56
<211> LENGTH: 24
<212> TYPE: DNA
<213> ORGANISM: Homo sapiens
<220> FEATURE:
<223> OTHER INFORMATION: sv40pA-AAVS1-probe-FAM-F1 primer 9.J.2

<400> SEQUENCE: 56
tgcggatcag gattggtgac agaa                                          24

<210> SEQ ID NO 57
<211> LENGTH: 26
<212> TYPE: DNA
<213> ORGANISM: Homo sapiens
<220> FEATURE:
<223> OTHER INFORMATION: TRAC_TCRA-ex1_R1 primer 10.A.9

<400> SEQUENCE: 57
gacttgtcac tggatttaga gtctct                                        26

<210> SEQ ID NO 58
<211> LENGTH: 23
<212> TYPE: DNA
<213> ORGANISM: Homo sapiens
<220> FEATURE:
<223> OTHER INFORMATION: TRAC_TCRA-promoter_F1 primer 10.A.10

<400> SEQUENCE: 58
ctgatcctct tgtcccacag ata                                           23

<210> SEQ ID NO 59
<211> LENGTH: 22
<212> TYPE: DNA
<213> ORGANISM: Homo sapiens
<220> FEATURE:
<223> OTHER INFORMATION: TRAC_probe (HEX) primer 10.B.6

<400> SEQUENCE: 59
atccagaacc ctgaccctgc cg                                            22

<210> SEQ ID NO 60
<211> LENGTH: 20
```

-continued

<212> TYPE: DNA
<213> ORGANISM: Homo sapiens
<220> FEATURE:
<223> OTHER INFORMATION: Pan-HLA_GT_F1 primer 8.B.3

<400> SEQUENCE: 60
aaggagggag ctactctcag                                           20

<210> SEQ ID NO 61
<211> LENGTH: 24
<212> TYPE: DNA
<213> ORGANISM: Homo sapiens
<220> FEATURE:
<223> OTHER INFORMATION: SV40pA_GT_R1 primer 15.H.2

<400> SEQUENCE: 61
cctctacaga tgtgatatgg cttg                                      24

<210> SEQ ID NO 62
<211> LENGTH: 27
<212> TYPE: DNA
<213> ORGANISM: Homo sapiens
<220> FEATURE:
<223> OTHER INFORMATION: 3xMyc_OE_R1 primer 10.C.4

<400> SEQUENCE: 62
ggagaacaaa agctcatctc tgaggag                                   27

<210> SEQ ID NO 63
<211> LENGTH: 29
<212> TYPE: DNA
<213> ORGANISM: Homo sapiens
<220> FEATURE:
<223> OTHER INFORMATION: CtermCysLink_OE_R1 primer 10.D.1

<400> SEQUENCE: 63
agatccagat ccaccggatg tagagcaac                                 29

<210> SEQ ID NO 64
<211> LENGTH: 20
<212> TYPE: DNA
<213> ORGANISM: Homo sapiens
<220> FEATURE:
<223> OTHER INFORMATION: Ef1a_intron_GT_F2 primer 15.H.4

<400> SEQUENCE: 64
tgggtggaga ctgaagttag                                           20

<210> SEQ ID NO 65
<211> LENGTH: 18
<212> TYPE: DNA
<213> ORGANISM: Homo sapiens
<220> FEATURE:
<223> OTHER INFORMATION: HCMVpp65_GT_F2ddPCR primer/probe 21.I.1

<400> SEQUENCE: 65
tcgacgccca aaaagcac                                             18

<210> SEQ ID NO 66
<211> LENGTH: 17
<212> TYPE: DNA
<213> ORGANISM: Homo sapiens
<220> FEATURE:
<223> OTHER INFORMATION: HCMVpp28_GT_F1 ddPCR primer/probe 21.I.2

<400> SEQUENCE: 66

```
<210> SEQ ID NO 67
<211> LENGTH: 19
<212> TYPE: DNA
<213> ORGANISM: Homo sapiens
<220> FEATURE:
<223> OTHER INFORMATION: HCMVpp52_GT_F1 ddPCR primer/probe 21.I.3

<400> SEQUENCE: 67
cgtccctaac accaagaag                                                19

<210> SEQ ID NO 68
<211> LENGTH: 19
<212> TYPE: DNA
<213> ORGANISM: Homo sapiens
<220> FEATURE:
<223> OTHER INFORMATION: Myc-Tag_GT_R1 ddPCR primer/probe 20.H.10

<400> SEQUENCE: 68
aaggtcctcc tcagagatg                                                19

<210> SEQ ID NO 69
<211> LENGTH: 27
<212> TYPE: DNA
<213> ORGANISM: Homo sapiens
<220> FEATURE:
<223> OTHER INFORMATION: Linker-Myc_Probe_Fam ddPCR primer/probe 20.H.9

<400> SEQUENCE: 69
cttttgttct ccagatccag atccacc                                       27

<210> SEQ ID NO 70
<211> LENGTH: 23
<212> TYPE: DNA
<213> ORGANISM: Homo sapiens
<220> FEATURE:
<223> OTHER INFORMATION: TRAC-TCRA-ex1-F1 ddPCR primer/probe 10.A.9

<400> SEQUENCE: 70
ctgatcctct tgtcccacag ata                                           23

<210> SEQ ID NO 71
<211> LENGTH: 26
<212> TYPE: DNA
<213> ORGANISM: Homo sapiens
<220> FEATURE:
<223> OTHER INFORMATION: TRAC-TCRA-ex1-F1 ddPCR primer/probe

<400> SEQUENCE: 71
gacttgtcac tggatttaga gtctct                                        26

<210> SEQ ID NO 72
<211> LENGTH: 22
<212> TYPE: DNA
<213> ORGANISM: Homo sapiens
<220> FEATURE:
<223> OTHER INFORMATION: TRAC-probe (HEX) ddPCR primer/probe

<400> SEQUENCE: 72
atccagaacc ctgaccctgc cg                                            22
```

The invention claimed is:

1. A method of selecting a component of or output from an analyte engineered antigen-presenting cell T-cell receptor (eAPC:T) system, wherein the eAPC-T system comprises an analyte engineered antigen-presenting cell (eAPC) and an analyte cell (analyte TC), wherein the eAPC is a cell that is engineered to lack endogenous expression of a target antigen-presenting complex and/or lacks endogenous expression of a target analyte antigenic molecule, wherein the eAPC comprises a genomic receiver site for integration of an open reading frame (ORF) encoding the target analyte antigen and wherein the analyte TC expresses on its surface a T cell receptor (analyte TCR), the method comprising:
(a) detecting a reported signal response from the eAPC: T system, wherein the reported signal response is based on an interaction between the target analyte antigen and the analyte TCR; and
(b) selecting a component of or a output from the eAPC: T system based on the presence or absence of the reported signal response, wherein the component is selected from the eAPC or the analyte TC, and wherein the output is selected from an affinity reagent or a non-cell based particle (NCBP).

2. The method of claim 1, wherein step (a) comprises detecting:
(i) a secreted biomolecule;
(ii) a secreted chemical;
(iii) an intracellular biomolecule;
(iv) an intracellular chemical;
(v) a surface expressed biomolecule;
(vi) a cytotoxic action of the analyte TC upon the analyte eAPC;
(vii) a paracrine action of the analyte TC upon the analyte eAPC;
(viii) proliferation of the analyte TC;
(ix) an immunological synapse between the analyte TC and the analyte eAPC.

3. The method of claim 2, wherein step (a) comprises detecting (vi) or (vii).

4. The method of claim 3, wherein step (a) further comprises detecting one or more of (i)-(v).

5. The method of claim 2, wherein step (a) comprises detecting (vii), and wherein (vii) is determined by detecting:
(1) a secreted biomolecule;
(2) a secreted chemical;
(3) an intracellular biomolecule;
(4) an intracellular chemical; or
(5) a surface expressed biomolecule.

6. The method of claim 1, wherein the reported signal response is a native signaling response.

7. The method of claim 1, wherein the reported signal response is a synthetic signaling response.

8. The method of claim 1, wherein the analyte TC is a primary T-cell, a recombinant T-cell or an engineered TCR presenting cell.

9. A method of selecting an analyte T cell receptor (analyte TCR), the method comprising:
(a) combining an analyte engineered antigen-presenting cell (eAPC) with an analyte TCR, wherein:
(i) the eAPC is engineered to lack endogenous surface expression of a target antigen-presenting complex (aAPX) and/or lacks endogenous expression of an analyte antigenic molecule (aAM);
(ii) the eAPC comprises a first genomic receiver site for integration of an open reading frame (ORF) encoding a target analyte antigen;
(iii) wherein the target analyte antigen is selected from:
(1) an aAPX: aAM complex;
(2) an aAM;
(3) an aAPX; or
(4) an aAPX: CM complex, wherein CM is a cargo molecule; and
(iv) the analyte TCR is a pair of TCR chains or TCR-mimic affinity reagent; and
(v) the analyte TCR is:
(1) a soluble reagent;
(2) an immobilised reagent;
(3) presented by a non-cell based particle (NCBP); or
(4) presented on the surface of a cell (TC),
(b) detecting the presence or absence of a formation of a complex between the target analyte antigen and the analyte TCR; and
(c) selecting the analyte TCR based on the detection of the presence or absence of the formation of the complex.

10. The method of claim 9, wherein step (b) comprises detecting a signal response induced by the formation of the complex, wherein the signal response is produced by (i) an analyte T cell (analyte TC) that expresses the analyte TCR or (ii) the eAPC.

11. The method of claim 9, wherein step (c) comprises performing single cell sorting and/or cell sorting to a pool.

12. The method of claim 11, further comprising, after single cell sorting, expanding the sorted single cell.

13. The method of claim 12, further comprising sequencing the analyte TCR of the sorted and/or expanded cell(s).

14. The method according to claim 13, further comprising, prior to the sequencing, one or more of: (1) extracting nucleic acids from the sorted and/or expanded cell(s), wherein the nucleic acids encode the analyte TCR, wherein the nucleic acids are genomic DNA or RNA; or (2) amplifying the nucleic acids by PCR or RT-PCR.

15. The method according to claim 11, further comprising, after cell sorting to a pool, expanding the sorted pool of cells.

16. The method of claim 15, further comprising sequencing the analyte TCR of the sorted and/or expanded cell(s).

17. The method according to claim 16, further comprising, prior to the sequencing, one or more of: (1) extracting nucleic acids from the sorted and/or expanded cell(s), wherein the nucleic acids encode the analyte TCR, wherein the nucleic acids are genomic DNA or RNA; or (2) amplifying the nucleic acids by PCR or RT-PCR.

18. The method of claim 9, wherein the signal response is a native signal response or synthetic signal response.

19. The method of claim 10, wherein the induced signal response is determined by detecting one or more of:
(1) a secreted biomolecule:
(2) a secreted chemical;
(3) an intracellular biomolecule;
(4) an intracellular chemical;
(5) a surface expressed biomolecule;
(6) a cytotoxic action of the analyte TC upon an analyte eAPC
(7) a paracrine action of the analyte TC upon an analyte eAPC;
(8) a proliferation of the analyte TC; or
(9) an immunological synapse between the analyte TC and an analyte eAPC.

* * * * *

UNITED STATES PATENT AND TRADEMARK OFFICE
CERTIFICATE OF CORRECTION

PATENT NO. : 12,270,047 B2
APPLICATION NO. : 16/863119
DATED : April 8, 2025
INVENTOR(S) : Reagan Micheal Jarvis et al.

It is certified that error appears in the above-identified patent and that said Letters Patent is hereby corrected as shown below:

On the Title Page

In item (57) Abstract, Under Column 2, Line 21, delete "recombinase mediated exchange" and insert -- recombinase mediated cassette exchange --.

In item (56) Other Publications, Under Column 2, Page 2, Line 4, delete "177, 3pages (2016)." and insert -- 177, 3 pages (2016). --.

In item (56) Other Publications, Under Column 2, Page 2, Line 16, delete "and γδT-Cell" and insert -- and γδ T-Cell --.

In the Drawings

Sheet 31 of 50, Figure 31, Line 1 (Y-Axis), delete "cout" and insert -- count --.

In the Specification

Under Column 1, Line 56, delete "The T-Cell/Receptor (TCR)" and insert -- The T-Cell Receptor (TCR) --.

Under Column 2, Line 32, delete "of a T-cells" and insert -- of αβ T-cells --.

Under Column 3, Line 16, delete "and germlineencoded mycolyl" and insert -- germline-encoded mycolyl --.

Under Column 5, Lines 62-63, delete "tumour immunuosurveillance and" and insert -- tumour immunosurveillance and --.

Under Column 6, Line 51, delete "glycopeptides, glycolipds and" and insert -- glycopeptides, glycolipids and --.

Signed and Sealed this
First Day of July, 2025

Coke Morgan Stewart
*Acting Director of the United States Patent and Trademark Office*

Under Column 8, Line 54, delete "matched as pairs" and insert -- matched αβ pairs --.

Under Column 10, Line 1, delete "paired as chains" and insert -- paired αβ chains --.

Under Column 11, Lines 52-55, delete "immunodiagnostics. Furthermore, the present invention relates to the use the multicomponent system to identify and characterise T-cell antigens and cognate TCRs for production of immunotherapeutics and immunodiagnostics." and insert -- immunodiagnostics. Furthermore, the present invention relates to the use of the multicomponent system to identify and characterise T-cell antigens and cognate TCRs for production of immunotherapeutics and immunodiagnostics. --.

Under Column 15, Line 15, delete "Akozak consensussequence. " and insert -- A kozak consensus sequence. --.

Under Column 16, Line 5, delete "Akozak consensussequence." and insert -- A kozak consensus sequence. --.

Under Column 19, Line 26, delete "HLA class" and insert -- HLA class II --.

Under Column 22, Line 61, delete "response circuit." and insert -- response circuit --.

Under Column 23, Line 21, delete "or NCBP" and insert -- or NCBP. --.

Under Column 24, Line 48, delete "in a an" and insert -- in an --.

Under Column 24, Line 54, delete "in a an" and insert -- in an --.

Under Column 25, Line 28, delete "pool of cells" and insert -- pool of cells. --.

Under Column 30, Line 17, delete "In STEP1 the" and insert -- In STEP 1 the --.

Under Column 30, Line 23, delete "In STEP2 the" and insert -- In STEP 2 the --.

Under Column 30, Line 23, delete "in STEP1 is" and insert -- in STEP 1 is --.

Under Column 30, Line 34, delete "In STEP1 the" and insert -- In STEP 1 the --.

Under Column 30, Line 40, delete "In STEP2 the" and insert -- In STEP 2 the --.

Under Column 30, Line 40, delete "in STEP1 is" and insert -- in STEP 1 is --.

Under Column 32, Line 15 (Approx.), delete "signal strength*, **" and insert -- signal strength *, ** --.

Under Column 32, Line 34, delete "analyte analyte TC" and insert -- analyte TC --.

CERTIFICATE OF CORRECTION (continued)　　　　　　　　　　　　　　　　　Page 3 of 6
U.S. Pat. No. 12,270,047 B2

Under Column 33, Line 29, delete "of Phase1, cells" and insert -- of Phase 1, cells --.

Under Column 36, Line 2, delete "as controls" and insert -- as controls. --.

Under Column 36, Line 38, delete "in monclones ACL-421" and insert -- in monoclones ACL-421 --.

Under Column 37, Line 2, delete "to 3reference gene" and insert -- to 3 reference gene --.

Under Column 37, Line 61, delete "post electoporation, individual" and insert -- post electroporation, individual --.

Under Column 38, Line 55, delete "outgrowth, ACL1050 cells" and insert -- outgrowth, ACL-1050 cells --.

Under Column 38, Line 59, delete "of ACL1050. c)" and insert -- of ACL-1050. c) --.

Under Column 39, Line 17, delete "(eAPC, HLA-1 null," and insert -- (eAPC, HLA-I null, --.

Under Column 40, Line 32 (Approx.), delete "with AnnexinV and" and insert -- with Annexin V and --.

Under Column 41, Line 18, delete "over 3kD columns." and insert -- over 3 kD columns. --.

Under Column 41, Line 50, delete "II V1.1.5 and V1.1.7. Variants" and insert -- II V1.I.5 and V1.I.7. Variants --.

Under Column 42, Line 5, delete "and jetPEI @ were" and insert -- and jetPEI® were --.

Under Column 42, Lines 29-30, delete "Trypsin (ThermoFisher Scientific)" and insert -- Trypsin (Thermo Fisher Scientific) --.

Under Column 42, Lines 48-49, delete "Trypsin (ThermoFisher Scientific)" and insert -- Trypsin (Thermo Fisher Scientific) --.

Under Column 43, Line 46, delete "the LRSFortessa™ (BD" and insert -- the LSRFortessa™ (BD --.

Under Column 43, Line 64, delete "DNA Minikit (Qiagen)." and insert -- DNA Mini Kit (Qiagen). --.

Under Column 44, Line 40 (Approx.), delete "using Q5@ Hot" and insert -- using Q5® Hot --.

Under Column 44, Line 48 (Approx.), delete "and 9.D. 1 to" and insert -- and 9.D.1 to --.

Under Column 44, Line 61 (Approx.), delete "Hot-Start Q5@ DNA" and insert -- Hot-Start Q5® DNA --.

CERTIFICATE OF CORRECTION (continued)
U.S. Pat. No. 12,270,047 B2

Under Column 44, Line 62 (Approx.), delete "and H₂0). PCR" and insert -- and H₂O). PCR --.

Under Column 44, Line 66 (Approx.), delete "of sybersafe and" and insert -- of sybr safe and --.

Under Column nos. 45-46, Line 29 (Table 5), delete "10.6.6" and insert -- 10.B.6 --.

Under Column 45, Line 64, delete "primers 4.1.9 and" and insert -- primers 4.I.9 and --.

Under Column 48, Line 9, delete "primer (SV40 pA_GT_R1" and insert -- primer (SV40pA_GT_R1 --.

Under Column 49, Line 18 (Table 8), delete "H20" and insert -- H2O --.

Under Column 49, Line 36 (Approx.), delete "of sybersafe and" and insert -- of sybr safe and --.

Under Column 49, Line 54 (Approx.), delete "well polysterene (wp)" and insert -- well polystyrene (wp) --.

Under Column 50, Line 67, delete "mix: AnnexinV BV711" and insert -- mix: Annexin V BV711 --.

Under Column 51, Line 17, delete "to HLA-A*24:02" and insert -- to HLA-A*24:02. --.

Under Column 51, Line 38, delete "over 3kD Nanosep" and insert -- over 3 kD Nanosep --.

Under Column 52, Line 4, delete "for κ min" and insert -- for 8 min --.

Under Column 52, Line 56, delete "encoded Cas9-P2 Å-GFP were" and insert -- encoded Cas9-P2A-GFP were --.

Under Column 53, Line 65, delete "encoded Cas9-P2 Å-GFP and" and insert -- encoded Cas9-P2A-GFP and --.

Under Column 53, Line 67, delete "for Cas9-P2 Å-GFP plasmid" and insert -- for Cas9-P2A-GFP plasmid --.

Under Column 54, Line 31, delete "Monoclones ACL469 and" and insert -- Monoclones ACL-469 and --.

Under Column 54, Line 35, delete "and ACL470 cell" and insert -- and ACL-470 cell --.

Under Column 54, Line 67, delete "for Cas9-P2 Å-GFP plasmid for Cas9-P2A-GFP plasmid".

Under Column 56, Line 13, delete "component C'HLA-A*24:02 and" and insert -- component $C'^{HLA-A*24:02}$ and --.

CERTIFICATE OF CORRECTION (continued)
U.S. Pat. No. 12,270,047 B2

Under Column 56, Line 20, delete "for Cas9-P2 Å-GFP plasmid" and insert -- for Cas9-P2A-GFP plasmid --.

Under Column 57, Line 7, delete "an HLADRA*01:01" and insert -- an HLA-DRA*01:01 --.

Under Column 58, Line 4, delete "for RMCE" and insert -- for RMCE. --.

Under Column 58, Line 29, delete "and ACL422, and" and insert -- and ACL-422, and --.

Under Column 63, Line 5, delete "provided exogeneously, and provided exogenously, and".

Under Column 63, Line 32 (Approx.), delete "(FIG. 46 a)." and insert -- (FIG. 46a). --.

Under Column 63, Line 49, delete "(ACL-390)" and insert -- (ACL-390). --.

Under Column 65, Line 13, delete "by AnnexinV and" and insert -- by Annexin V and --.

Under Column 65, Line 19, delete "(FIG. 48 a)." and insert -- (FIG. 48a). --.

Under Column 65, Line 26, delete "by AnnexinV and" and insert -- by Annexin V and --.

Under Column 66, Line 7, delete "affinity chromatopraphy as" and insert -- affinity chromatography as --.

Under Column 66, Line 38 (Approx.), delete "of T-cellreceptors and" and insert -- of T-cell receptors and --.

Under Column 67, Line 35 (Approx.), delete "<223> AAVSl_sg-sp-opti_3" and insert -- <223> AAVSI_sg-sp-opti_3 --.

Under Column 68, Line 18 (Approx.) , delete "primer 4.1.9" and insert -- primer 4.I.9 --.

Under Column 70, Line 22, delete "TRG TRCgamma" and insert -- TRG TRC gamma --.

Under Column 70, Line 62, delete "presenting complext" and insert -- presenting complex. --.

Under Column 71, Line 31 (Approx.), delete "Cargo molecules. peptide" and insert -- Cargo molecules peptide --.

Under Column 72, Line 6, delete "RNA polymerase and" and insert -- RNA polymerase II and --.

Under Column 76, Line 27, delete "HLA class" and insert -- HLA class II --.

Under Column 76, Line 67, delete "Akozak consensussequence" and insert -- A kozak consensus sequence --.

Under Column 81, Line 3, delete "an eAPCp and/or" and insert -- an eAPC-p and/or --.

Under Column 81, Line 44, delete "of cells" and insert -- of cells. --.

Under Column 82, Line 67, delete "an eAPCp and/or" and insert -- an eAPC-p and/or --.

Under Column 83, Line 8, delete "engineered cell" and insert -- engineered cell. --.

Under Column 83, Line 33 (Approx.), delete "signalling response" and insert -- signalling response. --.

In the Claims

In Claim 2, Column 221, Line 27, delete "(viii) proliferation of the analyte TC;" and insert -- (viii) proliferation of the analyte TC; or --.